United States Patent
Kim et al.

(10) Patent No.: US 10,266,607 B2
(45) Date of Patent: Apr. 23, 2019

(54) ANTIBODY BINDING TO TFPI AND COMPOSITION COMPRISING THE SAME

(71) Applicant: MOGAM INSTITUTE FOR BIOMEDICAL RESEARCH, Yongin-si, Gyeonggi-do (KR)

(72) Inventors: Dong-Sik Kim, Yongin-si (KR); Mi Jung Lee, Yongin-si (KR); Jae Chan Park, Yongin-si (KR); Sumin Lee, Yongin-si (KR); Heechun Kwak, Yongin-si (KR); SungHo Hwang, Yongin-si (KR); Hyung-Kwon Lim, Yongin-si (KR); Kisu Kim, Yongin-si (KR); Young Seoub Park, Yongin-si (KR); Junhong Jeong, Yongin-si (KR); Ki Joon Cho, Yongin-si (KR)

(73) Assignee: MOGAM INSTITUTE FOR BIOMEDICAL RESEARCH, Yongin-si (KR)

( * ) Notice: Subject to any disclaimer, the term of this patent is extended or adjusted under 35 U.S.C. 154(b) by 0 days.

(21) Appl. No.: 15/553,292

(22) PCT Filed: Dec. 29, 2015

(86) PCT No.: PCT/KR2015/014370
§ 371 (c)(1),
(2) Date: Aug. 24, 2017

(87) PCT Pub. No.: WO2016/137108
PCT Pub. Date: Sep. 1, 2016

(65) Prior Publication Data
US 2018/0030151 A1    Feb. 1, 2018

(30) Foreign Application Priority Data

Feb. 25, 2015 (KR) .................. 10-2015-0026555
Sep. 24, 2015 (KR) .................. 10-2015-0135761

(51) Int. Cl.
*C07K 16/38* (2006.01)
(52) U.S. Cl.
CPC .......... *C07K 16/38* (2013.01); *C07K 2317/24* (2013.01); *C07K 2317/34* (2013.01); *C07K 2317/565* (2013.01); *C07K 2317/622* (2013.01); *C07K 2317/72* (2013.01); *C07K 2317/92* (2013.01)

(58) Field of Classification Search
None
See application file for complete search history.

(56) References Cited

U.S. PATENT DOCUMENTS

| 5,378,614 A | 1/1995 | Petersen et al. | |
|---|---|---|---|
| 8,618,263 B2 * | 12/2013 | Hilden | C07K 16/38 424/145.1 |
| 2012/0269817 A1 * | 10/2012 | Wang | A61K 39/3955 424/142.1 |
| 2014/0275493 A1 | 9/2014 | Murphy et al. | |

FOREIGN PATENT DOCUMENTS

| CA | 2 745 317 | 7/2010 | |
|---|---|---|---|
| JP | 2012-512915 | 6/2012 | |
| JP | 2013-500701 | 1/2013 | |
| JP | 2014-511685 | 5/2014 | |
| KR | 10-2015-0026555 | * 2/2015 | |
| KR | 10-2016-0103767 A | 9/2016 | |
| WO | 2010/017196 A2 | 2/2010 | |
| WO | 2011/109452 A1 | 9/2011 | |
| WO | WO-2011130377 A2 * | 10/2011 | ......... C07K 14/4711 |
| WO | 2012/135671 A2 | 10/2012 | |
| WO | 2013/148248 | 10/2013 | |
| WO | 2014/144577 | 9/2014 | |
| WO | 2015/007880 | 1/2015 | |

OTHER PUBLICATIONS

Janeway et al., Immunobiology, 3rd edition, Garland Publications, Inc., 1997, pp. 3:1-3:11.*
UniProt entry Q6MZU6 downloaded from www.uniprot.org/uniprot/Q6MZU6 on Jul. 6, 2018, seqence in database on Jul. 5, 2004.*
Rudikoff et al., Proc Natl Acad Sci U S A. Mar. 1982;79(6):1979-83.*
Susan A. Maroney et al., "Absence of hematopoietic tissue factor pathway inhibitor mitigates bleeding in mice with hemophilia", PNAS, Mar. 6, 2012, pp. 3927-3931, vol. 109, No. 10.
Ruud M. T. De Wildt et al., "Analysis of Heavy and Light Chain Pairings Indicates that Receptor Editing Shapes the Human Antibody Repertoire", J. Mol. Biol., 1999, pp. 895-901, vol. 285.
Thomas Tiller et al., "A fully synthetic human Fab antibody library based on fixed VH/VL framework pairings with favorable biophysical properties", mAbs, May/Jun. 2013, pp. 445-470, vol. 5, Issue 3.
Stefan Ewert et al. "Stability improvement of antibodies for extracellular and intracellular applications: CDR grafting to stable frameworks and structure-based framework engineering", Methods, 2004, pp. 184-199, vol. 34.

(Continued)

*Primary Examiner* — Michael Szperka
(74) *Attorney, Agent, or Firm* — Sughrue Mion, PLLC

(57) ABSTRACT

The present invention relates to an antibody that binds specifically to a tissue factor pathway inhibitor (TFPI), a nucleic acid encoding the antibody, a vector comprising the nucleic acid, a host cell transformed with the vector, a method for producing the antibody, and a pharmaceutical composition for treating hemophilia, which comprises the antibody as an active ingredient. The antibody of the present invention, which binds specifically to TFPI, can activate the extrinsic pathway of blood coagulation by inhibiting TFPI. Thus, the antibody of the present invention can be effectively used for the treatment of antibody-induced hemophilia patients and for the prevention of blood coagulation disease in hemophilia-A or hemophilia-B patients.

6 Claims, 34 Drawing Sheets

Specification includes a Sequence Listing.

(56) References Cited

OTHER PUBLICATIONS

International Search Report for PCT/KR2015/014370, dated Apr. 8, 2016.
Korean Patent Office, communication dated Feb. 16, 2017 by the Korean Patent Office in copending Application No. 10-2015-0135761.
Korean Patent Office, communication dated Sep. 25, 2017 by the Korean Patent Office in copending Application No. 10-2015-0135761.
Australian Patent Office, communication dated Apr. 30, 2018 by the Australian Patent Office in copending Application No. 2015384281.
Canadian Patent Office, communication dated May 22, 2018 by the Canadian Patent Office in copending Application No. 2977621.
European Patent Office, communication dated Jun. 7, 2018 by the European Patent Office in copending Application No. 15 88 3495.
NCBI Reference Sequence NP_006278.1 tissue factor pathway inhibitor isoform a precursor [*Homo sapiens*].
GenBank: AA089075.1, tissue factor pathway inhibitor (lipoprotein-associated coagulation inhibitor) [*Homo sapiens*].
NCBI Reference Sequence: XP_004032982.1, Predicted: tissue factor pathway inhibitor isoform X1 [Gorilla gorilla gorilla].
Hilden et al., "Hemostatic effect of a monoclonal antibody MAb 2021 blocking the interaction between FXa and TFPI in a rabbit hemophilia model", Blood, vol. 119, No. 24, Jun. 2012, pp. 5871-5878.
WHO Drug Information, vol. 26, No. 4, 2012—Proposed International Nonproprietary Names, List 108 (2012; 135 pages).
Korean Patent Office: Communication dated Nov. 16, 2016 in counterpart application No. 10-2015-0026555.
Japanese Patent Office, Communication dated Sep. 4, 2018 by the Japanese Patent Office in copending Application No. 2017-545218.

\* cited by examiner

FIG. 4

Sequence alignment

```
VH              10         20         30         40        5052a
T417    EVHLVESGGDLVKPGGSLKLSCAASGFTFSSYAMSWVRQTPDKRLEWVATITTGGSYTY 59
308     EVQLVESGGGLVKPGGSLRLSCAASGFTFSSYAMNWVRQAPGKGLEWVSTITTGGSYTY 59
                  FR1              CDR1         FR2          CDR2

60         70       8082abc       90         100       110
T417    YPDSVKGRFTISRDNAKNTLYLQMSSLKSEDTAMYYCARQDGNFLMDYWGQGTTVTVSS 118
308     YADSVKGRFTISRDNAKNSLYLQMNSLRAEDTAVYYCARQDGNFLMDYWGQGTLVTVSS 118
                      FR3                     CDR3         FR4

VL              10         20       27abcd 30        40         50
T417    DVVMTQTPLTLSVTIGQPASISCKSSQSLIDSDGKTYLNWLLQRPGQSPKRLIYLVSKLDSGVP 59
308     DVVMTQTPLSLPVTLGQPASISCKSSQSLIDSDGKTYLNWLQQRPGQSPKRLIYLVSKLDSGVP 59
                  FR1              CDR1           FR2           CDR2

60         70        80         90        100
T417    DRFTGSGSGTDFTLKISRVEAEDLGVYYCWQGTHFPFTFGSGTKLEIKR 108
308     DRFTGSGSGTDFTLKISRVEAEDVGVYYCWQGTHFPFTFGQGTKVEIKR 108
                      FR3                CDR3         FR4
```

FIG. 5

Sequence alignment

```
VH              10        20        30        40        5052a
308     EVQLVESGGGLVKPGGSLRLSCAASGFTFS SYAMN VRQAPGKGLEWVS TITGGSITY  59
308-2   ..........................................................
308-4   ..........................................................

60        70       8082abc     90       100       110
308      KADSVKG RFTISRDNAKNSLYLQMNSLRAEDTAVYYCAR QDSNFLMDY WGQGTLVTVSS  118
308-2   .....Q....................................................
308-4   .....E....................................................
```

FIG. 18
Heavy Chain Variable Region
Hydrogen bond
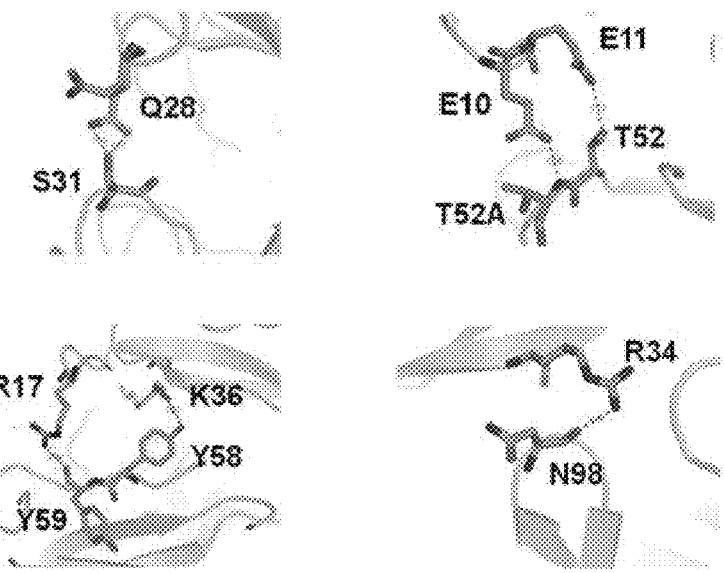
Salt bridge                Hydrophobic interaction
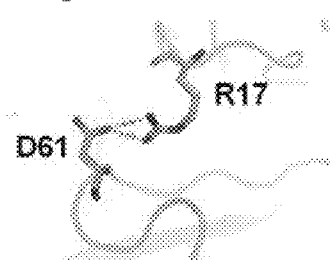 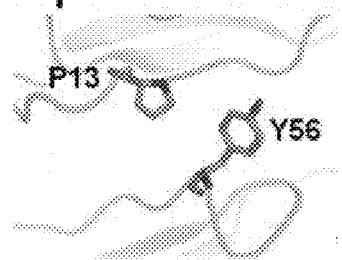

Light Chain Variable Region
Hydrogen bond

FIG. 30
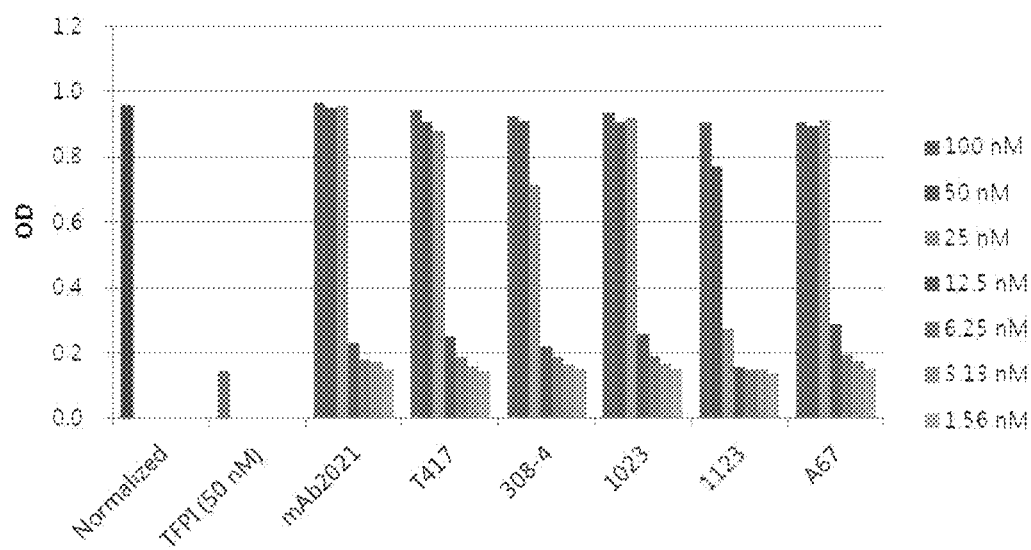
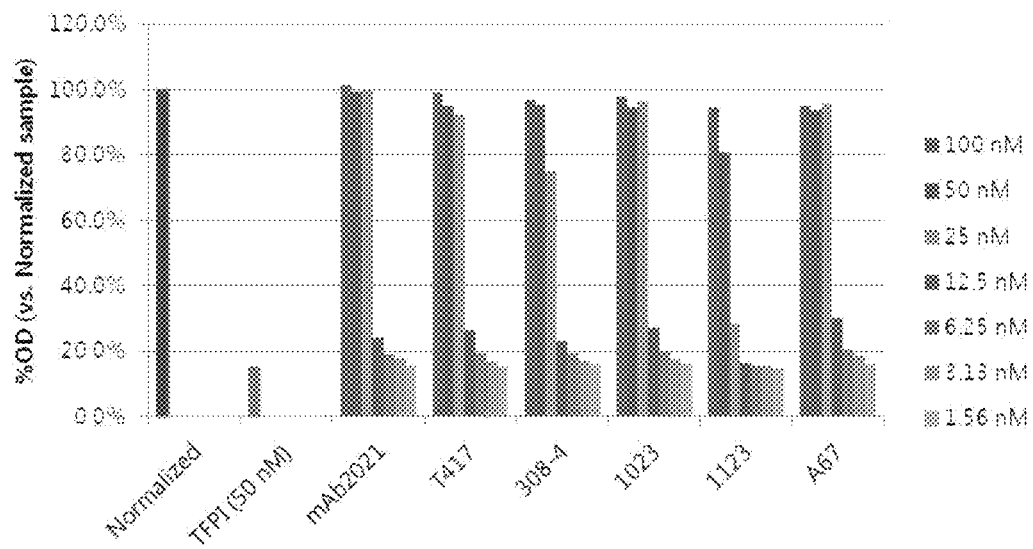

FIG. 32
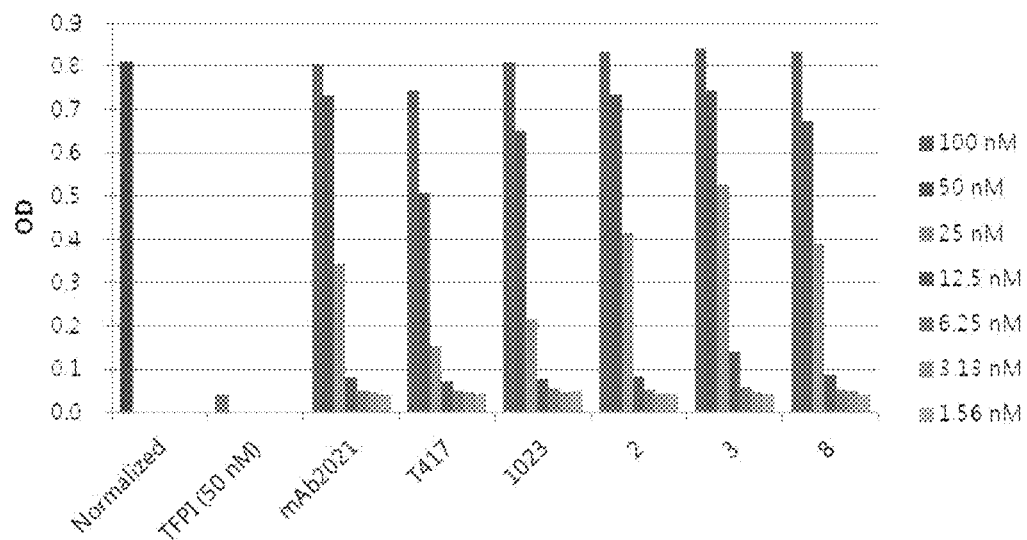
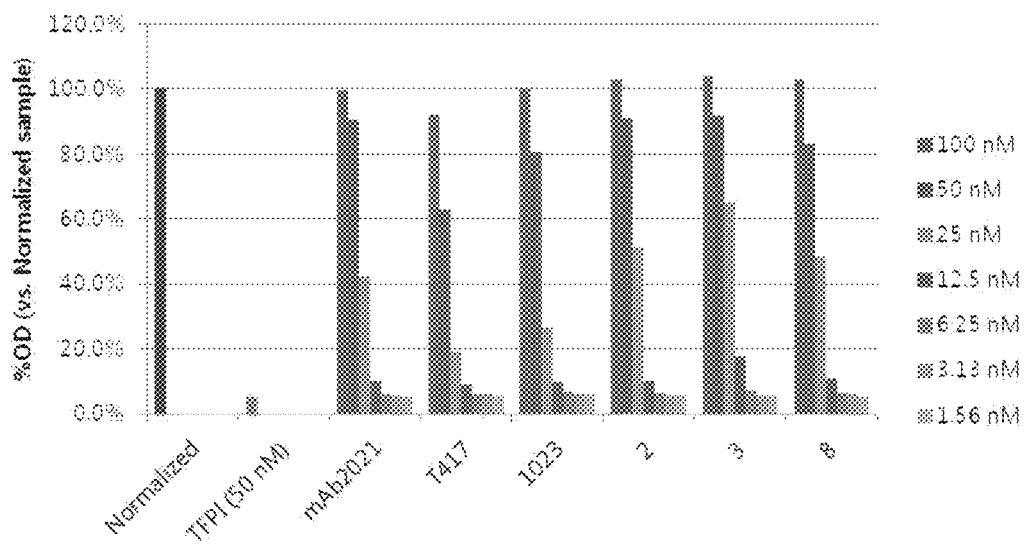

SEQUENCE LISTING

<160> NUMBER OF SEQ ID NOS: 204

<210> SEQ ID NO 1
<211> LENGTH: 118
<212> TYPE: PRT
<213> ORGANISM: Artificial Sequence
<220> FEATURE:
<223> OTHER INFORMATION: Clone T417_mouse Variable heavy chain

<400> SEQUENCE: 1

Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Asp Lys Arg Leu Glu Trp Val
        35                  40                  45

Ala Thr Ile Thr Thr Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Asp Gly Asn Phe Leu Met Asp Tyr Trp Gly Gln Gly Thr
            100                 105                 110

Thr Val Thr Val Ser Ser
        115

<210> SEQ ID NO 2
<211> LENGTH: 113
<212> TYPE: PRT
<213> ORGANISM: Artificial Sequence
<220> FEATURE:
<223> OTHER INFORMATION: Clone T417_mouse Variable light chain

<400> SEQUENCE: 2

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110

Arg

<210> SEQ ID NO 3
<211> LENGTH: 120
<212> TYPE: PRT
<213> ORGANISM: Artificial Sequence
<220> FEATURE:
<223> OTHER INFORMATION: Clone T308_mouse Variable heavy chain

<400> SEQUENCE: 3

Glu Val Lys Leu Val Glu Gly Gly Leu Val Lys Pro Gly
1               5                   10                  15

Ser Leu Lys Leu Ser Cys Ala Ala Ser Gly Phe Thr Phe Ser Asn Tyr
            20                  25                  30

Pro Met Ser Trp Val Arg Gln Thr Pro Glu Lys Arg Leu Glu Trp Val
            35                  40                  45

Ala Thr Ile Ser Asn Ser Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Arg Gln Val Tyr Gly Asn Tyr Glu Asp Phe Asp Tyr Trp Gly Gln
            100                 105                 110

Gly Thr Thr Leu Thr Val Ser Ser
        115                 120

<210> SEQ ID NO 4
<211> LENGTH: 113
<212> TYPE: PRT
<213> ORGANISM: Artificial Sequence
<220> FEATURE:
<223> OTHER INFORMATION: Clone T308_mouse Variable light chain

<400> SEQUENCE: 4

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Leu Lys
            100                 105                 110

Arg

<210> SEQ ID NO 5
<211> LENGTH: 5
<212> TYPE: PRT
<213> ORGANISM: Artificial Sequence
<220> FEATURE:
<223> OTHER INFORMATION: Clone T417_mouse Variable heavy chain CDR 1

<400> SEQUENCE: 5

Ser Tyr Ala Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Clone T417_mouse Variable heavy chain CDR 2

<400> SEQUENCE: 6

Thr Ile Thr Thr Gly Gly Ser Tyr Thr Tyr Tyr Pro Asp Ser Val Lys
1               5                   10                  15

Gly

<210> SEQ ID NO 7
<211> LENGTH: 9
<212> TYPE: PRT
<213> ORGANISM: Artificial Sequence
<220> FEATURE:
<223> OTHER INFORMATION: Clone T417_mouse Variable heavy chain CDR 3

<400> SEQUENCE: 7

Gln Asp Gly Asn Phe Leu Met Asp Tyr
1               5

<210> SEQ ID NO 8
<211> LENGTH: 16
<212> TYPE: PRT
<213> ORGANISM: Artificial Sequence
<220> FEATURE:
<223> OTHER INFORMATION: Clone T417_mouse Variable light chain CDR 1

<400> SEQUENCE: 8

Lys Ser Ser Gln Ser Leu Leu Asp Ser Asp Gly Lys Thr Tyr Leu Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Clone T417_mouse Variable light chain CDR 2

<400> SEQUENCE: 9

Leu Val Ser Lys Leu Asp Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Clone T417_mouse Variable light chain CDR 3

<400> SEQUENCE: 10

Trp Gln Gly Thr His Phe Pro Phe
1               5

<210> SEQ ID NO 11
<211> LENGTH: 5
<212> TYPE: PRT
<213> ORGANISM: Artificial Sequence
<220> FEATURE:
<223> OTHER INFORMATION: Clone T308_mouse Variable heavy chain CDR 1

<400> SEQUENCE: 11

Asn Tyr Pro Met Ser
1               5

<210> SEQ ID NO 12
<211> LENGTH: 17
<212> TYPE: PRT
<213> ORGANISM: Artificial Sequence
<220> FEATURE:
<223> OTHER INFORMATION: Clone T308_mouse Variable heavy chain CDR 2

```
<400> SEQUENCE: 12

Thr Ile Ser Asn Ser Gly Ser Tyr Thr Tyr Tyr Pro Asp Ser Val Lys
1               5                   10                  15

Gly

<210> SEQ ID NO 13
<211> LENGTH: 11
<212> TYPE: PRT
<213> ORGANISM: Artificial Sequence
<220> FEATURE:
<223> OTHER INFORMATION: Clone T308_mouse Variable heavy chain CDR 3

<400> SEQUENCE: 13

Gln Val Tyr Gly Asn Tyr Glu Asp Phe Asp Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Clone T308_mouse Variable light chain CDR 1

<400> SEQUENCE: 14

Lys Ser Ser Gln Ser Leu Leu Asp Ser Asp Gly Lys Thr Tyr Leu Asn
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Clone T308_mouse Variable light chain CDR 2

<400> SEQUENCE: 15

Leu Val Ser Lys Leu Asp Ser
1               5

<210> SEQ ID NO 16
<211> LENGTH: 8
<212> TYPE: PRT
<213> ORGANISM: Artificial Sequence
<220> FEATURE:
<223> OTHER INFORMATION: Clone T308_mouse Variable light chain CDR 3

<400> SEQUENCE: 16

Trp Gln Gly Thr His Phe Pro Tyr
1               5

<210> SEQ ID NO 17
<211> LENGTH: 87
<212> TYPE: DNA
<213> ORGANISM: Artificial Sequence
<220> FEATURE:
<223> OTHER INFORMATION: Primer_T417VH-F

<400> SEQUENCE: 17
gcggccgcca tgtatctggg tctgaactat gtctttatcg tgtttctgct gaatggtgtg    60
cagtctgagg tgcacctggt ggagtct                                        87

<210> SEQ ID NO 18
<211> LENGTH: 43
<212> TYPE: DNA
<213> ORGANISM: Artificial Sequence
<220> FEATURE:
```

<223> OTHER INFORMATION: Primer_T417VH Apa-R
<220> FEATURE:
<221> NAME/KEY: misc_feature
<222> LOCATION: (1)..(4)
<223> OTHER INFORMATION: n is a or g or c

<400> SEQUENCE: 18
nnnngggccc cttggtgctg gctgaggaga cggtgaccgt ggt                          43

<210> SEQ ID NO 19
<211> LENGTH: 95
<212> TYPE: DNA
<213> ORGANISM: Artificial Sequence
<220> FEATURE:
<223> OTHER INFORMATION: Primer_T417 VL-F

<400> SEQUENCE: 19
gcggccgcca tggatagcca ggctcaggtg ctgatgctgc tgctgctgtg ggtgtcaggg        60
acttgcgggg acgttgtgat gacccagact ccact                                   95

<210> SEQ ID NO 20
<211> LENGTH: 31
<212> TYPE: DNA
<213> ORGANISM: Artificial Sequence
<220> FEATURE:
<223> OTHER INFORMATION: Primer_VL-R
<220> FEATURE:
<221> NAME/KEY: misc_feature
<222> LOCATION: (1)..(4)
<223> OTHER INFORMATION: n is a or g or c

<400> SEQUENCE: 20
nnnnggtacc agatttcaac tgctcatcag a                                       31

<210> SEQ ID NO 21
<211> LENGTH: 118
<212> TYPE: PRT
<213> ORGANISM: Artificial Sequence
<220> FEATURE:
<223> OTHER INFORMATION: Clone 308_humanized Variable heavy chain

<400> SEQUENCE: 21

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 22
<211> LENGTH: 113
<212> TYPE: PRT
<213> ORGANISM: Artificial Sequence

```
<220> FEATURE:
<223> OTHER INFORMATION: Clone 308_humanized Variable light chain

<400> SEQUENCE: 22

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gln Gly Thr Lys Val Glu Ile Lys
            100                 105                 110

Arg

<210> SEQ ID NO 23
<211> LENGTH: 5
<212> TYPE: PRT
<213> ORGANISM: Artificial Sequence
<220> FEATURE:
<223> OTHER INFORMATION: Clone 308_humanized Variable heavy chain CDR 1

<400> SEQUENCE: 23

Ser Tyr Ala Met Asn
1               5

<210> SEQ ID NO 24
<211> LENGTH: 118
<212> TYPE: PRT
<213> ORGANISM: Artificial Sequence
<220> FEATURE:
<223> OTHER INFORMATION: Clone 308-2_humanized and mutated Variable
      heavy chain

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 25
<211> LENGTH: 118
```

```
<212> TYPE: PRT
<213> ORGANISM: Artificial Sequence
<220> FEATURE:
<223> OTHER INFORMATION: Clone 308-4_humanized and mutated Variable
      heavy chain

<400> SEQUENCE: 25

Glu Val Gln Leu Val Glu Ser Gly Gly Gly Leu Val Lys Pro Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 26
<211> LENGTH: 17
<212> TYPE: PRT
<213> ORGANISM: Artificial Sequence
<220> FEATURE:
<223> OTHER INFORMATION: Clone 308-2_humanized and mutated Variable
      heavy chain CDR 2

<400> SEQUENCE: 26

Thr Ile Thr Thr Gly Gly Ser Tyr Thr Tyr Tyr Pro Asp Ser Val Gln
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Clone 308-4_humanized and mutated Variable
      heavy chain CDR 2

<400> SEQUENCE: 27

Thr Ile Thr Thr Gly Gly Ser Tyr Thr Tyr Tyr Pro Asp Ser Val Glu
1               5                   10                  15

Gly

<210> SEQ ID NO 28
<211> LENGTH: 50
<212> TYPE: DNA
<213> ORGANISM: Artificial Sequence
<220> FEATURE:
<223> OTHER INFORMATION: Primer_VH Fo

<400> SEQUENCE: 28
tgctgtgggt gagtggtacc tgtggggaag tgcagctcgt ggagagcggt          50

<210> SEQ ID NO 29
<211> LENGTH: 56
```

<212> TYPE: DNA
<213> ORGANISM: Artificial Sequence
<220> FEATURE:
<223> OTHER INFORMATION: Primer_VH Re

<400> SEQUENCE: 29
agtgggaaca cggagggccc cttggtgctg gcggatgaga cagtcacaag tgtccc    56

<210> SEQ ID NO 30
<211> LENGTH: 58
<212> TYPE: PRT
<213> ORGANISM: Artificial Sequence
<220> FEATURE:
<223> OTHER INFORMATION: Human_TFPI Kunitz domain 2

<400> SEQUENCE: 30

Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
        35                  40                  45

Glu Glu Cys Lys Asn Ile Cys Glu Asp Gly
    50                  55

<210> SEQ ID NO 31
<211> LENGTH: 58
<212> TYPE: PRT
<213> ORGANISM: Artificial Sequence
<220> FEATURE:
<223> OTHER INFORMATION: Rabbit_TFPI Kunitz domain 2

<400> SEQUENCE: 31

Lys Pro Asp Phe Cys Phe Leu Glu Glu Asp Pro Gly Ile Cys Arg Gly
1               5                   10                  15

Phe Met Thr Arg Tyr Phe Tyr Asn Asn Gln Ser Lys Gln Cys Glu Gln
            20                  25                  30

Phe Lys Tyr Gly Gly Cys Leu Gly Asn Ser Asn Asn Phe Glu Thr Leu
        35                  40                  45

Glu Glu Cys Arg Asn Thr Cys Glu Asp Pro
    50                  55

<210> SEQ ID NO 32
<211> LENGTH: 58
<212> TYPE: PRT
<213> ORGANISM: Artificial Sequence
<220> FEATURE:
<223> OTHER INFORMATION: Mouse_TFPI Kunitz domain 2

<400> SEQUENCE: 32

Arg Pro Asp Phe Cys Phe Leu Glu Glu Asp Pro Gly Leu Cys Arg Gly
1               5                   10                  15

Tyr Met Lys Arg Tyr Leu Tyr Asn Asn Gln Thr Lys Gln Cys Glu Arg
            20                  25                  30

Phe Val Tyr Gly Gly Cys Leu Gly Asn Arg Asn Asn Phe Glu Thr Leu
        35                  40                  45

Asp Glu Cys Lys Lys Ile Cys Glu Asn Pro
    50                  55

<210> SEQ ID NO 33
<211> LENGTH: 29
<212> TYPE: DNA

```
<213> ORGANISM: Artificial Sequence
<220> FEATURE:
<223> OTHER INFORMATION: Primer_HTK2 For

<400> SEQUENCE: 33
ccatggaaac ccgactttg cttcctgga                                      29

<210> SEQ ID NO 34
<211> LENGTH: 30
<212> TYPE: DNA
<213> ORGANISM: Artificial Sequence
<220> FEATURE:
<223> OTHER INFORMATION: Primer_RTK2 For

<400> SEQUENCE: 34
ccatggaaac ccgatttctg ctttctggag                                    30

<210> SEQ ID NO 35
<211> LENGTH: 30
<212> TYPE: DNA
<213> ORGANISM: Artificial Sequence
<220> FEATURE:
<223> OTHER INFORMATION: Primer_MTK2 For

<400> SEQUENCE: 35
ccatggagac ctgacttctg ctttctggag                                    30

<210> SEQ ID NO 36
<211> LENGTH: 33
<212> TYPE: DNA
<213> ORGANISM: Artificial Sequence
<220> FEATURE:
<223> OTHER INFORMATION: Primer_HTK2 Re

<400> SEQUENCE: 36
gcggccgcct agccgtcttc acagatgttc ttg                                33

<210> SEQ ID NO 37
<211> LENGTH: 30
<212> TYPE: DNA
<213> ORGANISM: Artificial Sequence
<220> FEATURE:
<223> OTHER INFORMATION: Primer_RTK2 Re

<400> SEQUENCE: 37
gcggccgcct aggggtcctc acaggtgttg                                    30

<210> SEQ ID NO 38
<211> LENGTH: 37
<212> TYPE: DNA
<213> ORGANISM: Artificial Sequence
<220> FEATURE:
<223> OTHER INFORMATION: Primer_MTK2 Re

<400> SEQUENCE: 38
gcggccgcct aggggttctc acagattttc ttgcatt                            37

<210> SEQ ID NO 39
<211> LENGTH: 304
<212> TYPE: PRT
<213> ORGANISM: Artificial Sequence
<220> FEATURE:
<223> OTHER INFORMATION: HUMAN Tissue factor pathway inhibitor

<400> SEQUENCE: 39

Met Ile Tyr Thr Met Lys Lys Val His Ala Leu Trp Ala Ser Val Cys
```

```
            1               5              10              15
          Leu Leu Leu Asn Leu Ala Pro Ala Pro Leu Asn Ala Asp Ser Glu Glu
                         20                  25                  30

Asp Glu Glu His Thr Ile Ile Thr Asp Thr Glu Leu Pro Pro Leu Lys
                         35                  40                  45

Leu Met His Ser Phe Cys Ala Phe Lys Ala Asp Gly Pro Cys Lys
           50                  55                  60

Ala Ile Met Lys Arg Phe Phe Asn Ile Phe Thr Arg Gln Cys Glu
           65                  70                  75                  80

Glu Phe Ile Tyr Gly Gly Cys Glu Gly Asn Gln Asn Arg Phe Glu Ser
                         85                  90                  95

Leu Glu Glu Cys Lys Lys Met Cys Thr Arg Asp Asn Ala Asn Arg Ile
                        100                 105                 110

Ile Lys Thr Thr Leu Gln Gln Glu Lys Pro Asp Phe Cys Phe Leu Glu
                        115                 120                 125

Glu Asp Pro Gly Ile Cys Arg Gly Tyr Ile Thr Arg Tyr Phe Tyr Asn
                   130                 135                 140

Asn Gln Thr Lys Gln Cys Glu Arg Phe Lys Tyr Gly Gly Cys Leu Gly
          145                 150                 155                 160

Asn Met Asn Asn Phe Glu Thr Leu Glu Glu Cys Lys Asn Ile Cys Glu
                        165                 170                 175

Asp Gly Pro Asn Gly Phe Gln Val Asp Asn Tyr Gly Thr Gln Leu Asn
                        180                 185                 190

Ala Val Asn Asn Ser Leu Thr Pro Gln Ser Thr Lys Val Pro Ser Leu
                        195                 200                 205

Phe Glu Phe His Gly Pro Ser Trp Cys Leu Thr Pro Ala Asp Arg Gly
                        210                 215                 220

Leu Cys Arg Ala Asn Glu Asn Arg Phe Tyr Tyr Asn Ser Val Ile Gly
          225                 230                 235                 240

Lys Cys Arg Pro Phe Lys Tyr Ser Gly Cys Gly Gly Asn Glu Asn Asn
                        245                 250                 255

Phe Thr Ser Lys Gln Glu Cys Leu Arg Ala Cys Lys Lys Gly Phe Ile
                        260                 265                 270

Gln Arg Ile Ser Lys Gly Gly Leu Ile Lys Thr Lys Arg Lys Arg Lys
                        275                 280                 285

Lys Gln Arg Val Lys Ile Ala Tyr Glu Glu Ile Phe Val Lys Asn Met
                        290                 295                 300

<210> SEQ ID NO 40
<211> LENGTH: 27
<212> TYPE: DNA
<213> ORGANISM: Artificial Sequence
<220> FEATURE:
<223> OTHER INFORMATION: VH FR1 Fo

<400> SEQUENCE: 40
gaagtccagc tggtggagtc tggaggt                                                27

<210> SEQ ID NO 41
<211> LENGTH: 57
<212> TYPE: DNA
<213> ORGANISM: Artificial Sequence
<220> FEATURE:
<223> OTHER INFORMATION: VH FR1 Re_S

<400> SEQUENCE: 41
cggggcctga cgaacccagt tcatggcata gctgctgaag gtgaagccgc tcgctgc              57
```

<210> SEQ ID NO 42
<211> LENGTH: 57
<212> TYPE: DNA
<213> ORGANISM: Artificial Sequence
<220> FEATURE:
<223> OTHER INFORMATION: VH FR1 Re_H

<400> SEQUENCE: 42
cggggcctga cgaacccagt tcatggcata atggctgaag gtgaagccgc tcgctgc    57

<210> SEQ ID NO 43
<211> LENGTH: 57
<212> TYPE: DNA
<213> ORGANISM: Artificial Sequence
<220> FEATURE:
<223> OTHER INFORMATION: VH FR1 Re_K

<400> SEQUENCE: 43
cggggcctga cgaacccagt tcatggcata tttgctgaag gtgaagccgc tcgctgc    57

<210> SEQ ID NO 44
<211> LENGTH: 57
<212> TYPE: DNA
<213> ORGANISM: Artificial Sequence
<220> FEATURE:
<223> OTHER INFORMATION: VH FR1 Re_R

<400> SEQUENCE: 44
cggggcctga cgaacccagt tcatggcata tctgctgaag gtgaagccgc tcgctgc    57

<210> SEQ ID NO 45
<211> LENGTH: 57
<212> TYPE: DNA
<213> ORGANISM: Artificial Sequence
<220> FEATURE:
<223> OTHER INFORMATION: VH FR1 Re_T

<400> SEQUENCE: 45
cggggcctga cgaacccagt tcatggcata agtgctgaag gtgaagccgc tcgctgc    57

<210> SEQ ID NO 46
<211> LENGTH: 57
<212> TYPE: DNA
<213> ORGANISM: Artificial Sequence
<220> FEATURE:
<223> OTHER INFORMATION: VH FR1 Re_Y

<400> SEQUENCE: 46
cggggcctga cgaacccagt tcatggcata atagctgaag gtgaagccgc tcgctgc    57

<210> SEQ ID NO 47
<211> LENGTH: 57
<212> TYPE: DNA
<213> ORGANISM: Artificial Sequence
<220> FEATURE:
<223> OTHER INFORMATION: VH FR1 Re_I

<400> SEQUENCE: 47
cggggcctga cgaacccagt tcatggcata aatgctgaag gtgaagccgc tcgctgc    57

<210> SEQ ID NO 48
<211> LENGTH: 57
<212> TYPE: DNA
<213> ORGANISM: Artificial Sequence
<220> FEATURE:

<223> OTHER INFORMATION: VH FR1 Re_L

<400> SEQUENCE: 48
cggggcctga cgaacccagt tcatggcata aggctgaag gtgaagccgc tcgctgc    57

<210> SEQ ID NO 49
<211> LENGTH: 27
<212> TYPE: DNA
<213> ORGANISM: Artificial Sequence
<220> FEATURE:
<223> OTHER INFORMATION: VH FR2 Fo

<400> SEQUENCE: 49
tatgccatga actgggttcg tcaggcc    27

<210> SEQ ID NO 50
<211> LENGTH: 93
<212> TYPE: DNA
<213> ORGANISM: Artificial Sequence
<220> FEATURE:
<223> OTHER INFORMATION: VH FR2 Re_T-YH-EQDH

<400> SEQUENCE: 50
gttatcgcgg gaaatggtga agcgcccttg aacgctatcg gcgtagtagg tgtttgaccc    60
accggttgtg atggtgctga cccattccaa gcc    93

<210> SEQ ID NO 51
<211> LENGTH: 93
<212> TYPE: DNA
<213> ORGANISM: Artificial Sequence
<220> FEATURE:
<223> OTHER INFORMATION: VH FR2 Re_T-RK-EQDH

<400> SEQUENCE: 51
gttatcgcgg gaaatggtga agcgcccttg aacgctatcg gcgtagtagg ttyttgaccc    60
accggttgtg atggtgctga cccattccaa gcc    93

<210> SEQ ID NO 52
<211> LENGTH: 93
<212> TYPE: DNA
<213> ORGANISM: Artificial Sequence
<220> FEATURE:
<223> OTHER INFORMATION: VH FR2 Re_FYLH-YH-EQDH

<400> SEQUENCE: 52
gttatcgcgg gaaatggtga agcgcccttg aacgctatcg gcgtagtagg tgtttgaccc    60
acctwrtgtg atggtgctga cccattccaa gcc    93

<210> SEQ ID NO 53
<211> LENGTH: 93
<212> TYPE: DNA
<213> ORGANISM: Artificial Sequence
<220> FEATURE:
<223> OTHER INFORMATION: VH FR2 Re_FYLH-RK-EQDH

<400> SEQUENCE: 53
gttatcgcgg gaaatggtga agcgcccttg aacgctatcg gcgtagtagg ttyttgaccc    60
acctwrtgtg atggtgctga cccattccaa gcc    93

<210> SEQ ID NO 54
<211> LENGTH: 93
<212> TYPE: DNA
<213> ORGANISM: Artificial Sequence

```
<220> FEATURE:
<223> OTHER INFORMATION: VH FR2 Re_KRI-YH-EQDH

<400> SEQUENCE: 54
gttatcgcgg gaaatggtga agcgcccttg aacgctatcg gcgtagtagg tgtttgaccc    60
accthttgtg atggtgctga cccattccaa gcc                                 93

<210> SEQ ID NO 55
<211> LENGTH: 93
<212> TYPE: DNA
<213> ORGANISM: Artificial Sequence
<220> FEATURE:
<223> OTHER INFORMATION: VH FR2 Re_KRI-RK-EQDH

<400> SEQUENCE: 55
gttatcgcgg gaaatggtga agcgcccttg aacgctatcg gcgtagtagg ttyttgaccc    60
accthttgtg atggtgctga cccattccaa gcc                                 93

<210> SEQ ID NO 56
<211> LENGTH: 93
<212> TYPE: DNA
<213> ORGANISM: Artificial Sequence
<220> FEATURE:
<223> OTHER INFORMATION: VH FR2 Re_T-YH-EQDH_#2
<220> FEATURE:
<221> NAME/KEY: misc_feature
<222> LOCATION: (28)
<223> OTHER INFORMATION: a or g or c

<400> SEQUENCE: 56
gttatcgcgg gaaatggtga agcgcccnts aacgctatcg gcgtagtagg tatrtgaccc    60
accggttgtg atggtgctga cccattccaa gcc                                 93

<210> SEQ ID NO 57
<211> LENGTH: 93
<212> TYPE: DNA
<213> ORGANISM: Artificial Sequence
<220> FEATURE:
<223> OTHER INFORMATION: VH FR2 Re_T-RK-EQDH_#2
<220> FEATURE:
<221> NAME/KEY: misc_feature
<222> LOCATION: (28)
<223> OTHER INFORMATION: a or g or c

<400> SEQUENCE: 57
gttatcgcgg gaaatggtga agcgcccnts aacgctatcg gcgtagtagg ttyttgaccc    60
accggttgtg atggtgctga cccattccaa gcc                                 93

<210> SEQ ID NO 58
<211> LENGTH: 93
<212> TYPE: DNA
<213> ORGANISM: Artificial Sequence
<220> FEATURE:
<223> OTHER INFORMATION: VH FR2 Re_FYLH-YH-EQDH_#2
<220> FEATURE:
<221> NAME/KEY: misc_feature
<222> LOCATION: (28)
<223> OTHER INFORMATION: a or g or c

<400> SEQUENCE: 58
gttatcgcgg gaaatggtga agcgcccnts aacgctatcg gcgtagtagg tatrtgaccc    60
acctwrtgtg atggtgctga cccattccaa gcc                                 93

<210> SEQ ID NO 59
```

```
<211> LENGTH: 93
<212> TYPE: DNA
<213> ORGANISM: Artificial Sequence
<220> FEATURE:
<223> OTHER INFORMATION: VH FR2 Re_FYLH-RK-EQDH_#2
<220> FEATURE:
<221> NAME/KEY: misc_feature
<222> LOCATION: (28)
<223> OTHER INFORMATION: a or g or c

<400> SEQUENCE: 59
gttatcgcgg gaaatggtga agcgcccnts aacgctatcg gcgtagtagg ttyttgaccc      60
acctwrtgtg atggtgctga cccattccaa gcc                                  93

<210> SEQ ID NO 60
<211> LENGTH: 93
<212> TYPE: DNA
<213> ORGANISM: Artificial Sequence
<220> FEATURE:
<223> OTHER INFORMATION: VH FR2 Re_KRI-YH-EQDH_#2
<220> FEATURE:
<221> NAME/KEY: misc_feature
<222> LOCATION: (28)
<223> OTHER INFORMATION: a or g or c

<400> SEQUENCE: 60
gttatcgcgg gaaatggtga agcgcccnts aacgctatcg gcgtagtagg tatrtgaccc      60
accthttgtg atggtgctga cccattccaa gcc                                  93

<210> SEQ ID NO 61
<211> LENGTH: 93
<212> TYPE: DNA
<213> ORGANISM: Artificial Sequence
<220> FEATURE:
<223> OTHER INFORMATION: VH FR2 Re_KRI-RK-EQDH_#2
<220> FEATURE:
<221> NAME/KEY: misc_feature
<222> LOCATION: (28)
<223> OTHER INFORMATION: a or g or c

<400> SEQUENCE: 61
gttatcgcgg gaaatggtga agcgcccnts aacgctatcg gcgtagtagg ttyttgaccc      60
accthttgtg atggtgctga cccattccaa gcc                                  93

<210> SEQ ID NO 62
<211> LENGTH: 27
<212> TYPE: DNA
<213> ORGANISM: Artificial Sequence
<220> FEATURE:
<223> OTHER INFORMATION: VH FR3 Fo

<400> SEQUENCE: 62
gggcgcttca ccatttcccg cgataac                                         27

<210> SEQ ID NO 63
<211> LENGTH: 60
<212> TYPE: DNA
<213> ORGANISM: Artificial Sequence
<220> FEATURE:
<223> OTHER INFORMATION: VH FR3 Re_N

<400> SEQUENCE: 63
gccctggccc caataatcca tcagaaaatt gccatcctgg cgcgcgcaat aatataccgc      60

<210> SEQ ID NO 64
<211> LENGTH: 60
```

<212> TYPE: DNA
<213> ORGANISM: Artificial Sequence
<220> FEATURE:
<223> OTHER INFORMATION: VH FR3 Re_F

<400> SEQUENCE: 64
gccctggccc caataatcca tcagaaaaaa gccatcctgg cgcgcgcaat aatataccgc    60

<210> SEQ ID NO 65
<211> LENGTH: 60
<212> TYPE: DNA
<213> ORGANISM: Artificial Sequence
<220> FEATURE:
<223> OTHER INFORMATION: VH FR3 Re_H

<400> SEQUENCE: 65
gccctggccc caataatcca tcagaaaatg gccatcctgg cgcgcgcaat aatataccgc    60

<210> SEQ ID NO 66
<211> LENGTH: 60
<212> TYPE: DNA
<213> ORGANISM: Artificial Sequence
<220> FEATURE:
<223> OTHER INFORMATION: VH FR3 Re_K

<400> SEQUENCE: 66
gccctggccc caataatcca tcagaaattt gccatcctgg cgcgcgcaat aatataccgc    60

<210> SEQ ID NO 67
<211> LENGTH: 60
<212> TYPE: DNA
<213> ORGANISM: Artificial Sequence
<220> FEATURE:
<223> OTHER INFORMATION: VH FR3 Re_Q

<400> SEQUENCE: 67
gccctggccc caataatcca tcagaaattg gccatcctgg cgcgcgcaat aatataccgc    60

<210> SEQ ID NO 68
<211> LENGTH: 60
<212> TYPE: DNA
<213> ORGANISM: Artificial Sequence
<220> FEATURE:
<223> OTHER INFORMATION: VH FR3 Re_R

<400> SEQUENCE: 68
gccctggccc caataatcca tcagaaatct gccatcctgg cgcgcgcaat aatataccgc    60

<210> SEQ ID NO 69
<211> LENGTH: 60
<212> TYPE: DNA
<213> ORGANISM: Artificial Sequence
<220> FEATURE:
<223> OTHER INFORMATION: VH FR3 Re_Y

<400> SEQUENCE: 69
gccctggccc caataatcca tcagaaaata gccatcctgg cgcgcgcaat aatataccgc    60

<210> SEQ ID NO 70
<211> LENGTH: 54
<212> TYPE: DNA
<213> ORGANISM: Artificial Sequence
<220> FEATURE:
<223> OTHER INFORMATION: VH Final Fo

<400> SEQUENCE: 70
ggttctggtg gtggtggttc tgctagcgac gtggtgatga cacagacgcc gctg       54

<210> SEQ ID NO 71
<211> LENGTH: 48
<212> TYPE: DNA
<213> ORGANISM: Artificial Sequence
<220> FEATURE:
<223> OTHER INFORMATION: VH Final Re

<400> SEQUENCE: 71
ggagctcaca gtcaccagcg tgccctggcc ccaataatcc atcagaaa              48

<210> SEQ ID NO 72
<211> LENGTH: 27
<212> TYPE: DNA
<213> ORGANISM: Artificial Sequence
<220> FEATURE:
<223> OTHER INFORMATION: VL FR1 Fo

<400> SEQUENCE: 72
gacgtggtga tgacacagac gccgctg                                    27

<210> SEQ ID NO 73
<211> LENGTH: 57
<212> TYPE: DNA
<213> ORGANISM: Artificial Sequence
<220> FEATURE:
<223> OTHER INFORMATION: VL FR1 Re_S

<400> SEQUENCE: 73
gagccaattc agatacgtct tgccgtcgga gtccagcagc gactggcttg atttgca    57

<210> SEQ ID NO 74
<211> LENGTH: 57
<212> TYPE: DNA
<213> ORGANISM: Artificial Sequence
<220> FEATURE:
<223> OTHER INFORMATION: VL FR1 Re_I

<400> SEQUENCE: 74
gagccaattc agatacgtct tgccgtcaat gtccagcagc gactggcttg atttgca    57

<210> SEQ ID NO 75
<211> LENGTH: 57
<212> TYPE: DNA
<213> ORGANISM: Artificial Sequence
<220> FEATURE:
<223> OTHER INFORMATION: VL FR1 Re_L

<400> SEQUENCE: 75
gagccaattc agatacgtct tgccgtcaag gtccagcagc gactggcttg atttgca    57

<210> SEQ ID NO 76
<211> LENGTH: 57
<212> TYPE: DNA
<213> ORGANISM: Artificial Sequence
<220> FEATURE:
<223> OTHER INFORMATION: VL FR1 Re_N

<400> SEQUENCE: 76
gagccaattc agatacgtct tgccgtcagc gtccagcagc gactggcttg atttgca    57

<210> SEQ ID NO 77
<211> LENGTH: 57
<212> TYPE: DNA
<213> ORGANISM: Artificial Sequence

```
<220> FEATURE:
<223> OTHER INFORMATION: VL FR1 Re_Q

<400> SEQUENCE: 77
gagccaattc agatacgtct tgccgtcttg gtccagcagc gactggcttg atttgca      57

<210> SEQ ID NO 78
<211> LENGTH: 57
<212> TYPE: DNA
<213> ORGANISM: Artificial Sequence
<220> FEATURE:
<223> OTHER INFORMATION: VL FR1 Re_R

<400> SEQUENCE: 78
gagccaattc agatacgtct tgccgtctct gtccagcagc gactggcttg atttgca      57

<210> SEQ ID NO 79
<211> LENGTH: 57
<212> TYPE: DNA
<213> ORGANISM: Artificial Sequence
<220> FEATURE:
<223> OTHER INFORMATION: VL FR1 Re_F

<400> SEQUENCE: 79
gagccaattc agatacgtct tgccgtcaaa gtccagcagc gactggcttg atttgca      57

<210> SEQ ID NO 80
<211> LENGTH: 57
<212> TYPE: DNA
<213> ORGANISM: Artificial Sequence
<220> FEATURE:
<223> OTHER INFORMATION: VL FR1 Re_K

<400> SEQUENCE: 80
gagccaattc agatacgtct tgccgtcttt gtccagcagc gactggcttg atttgca      57

<210> SEQ ID NO 81
<211> LENGTH: 57
<212> TYPE: DNA
<213> ORGANISM: Artificial Sequence
<220> FEATURE:
<223> OTHER INFORMATION: VL FR1 Re_T

<400> SEQUENCE: 81
gagccaattc agatacgtct tgccgtcagt gtccagcagc gactggcttg atttgca      57

<210> SEQ ID NO 82
<211> LENGTH: 57
<212> TYPE: DNA
<213> ORGANISM: Artificial Sequence
<220> FEATURE:
<223> OTHER INFORMATION: VL FR1 Re_V

<400> SEQUENCE: 82
gagccaattc agatacgtct tgccgtcaac gtccagcagc gactggcttg atttgca      57

<210> SEQ ID NO 83
<211> LENGTH: 30
<212> TYPE: DNA
<213> ORGANISM: Artificial Sequence
<220> FEATURE:
<223> OTHER INFORMATION: VL FR2 Fo

<400> SEQUENCE: 83
gacggcaaga cgtatctgaa ttggctccag      30
```

<210> SEQ ID NO 84
<211> LENGTH: 75
<212> TYPE: DNA
<213> ORGANISM: Artificial Sequence
<220> FEATURE:
<223> OTHER INFORMATION: VL FR2 Re_T-YH

<400> SEQUENCE: 84
gcgtttaatt tcaaccttag tgccttggcc gaacgtaaac ggaaagtrgg tgccctgcca    60
gcaatagtag acgcc    75

<210> SEQ ID NO 85
<211> LENGTH: 75
<212> TYPE: DNA
<213> ORGANISM: Artificial Sequence
<220> FEATURE:
<223> OTHER INFORMATION: VL FR2 Re_T-LIHQNK

<400> SEQUENCE: 85
gcgtttaatt tcaaccttag tgccttggcc gaacgtaaac ggaaawwkgg tgccctgcca    60
gcaatagtag acgcc    75

<210> SEQ ID NO 86
<211> LENGTH: 75
<212> TYPE: DNA
<213> ORGANISM: Artificial Sequence
<220> FEATURE:
<223> OTHER INFORMATION: VL FR2 Re_FYIN-YH

<400> SEQUENCE: 86
gcgtttaatt tcaaccttag tgccttggcc gaacgtaaac ggaaagtraw wgccctgcca    60
gcaatagtag acgcc    75

<210> SEQ ID NO 87
<211> LENGTH: 75
<212> TYPE: DNA
<213> ORGANISM: Artificial Sequence
<220> FEATURE:
<223> OTHER INFORMATION: VL FR2 Re_FYIN-LIHQNK

<400> SEQUENCE: 87
gcgtttaatt tcaaccttag tgccttggcc gaacgtaaac ggaaawwkaw wgccctgcca    60
gcaatagtag acgcc    75

<210> SEQ ID NO 88
<211> LENGTH: 39
<212> TYPE: DNA
<213> ORGANISM: Artificial Sequence
<220> FEATURE:
<223> OTHER INFORMATION: VL Final Re

<400> SEQUENCE: 88
gcgtttaatt tcaaccttag tgccttggcc gaacgtaaa    39

<210> SEQ ID NO 89
<211> LENGTH: 43
<212> TYPE: DNA
<213> ORGANISM: Artificial Sequence
<220> FEATURE:
<223> OTHER INFORMATION: VL Final Fo SfiI

<400> SEQUENCE: 89
cgtggcccag gcggccgacg tggtgatgac acagacgccg ctg    43

<210> SEQ ID NO 90
<211> LENGTH: 33
<212> TYPE: DNA
<213> ORGANISM: Artificial Sequence
<220> FEATURE:
<223> OTHER INFORMATION: VL Final Fo NruI

<400> SEQUENCE: 90
ctatcgcgat tgcagtggca ctggctggtt tcg                                  33

<210> SEQ ID NO 91
<211> LENGTH: 96
<212> TYPE: DNA
<213> ORGANISM: Artificial Sequence
<220> FEATURE:
<223> OTHER INFORMATION: VL Overlapping Fo

<400> SEQUENCE: 91
ggcacgctgg tgactgtgag ctccggaggc ggcggaagtg gcggaggagg cagcggcgga     60
ggcgggagtg acgtggtgat gacacagacg ccgctg                              96

<210> SEQ ID NO 92
<211> LENGTH: 72
<212> TYPE: DNA
<213> ORGANISM: Artificial Sequence
<220> FEATURE:
<223> OTHER INFORMATION: VL Final Re

<400> SEQUENCE: 92
gtcctcttca gaaataagct tttgttcgga tccgcgttta atttcaacct tagtgccttg     60
gccgaacgta aa                                                        72

<210> SEQ ID NO 93
<211> LENGTH: 66
<212> TYPE: DNA
<213> ORGANISM: Artificial Sequence
<220> FEATURE:
<223> OTHER INFORMATION: VH Homologous recombination

<400> SEQUENCE: 93
gctctgcagg ctagtggtgg tggtggttct ggtggtggtg gttctggtgg tggtggttct     60
gctagc                                                               66

<210> SEQ ID NO 94
<211> LENGTH: 60
<212> TYPE: DNA
<213> ORGANISM: Artificial Sequence
<220> FEATURE:
<223> OTHER INFORMATION: VL Homologous recombination

<400> SEQUENCE: 94
ttgttatcag atctcgagct attacaagtc ctcttcagaa ataagctttt gttcggatcc     60

<210> SEQ ID NO 95
<211> LENGTH: 118
<212> TYPE: PRT
<213> ORGANISM: Artificial Sequence
<220> FEATURE:
<223> OTHER INFORMATION: Clone 1001_Variable heavy chain

<400> SEQUENCE: 95

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Gly Thr Ile Thr Thr Gly Gly Ser Tyr Thr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
            115

<210> SEQ ID NO 96
<211> LENGTH: 113
<212> TYPE: PRT
<213> ORGANISM: Artificial Sequence
<220> FEATURE:
<223> OTHER INFORMATION: Clone 1001_Variable light chain

<400> SEQUENCE: 96

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Ile
            20                  25                  30

Asp Gly Lys Thr Tyr Leu Asn Trp Leu Gln Gln Arg Pro Gly Gln Ser
            35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gln Gly Thr Lys Val Glu Ile Lys
            100                 105                 110

Arg

<210> SEQ ID NO 97
<211> LENGTH: 118
<212> TYPE: PRT
<213> ORGANISM: Artificial Sequence
<220> FEATURE:
<223> OTHER INFORMATION: Clone 1015_Variable heavy chain

<400> SEQUENCE: 97

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Thr Thr Gly Gly Ser His Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 98
<211> LENGTH: 118
<212> TYPE: PRT
<213> ORGANISM: Artificial Sequence
<220> FEATURE:
<223> OTHER INFORMATION: Clone 1021_Variable heavy chain

<400> SEQUENCE: 98

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly His Phe Leu Met Asp Tyr Trp Gly Gln Gly Thr
            100                 105                 110

Leu Val Thr Val Ser Ser
        115

<210> SEQ ID NO 99
<211> LENGTH: 118
<212> TYPE: PRT
<213> ORGANISM: Artificial Sequence
<220> FEATURE:
<223> OTHER INFORMATION: Clone 1023_Variable heavy chain

<400> SEQUENCE: 99

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115
```

```
<210> SEQ ID NO 100
<211> LENGTH: 118
<212> TYPE: PRT
<213> ORGANISM: Artificial Sequence
<220> FEATURE:
<223> OTHER INFORMATION: Clone 1024_Variable heavy chain

<400> SEQUENCE: 100
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

```
<210> SEQ ID NO 101
<211> LENGTH: 113
<212> TYPE: PRT
<213> ORGANISM: Artificial Sequence
<220> FEATURE:
<223> OTHER INFORMATION: Clone 1024_Variable light chain

<400> SEQUENCE: 101
```

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Leu
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gln Gly Thr Lys Val Glu Ile Lys
            100                 105                 110

Arg

```
<210> SEQ ID NO 102
<211> LENGTH: 118
<212> TYPE: PRT
<213> ORGANISM: Artificial Sequence
<220> FEATURE:
<223> OTHER INFORMATION: Clone 1104_Variable heavy chain

<400> SEQUENCE: 102
```

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Gly Thr Ile Thr Thr Gly Gly Ser His Thr Tyr Tyr Ala Asp Ser Val
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
            115
```

<210> SEQ ID NO 103
<211> LENGTH: 113
<212> TYPE: PRT
<213> ORGANISM: Artificial Sequence
<220> FEATURE:
<223> OTHER INFORMATION: Clone 1104_Variable light chain

<400> SEQUENCE: 103

```
Asp Val Val Met Thr Gln Thr Pro Leu Ser Leu Pro Val Thr Leu Gly
 1               5                  10                  15

Gln Pro Ala Ser Ile Ser Cys Lys Ser Ser Gln Ser Leu Leu Asp Val
            20                  25                  30

Asp Gly Lys Thr Tyr Leu Asn Trp Leu Gln Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gln Gly Thr Lys Val Glu Ile Lys
            100                 105                 110

Arg
```

<210> SEQ ID NO 104
<211> LENGTH: 118
<212> TYPE: PRT
<213> ORGANISM: Artificial Sequence
<220> FEATURE:
<223> OTHER INFORMATION: Clone 1123_Variable heavy chain

<400> SEQUENCE: 104

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Thr Thr Gly Gly Ser His Thr Tyr Tyr Ala Asp Ser Val
 50                  55                  60

Glu Gly Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
                 85                  90                  95

Ala Arg Gln Asp Gly His Phe Leu Met Asp Tyr Trp Gly Gln Gly Thr
            100                 105                 110

Leu Val Thr Val Ser Ser
        115

<210> SEQ ID NO 105
<211> LENGTH: 118
<212> TYPE: PRT
<213> ORGANISM: Artificial Sequence
<220> FEATURE:
<223> OTHER INFORMATION: Clone 1202_Variable heavy chain

<400> SEQUENCE: 105

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Gly Thr Ile Thr Thr Gly Gly Ser Tyr Thr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Lys Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 106
<211> LENGTH: 113
<212> TYPE: PRT
<213> ORGANISM: Artificial Sequence
<220> FEATURE:
<223> OTHER INFORMATION: Clone 1208_Variable light chain

<400> SEQUENCE: 106

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Val
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Tyr Leu Pro Phe Thr Phe Gly Gln Gly Thr Lys Val Glu Ile Lys
            100                 105                 110

Arg

<210> SEQ ID NO 107
<211> LENGTH: 118
```

<212> TYPE: PRT
<213> ORGANISM: Artificial Sequence
<220> FEATURE:
<223> OTHER INFORMATION: Clone 1216_Variable heavy chain

<400> SEQUENCE: 107

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser His Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly His Phe Leu Met Asp Tyr Trp Gly Gln Gly Thr
            100                 105                 110

Leu Val Thr Val Ser Ser
        115

<210> SEQ ID NO 108
<211> LENGTH: 113
<212> TYPE: PRT
<213> ORGANISM: Artificial Sequence
<220> FEATURE:
<223> OTHER INFORMATION: Clone 1216_Variable light chain

<400> SEQUENCE: 108

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Ile
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Leu Pro Phe Thr Phe Gly Gln Gly Thr Lys Val Glu Ile Lys
            100                 105                 110

Arg

<210> SEQ ID NO 109
<211> LENGTH: 118
<212> TYPE: PRT
<213> ORGANISM: Artificial Sequence
<220> FEATURE:
<223> OTHER INFORMATION: Clone 1223_Variable heavy chain

<400> SEQUENCE: 109

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

```
Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Gly His Phe Leu Met Asp Tyr Trp Gly Gln Gly Thr
            100                 105                 110

Leu Val Thr Val Ser Ser
            115

<210> SEQ ID NO 110
<211> LENGTH: 118
<212> TYPE: PRT
<213> ORGANISM: Artificial Sequence
<220> FEATURE:
<223> OTHER INFORMATION: Clone 1234_Variable heavy chain

<400> SEQUENCE: 110

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Gly Asn Phe Leu Met Asp Tyr Trp Gly Gln Gly Thr
            100                 105                 110

Leu Val Thr Val Ser Ser
            115

<210> SEQ ID NO 111
<211> LENGTH: 113
<212> TYPE: PRT
<213> ORGANISM: Artificial Sequence
<220> FEATURE:
<223> OTHER INFORMATION: Clone 1234_Variable light chain

<400> SEQUENCE: 111

Asp Val Val Met Thr Gln Thr Pro Leu Ser Leu Pro Val Thr Leu Gly
 1               5                  10                  15

Gln Pro Ala Ser Ile Ser Cys Lys Ser Ser Gln Ser Leu Leu Asp Ile
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Glu Ile
 65                  70                  75                  80

Ser Arg Val Glu Ala Glu Asp Val Gly Val Tyr Tyr Cys Trp Gln Gly
```

```
                    85                  90                  95
Thr His Phe Pro Phe Thr Phe Gly Gln Gly Thr Lys Val Glu Ile Lys
                100                 105                 110
Arg

<210> SEQ ID NO 112
<211> LENGTH: 118
<212> TYPE: PRT
<213> ORGANISM: Artificial Sequence
<220> FEATURE:
<223> OTHER INFORMATION: Clone 1243_Variable heavy chain

<400> SEQUENCE: 112

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
    50                  55                  60

His Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly His Phe Leu Met Asp Tyr Trp Gly Gln Gly Thr
                100                 105                 110

Leu Val Thr Val Ser Ser
            115

<210> SEQ ID NO 113
<211> LENGTH: 118
<212> TYPE: PRT
<213> ORGANISM: Artificial Sequence
<220> FEATURE:
<223> OTHER INFORMATION: Clone 1248_Variable heavy chain

<400> SEQUENCE: 113

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly His Phe Leu Met Asp Tyr Trp Gly Gln Gly Thr
                100                 105                 110

Leu Val Thr Val Ser Ser
            115

<210> SEQ ID NO 114
<211> LENGTH: 118
<212> TYPE: PRT
```

<213> ORGANISM: Artificial Sequence
<220> FEATURE:
<223> OTHER INFORMATION: Clone 3007_Variable heavy chain

<400> SEQUENCE: 114

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Ser Tyr
            20                  25                  30

Ala Met Asn Trp Val Arg Gln Ala Pro Gly Lys Gly Leu Glu Trp Val
        35                  40                  45

Ser Thr Ile Thr Leu Gly Gly Ser Tyr Thr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 115
<211> LENGTH: 118
<212> TYPE: PRT
<213> ORGANISM: Artificial Sequence
<220> FEATURE:
<223> OTHER INFORMATION: Clone 3016_Variable heavy chain

<400> SEQUENCE: 115

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 116
<211> LENGTH: 113
<212> TYPE: PRT
<213> ORGANISM: Artificial Sequence
<220> FEATURE:
<223> OTHER INFORMATION: Clone 3016_Variable light chain

<400> SEQUENCE: 116

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

```
Asp Gly Lys Thr Tyr Leu Asn Trp Leu Gln Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Leu Pro Phe Thr Phe Gly Gln Gly Thr Lys Val Glu Ile Lys
                100                 105                 110

Arg

<210> SEQ ID NO 117
<211> LENGTH: 118
<212> TYPE: PRT
<213> ORGANISM: Artificial Sequence
<220> FEATURE:
<223> OTHER INFORMATION: Clone 3024_Variable heavy chain

<400> SEQUENCE: 117

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Thr Ile Thr Thr Gly Gly Ser Tyr Thr Tyr Tyr Ala Asp Ser Val
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Gly Asn Phe Leu Met Asp Tyr Trp Gly Gln Gly Thr
                100                 105                 110

Leu Val Thr Val Ser Ser
            115

<210> SEQ ID NO 118
<211> LENGTH: 118
<212> TYPE: PRT
<213> ORGANISM: Artificial Sequence
<220> FEATURE:
<223> OTHER INFORMATION: Clone 3120_Variable heavy chain

<400> SEQUENCE: 118

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Thr Ile Thr Thr Gly Gly Ser Tyr Thr Tyr Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Ala Arg Gln Asp Gly Tyr Phe Leu Met Asp Tyr Trp Gly Gln Gly Thr
            100                 105                 110

Leu Val Thr Val Ser Ser
        115

<210> SEQ ID NO 119
<211> LENGTH: 118
<212> TYPE: PRT
<213> ORGANISM: Artificial Sequence
<220> FEATURE:
<223> OTHER INFORMATION: Clone 3131_Variable heavy chain

<400> SEQUENCE: 119

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Gln Phe Leu Met Asp Tyr Trp Gly Gln Gly Thr
            100                 105                 110

Leu Val Thr Val Ser Ser
        115

<210> SEQ ID NO 120
<211> LENGTH: 118
<212> TYPE: PRT
<213> ORGANISM: Artificial Sequence
<220> FEATURE:
<223> OTHER INFORMATION: Clone 3203_Variable heavy chain

<400> SEQUENCE: 120

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 121
<211> LENGTH: 118
<212> TYPE: PRT

<213> ORGANISM: Artificial Sequence
<220> FEATURE:
<223> OTHER INFORMATION: Clone 4011_Variable heavy chain

<400> SEQUENCE: 121

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Tyr Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
            115
```

<210> SEQ ID NO 122
<211> LENGTH: 113
<212> TYPE: PRT
<213> ORGANISM: Artificial Sequence
<220> FEATURE:
<223> OTHER INFORMATION: Clone 4011_Variable light chain

<400> SEQUENCE: 122

```
Asp Val Val Met Thr Gln Thr Pro Leu Ser Leu Pro Val Thr Leu Gly
1               5                   10                  15

Gln Pro Ala Ser Ile Ser Cys Lys Ser Gln Ser Leu Leu Asp Val
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Leu Pro Phe Thr Phe Gly Gln Gly Thr Lys Val Glu Ile Lys
            100                 105                 110

Arg
```

<210> SEQ ID NO 123
<211> LENGTH: 118
<212> TYPE: PRT
<213> ORGANISM: Artificial Sequence
<220> FEATURE:
<223> OTHER INFORMATION: Clone 4017_Variable heavy chain

<400> SEQUENCE: 123

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

```
Ala Met Asn Trp Val Arg Gln Ala Pro Gly Lys Gly Leu Glu Trp Val
        35                  40                  45

Gly Thr Ile Thr Thr Gly Gly Ser Tyr Thr Tyr Tyr Ala Asp Ser Val
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
            85                  90                  95

Ala Arg Gln Asp Gly Tyr Phe Leu Met Asp Tyr Trp Gly Gln Gly Thr
            100                 105                 110

Leu Val Thr Val Ser Ser
            115

<210> SEQ ID NO 124
<211> LENGTH: 118
<212> TYPE: PRT
<213> ORGANISM: Artificial Sequence
<220> FEATURE:
<223> OTHER INFORMATION: Clone 4034_Variable heavy chain

<400> SEQUENCE: 124

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Thr Ile Thr Thr Gly Gly Ser His Thr Tyr Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Gln Asp Gly Tyr Phe Leu Met Asp Tyr Trp Gly Gln Gly Thr
             100                 105                 110

Leu Val Thr Val Ser Ser
            115

<210> SEQ ID NO 125
<211> LENGTH: 118
<212> TYPE: PRT
<213> ORGANISM: Artificial Sequence
<220> FEATURE:
<223> OTHER INFORMATION: Clone 4041_Variable heavy chain

<400> SEQUENCE: 125

Glu Val Gln Leu Val Glu Ser Gly Gly Gly Leu Val Lys Pro Gly Gly
 1               5                  10                  15

Ser Leu Arg Leu Ser Cys Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Thr Ile Thr Thr Gly Gly Ser His Thr Tyr Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95
```

Ala Arg Gln Asp Gly Tyr Phe Leu Met Asp Tyr Trp Gly Gln Gly Thr
            100                 105                 110

Leu Val Thr Val Ser Ser
        115

<210> SEQ ID NO 126
<211> LENGTH: 118
<212> TYPE: PRT
<213> ORGANISM: Artificial Sequence
<220> FEATURE:
<223> OTHER INFORMATION: Clone 4141_Variable heavy chain

<400> SEQUENCE: 126

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Gly Thr Ile Thr Thr Gly Gly Ser His Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Tyr Phe Leu Met Asp Tyr Trp Gly Gln Gly Thr
            100                 105                 110

Leu Val Thr Val Ser Ser
        115

<210> SEQ ID NO 127
<211> LENGTH: 118
<212> TYPE: PRT
<213> ORGANISM: Artificial Sequence
<220> FEATURE:
<223> OTHER INFORMATION: Clone 4146_Variable heavy chain

<400> SEQUENCE: 127

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Tyr Phe Leu Met Asp Tyr Trp Gly Gln Gly Thr
            100                 105                 110

Leu Val Thr Val Ser Ser
        115

<210> SEQ ID NO 128
<211> LENGTH: 118
<212> TYPE: PRT

<213> ORGANISM: Artificial Sequence
<220> FEATURE:
<223> OTHER INFORMATION: Clone 4206_Variable heavy chain

<400> SEQUENCE: 128

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 129
<211> LENGTH: 118
<212> TYPE: PRT
<213> ORGANISM: Artificial Sequence
<220> FEATURE:
<223> OTHER INFORMATION: Clone 4208_Variable heavy chain

<400> SEQUENCE: 129

Glu Val Gln Leu Val Glu Ser Gly Gly Gly Leu Val Lys Ser Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Thr Ile Thr Thr Gly Gly Ser Tyr Thr Tyr Tyr Ala Asp Ser Val
50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 130
<211> LENGTH: 113
<212> TYPE: PRT
<213> ORGANISM: Artificial Sequence
<220> FEATURE:
<223> OTHER INFORMATION: Clone 4208_Variable light chain

<400> SEQUENCE: 130

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Thr
            20                  25                  30

```
Asp Gly Lys Thr Tyr Leu Asn Trp Leu Gln Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gln Gly Thr Lys Val Glu Ile Lys
                100                 105                 110

Arg

<210> SEQ ID NO 131
<211> LENGTH: 120
<212> TYPE: PRT
<213> ORGANISM: Artificial Sequence
<220> FEATURE:
<223> OTHER INFORMATION: Clone 4278_Variable heavy chain

<400> SEQUENCE: 131

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Lys Tyr
                20                  25                  30

Ala Met Asn Trp Phe Arg Gln Ala Pro Gly Lys Gly Leu Glu Trp Val
            35                  40                  45

Ser Thr Ile Thr Leu Gly Gly Ser Tyr Thr Tyr Tyr Ala Asp Ser Val
 50                  55                  60

Asp Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gln Tyr Leu Asp Gly Asn Phe Leu Met Asp Tyr Trp Gly Gln
                100                 105                 110

Gly Thr Leu Val Thr Val Ser Ser
            115                 120

<210> SEQ ID NO 132
<211> LENGTH: 120
<212> TYPE: PRT
<213> ORGANISM: Artificial Sequence
<220> FEATURE:
<223> OTHER INFORMATION: Clone 4287_Variable heavy chain

<400> SEQUENCE: 132

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Lys Tyr
                20                  25                  30

Ala Met Asn Trp Phe Arg Gln Ala Pro Gly Lys Gly Leu Glu Trp Val
            35                  40                  45

Ser Thr Ile Thr Thr Gly Gly Ser Tyr Thr Tyr Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95
```

-continued

Ala Arg Gln His Pro Tyr Gly Asn Phe Leu Met Asp Tyr Trp Gly Gln
            100                 105                 110

Gly Thr Leu Val Thr Val Ser Ser
        115                 120

<210> SEQ ID NO 133
<211> LENGTH: 118
<212> TYPE: PRT
<213> ORGANISM: Artificial Sequence
<220> FEATURE:
<223> OTHER INFORMATION: Clone 4_Variable heavy chain

<400> SEQUENCE: 133

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Gly Thr Ile Thr Thr Gly Gly Ser His Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 134
<211> LENGTH: 118
<212> TYPE: PRT
<213> ORGANISM: Artificial Sequence
<220> FEATURE:
<223> OTHER INFORMATION: Clone 6_Variable heavy chain

<400> SEQUENCE: 134

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Gly Thr Ile Thr Thr Gly Gly Ser Tyr Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 135
<211> LENGTH: 118
<212> TYPE: PRT

<213> ORGANISM: Artificial Sequence
<220> FEATURE:
<223> OTHER INFORMATION: Clone 9_Variable heavy chain

<400> SEQUENCE: 135

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Gly Thr Ile Thr Thr Gly Gly Ser Tyr Thr Tyr Tyr Ala Asp Ser Val
50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 136
<211> LENGTH: 118
<212> TYPE: PRT
<213> ORGANISM: Artificial Sequence
<220> FEATURE:
<223> OTHER INFORMATION: Clone 11_Variable heavy chain

<400> SEQUENCE: 136

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Gly Thr Ile Thr Thr Gly Gly Ser Tyr Thr Tyr Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 137
<211> LENGTH: 118
<212> TYPE: PRT
<213> ORGANISM: Artificial Sequence
<220> FEATURE:
<223> OTHER INFORMATION: Clone 12_Variable heavy chain

<400> SEQUENCE: 137

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Gly Thr Ile Thr Thr Gly Gly Ser His Thr Tyr Tyr Ala Asp Ser Val
 50                  55                  60

Glu Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Gln Asp Gly His Phe Leu Met Asp Tyr Trp Gly Gln Gly Thr
            100                 105                 110

Leu Val Thr Val Ser Ser
            115

<210> SEQ ID NO 138
<211> LENGTH: 118
<212> TYPE: PRT
<213> ORGANISM: Artificial Sequence
<220> FEATURE:
<223> OTHER INFORMATION: Clone 13_Variable heavy chain

<400> SEQUENCE: 138

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Gly Thr Ile Thr Thr Gly Gly Ser His Thr Tyr Tyr Ala Asp Ser Val
 50                  55                  60

Glu Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
            115

<210> SEQ ID NO 139
<211> LENGTH: 113
<212> TYPE: PRT
<213> ORGANISM: Artificial Sequence
<220> FEATURE:
<223> OTHER INFORMATION: Clone 14_Variable light chain

<400> SEQUENCE: 139

Asp Val Val Met Thr Gln Thr Pro Leu Ser Leu Pro Val Thr Leu Gly
1               5                   10                  15

Gln Pro Ala Ser Ile Ser Cys Lys Ser Ser Pro Ser Leu Leu Asp Ser
            20                  25                  30

Asp Gly Lys Thr Tyr Leu Asn Trp Leu Gln Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
65                   70                  75                  80

Ser Arg Val Glu Ala Glu Asp Val Gly Val Tyr Tyr Cys Trp Gln Gly

Thr Tyr Phe Pro Phe Thr Phe Gly Gln Gly Thr Lys Val Glu Ile Lys
                100                 105                 110

Arg

<210> SEQ ID NO 140
<211> LENGTH: 113
<212> TYPE: PRT
<213> ORGANISM: Artificial Sequence
<220> FEATURE:
<223> OTHER INFORMATION: Clone 15_Variable light chain

<400> SEQUENCE: 140

Asp Val Val Met Thr Gln Thr Pro Leu Ser Leu Pro Val Thr Leu Gly
1               5                   10                  15

Gln Pro Ala Ser Ile Ser Cys Lys Ser Ser Pro Ser Leu Leu Asp Ser
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Phe Tyr Phe Pro Phe Thr Phe Gly Gln Gly Thr Lys Val Glu Ile Lys
                100                 105                 110

Arg

<210> SEQ ID NO 141
<211> LENGTH: 118
<212> TYPE: PRT
<213> ORGANISM: Artificial Sequence
<220> FEATURE:
<223> OTHER INFORMATION: Clone 16_Variable heavy chain

<400> SEQUENCE: 141

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser His Tyr
            20                  25                  30

Ala Met Thr Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
                100                 105                 110

Leu Val Thr Val Ser Ser
        115

<210> SEQ ID NO 142
<211> LENGTH: 118
<212> TYPE: PRT
<213> ORGANISM: Artificial Sequence
<220> FEATURE:
<223> OTHER INFORMATION: Clone 17_Variable heavy chain

<400> SEQUENCE: 142

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 143
<211> LENGTH: 118
<212> TYPE: PRT
<213> ORGANISM: Artificial Sequence
<220> FEATURE:
<223> OTHER INFORMATION: Clone 18_Variable heavy chain

<400> SEQUENCE: 143

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser His Tyr
            20                  25                  30

Ala Met Thr Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 144
<211> LENGTH: 118
<212> TYPE: PRT
<213> ORGANISM: Artificial Sequence
<220> FEATURE:
<223> OTHER INFORMATION: Clone 19_Variable heavy chain

<400> SEQUENCE: 144

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gln Tyr
            20                  25                  30

```
Ala Met Asn Trp Val Arg Gln Ala Pro Gly Lys Gly Leu Glu Trp Val
            35                  40                  45

Ser Thr Ile Thr Lys Lys Gly Ser Phe Thr Tyr Tyr Ala Asp Ser Val
 50                  55                  60

Asp Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Gln Asp Gly Glu Phe Leu Met Asp Tyr Trp Gly Gln Gly Thr
            100                 105                 110

Leu Val Thr Val Ser Ser
            115

<210> SEQ ID NO 145
<211> LENGTH: 118
<212> TYPE: PRT
<213> ORGANISM: Artificial Sequence
<220> FEATURE:
<223> OTHER INFORMATION: Clone 20_Variable heavy chain

<400> SEQUENCE: 145

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gln Tyr
            20                  25                  30

Ala Met Asn Trp Val Arg Gln Ala Pro Gly Lys Gly Leu Glu Trp Val
            35                  40                  45

Ser Thr Ile Lys Lys Gly Gly Ser Phe Thr Tyr Tyr Ala Asp Ser Val
 50                  55                  60

Asp Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Gln Asp Gly Glu Phe Leu Met Asp Tyr Trp Gly Gln Gly Thr
            100                 105                 110

Leu Val Thr Val Ser Ser
            115

<210> SEQ ID NO 146
<211> LENGTH: 118
<212> TYPE: PRT
<213> ORGANISM: Artificial Sequence
<220> FEATURE:
<223> OTHER INFORMATION: Clone 21_Variable heavy chain

<400> SEQUENCE: 146

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Thr Lys Gly Gly Ser Tyr Thr Tyr Tyr Ala Asp Ser Val
 50                  55                  60

Asp Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95
```

-continued

Ala Arg Gln Asp Gly Asn Phe Leu Met Asp Tyr Trp Gly Gln Gly Thr
                100                 105                 110

Leu Val Thr Val Ser Ser
        115

<210> SEQ ID NO 147
<211> LENGTH: 113
<212> TYPE: PRT
<213> ORGANISM: Artificial Sequence
<220> FEATURE:
<223> OTHER INFORMATION: Clone 22_Variable light chain

<400> SEQUENCE: 147

Asp Val Val Met Thr Gln Thr Pro Leu Ser Leu Pro Val Thr Leu Gly
1               5                   10                  15

Gln Pro Ala Ser Ile Ser Cys Lys Ser Ser Pro Ser Leu Leu Asp Val
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Tyr Phe Pro Phe Thr Phe Gly Gln Gly Thr Lys Val Glu Ile Lys
            100                 105                 110

Arg

<210> SEQ ID NO 148
<211> LENGTH: 118
<212> TYPE: PRT
<213> ORGANISM: Artificial Sequence
<220> FEATURE:
<223> OTHER INFORMATION: Clone 23_Variable heavy chain

<400> SEQUENCE: 148

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser His Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly His Phe Leu Met Asp Tyr Trp Gly Gln Gly Thr
            100                 105                 110

Leu Val Thr Val Ser Ser
        115

<210> SEQ ID NO 149
<211> LENGTH: 5
<212> TYPE: PRT
<213> ORGANISM: Artificial Sequence

```
<220> FEATURE:
<223> OTHER INFORMATION: Clone 1001_Variable heavy chain CDR 1

<400> SEQUENCE: 149

Ser Tyr Ala Met Asn
1               5

<210> SEQ ID NO 150
<211> LENGTH: 17
<212> TYPE: PRT
<213> ORGANISM: Artificial Sequence
<220> FEATURE:
<223> OTHER INFORMATION: Clone 1001_Variable heavy chain CDR 2

<400> SEQUENCE: 150

Thr Ile Thr Thr Gly Gly Ser Tyr Thr Tyr Tyr Ala Asp Ser Val Asp
1               5                   10                  15

Gly

<210> SEQ ID NO 151
<211> LENGTH: 9
<212> TYPE: PRT
<213> ORGANISM: Artificial Sequence
<220> FEATURE:
<223> OTHER INFORMATION: Clone 1001_Variable heavy chain CDR 3

<400> SEQUENCE: 151

Gln Asp Gly Asn Phe Leu Met Asp Tyr
1               5

<210> SEQ ID NO 152
<211> LENGTH: 16
<212> TYPE: PRT
<213> ORGANISM: Artificial Sequence
<220> FEATURE:
<223> OTHER INFORMATION: Clone 1001_Variable light chain CDR 1

<400> SEQUENCE: 152

Lys Ser Ser Gln Ser Leu Leu Asp Ile Asp Gly Lys Thr Tyr Leu Asn
1               5                   10                  15

<210> SEQ ID NO 153
<211> LENGTH: 7
<212> TYPE: PRT
<213> ORGANISM: Artificial Sequence
<220> FEATURE:
<223> OTHER INFORMATION: Clone 1001_Variable light chain CDR 2

<400> SEQUENCE: 153

Leu Val Ser Lys Leu Asp Ser
1               5

<210> SEQ ID NO 154
<211> LENGTH: 8
<212> TYPE: PRT
<213> ORGANISM: Artificial Sequence
<220> FEATURE:
<223> OTHER INFORMATION: Clone 1001_Variable light chain CDR 3

<400> SEQUENCE: 154

Trp Gln Gly Thr His Phe Pro Phe
1               5

<210> SEQ ID NO 155
<211> LENGTH: 17
<212> TYPE: PRT
```

```
<213> ORGANISM: Artificial Sequence
<220> FEATURE:
<223> OTHER INFORMATION: Clone 1015_Variable heavy chain CDR 2

<400> SEQUENCE: 155

Thr Ile Thr Thr Gly Gly Ser His Thr Tyr Tyr Ala Asp Ser Val Glu
1               5                   10                  15

Gly

<210> SEQ ID NO 156
<211> LENGTH: 9
<212> TYPE: PRT
<213> ORGANISM: Artificial Sequence
<220> FEATURE:
<223> OTHER INFORMATION: Clone 1021_Variable heavy chain CDR 3

<400> SEQUENCE: 156

Gln Asp Gly His Phe Leu Met Asp Tyr
1               5

<210> SEQ ID NO 157
<211> LENGTH: 5
<212> TYPE: PRT
<213> ORGANISM: Artificial Sequence
<220> FEATURE:
<223> OTHER INFORMATION: Clone 1024_Variable heavy chain CDR 1

<400> SEQUENCE: 157

Ser Tyr Ala Met Ser
1               5

<210> SEQ ID NO 158
<211> LENGTH: 16
<212> TYPE: PRT
<213> ORGANISM: Artificial Sequence
<220> FEATURE:
<223> OTHER INFORMATION: Clone 1024_Variable light chain CDR 1

<400> SEQUENCE: 158

Lys Ser Ser Gln Ser Leu Leu Asp Leu Asp Gly Lys Thr Tyr Leu Asn
1               5                   10                  15

<210> SEQ ID NO 159
<211> LENGTH: 17
<212> TYPE: PRT
<213> ORGANISM: Artificial Sequence
<220> FEATURE:
<223> OTHER INFORMATION: Clone 1104_Variable heavy chain CDR 2

<400> SEQUENCE: 159

Thr Ile Thr Thr Gly Gly Ser His Thr Tyr Tyr Ala Asp Ser Val Gln
1               5                   10                  15

Gly

<210> SEQ ID NO 160
<211> LENGTH: 16
<212> TYPE: PRT
<213> ORGANISM: Artificial Sequence
<220> FEATURE:
<223> OTHER INFORMATION: Clone 1104_Variable light chain CDR 1

<400> SEQUENCE: 160

Lys Ser Ser Gln Ser Leu Leu Asp Val Asp Gly Lys Thr Tyr Leu Asn
1               5                   10                  15
```

```
<210> SEQ ID NO 161
<211> LENGTH: 8
<212> TYPE: PRT
<213> ORGANISM: Artificial Sequence
<220> FEATURE:
<223> OTHER INFORMATION: Clone 1208_Variable light chain CDR 3

<400> SEQUENCE: 161

Trp Gln Gly Thr Tyr Leu Pro Phe
1               5

<210> SEQ ID NO 162
<211> LENGTH: 17
<212> TYPE: PRT
<213> ORGANISM: Artificial Sequence
<220> FEATURE:
<223> OTHER INFORMATION: Clone 1214_Variable heavy chain CDR 2

<400> SEQUENCE: 162

Thr Ile Thr Thr Gly Gly Ser Tyr Thr Tyr Tyr Ala Asp Ser Val Glu
1               5                   10                  15

Gly

<210> SEQ ID NO 163
<211> LENGTH: 5
<212> TYPE: PRT
<213> ORGANISM: Artificial Sequence
<220> FEATURE:
<223> OTHER INFORMATION: Clone 1216_Variable heavy chain CDR 1

<400> SEQUENCE: 163

His Tyr Ala Met Asn
1               5

<210> SEQ ID NO 164
<211> LENGTH: 8
<212> TYPE: PRT
<213> ORGANISM: Artificial Sequence
<220> FEATURE:
<223> OTHER INFORMATION: Clone 1216_Variable light chain CDR 3

<400> SEQUENCE: 164

Trp Gln Gly Thr His Leu Pro Phe
1               5

<210> SEQ ID NO 165
<211> LENGTH: 17
<212> TYPE: PRT
<213> ORGANISM: Artificial Sequence
<220> FEATURE:
<223> OTHER INFORMATION: Clone 1234_Variable heavy chain CDR 2

<400> SEQUENCE: 165

Thr Ile Thr Thr Gly Gly Ser Tyr Thr Tyr Tyr Ala Asp Ser Val Gln
1               5                   10                  15

Gly

<210> SEQ ID NO 166
<211> LENGTH: 17
<212> TYPE: PRT
<213> ORGANISM: Artificial Sequence
<220> FEATURE:
<223> OTHER INFORMATION: Clone 1243_Variable heavy chain CDR 2

<400> SEQUENCE: 166

Thr Ile Thr Thr Gly Gly Ser His Thr Tyr Tyr Ala Asp Ser Val His
```

```
1               5                   10                  15
Gly

<210> SEQ ID NO 167
<211> LENGTH: 17
<212> TYPE: PRT
<213> ORGANISM: Artificial Sequence
<220> FEATURE:
<223> OTHER INFORMATION: Clone 1248_Variable heavy chain CDR 2

<400> SEQUENCE: 167

Thr Ile Thr Thr Gly Gly Ser His Thr Tyr Tyr Ala Asp Ser Val Asp
1               5                   10                  15
Gly

<210> SEQ ID NO 168
<211> LENGTH: 17
<212> TYPE: PRT
<213> ORGANISM: Artificial Sequence
<220> FEATURE:
<223> OTHER INFORMATION: Clone 3007_Variable heavy chain CDR 2

<400> SEQUENCE: 168

Thr Ile Thr Leu Gly Gly Ser Tyr Thr Tyr Tyr Ala Asp Ser Val Gln
1               5                   10                  15
Gly

<210> SEQ ID NO 169
<211> LENGTH: 16
<212> TYPE: PRT
<213> ORGANISM: Artificial Sequence
<220> FEATURE:
<223> OTHER INFORMATION: Clone 3016_Variable light chain CDR 1

<400> SEQUENCE: 169

Lys Ser Ser Gln Ser Leu Leu Asp Ser Asp Gly Lys Thr Tyr Leu Asn
1               5                   10                  15

<210> SEQ ID NO 170
<211> LENGTH: 9
<212> TYPE: PRT
<213> ORGANISM: Artificial Sequence
<220> FEATURE:
<223> OTHER INFORMATION: Clone 3120_Variable heavy chain CDR 3

<400> SEQUENCE: 170

Gln Asp Gly Tyr Phe Leu Met Asp Tyr
1               5

<210> SEQ ID NO 171
<211> LENGTH: 9
<212> TYPE: PRT
<213> ORGANISM: Artificial Sequence
<220> FEATURE:
<223> OTHER INFORMATION: Clone 3131_Variable heavy chain CDR 3

<400> SEQUENCE: 171

Gln Asp Gly Gln Phe Leu Met Asp Tyr
1               5

<210> SEQ ID NO 172
<211> LENGTH: 5
<212> TYPE: PRT
<213> ORGANISM: Artificial Sequence
<220> FEATURE:
```

```
<223> OTHER INFORMATION: Clone 4278_Variable heavy chain CDR 1

<400> SEQUENCE: 172

Lys Tyr Ala Met Asn
1               5

<210> SEQ ID NO 173
<211> LENGTH: 17
<212> TYPE: PRT
<213> ORGANISM: Artificial Sequence
<220> FEATURE:
<223> OTHER INFORMATION: Clone 4278_Variable heavy chain CDR 2

<400> SEQUENCE: 173

Thr Ile Thr Leu Gly Gly Ser Tyr Thr Tyr Tyr Ala Asp Ser Val Asp
1               5                   10                  15
Gly

<210> SEQ ID NO 174
<211> LENGTH: 11
<212> TYPE: PRT
<213> ORGANISM: Artificial Sequence
<220> FEATURE:
<223> OTHER INFORMATION: Clone 4278_Variable heavy chain CDR 3

<400> SEQUENCE: 174

Gln Tyr Leu Asp Gly Asn Phe Leu Met Asp Tyr
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Clone 4287_Variable heavy chain CDR 3

<400> SEQUENCE: 175

Gln His Pro Tyr Gly Asn Phe Leu Met Asp Tyr
1               5                   10

<210> SEQ ID NO 176
<211> LENGTH: 16
<212> TYPE: PRT
<213> ORGANISM: Artificial Sequence
<220> FEATURE:
<223> OTHER INFORMATION: Clone 1_Variable light chain CDR 1

<400> SEQUENCE: 176

Lys Ser Ser Pro Ser Leu Leu Asp Ser Asp Gly Lys Thr Tyr Leu Asn
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Clone 2_Variable light chain CDR 1

<400> SEQUENCE: 177

Lys Ser Ser Pro Ser Leu Leu Asp Ile Asp Gly Lys Thr Tyr Leu Asn
1               5                   10                  15

<210> SEQ ID NO 178
<211> LENGTH: 16
<212> TYPE: PRT
<213> ORGANISM: Artificial Sequence
```

```
<220> FEATURE:
<223> OTHER INFORMATION: Clone 3_Variable light chain CDR 1

<400> SEQUENCE: 178

Lys Ser Ser Pro Ser Leu Leu Asp Val Asp Gly Lys Thr Tyr Leu Asn
1               5                   10                  15

<210> SEQ ID NO 179
<211> LENGTH: 8
<212> TYPE: PRT
<213> ORGANISM: Artificial Sequence
<220> FEATURE:
<223> OTHER INFORMATION: Clone 14_Variable light chain CDR 3

<400> SEQUENCE: 179

Trp Gln Gly Thr Tyr Phe Pro Phe
1               5

<210> SEQ ID NO 180
<211> LENGTH: 8
<212> TYPE: PRT
<213> ORGANISM: Artificial Sequence
<220> FEATURE:
<223> OTHER INFORMATION: Clone 15_Variable light chain CDR 3

<400> SEQUENCE: 180

Trp Gln Gly Phe Tyr Phe Pro Phe
1               5

<210> SEQ ID NO 181
<211> LENGTH: 5
<212> TYPE: PRT
<213> ORGANISM: Artificial Sequence
<220> FEATURE:
<223> OTHER INFORMATION: Clone 16_Variable heavy chain CDR 1

<400> SEQUENCE: 181

His Tyr Ala Met Thr
1               5

<210> SEQ ID NO 182
<211> LENGTH: 5
<212> TYPE: PRT
<213> ORGANISM: Artificial Sequence
<220> FEATURE:
<223> OTHER INFORMATION: Clone 17_Variable heavy chain CDR 1

<400> SEQUENCE: 182

Ser Tyr Ala Met Thr
1               5

<210> SEQ ID NO 183
<211> LENGTH: 5
<212> TYPE: PRT
<213> ORGANISM: Artificial Sequence
<220> FEATURE:
<223> OTHER INFORMATION: Clone 19_Variable heavy chain CDR 1

<400> SEQUENCE: 183

Gln Tyr Ala Met Asn
1               5

<210> SEQ ID NO 184
<211> LENGTH: 17
<212> TYPE: PRT
<213> ORGANISM: Artificial Sequence
<220> FEATURE:
```

<223> OTHER INFORMATION: Clone 19_Variable heavy chain CDR 2

<400> SEQUENCE: 184

Thr Ile Thr Lys Lys Gly Ser Phe Thr Tyr Tyr Ala Asp Ser Val Asp
1               5                   10                  15

Gly

<210> SEQ ID NO 185
<211> LENGTH: 9
<212> TYPE: PRT
<213> ORGANISM: Artificial Sequence
<220> FEATURE:
<223> OTHER INFORMATION: Clone 19_Variable heavy chain CDR 3

<400> SEQUENCE: 185

Gln Asp Gly Glu Phe Leu Met Asp Tyr
1               5

<210> SEQ ID NO 186
<211> LENGTH: 17
<212> TYPE: PRT
<213> ORGANISM: Artificial Sequence
<220> FEATURE:
<223> OTHER INFORMATION: Clone 20_Variable heavy chain CDR 2

<400> SEQUENCE: 186

Thr Ile Lys Lys Gly Gly Ser Phe Thr Tyr Tyr Ala Asp Ser Val Asp
1               5                   10                  15

Gly

<210> SEQ ID NO 187
<211> LENGTH: 17
<212> TYPE: PRT
<213> ORGANISM: Artificial Sequence
<220> FEATURE:
<223> OTHER INFORMATION: Clone 21_Variable heavy chain CDR 2

<400> SEQUENCE: 187

Thr Ile Thr Lys Gly Gly Ser Tyr Thr Tyr Tyr Ala Asp Ser Val Asp
1               5                   10                  15

Gly

<210> SEQ ID NO 188
<211> LENGTH: 5
<212> TYPE: PRT
<213> ORGANISM: Artificial Sequence
<220> FEATURE:
<223> OTHER INFORMATION: Clone 23_Variable heavy chain CDR 1

<400> SEQUENCE: 188

His Tyr Ala Met Asn
1               5

<210> SEQ ID NO 189
<211> LENGTH: 53
<212> TYPE: DNA
<213> ORGANISM: Artificial Sequence
<220> FEATURE:
<223> OTHER INFORMATION: VH Fo

<400> SEQUENCE: 189
tgctgtgggt gagtggtacc tgtggggaag tccagctggt ggagtctgga ggt            53

<210> SEQ ID NO 190

```
<211> LENGTH: 56
<212> TYPE: DNA
<213> ORGANISM: Artificial Sequence
<220> FEATURE:
<223> OTHER INFORMATION: VH Re

<400> SEQUENCE: 190
agtgggaaca cggagggccc cttggtgctg gcggagctca cagtcaccag cgtgcc      56

<210> SEQ ID NO 191
<211> LENGTH: 53
<212> TYPE: DNA
<213> ORGANISM: Artificial Sequence
<220> FEATURE:
<223> OTHER INFORMATION: VL Fo

<400> SEQUENCE: 191
tgctgtgggt gagtggtacc tgtggggacg tggtgatgac acagacgccg ctg         53

<210> SEQ ID NO 192
<211> LENGTH: 66
<212> TYPE: DNA
<213> ORGANISM: Artificial Sequence
<220> FEATURE:
<223> OTHER INFORMATION: VL Re_CL overlap

<400> SEQUENCE: 192
gatgaacaca gaaggggcag ccaccgtgcg tttaatttca accttagtgc cttggccgaa  60
cgtaaa                                                              66

<210> SEQ ID NO 193
<211> LENGTH: 27
<212> TYPE: DNA
<213> ORGANISM: Artificial Sequence
<220> FEATURE:
<223> OTHER INFORMATION: Ck Fo

<400> SEQUENCE: 193
acggtggctg ccccttctgt gttcatc                                      27

<210> SEQ ID NO 194
<211> LENGTH: 45
<212> TYPE: DNA
<213> ORGANISM: Artificial Sequence
<220> FEATURE:
<223> OTHER INFORMATION: Ck Re

<400> SEQUENCE: 194
gattggatcc aagcttacta gcactcaccc ctgttgaaag actta                  45

<210> SEQ ID NO 195
<211> LENGTH: 118
<212> TYPE: PRT
<213> ORGANISM: Artificial Sequence
<220> FEATURE:
<223> OTHER INFORMATION: Clone A24_Variable heavy chain

<400> SEQUENCE: 195

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe His Ser Tyr
            20                  25                  30

Ala Met Asn Trp Val Arg Gln Ala Pro Gly Lys Gly Leu Glu Trp Val
        35                  40                  45
```

Ser Thr Ile Thr Thr Arg Gly Ser Tyr Thr Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
            115

<210> SEQ ID NO 196
<211> LENGTH: 113
<212> TYPE: PRT
<213> ORGANISM: Artificial Sequence
<220> FEATURE:
<223> OTHER INFORMATION: Clone A25_Variable light chain

<400> SEQUENCE: 196

Asp Val Val Met Thr Gln Thr Pro Leu Ser Leu Pro Val Thr Leu Gly
1               5                   10                  15

Gln Pro Ala Ser Ile Ser Cys Lys Ser Ser Gln Ser Leu Leu Asp Arg
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gln Gly Thr Lys Val Glu Ile Lys
            100                 105                 110

Arg

<210> SEQ ID NO 197
<211> LENGTH: 118
<212> TYPE: PRT
<213> ORGANISM: Artificial Sequence
<220> FEATURE:
<223> OTHER INFORMATION: Clone A52_Variable heavy chain

<400> SEQUENCE: 197

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser His Thr Tyr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

```
Leu Val Thr Val Ser Ser
        115

<210> SEQ ID NO 198
<211> LENGTH: 118
<212> TYPE: PRT
<213> ORGANISM: Artificial Sequence
<220> FEATURE:
<223> OTHER INFORMATION: Clone A63_Variable heavy chain

<400> SEQUENCE: 198

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 199
<211> LENGTH: 118
<212> TYPE: PRT
<213> ORGANISM: Artificial Sequence
<220> FEATURE:
<223> OTHER INFORMATION: Clone A71_Variable heavy chain

<400> SEQUENCE: 199

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

His Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 200
<211> LENGTH: 118
<212> TYPE: PRT
<213> ORGANISM: Artificial Sequence
<220> FEATURE:
<223> OTHER INFORMATION: Clone A74_Variable heavy chain
```

<400> SEQUENCE: 200

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Thr Ile Thr Thr Gly Gly Ser Tyr Thr Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Gly Asn Phe Leu Met Asp Tyr Trp Gly Gln Gly Thr
            100                 105                 110

Leu Val Thr Val Ser Ser
        115

<210> SEQ ID NO 201
<211> LENGTH: 16
<212> TYPE: PRT
<213> ORGANISM: Artificial Sequence
<220> FEATURE:
<223> OTHER INFORMATION: Clone A25_Variable light chain CDR 1

<400> SEQUENCE: 201

Lys Ser Ser Gln Ser Leu Leu Asp Arg Asp Gly Lys Thr Tyr Leu Asn
1               5                   10                  15

<210> SEQ ID NO 202
<211> LENGTH: 17
<212> TYPE: PRT
<213> ORGANISM: Artificial Sequence
<220> FEATURE:
<223> OTHER INFORMATION: Clone A71_Variable heavy chain CDR 2

<400> SEQUENCE: 202

Thr Ile Thr Thr Gly Gly Ser Tyr Thr Tyr Tyr Ala Asp Ser Val His
1               5                   10                  15

Gly

<210> SEQ ID NO 203
<211> LENGTH: 5
<212> TYPE: PRT
<213> ORGANISM: Artificial Sequence
<220> FEATURE:
<223> OTHER INFORMATION: Clone A74_Variable heavy chain CDR 1

<400> SEQUENCE: 203

Ser Tyr Ala Met His
1               5

<210> SEQ ID NO 204
<211> LENGTH: 17
<212> TYPE: PRT
<213> ORGANISM: Artificial Sequence
<220> FEATURE:
<223> OTHER INFORMATION: Clone A24_Variable heavy chain CDR 2

<400> SEQUENCE: 204

Thr Ile Thr Thr Arg Gly Ser Tyr Thr Tyr Tyr Ala Asp Ser Val Glu
1               5                   10                  15

Gly

ANTIBODY BINDING TO TFPI AND COMPOSITION COMPRISING THE SAME

CROSS REFERENCE TO RELATED APPLICATIONS

This application is a National Stage of International Application No. PCT/KR2015/014370 filed Dec. 29, 2015, claiming priority based on Korean Patent Application No. 10-2015-0026555 filed Feb. 25, 2015 and Korean Patent Application No. 10-2015-0135761 filed Sep. 24, 2015, the contents of all of which are incorporated herein by reference in their entirety.

TECHNICAL FIELD

The present invention relates to an antibody that binds specifically to a tissue factor pathway inhibitor (TFPI), a nucleic acid encoding the antibody, a vector comprising the nucleic acid, a host cell comprising the vector, a method for producing the antibody, and a pharmaceutical composition for treating hemophilia, which comprises the antibody as an active ingredient.

BACKGROUND ART

It is known that, in about 30% of patients with hemophilia A and B, an antibody against the FVIII (factor VIII) or FIX (factor IX) protein used for treatment is produced to significantly reduce the therapeutic effect of the protein. As an alternative to the protein, activated factor VIIa or aPCC (plasma-derived activated prothrombin complex concentrate) has been administered.

The above-described recombinant protein is administered to hemophilia patients by intravenous injection twice or more a week, but inconvenience caused by repeated administration of the recombinant protein has been constantly presented. Thus, studies on long-acting recombinant proteins having an increased half-life have been actively conducted.

In hemophilia models, an approach against TFPI (tissue factor pathway inhibitor) has recently been attempted. TFPI is involved in the extrinsic pathway of blood coagulation, and functions to inhibit blood coagulation by preventing factor X activation with TF/FVIIa (see FIG. 1). Thus, when TFPI is inhibited by an anti-TFPI antibody, blood coagulation during bleeding can be activated by the extrinsic pathway.

TFPI consists of three KPI domains (Kunitz-type domains or Kunitz domains), and KPI-2 (Kunitz domain 2) inhibits FXa by binding directly to FXa (see FIG. 2). This means that KPI-2 forms a complex of TF/FVIIa/FXa/TFPI, resulting in direct inhibition of production of FXa.

An anti-TFPI antibody may be used in patients in which an antibody against the FVIII or FIX protein has been produced. In addition, the anti-TFPI antibody has a very long half-life (about 2 weeks), and thus the number of administrations thereof can be reduced.

Hemophilia therapeutic agents against TFPI are mostly in the research stage or the initial development stage. For example, the humanized monoclonal antibody (mAb) mAb2021 developed by Novo Nordisk is a humanized antibody (IgG4) that is an anti-TFPI monoclonal antibody, and is in the phase 1 clinical stage. In addition, ARC19499 developed by Baxter is a PEGylated aptamer targeting TFPI and is in the preclinical stage. Furthermore, JBT2329 developed by Baxter & 3B Pharmaceuticals is a Pegylated anti-human TFPI 20mer peptide and is in the preclinical stage.

The need for a new agent for treating hemophilia has been constantly proposed, and the development of therapeutic agents that are approaches other than a bypassing agent such as FVIIa is urgently required. In particular, an approach to a drug that inhibits the TFPI pathway is preferred. Among hemophilia patients who are administered with a blood coagulation factor, a number of patients having resistance to the factor exist, and thus require a new drug. However, medical issues such as antigen (Ag)-antibody (Ab) complex clearance should be taken into consideration.

Accordingly, the present inventors have made extensive efforts to develop a novel antibody that binds specifically to TFPI, and as a result, have found that the use of the antibody can activate the extrinsic pathway of blood coagulation by inhibiting the anticoagulation mechanism of TFPI, thereby completing the present invention.

DISCLOSURE OF INVENTION

Technical Problem

It is an object of the present invention to provide a novel antibody that binds specifically to TFPI, a nucleic acid encoding the antibody, a vector comprising the nucleic acid, a host cell comprising the vector, a method for producing the antibody, and a pharmaceutical composition for treating antibody-induced hemophilia or preventing a blood coagulation disorder in hemophilia-A and hemophilia-B patients, the pharmaceutical composition comprising the antibody as an active ingredient and being capable of inhibiting TFPI to thereby activate the extrinsic pathway of blood coagulation.

Technical Solution

To achieve the above object, the present invention provides an antibody that binds specifically to a TFPI (tissue factor pathway inhibitor) represented by SEQ ID NO: 39.

The present invention also provides: a nucleic acid encoding an anti-TFPI antibody; a vector containing the nucleic acid; and a cell having the vector introduced therein.

The present invention also provides a pharmaceutical composition for treating hemophilia, which comprises an anti-TFPI antibody as an active ingredient.

BRIEF DESCRIPTION OF THE DRAWINGS

FIG. 4 shows the amino acid sequences of clone T417 and humanized antibody clone 308 among anti-TFPI antibodies.

FIG. 5 shows the amino acid sequences of 308-2 and 302-4 clone antibodies that are clone 308 antibody mutants among anti-TFPI antibodies.

FIG. 18 shows the predicted binding between the heavy-chain variable region of clone 308 among anti-TFPI antibodies and a human TFPI antigen.

FIGS. 29 to 33 show the results of evaluating the effects of affinity-matured anti-TFPI antibodies by a TF/FVIIa/FX complex assay.

BEST MODE FOR CARRYING OUT THE INVENTION

Figure 1:
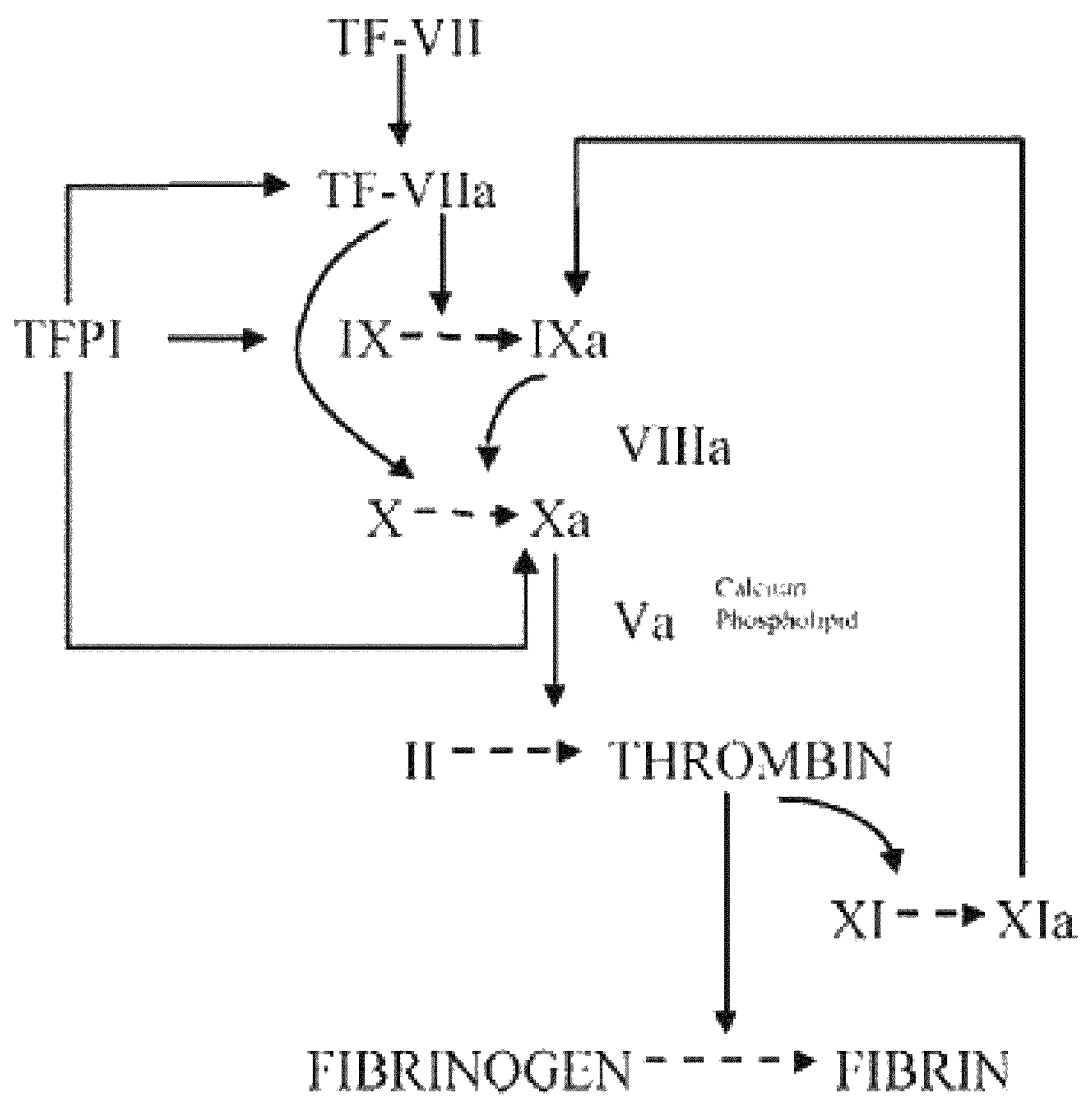
FIG. 1 shows the extrinsic pathway of blood coagulation and TFPI.
Figure 2:
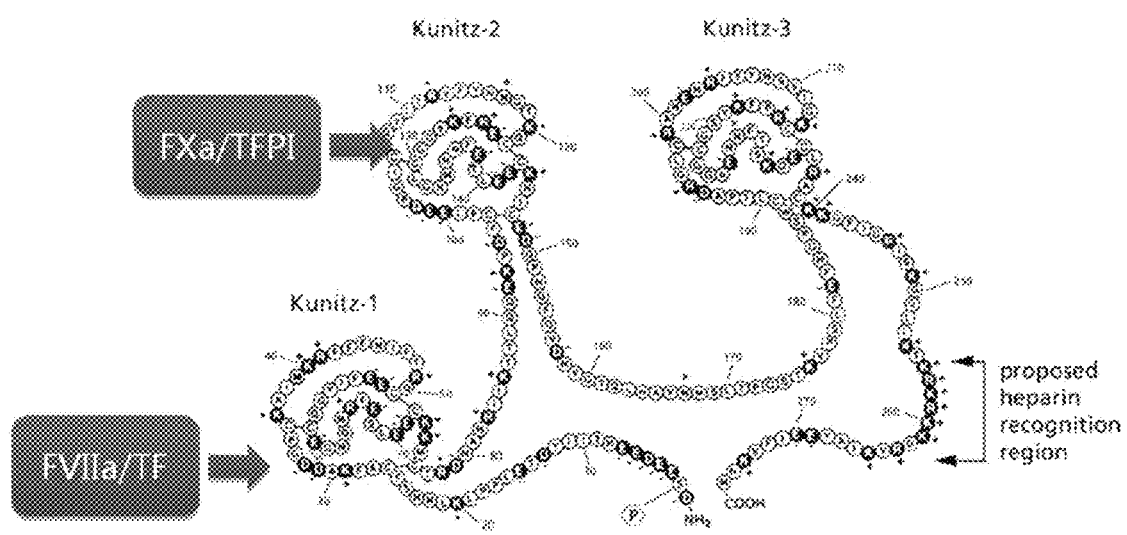
FIG. 2 shows the schematic protein structure of TFPI and the function of KPI domains.

It was reported that TFPI (tissue factor pathway inhibitor) is involved in the extrinsic pathway of blood coagulation and inhibits blood coagulation by preventing factor X activation with TF/FVIIa. Thus, the present inventors have attempted to construct an antibody for treating or preventing hemophilia. In particular, it is the subject matter of the present invention to activate the extrinsic pathway of blood coagulation by an antibody that inhibits the KPI-2 of TFPI. The antigen region that is targeted by the antibody is the KPI-2 domain of TFPI, which has an amino acid sequence having an identity of 90% or higher between humans, rabbits and monkeys. Thus, when the KPI-2 domain of TFPI is used, an animal study is easily designed, and a simple model for measuring the rate of blood coagulation can be introduced.

As used herein, the term "tissue factor pathway inhibitor" or "TFPI" refers to any variant, isoform and species homolog of human TFPI that is naturally expressed by cells.

In a preferred embodiment of the invention, the binding of an antibody of the invention to TFPI reduces the blood coagulation time.

In an example of the present invention, "clone 308", "clone 308-2", and "clone 308-4" were prepared, which are isolated human monoclonal antibodies having a structural characteristic that binds specifically to a TFPI (tissue factor pathway inhibitor) represented by SEQ ID NO: 39. The amino acid sequences of the heavy-chain CDR and light-chain CDR of each of the antibodies are as shown in Tables 5 and 7 below. As shown in Tables 4 and 6 below, anti-TFPI antibodies may comprise the amino acid sequences of a heavy-chain variable region and a light-chain variable region and sequences homologous thereto.

In another example of the present invention, the quantitative affinity of the purified antibody clone T417, clone T308, clone 308, clone 308-2 or clone 308-4 for recombinant human TFPI was measured using a Biacore T-200 biosensor (GE Healthcare, USA) (Example 6). As a result, as shown in Table 13 and FIG. 8, all the prepared clone antibodies affinities which were somewhat different from one another. Particularly, it was shown that the affinities of clone 308-2 and clone 308-4 were very higher than that of clone 308.

Thus, in one aspect, the present invention is directed to an antibody that binds specifically to a TFPI (tissue factor pathway inhibitor) represented by SEQ ID NO: 39.

In the present invention, the antibody may contain a heavy-chain variable region comprising: a heavy-chain CDR1 comprising an amino acid sequence of SEQ ID NO: 5, 11 or 23; a heavy-chain CDR2 comprising an amino acid sequence of SEQ ID NO: 6, 12, 26 or 27; and a heavy-chain CDR3 comprising an amino acid sequence of SEQ ID NO: 7 or 13.

In the present invention, the antibody may contain a heavy-chain variable region comprising: a light-chain CDR1 comprising an amino acid sequence of SEQ ID NO: 8 or 14; a light-chain CDR2 comprising an amino acid sequence of SEQ ID NO: 9 or 15; and a light-chain CDR3 comprising an amino acid sequence of SEQ ID NO: 10 or 16.

In the present invention, the antibody may contain a heavy-chain variable region comprising a sequence having a homology of at least 80%, preferably at least 90%, more preferably 100%, to an amino acid sequence of SEQ ID NO: 1, 3, 21, 24 or 25, and the antibody may contain a light-chain variable region comprising a sequence having a homology of at least 80%, preferably at least 90%, more preferably 100%, to an amino acid sequence of SEQ ID NO: 2, 4 or 22.

In the present invention, the antibody may contain a heavy-chain variable region comprising an amino acid sequence of SEQ ID NO: 1, 3, 21, 24 or 25, and a light-chain variable region comprising an amino acid sequence of SEQ ID NO: 2, 4 or 22. The antibody may be a human monoclonal antibody, but is not limited thereto.

In an example of the present invention, "clone 1001", "clone 1015", "clone 1021", "clone 1023" "clone 1024", "clone 1104", "clone 1123", "clone 1202", "clone 1208", "clone 1214", "clone 1216", "clone 1223", "clone 1224", "clone 1232", "clone 1234", "clone 1238", "clone 1243", "clone 1248", "clone 3007", "clone 3016", "clone 3024", "clone 3115", "clone 3120", "clone 3131", "clone 3203", "clone 3241", "clone 4011", "clone 4017", "clone 4034", "clone 4041", "clone 4141", "clone 4146", "clone 4206", "clone 4208", "clone 4278", "clone 4287", "clone 1", "clone 2", "clone 3", "clone 4", "clone 5", "clone 6", "clone 7", "clone 8", "clone 9", "clone 10", "clone 11", "clone 12", "clone 13", "clone 14", "clone 15", "clone 16", "clone 17", "clone 18", "clone 19", "clone 20", "clone 21", "clone 22", "clone 23", "clone A24", "clone A25", "clone A52", "clone A63", "clone A67", "clone A71", and "clone A74" were prepared, which are isolated monoclonal antibodies having a structural characteristic that binds specifically to a TFPI (tissue factor pathway inhibitor) represented by SEQ ID NO: 39. The amino acid sequences of the heavy-chain CDR and light-chain CDR of each of the antibodies are as shown in Tables 20 and below. As shown in Tables 19 and 22 below, anti-TFPI antibodies may comprise the amino acid sequences of a heavy-chain variable region and a light-chain variable region and sequences homologous thereto.

In another example of the present invention, the quantitative binding affinities of clone 12, clone 1023, clone 1202 and clone 3241, which are purified antibodies, for recombinant human TFPI, were measured using a Biacore T-200 biosensor (GE Healthcare, USA) (Example 13). As a result, as shown in Table 24 below, all the prepared clone antibodies showed affinities which were somewhat different from one another.

Thus, in one aspect, the present invention is directed to an antibody that binds specifically to a TFPI (tissue factor pathway inhibitor) represented by SEQ ID NO: 39.

In the present invention, the antibody may contain a heavy-chain variable region comprising: a heavy-chain CDR1 comprising an amino acid sequence of SEQ ID NO: 149, 157, 163, 172, 181, 182, 183, 188, 201 or 203; a heavy-chain CDR2 comprising an amino acid sequence of SEQ ID NO: 150, 155, 159, 162, 165, 166, 167, 168, 173, 184, 186, 187 or 202; and a heavy-chain CDR3 comprising an amino acid sequence of SEQ ID NO: 151, 156, 170, 174, 175 or 185.

In the present invention, the antibody may contain a heavy-chain variable region comprising: a light-chain CDR1 comprising an amino acid sequence of SEQ ID NO: 152, 158, 160, 169, 171, 176, 177 or 178; a light-chain CDR2 comprising an amino acid sequence of SEQ ID NO: 153; and a light-chain CDR3 comprising an amino acid sequence of SEQ ID NO: 154, 161, 164, 179 or 180.

In the present invention, the antibody may contain a heavy-chain variable region comprising a sequence having a homology of at least 80%, preferably at least 90%, more preferably 100%, to an amino acid sequence of SEQ ID NO: 95, 97, 98, 99, 100, 102, 104, 105, 107, 109, 110, 112, 113, 114, 115, 117, 118, 119, 120, 121, 123, 124, 125, 126, 127, 128, 129, 131, 132, 133, 134, 135, 136, 137, 138, 141, 142, 143, 144, 145, 146, 148, 195, 197, 198, 199 or 200, and the antibody may contain a light-chain variable region comprising a sequence having a homology of at least 80%, preferably at least 90%, more preferably 100%, to an amino acid sequence of SEQ ID NO: 96, 101, 103, 106, 108, 111, 116, 122, 130, 139, 140, 147 or 196.

In the present invention, the antibody may contain a heavy-chain variable region comprising an amino acid sequence of SEQ ID NO: 95, 97, 98, 99, 100, 102, 104, 105, 107, 109, 110, 112, 113, 114, 115, 117, 118, 119, 120, 121, 123, 124, 125, 126, 127, 128, 129, 131, 132, 133, 134, 135, 136, 137, 138, 141, 142, 143, 144, 145, 146, 148, 195, 197, 198, 199 or 200, and a light-chain variable region comprising an amino acid sequence of SEQ ID NO: 96, 101, 103, 106, 108, 111, 116, 122, 130, 139, 140, 147 or 196. The antibody may be a human monoclonal antibody, but is not limited thereto.

The amino acid sequence of the antibody can be replaced by conservative substitution. As used herein, the term "conservative substitution" refers to modifications of a polypeptide that involve the substitution of one or more amino acids for amino acids having similar biochemical properties that do not result in loss of the biological or biochemical function of the polypeptide. A "conservative amino acid substitution" is one in which the amino acid residue is replaced with an amino acid residue having a similar side chain. Families of amino acid residues having similar side chains have been defined in the art to which the present invention pertains. These families include amino acids (e.g., lysine, arginine and histidine with basic side chains, amino acids (e.g., aspartic acid and glutamic acid) with acidic side chains, amino acids (e.g., glycine, aspargin, glutamine, serine, threonine, tyrosine, and cysteine) with uncharged polar side chains, amino acids (e.g., alanine, valine, leucine, isoleucine, proline, phenylalanine, methionine, and tryptophan) with nonpolar side chains, amino acids (e.g., threonine, valine, and isoleucine) with beta-branched side chains, and amino acids (e.g., tyrosine, phenylalanine, tryptophan, and histidine) with aromatic side chains. It is envisioned that the antibodies of the present invention may have conservative amino acid substitutions and still retain activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, preferably at least about 90%, 91%, 92%, 93%, 94%, or 95%, more preferably at least about 96%, 97%, 98%, 99%, 99.1%, 99.2%, 99.3%, 99.4% or 99.5% of the nucleotides or amino acids. Alternatively, substantial homology for nucleic acids exists when the segments will hybridize under selective hybridization conditions to the complement of the strand. Also included are nucleic acid sequences and polypeptide sequences having substantial homology to the specific nucleic acid sequences and amino acid sequences recited herein.

As shown in Tables 2, 5 and 7 below, in the antibodies according to the present invention, the heavy-chain ($V_H$) CDR1, CDR2 and CDR3 sequences and the light-chain ($V_L$) CDR1, CDR2 and CDR3 sequences may be composed of a mixture of structurally similar heavy-chain ($V_H$) and light-chain ($V_L$) sequences which form CDR1, CDR2 and CDR3, each consisting of a heavy chain ($V_H$)/light chain ($V_L$) pair.

As shown in Tables 20 and 23 below, in the antibodies according to the present invention, the heavy-chain ($V_H$) CDR1, CDR2 and CDR3 sequences and the light-chain ($V_L$) CDR1, CDR2 and CDR3 sequences may be composed of a mixture of structurally similar heavy-chain ($V_H$) and light-chain ($V_L$) sequences which form CDR1, CDR2 and CDR3, each consisting of a heavy chain ($V_H$)/light chain ($V_L$) pair.

As used herein, the term "antibody" or "antibody composition" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity that have variable and constant regions derived from human germline immunoglobulin sequences. The human antibodies of the present invention can include amino acid residues not encoded by human germline immunoglobulin sequences (e.g., mutations introduced by random or site-specific mutagenesis vitro or by somatic mutation in vivo).

As used herein, the term "antibody" refers to a protein molecule which comprises an immunoglobulin molecule immunologically reactive with a particular antigen, and which serves as a receptor that specifically recognizes an antigen. The term may include all polyclonal antibodies, monoclonal antibodies, full-length antibodies, and antibody fragments. In addition, the term may include chimeric antibodies (e.g., humanized murine antibodies), bivalent or bispecific molecules (e.g., bispecific antibodies), diabodies, triabodies and tetrabodies.

A full-length antibody has two full-length light chains and two full-length heavy chains, in which each of the light chains is linked to the heavy chain by a disulfide bond. The full-length antibody comprises IgA, IgD, IgE, IgM and IgG, and subtypes of IgG include IgG1, IgG2, IgG3 and IgG4. The term "antibody fragment" refers to a fragment having an antigen-binding function, and is intended to include Fab, Fab', F(ab')2, scFv and Fv.

Fab comprises light-chain and heavy-chain variable regions, a light-chain constant region, and a heavy-chain first constant domain (CH1), and has one antigen-binding site. Fab' differs from Fab in that it has a hinge region including one or more cysteine residues at the C-terminus of the heavy-chain CH1 domain. An F(ab')$_2$ antibody is formed by a disulfide bond between the cysteine residues of the hinge region of Fab'.

Fv (variable fragment) means a minimal antibody fragment having only a heavy-chain variable region and a light-chain variable region. dsFv is has a structure in which a heavy-chain variable region and a light-chain variable region are linked to each other by a disulfide bond, and scFV generally has a structure in which a heavy-chain variable region and a light-chain variable region are covalently linked to each other by a peptide linker. These antibody fragments can be obtained using proteases (for example, Fab fragments can be obtained by digesting a full-length antibody with papain, and F(ab')$_2$ fragments can be obtained by digesting a full-length antibody with pepsin). Preferably, these antibody fragments can be produced by a genetic recombinant technique (for example, performing amplification by PCR (polymerase chain reaction) using as a template a DNA encoding the heavy chain of the antibody or the variable region thereof and a DNA encoding the light chain or the variable region thereof together with a primer pair, and performing amplification using a combination of primer pairs such that a DNA encoding a peptide linker is connected with the heavy chain or the variable region thereof and the light chain and the variable region thereof).

An immunoglobulin has heavy chains and light chains, and each heavy and light chain contains a constant region and a variable region (the regions are also known domains). Light and heavy chain variable regions contain four framework regions and three hypervariable regions, also called "complementarity-determining regions" (hereinafter referred to as "CDRs"). The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

The terms "monoclonal antibody", as used herein, refers to antibody molecules having a single molecular composition, obtained from a population of essentially identical antibodies. This monoclonal antibody can display a single binding specificity and affinity for a particular epitope.

As used herein, the term "monoclonal antibody" refers to a molecule derived from human immunoglobulin, in which the full-length amino acid sequence of the antibody, including complementarity-determining regions and framework regions, consists of the amino acid sequence of human immunoglobulin. Human antibodies are generally used for the treatment of human diseases and have the following advantages. First, the human antibody can more easily interact with the human immune system so that target cells can be more efficiently destroyed by, for example, complement-dependent cytotoxicity (CDC) or antibody-dependent cell-mediated cytotoxicity (ADCC). Second, the human immune system does not recognize the antibody as an external antibody. Third, even when the antibody is administered in a smaller mount at a lower frequency, the half-life thereof in the human circulatory system is similar to that of a naturally occurring antibody.

Thus, the antibody according to the present invention is a monoclonal antibody that binds specifically to TFPI, and can show a high affinity and specificity for TFPI. In addition, because the antibody of the present invention is of human origin, it shows low immunogenicity, and thus is effectively used for the treatment of diseases such as antibody-induced hemophilia (hemophilia-A or hemophilia-B).

As used herein, the term "clone T417", "clone T308", "clone 308", "clone 308-2" or "clone 308-4" that binds specifically to TFPI means an antibody that binds to TFPI, resulting in inhibition of the biological activity of TFPI. The term can be used interchangeably with the term "anti-TFPI antibody". Herein, clone T417 and clone T308 is an antibody are antibodies isolated after immunization of mice with recombinant human TFPI, and clone 308 is an antibody prepared by humanization of clone T417. In addition, clone 308-2 and clone 308-4 are antibodies prepared by mutating the lysine (K) of the heavy chain of clone 308 with glutamine (Q) or glutamate (E) as shown in FIG. 5.

The equilibrium dissociation constant ($K_D$) of the anti-TFPI antibody may be, for example, as follows. The $K_D$ of clone 308 may be $5.5 \times 10^{-11}$ M or lower, preferably $5.25 \times 10^{-11}$ M or lower, more preferably $5.0 \times 10^{-12}$ M or lower; the $K_D$ of clone 308-2 may be $3.63 \times 10^{-11}$ M or lower, preferably $3.465 \times 10^{-11}$ M or lower, more preferably $3.3 \times 10^{-11}$ M or lower; and the $K_D$ of clone 308-4 may be $2.64 \times 10^{-11}$ M or lower, preferably $2.52 \times 10^{-11}$ M or lower, more preferably $2.4 \times 10^{11}$ M or lower.

As used herein, the term "clone 1001", "clone 1015", "clone 1021", "clone 1023", "clone 1024", "clone 1104", "clone 1123", "clone 1202", "clone 1208", "clone 1214", "clone 1216", "clone 1223", "clone 1224", "clone 1232", "clone 1234", "clone 1238", "clone 1243", "clone 1248", "clone 3007", "clone 3016", "clone 3024", "clone 3115", "clone 3120", "clone 3131", "clone 3203", "clone 3241", "clone 4011", "clone 4017", "clone 4034", "clone 4041", "clone 4141", "clone 4146", "clone 4206", "clone 4208", "clone 4278", "clone 4287", "clone 1", "clone 2", "clone 3", "clone 4", "clone 5", "clone 6", "clone 7", "clone 8", "clone 9", "clone 10", "clone 11", "clone 12", "clone 13", "clone 14", "clone 15", "clone 16", "clone 17", "clone 18", "clone 19", "clone 20", "clone 21", "clone 22", "clone 23", "clone A24", "clone A25", "clone A52", "clone A63", "clone A67", "clone A71" or "clone A74" that binds specifically to TFPI means an antibody that binds to TFPI, resulting in inhibition of the biological activity of TFPI. The term can be used interchangeably with the term "anti-TFPI antibody".

In addition, as used herein, the term "clone T417", "clone T308", "clone 308", "clone 308-2" or "clone 308-4" that binds specifically to TFPI means an antibody that binds to TFPI, resulting in inhibition of the biological activity of TFPI. The term can be used interchangeably with the term "anti-TFPI antibody". Herein, clone T417 and clone T308 is an antibody are antibodies isolated after immunization of mice with recombinant human TFPI, and clone 308 is an antibody prepared by humanization of clone T417. In addition, clone 308-2 and clone 308-4 are antibodies prepared by mutating the lysine (K) of the heavy chain of clone 308 with glutamine (Q) or glutamate (E) as shown in FIG. 5.

The equilibrium dissociation constant ($K_D$) of the anti-TFPI antibody may be, for example, as follows. The $K_D$ of clone 12 may be $9.009 \times 10^{-12}$ M or lower, preferably $8.59 \times 10^{-12}$ M or lower, more preferably $8.19 \times 10^{-12}$ M or lower; the $K_D$ of clone 1023 may be $3.31 \times 10^{-11}$ M or lower, preferably $3.16 \times 10^{-11}$ M or lower, more preferably $3.01 \times 10^{-11}$ M or lower; the $K_D$ of clone 1202 may be $10.42 \times 10^{-12}$ M or lower, preferably $9.94 \times 10^{-12}$ M or lower, more preferably $9.47 \times 10^{-12}$ M or lower; and the $K_D$ of clone 3241 may be $8.14 \times 10^{-11}$ M or lower, preferably $7.77 \times 10^{-11}$ M or lower, more preferably $7.4 \times 10^{-11}$ M or lower.

In another example of the present invention, the heavy chain variable region and light chain variable region genes that bind to human TFPI were examined, and then the heavy chain variable region gene was linked to the human IgG4 heavy chain constant region, and the light chain variable region gene was linked to the human light-chain constant region. Next, each of these genes was inserted into a protein expression vector for an animal cell to thereby construct vectors. The constructed vectors were transfected into the Expi293 cell line which was then cultured to produce antibodies. The produced antibodies were purified with protein A (Example 1).

In another example of the present invention, the heavy chain variable region and light chain variable region genes that bind to human TFPI were examined, and then the heavy chain variable region gene was linked to the human IgG4 heavy chain constant region, and the light chain variable region gene was linked to the human light-chain constant region. Next, each of these genes was inserted into a protein expression vector for an animal cell to thereby construct vectors. The constructed vectors were transfected into the Expi293 cell line which was then cultured to produce antibodies. The produced antibodies were purified with protein A (Examples 11 and 12).

Thus, in another aspect, the present invention is directed to a nucleic acid encoding the antibody. The nucleic acids that are used in the present invention may be present in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. The nucleic acid in the present invention may be, for example, DNA or RNA, and may comprise or may not comprise an intron sequence.

In still another aspect, the present invention is directed to a vector comprising the nucleic acid. For expression of an antibody or an antibody fragment thereof, a DNA encoding a partial or full-length light chain and heavy chain can be obtained by standard molecular biology techniques (e.g., PCR amplification or cDNA cloning using a hybridoma that expresses the antibody of interest), and the DNA can be inserted into an expression vector such that it is operatively linked to transcriptional and translational control sequences.

As used herein, the term "operatively linked" is intended to mean that an antibody gene is ligated into a vector such that transcriptional and translational control sequences serve their intended function of regulating the transcription and translation of the antibody gene. The expression vector and expression control sequences are chosen to be compatible with the expression host cell used. An antibody heavy chain gene and an antibody light chain gene can be inserted into separate vectors, or both genes are inserted into the same expression vector. The antibody genes are inserted into the expression vector by standard methods (e.g., ligation of complementary restriction sites on the antibody gene fragment and vector, or blunt end ligation if no restriction sites are present). In some cases, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein). In addition, the recombinant expression vectors carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. It will be appreciated by those skilled in the art that the design of the expression vector, including the selection of regulatory sequences, may depend on such factors as the choice of the host cell to be transformed, the level of expression of protein desired, etc.

In yet another aspect, the present invention is directed to a host cell comprising the nucleic acid or the vector. The nucleic acid or the vector is transfected into a host cell. Transfection can be performed using various techniques that are generally used to introduce foreign nucleic acid (DNA or RNA) into procaryotic or eukaryotic cells, for example, electrophoresis, calcium phosphate precipitation, DEAE-dextran transfection or lipofection. The antibody according to the present invention can be expressed in eukaryotic cells, preferably mammalian host cells, in view of its applicability to mammalian cells. Examples of mammalian host cells suitable for expression of the antibody include Chinese hamster ovary (CHO) cells (including dhfr-CHO cells that are used together with, for example, a DHFR selectable marker), NSO myeloma cells, COS cells, and SP2 cells.

In yet another aspect, the present invention is directed to a method for producing an antibody, which comprises culturing a host cell to express the antibody. When a recombinant expression vector encoding the antibody gene is introduced into mammalian host cells, the antibody gene can be produced by culturing the host cells for a period of time such that the antibody is expressed in the host cells, preferably a period of time such that the antibody is secreted into the medium during culture of the host cells.

In some cases, the expressed antibody can be isolated and purified from the host cells. Isolation or purification of the antibody can be performed by conventional isolation/purification methods (e.g., chromatography) that are used for proteins. Examples of the chromatography include affinity chromatography including a protein A column and a protein G column, ion exchange chromatography, and hydrophobic chromatography. In addition to the chromatography, a combination of filtration, ultrafiltration, salting out, dialysis and the like may be used to isolate and purify the antibody.

Figure 9:
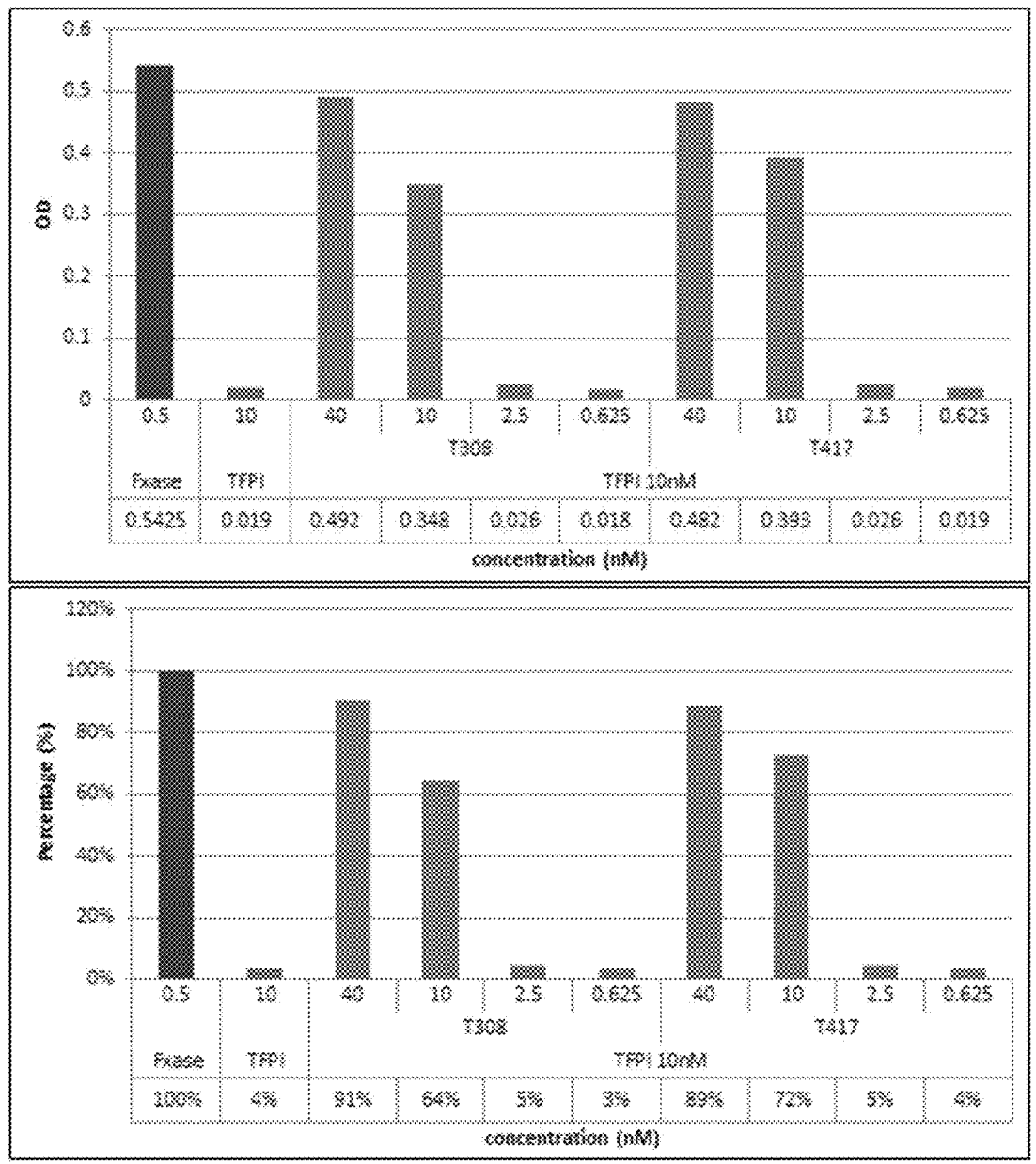
FIG. 9 graphically shows the results of evaluating the effects of chimeric antibodies among anti-TFPI antibodies by an FXa activity assay.

In still another example of the present invention, an FXa activity assay was performed to evaluate the effects of anti-TFPI antibodies (Example 7). As a result, as shown in FIG. 9, it was found that absorbance increased in a concentration-dependent manner in both clone T308 and clone T417 which are chimeric antibodies among anti-TFPI antibody candidates, indicating that the TFPI inhibitory effects of the two antibodies increase in an antibody concentration-dependent manner. When the effects were compared at a TFPI concentration of 10 nM, it could be seen that the TFPI inhibitory activity of clone T417 is better than that of clone T308.

Figure 10:
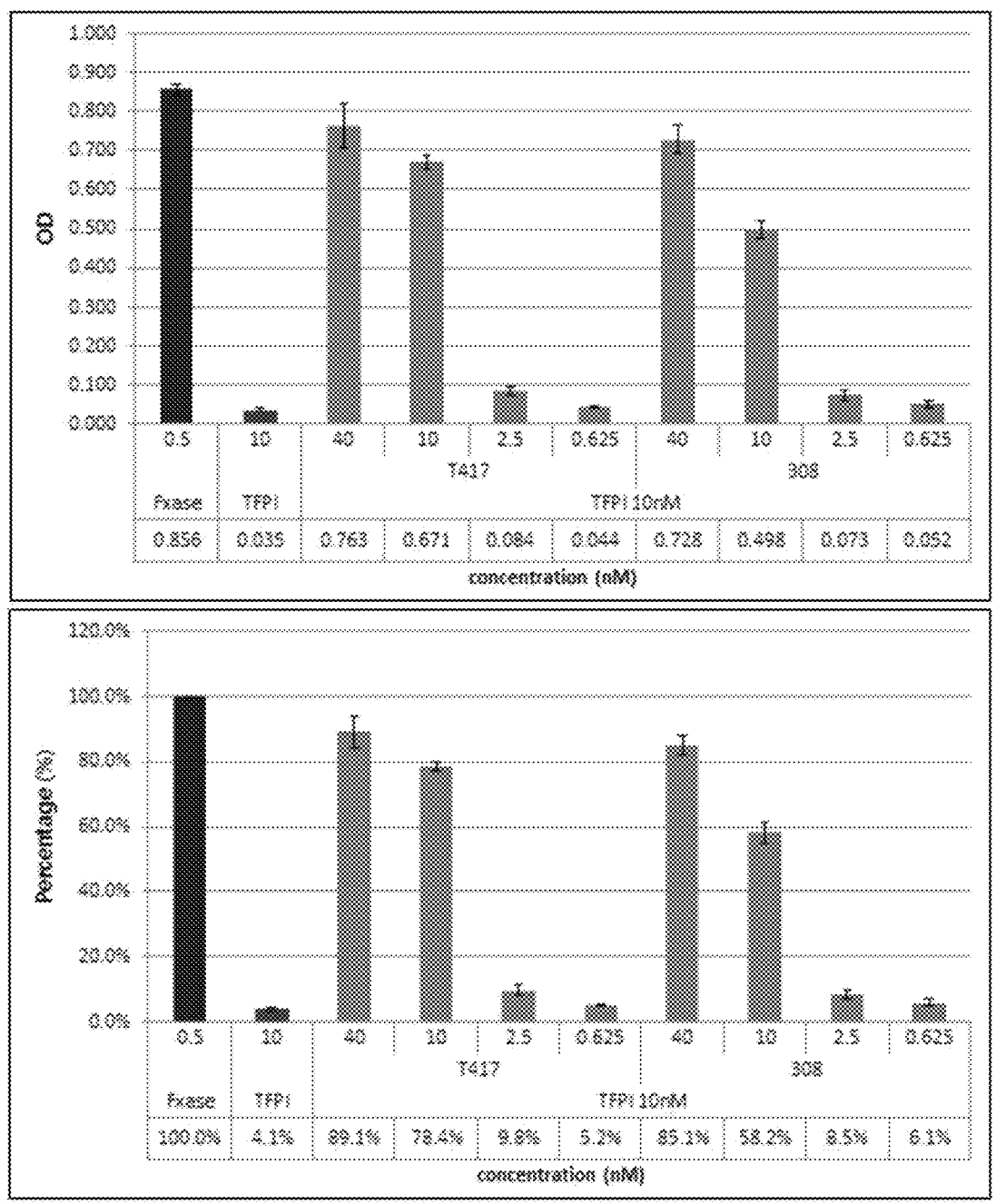
FIG. 10 graphically shows the results of evaluating the effects of humanized antibodies among anti-TFPI antibodies by an FXa activity assay.

In addition, as shown in FIG. 10, clone 308 was obtained by a humanization process using clone T417 determined to have a better effect in the above-described assay. Clone 308 also showed a concentration-dependent increase in absorbance, indicating that it could inhibit TFPI.

Figure 11:
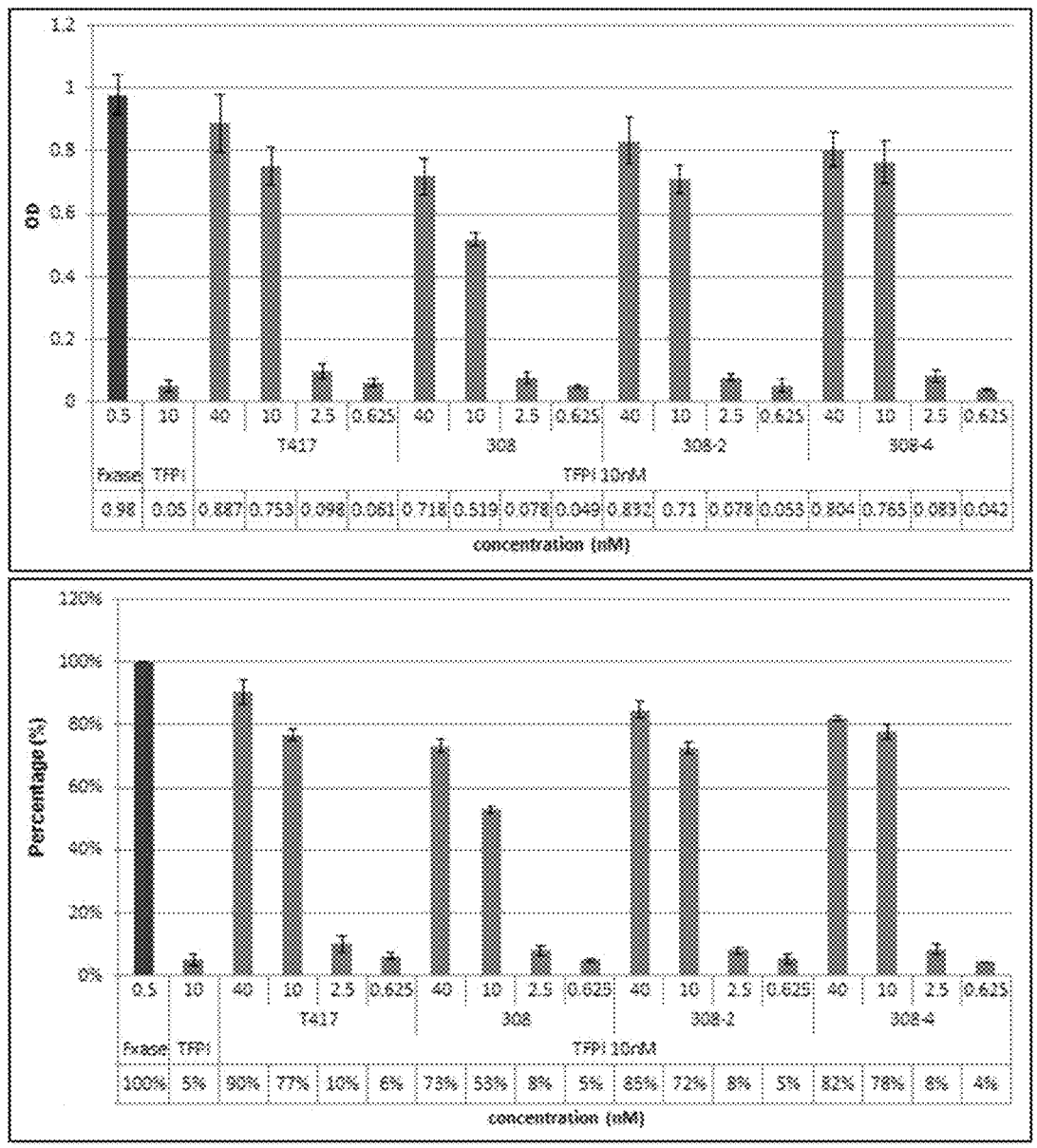
FIG. 11 graphically shows the results of evaluating the effects of back-mutated antibodies among anti-TFPI antibodies by an FXa activity assay.

Furthermore, as shown in FIG. 11, back mutation was performed in order to increase the effect of clone 308, and clone 308-2 and clone 308-4 were obtained. It could be seen that both clone 308-2 and clone 308-4 inhibited TFPI in a concentration-dependent manner. Also, when samples treated with 40 nM and 10 nM were compared, it could be seen that the TFPI inhibitory activities of clone 308-2 and clone 308-4 increased compared to that of clone 308. At a concentration of 40 nM, clone 308-2 and clone 308-4 showed TFPI inhibitory activities of 85% and 82%, respectively, compared to a positive control (mAb2021 or anti-TFPI Ab), but at a concentration of 10 nM, clone 308-2 showed a TFPI inhibitory activity of 72%, and clone 308-4 showed a TFPI inhibitory activity of 78%, which was better than that of clone 308-2. In addition, it was found that the clone antibodies showed TFPI inhibitory activities equal to that of clone T417 chimeric antibody showing a TFPI inhibitory activity of 77%.

In still another example of the present invention, a TF/FVIIa/FXa complex assay was performed to evaluate the effects of anti-TFPI antibodies (Example 8). Specifically, in a state in which TFPI was present together with or independently of anti-TFPI antibodies, the extents of production and inhibition of FXa by a TF/FVIIa complex were evaluated based on FXa activity.

Figure 12:
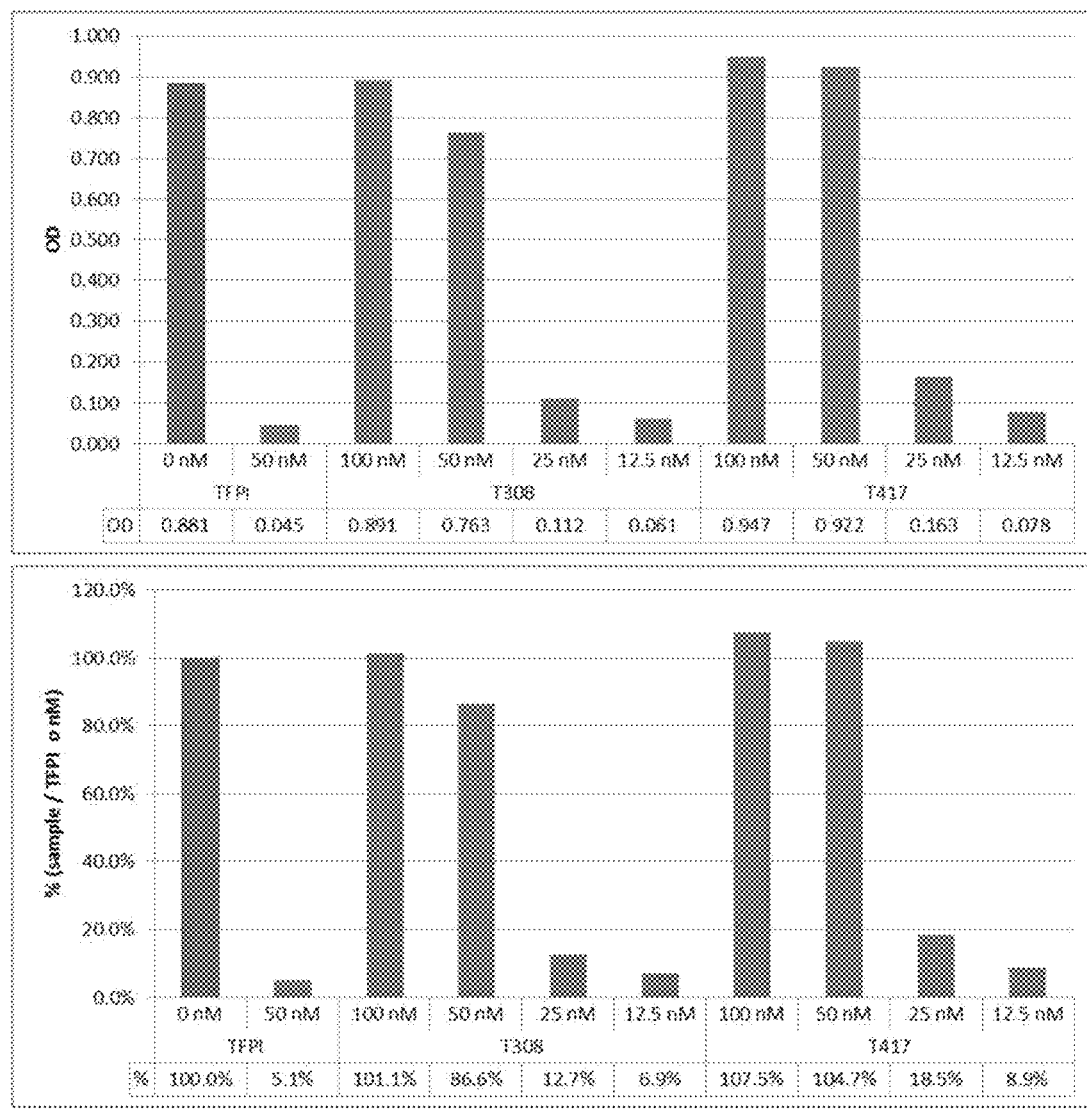
FIG. 12 graphically shows the results of evaluating the effects of chimeric antibodies among anti-TFPI antibodies by a TF/FVIIa/FXa complex assay.

As a result, as shown in FIG. 12, clone T308 and clone T417 antibodies that are chimeric antibodies among anti-TFPI antibody candidates showed a concentration-dependent increase in absorbance, indicating that the TFPI inhibitory effects of the two antibodies increase in a concentration-dependent manner. Particularly, it could be seen that the TFPI inhibitory activity of clone T417 was better than that of clone T308.

Figure 13:
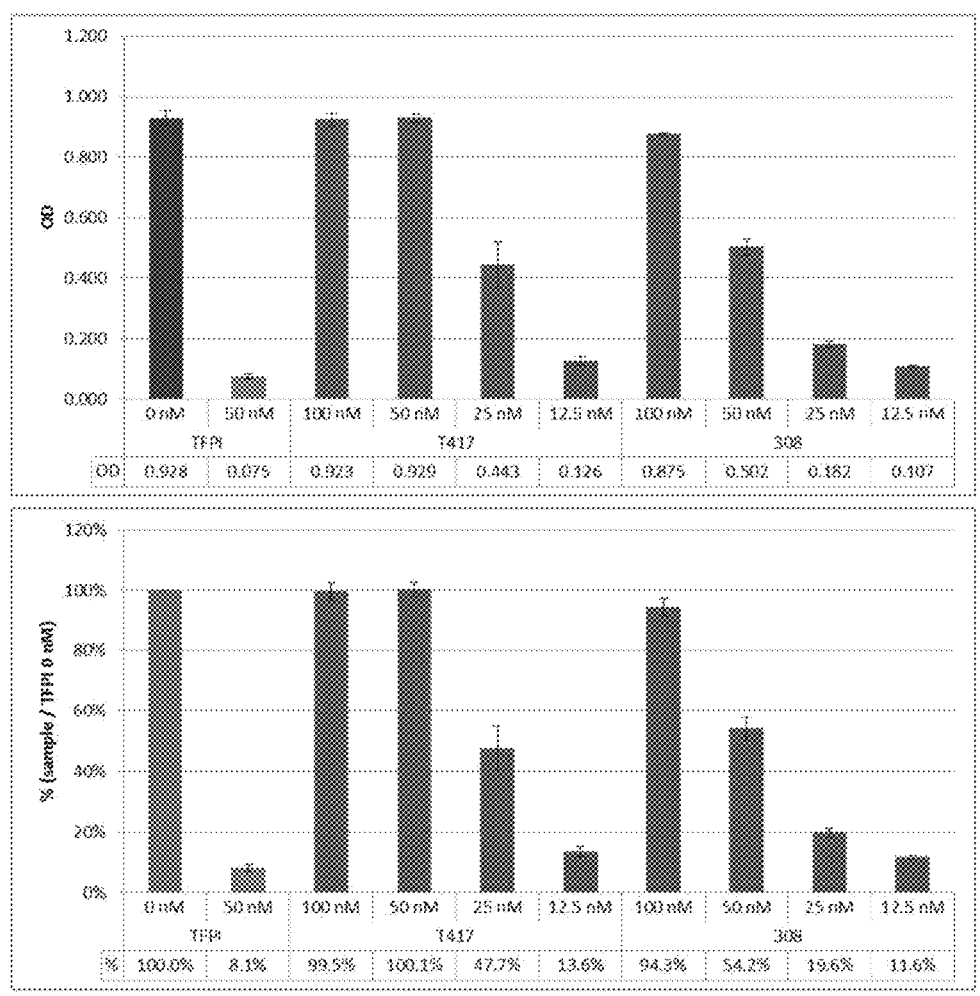
FIG. 13 graphically shows the results of evaluating the effects of humanized antibodies among anti-TFPI antibodies by a TF/FVIIa/FXa complex assay.

In addition, as shown in FIG. 13, clone 308 was obtained by a humanization process using clone T417 antibody having a better effect than clone T308. It could be seen that clone 308 also showed a concentration-dependent increase in absorbance, indicating that it inhibits TFPI.

Figure 14:
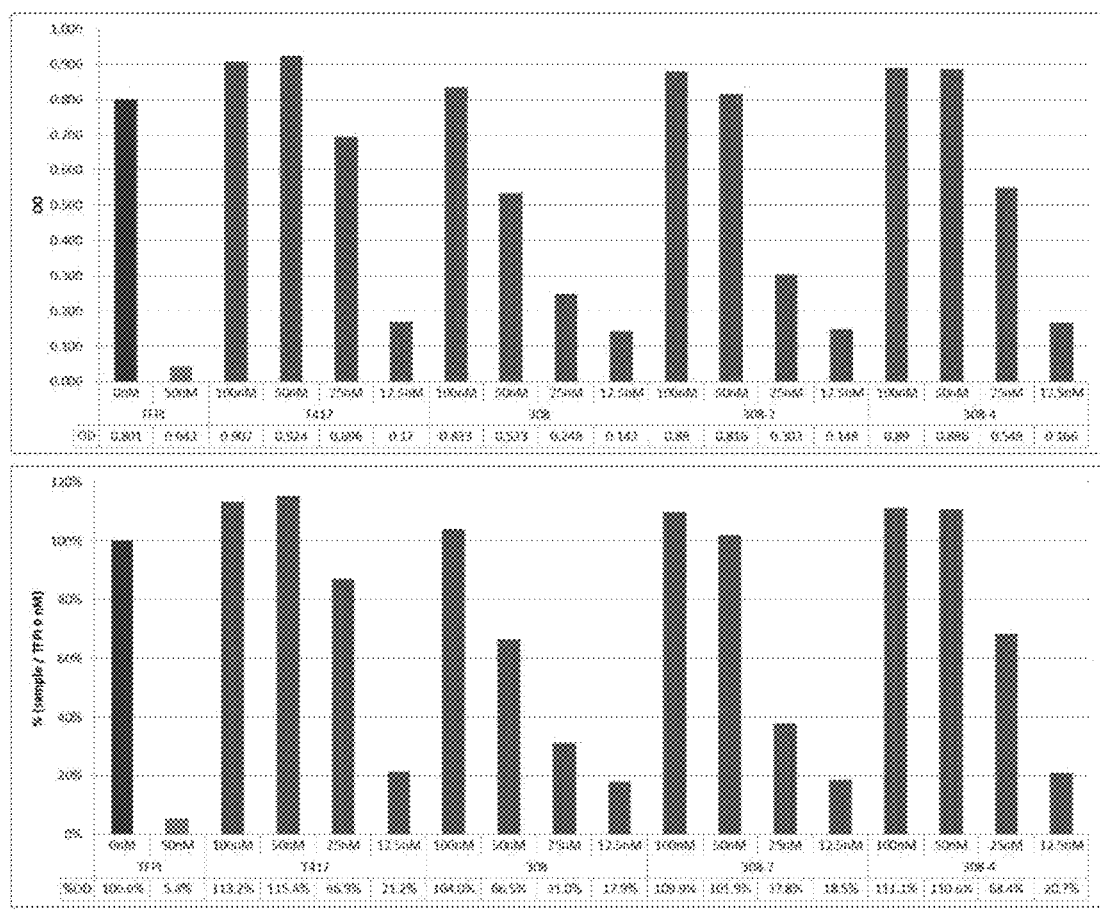
FIG. 14 graphically shows the results of evaluating the effects of back-mutated antibodies among anti-TFPI antibodies by a TF/FVIIa/FXa complex assay.

Furthermore, as shown in FIG. 14, back mutation was performed in order to increase the effect of clone 308 humanized antibody. As a result, the TFPI inhibitory activity of clone 308-2 or clone 308-4 increased compared to that of clone 308. At a concentration of 25 nM, clone 308-2 showed a TFPI inhibitory activity of 37.8%, and clone 308-4 showed a TFPI inhibitory activity of 68.4%, which was higher than that of clone 308-2.

Figure 15:
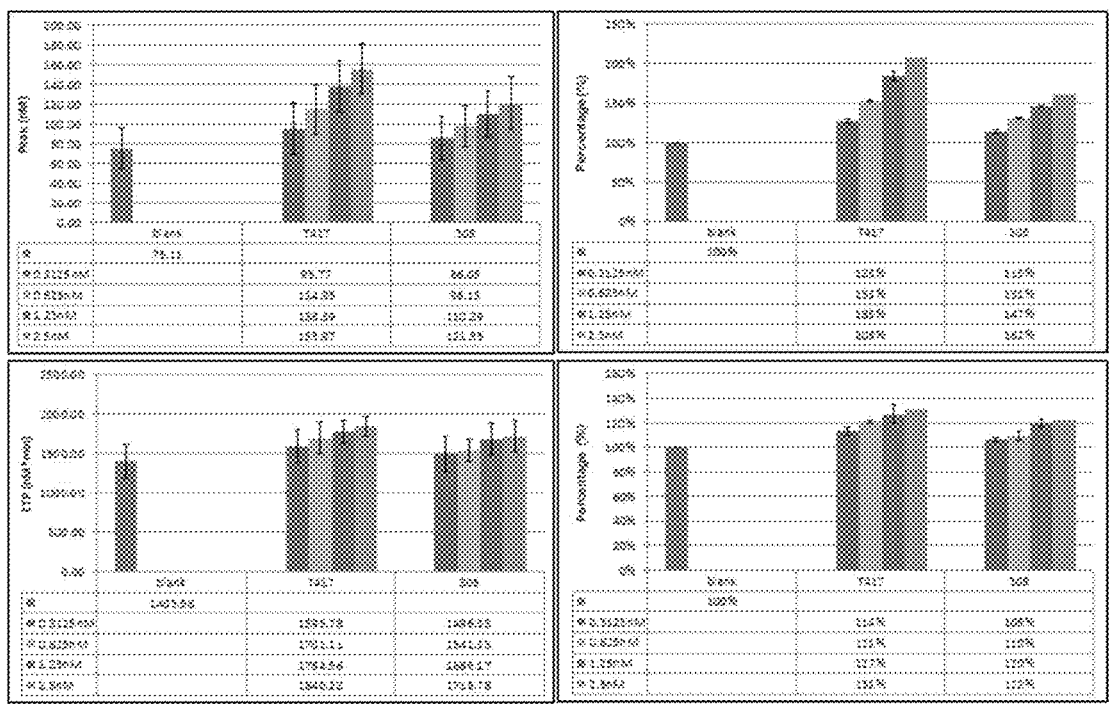
FIG. 15 graphically shows the results of evaluating the effects of chimeric and humanized antibodies among anti-TFPI antibodies by a thrombin generation assay.

In still another example of the present invention, a thrombin generation assay for clone 308-2 and clone 308-4, selected through the FXa activity assay and the TF/FVIIa/FXa complex assay, was performed (Example 9). As a result, as shown in FIG. 15, both clone T417 and clone 308 showed increases in the thrombin generation peak and the thrombin generation compared to a negative control group (having no antibody). In samples treated with 2.5 nM, clone T417 and clone 308 showed thrombin peak values of 208% and 162%, respectively, compared to a negative control group (having no antibody), and the ETP values indicating thrombin generation were 131% in clone T417 and 122% in clone 308. Thus, it was found that clone T417 has a better effect than clone 308 antibody.

Figure 16:
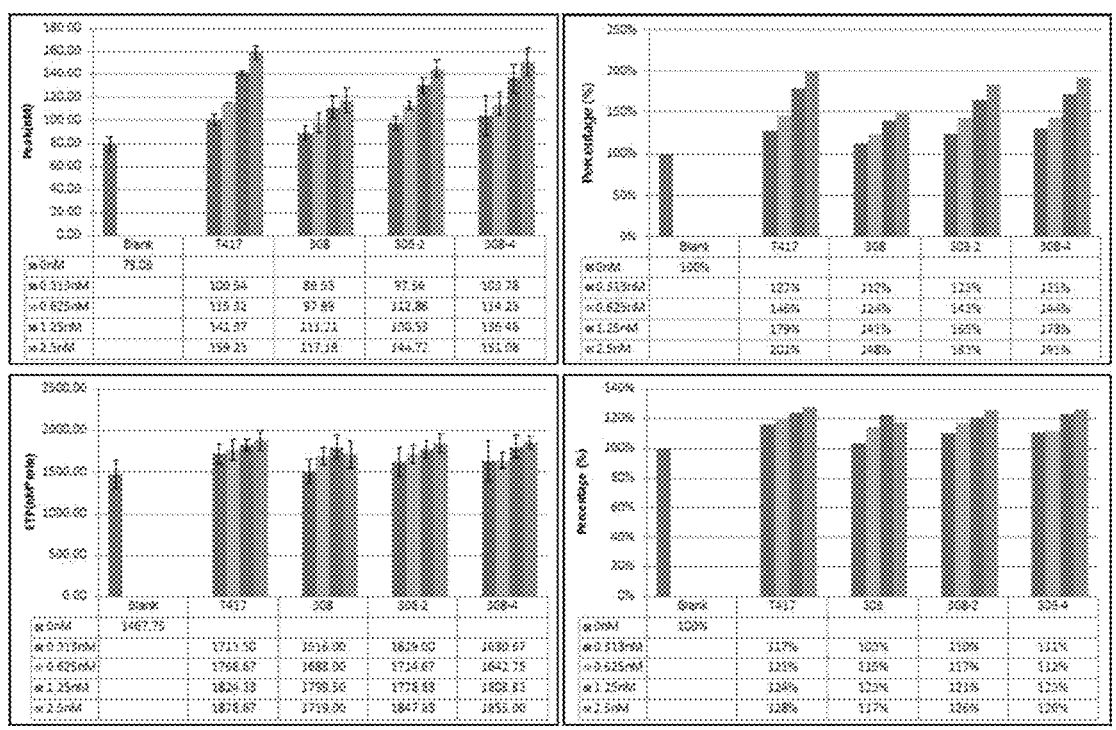
FIG. 16 graphically shows the results of evaluating the effects of back-mutated antibodies among anti-TFPI antibodies by a thrombin generation assay.

Moreover, as shown in FIG. 16, clone 308-2 and clone 308-4 showed increases in the thrombin generation peak and the total thrombin generation compared to clone 308 antibody. In particular, in samples treated with 2.5 nM, both clone 308-2 and clone 308-4 showed increases in thrombin peak value of 183% and 191%, respectively, compared to a negative control group (having no antibody), and the ETP value was 126% in both clone 308-2 and clone 308-4, indicating that the clone antibodies have an increased ability to produce thrombin.

In another example of the present invention, an FXa activity assay was performed to evaluate the effects of anti-TFPI antibodies (Example 14). As a result, as shown in FIGS. 20 to 28, the effects of affinity-matured antibodies among anti-TFPI antibody candidates were demonstrated. It was found that the antibodies showed increases in the absorbance in an antibody concentration-dependent manner, indicating that the TFPI inhibitory effect of the antibodies increases in an antibody concentration-dependent manner.

In another example of the present invention, a TF/FVIIa/FXa complex assay was performed to evaluate the effects of anti-TFPI antibodies (Example 15). Specifically, the extents of production and inhibition of FXa by a TF/FVIIa complex were evaluated based on FXa activity in a state in which TFPI were present together with or independently of anti-TFPI antibodies. As a result, as shown in FIGS. 29 to 33 and tables 27 to 36, the effects of affinity-matured antibodies among anti-TFPI antibody MG1113 candidates were demonstrated. It was found that the antibodies showed increases in the absorbance in an antibody concentration-dependent manner, indicating that the TFPI inhibitory effect of the candidate antibodies increases in an antibody concentration-dependent manner.

Figure 34:
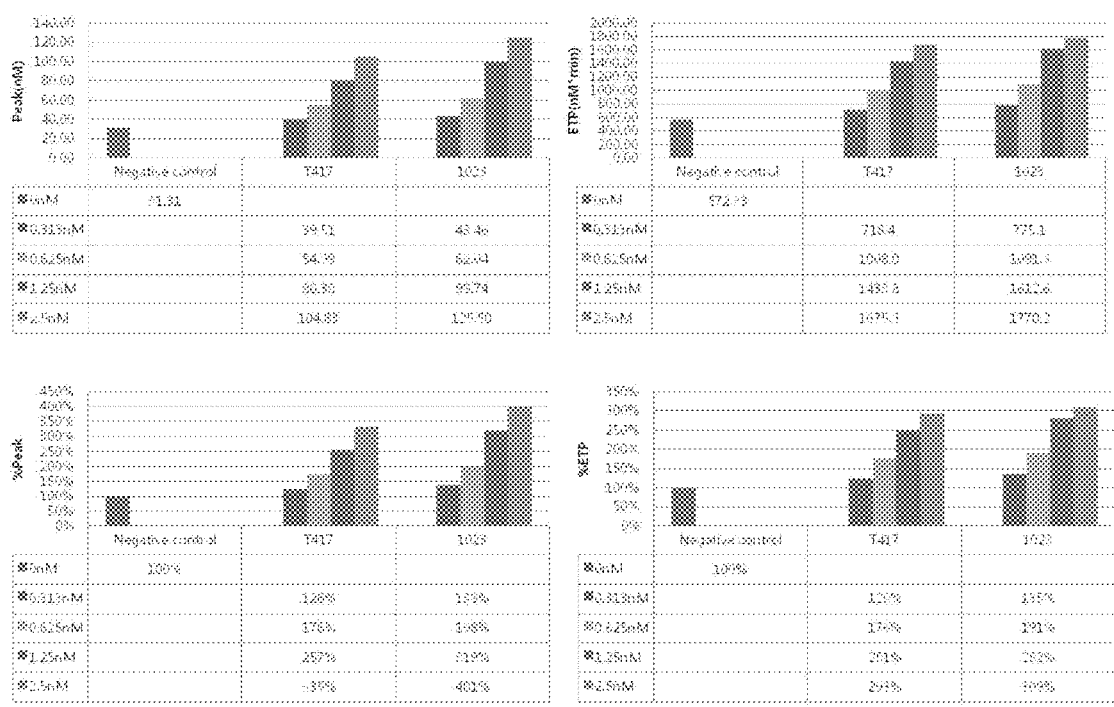
FIG. 34 shows the results of evaluating the effects of affinity-matured anti-TFPI antibodies by a thrombin generation assay.

In still another example of the present invention, a thrombin generation assay for anti-TFPI antibodies selected through the FXa activity assay was performed (Example 16). As a result, as shown in FIG. 34, for No. 1023 antibody among affinity-matured antibody candidates selected through the Fxa activity assay and the TF/FVIIa/FXa complex assay, a thrombin generation comparison assay was performed using T417 chimeric antibody. At 2.5 nM, T417 antibody showed an increase in thrombin peak of about 335% compared to a blank treated with only a sample dilution, and No. 1023 antibody showed an increase in thrombin peak of about 401% compared with the blank. In addition, in the case of ETP indicating the total generation of thrombin, T417 antibody showed an increase in ETP of about 293% compared to a negative control group (having no antibody) at a concentration of 2.5 nM, and No. 1023 antibody showed an increase in ETP of about 309% compared to the negative control group. The comparison between the two antibodies indicated that No. 1023 antibody obtained from affinity maturation has a better effect than the T417 antibody.

In a further aspect, the present invention is directed to a pharmaceutical composition for treating hemophilia, which comprises an anti-TFPI antibody as an active ingredient.

The present invention also provides a pharmaceutical composition comprising a therapeutically effective amount of an anti-TFPI antibody and a pharmaceutically acceptable carrier. The term "pharmaceutically acceptable carrier" refers to a substance which can be added to the active ingredient to help formulate or stabilize the preparation and causes no significant adverse toxicological effects to the patient.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the composition of the present invention may be formulated as injectable forms such as aqueous solutions, suspensions or emulsions with the aid of diluents, dispersants, surfactants, binders and lubricants. In addition, the composition according to the present invention may be formulated in the form of pills, capsules, granules, or tablets. Other carriers are described in a literature [Remington's Pharmaceutical Sciences (E. W. Martin)]. This composition may contain a therapeutically effective amount of at least one anti-TFPI antibody.

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. The composition is preferably formulated for parenteral injection. The composition can be formulated as a solid, a solution, a microemulsion, a liposome, or other ordered structures suitable to high drug concentration. The carrier may be a solvent or dispersion medium containing, for example, water, ethanol, polyol (e.g., glycerol, propylene glycol and liquid polyethylene glycol), and suitable mixtures thereof. In some cases, the composition may contain an isotonic agent, for example, sugar, polyalcohol, sorbitol or sodium chloride. Sterile injectable solutions can be prepared by the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Anti-TFPI antibodies can be used for therapeutic purposes for treating genetic and acquired deficiencies or defects in coagulation. For example, the antibodies can be used to block the interaction between TFPI and FXa, or to prevent the TFPI-dependent inhibition of TF/FVIIa activity. Additionally, the human monoclonal antibody may also be used to restore the TF/FVIIa-driven generation of FXa to bypass the insufficiency of FVIII- or FIX-dependent amplification of FXa.

The antibodies have therapeutic use in the treatment of disorders of hemostasis such as thrombocytopenia, platelet disorders and bleeding disorders (e.g., hemophilia A and hemophilia B). Such disorders may be treated by administering a therapeutically effective amount of the anti-TFPI antibody to a patient in need thereof. The antibodies also have therapeutic use in the treatment of uncontrolled bleeds in indications such as trauma and hemorrhagic stroke. Thus, the present invention also provides a method for shortening the bleeding time comprising administering a therapeutically effective amount of the anti-TFPI antibody to a patient in need thereof.

The antibody can be used as monotherapy or in combination with other therapies to address a hemostatic disorder. For example, co-administration of one or more antibodies of the present invention with a clotting factor such as TF (tissue factor), FVII (factor VII) or FX (factor X) is believed useful for treating hemophilia. By co-administration or combination therapy of the antibody with a clotting factor is meant administration of the two therapeutic drugs each formulated separately or formulated together in one composition, and, when formulated separately, administered either at approximately the same time or at different times, but over the same therapeutic period.

The pharmaceutical compositions may be parenterally administered to subjects suffering from hemophilia A or B at a dosage and frequency that may vary with the severity of the bleeding episode or, in the case of prophylactic therapy, may vary with the severity of the patient's clotting deficiency. The compositions may be administered to patients in need as a bolus or by continuous infusion. For example, a bolus administration of the inventive antibody present as a Fab fragment may be in an amount of from 0.0025 to 100 mg/kg body weight, 0.025 to 0.25 mg/kg, 0.010 to 0.10 mg/kg or 0.10-0.50 mg/kg. For continuous infusion, the inventive antibody present as an Fab fragment may be administered at 0.001 to 100 mg/kg body weight/minute, 0.0125 to 1.25 mg/kg/min, 0.010 to 0.75 mg/kg/min, 0.010 to 1.0 mg/kg/min or 0.10-0.50 mg/kg/min for a period of 1-24 hours, 1-12 hours, 2-12 hours, 6-12 hours, 2-8 hours, or 1-2 hours. For administration of the inventive antibody present as a full-length antibody (with full constant regions), dosage amounts may be about 1-10 mg/kg body weight, 2-8 mg/kg, or 5-6 mg/kg. Such full-length antibodies would typically be administered by infusion extending for a period of 30 minutes to 35 minutes. The frequency of the administration would depend upon the severity of the condition. Frequency could range from three times per week to once every one week or two weeks.

Additionally, the compositions may be administered to patients via subcutaneous injection. For example, a dose of 10 to 100 mg anti-TFPI antibody can be administered to patients via subcutaneous injection weekly, biweekly or monthly.

As used herein, "therapeutically effective amount" means an amount of an anti-TFPI antibody variant or of a combination of such antibody and TF (tissue factor), FVII (factor VII) or FX (factor X) that is needed to effectively increase the clotting time in vivo or otherwise cause a measurable benefit in vivo to a patient in need. The precise amount will depend upon numerous factors, including, but not limited to the components and physical characteristics of the therapeutic composition, intended patient population, individual patient considerations, and the like, and can readily be determined by one skilled in the art. When these factors are completely considered, it is important to administer the minimum amount sufficient for achieving the highest effect without causing side effects, and this dose can be easily determined by those skilled in the art.

The dose of the pharmaceutical composition of the present invention may vary depending on various factors, including a patient's health condition and weight, severity of a disease, the type of drug, and the route and period of administration. The composition may be administered in a single dose or in multiple doses per day into mammals including rats, mice, domestic animals, humans, etc. via any typically accepted route, for example, orally, rectally, intravenously, subcutaneously, intrauterinely, or intracerebrovascularly.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Preparation of Anti-TFPI Antibody

As an antibody against TFPI (tissue factor pathway inhibitor) that inhibits the factor X activity, an antibody for treating or preventing hemophilia, which can prevent the inhibition of blood coagulation, was prepared.

1-1: Selection of Antibody

Mice were immunized with recombinant human TFPI, and the spleens were extracted from the mice. B lymphocytes were extracted from the spleens, total RNA was isolated therefrom, and then synthesized into cDNA. From the synthesized cDNA, various mouse antibody genes were cloned by PCR (polymerase chain reaction), and inserted into pComb3X phagemids, thereby constructing an antibody library displaying antibody fragments having various sequences. In order to select a human TFPI-specific antibody from the antibody library, TFPI-immobilized magnetic beads and the antibody library were mixed with each other, and clones binding to the target antigen were separated and cultured. Then, clones (T417 or T308 clone cells) binding specifically to the target antigen (human TFPI) were individually selected by ELISA (enzyme linked immunosorbent assay), and the amino acid sequences of the antibody genes were identified by sequencing.

As a result, as shown in Table 1 below, clone T417 and clone T308, which bind specifically to human TFPI, could be selected, and the amino acid sequences thereof were identified.

Table 2 below the CDR amino acid sequences of the clone antibodies of Table 1, identified based on the Kabat numbering system.

TABLE 1

| Clones | Variable Regions | AA Sequences | SEQ ID NOS: |
|---|---|---|---|
| T417 | VH | EVHLVESGGDLVKPGGSLKLSCAASGFTF SSYAMSWVRQTPDKRLEWVATITTGGSYT YYPDSVKGRFTISRDNAKNTLYLQMSSLK SEDTAMYYCARQDGNFLMDYWGQGTTVTV SS | 1 |
| | VL | DVVMTQTPLTLSVTIGQPASISCKSSQSL LDSDGKTYLNWLLQRPGQSPKRLIYLVSK LDSGVPDRFTGSGSGTDFTLKISRVEAED LGVYYCWQGTHFPFTFGSGTKLEIKR | 2 |
| T308 | VH | EVKLVESGGGLVKPGGSLKLSCAASGFTF SNYPMSWVRQTPEKRLEWVATISNSGSY TYYPDSVKGRFTISRDNAKNTLYLQMNSL RSEDTAMYYCARQVYGNYEDFDYWGQGT TLTVSS | 3 |

TABLE 1-continued

| Clones | Variable Regions | AA Sequences | SEQ ID NOS: |
|---|---|---|---|
| | VL | DVVMTQTPLTLSVTIGQPASISCKSSQSL LDSDGKTYLNWLLQRPGQSPKRLIYLVS KLDSGVPDRFTGSGSGTDFTLKISRVEA EDLGVYYCWQGTHFPYTFGGGTKLELKR | 4 |

TABLE 2

| Clones | Variable Regions | CDR1 | CDR2 | CDR3 |
|---|---|---|---|---|
| T417 | Heavy Chain | SYAMS (SEQ ID NO: 5) | TITTGGSYTYY PDSVKG (SEQ ID NO: 6) | QDGNFLMDY (SEQ ID NO: 7) |
| | Light Chain | KSSQSLLDSDG KTYLN (SEQ ID NO: 8) | LVSKLDS (SEQ ID NO: 9) | WQGTHFPF (SEQ ID NO: 10) |
| T308 | Heavy Chain | NYPMS (SEQ ID NO: 11) | TISNSGSYTYY PDSVKG (SEQ ID NO: 12) | QVYGNYEDF DY (SEQ ID NO: 13) |
| | Light Chain | KSSQSLLDSDG KTYLN (SEQ ID NO: 14) | LVSKLDS (SEQ ID NO: 15) | WQGTHFPY (SEQ ID NO: 16) |

1-2: Cloning of IgG Genes of T417 and T308 Clone Antibodies

From the T417 and T308 clone cells, pComb3X phagemids containing the genes encoding the heavy-chain variable regions of the T417 and T308 clone antibodies were extracted. Using each of the extracted pComb3X phagemids as a template, PCR was performed using Accupower Pfu PCR premix (Bioneer) together with an NotI-containing forward primer (Table 3; SEQ ID NO: 17) and an ApaI-containing reverse primer (Table 3; SEQ ID NO: 18). The PCR was performed under the following conditions: 10 min at 94° C.; and then 30 cycles, each consisting of 15 sec at 94° C., 30 sec at 56° C. and 90 sec at 72° C.; followed by 10 min at 72° C. The amplified genes were electrophoresed on 1% agarose gel to confirm the DNA bands having the expected sizes, and were isolated using a gel extraction kit. Next, each of the isolated genes was treated with NotI and ApaI restriction enzymes at 37° C. for 12 hours or more. The gene treated with the restriction enzyme was separated on 1% agarose gel. A pcIW plasmid vector containing the IgG4 heavy chain constant region gene was also digested in the same manner and separated on agarose gel. Using T4 DNA ligase (Cat.No.M0203S, New England BioLabs (NEB)), each of the isolated T417 and T308 heavy-chain variable region genes was ligated into the KpnI and ApaI sites of a linear pcIw vector containing the human heavy-chain constant region. The ligation product was transformed into XL1-Blue bacteria (Electroporation-Competent Cells; Cat.No.200228, Stratagene), and the bacterial cells were plated on a carbenicillin-containing LB plate (Cat.No.LN004CA, NaraeBiotech), and then cultured at 37° C. for 12 hours or more. Next, single colonies were selected from the plate and cultured, and a plasmid was separated therefrom using a plasmid mini-kit (Cat.No.27405, QIAGEN) and identified by DNA sequencing.

From the T417 and T308 clone cells, pComb3X phagemids containing the genes encoding the light-chain variable regions of the T417 and T308 clone antibodies were extracted. Using each of the extracted pComb3X phagemids as a template, PCR was performed using Accupower Pfu PCR premix together with an NotI-containing forward primer (Table 3; SEQ ID NO: 19) and a KpnI-containing reverse primer (Table 3; SEQ ID NO: 20). The PCR was performed under the following conditions: 10 min at 94° C.; and then 30 cycles, each consisting of 15 sec at 94° C., 30 sec at 56° C. and 90 sec at 72° C.; followed by 10 min at 72° C. The amplified genes were electrophoresed on 1% agarose gel to confirm the DNA bands having the expected sizes, and were isolated using a gel extraction kit. Next, each of the isolated genes was treated with NotI and KpnI restriction enzymes at 37° C. for 12 hours or more. The gene treated with the restriction enzyme was separated on 1% agarose gel. A pcIW plasmid vector was also digested in the same manner and separated on agarose gel. Using T4 DNA ligase (Cat.No.M0203S, New England BioLabs(NEB)), each of the isolated T417 and T308 light-chain variable region genes was ligated into the NotI and KpnI sites of a linear pcIw vector containing the human light-chain constant region. The ligation product was transformed into XL1-Blue bacteria (Electroporation-Competent Cells; Cat.No.200228, Stratagene), and the bacterial cells were plated on a carbenicillin-containing LB plate (Cat.No.LN004CA, NaraeBiotech), and then cultured at 37° C. for 12 hours or more. Next, single colonies were selected from the plate and cultured, and a plasmid was separated therefrom using a plasmid mini-kit (Cat.No.27405, QIAGEN) and identified by DNA sequencing.

TABLE 3

| Names | DNA Sequences | SEQ ID NOS: |
|---|---|---|
| T417VH-F | GCGGCCGCCATGTATCTGGG TCTGAACTATGTCTTTATCG TGTTTCTGCTGAATGGTGTG CAGTCTGAGGTGCACCTGGT GGAGTCT | 17 |
| T417VH Apa-R | NNNNGGGCCCCTTGGTGCTG GCTGAGGAGACGGTGACCGT GGT | 18 |
| T417 VL-F | GCGGCCGCCATGGATAGCCA GGCTCAGGTGCTGATGCTGC TGCTGCTGTGGGTGTCAGGG ACTTGCGGGGACGTTGTGAT GACCCAGACTCCACT | 19 |
| VL-R | NNNNGGTACCAGATTTCAAC TGCTCATCAGA | 20 |

1-3: Production and Purification of Anti-TFPI T417, T308 Clone Antibody Mutant IgG In order to produce and purify the anti-TFPI clone T417 and T308 clones obtained by mouse immunization, Expi293F™ cells were seeded at a concentration of $2.5 \times 10^6$ cells/mL on one day before transfection. After 24 hours of culture (37° C., 8% $CO_2$, 125 rpm), Expi293™ Expression medium (Cat.No.A1435101, Gibco) was added to prepare 30 mL of the cells at a concentration of $2.5 \times 10^6$ cells/mL (viability ≥95%). 30 μg of DNA (pcIw-anti-TFPI heavy chain: 15 μg, pcIw-anti-TFPI light chain: 15 μg) was diluted in 1.5 mL of OptiPro™SEM medium (Cat.No.12309019, Gibco) to a total volume of 1.5 mL and incubated at room temperature for 5 minutes. 80 μL of ExpiFectamine™293 reagent (Cat.No.A14524, Gibco) was added to 1.5 mL of OptiPro™SEM medium (Cat.No.12309019, Gibco) to a total volume of 1.5 mL, and then incubated at room temperature for 5 minutes. After 5 minutes of incubation, 1.5 mL of the diluted DNA and 1.5 mL of the ExpiFectamine™ 293 reagent were mixed well with each other and incubated at room temperature for 20-30 minutes. Expi293F™ cells were treated with 3 mL of the mixture of the DNA and the ExpiFectamine™ 293 reagent. After 16-18 hours of suspension culture (37° C., 8% $CO_2$, 125 rpm), 150 μL of ExpiFectamine™ 293 Enhancer 1 (Cat.No.A14524, Gibco) and 1.5 mL of ExpiFectamine™ 293 Enhancer 2 (Cat.No.A14524, Gibco) were added to the cells, followed by suspension culture for 5 days. After completion of the culture, the cells were centrifuged at 4000 rpm for 20 minutes to remove cell debris, and the supernatant was passed through a 0.22 μm filter. 100 μL of the protein A resin MabSelect Xtra (Cat.No.17-5269-02, GE Healthcare) was prepared per 30 mL of the culture medium, centrifuged at 1000 rpm for 2 minutes to remove the storage solution, and washed three times with 400 μL of protein A binding buffer (Cat.No.21007, Pierce) for each washing. Protein A resin was added to the prepared culture medium, followed by rotating incubation at room temperature for 30 minutes. The mixture of the culture medium and the resin was added to the Pierce spin column-snap cap (Cat.No.69725, Thermo), and extracted using the QIAvac 24 Plus (Cat.No.19413, QIAGEN) vacuum manifold so that only the resin remained in the column. The resin was washed with 5 mL of protein A binding buffer, and then resuspended in 200 μL of protein A elution buffer (Cat.No.21009, Pierce), after which it was incubated at room temperature for 2 minutes and eluted by centrifugation at 1000 rpm for 1 minute. The eluate was neutralized by addition of 2.5 μL of 1.5M Tris-HCl (pH 9.0). Elution was performed 4-6 times, and each fraction was quantified using Nanodrop 200C (Thermo Scientific). Fractions having the protein detected therein were collected, and the buffer was replaced with PBS (phosphate-buffered saline) buffer using 5 mL of 7K MWCO (Cat.No.0089892, Pierce) in Zeba Spin Desalting Columns. Next, electrophoresis (SDS-PAGE) of the protein was performed under reducing and non-reducing conditions to finally quantify the concentration of the antibody and verify the state of the antibody, and the antibody was stored at 4° C.

Figure 3:
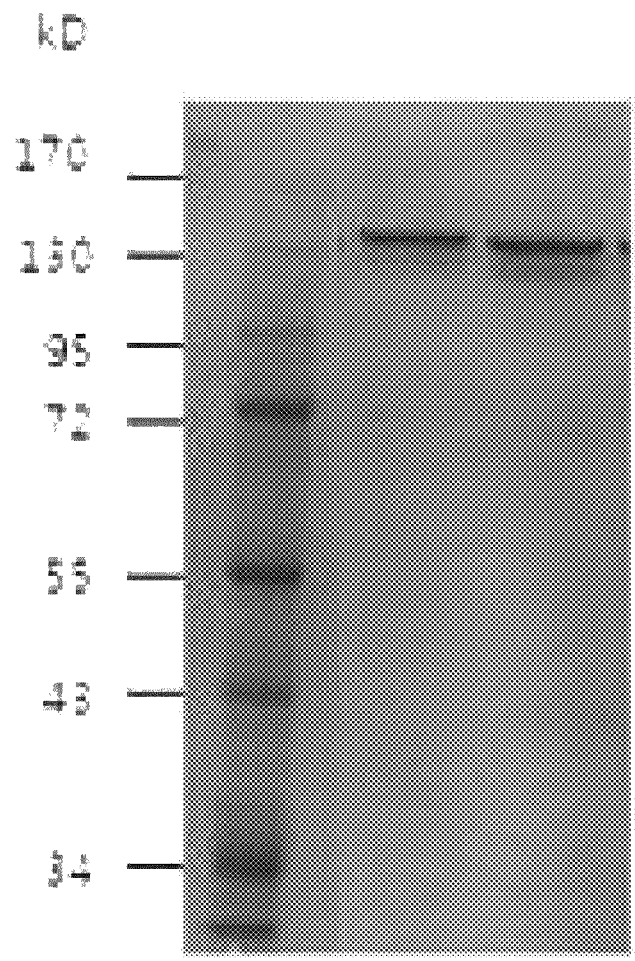
FIG. 3 shows the results of protein electrophoresis (SDS-PAGE) of T417 and T308 clone antibodies among purified anti-TFPI antibodies.

As a result, as shown in FIG. 3, protein electrophoresis (SDS-PAGE) indicated that the T417 and T308 clone antibodies were purified in a good state.

Example 2: Construction of Humanized Antibody by CDR-Grafting to Stable Framework When the quantitative binding affinities of the TFPI antigen (full-length human TFPI protein) (Cat.No.TFPI-875H; Creative Biomart, USA) for the T417 and T308 clone antibodies were evaluated, the clone T417 antibody showed the best effect (see FIG. 8 and Example 6). Thus, humanization of clone T417 was performed in order to clone 308.

In order to humanize the mouse-derived clone T417 antibody, CDR-grafting that is most widely used for humanization was selected. Specifically, the structure of clone T417 was predicted through a sample showing the highest QMEAN, GMQE and homology values among 50 samples obtained from Swiss-Model (http://swissmodel.expasy.org/) that is a structure prediction site, and the CDRs binding to the antigen and a framework other than the CDRs were identified using the Kabat and Chothia numbering scheme. Then, a human framework having the highest homology was searched using IgBLAST (http://www.ncbi.nlm.nih.gov/igblast/). From several combinations of several heavy-chain variable regions and light-chain variable regions obtained by the search, VH3-21/VK2-30 showing the highest formation rate in human germline cell analysis was selected (de Wildt R M et al., *J. Mol. Biol.*, 285:895-901, 1999; mAbs, 5:3, 445-470). Next, clone 308 that is a humanized antibody of clone T417 was constructed, which comprises: the light-chain variable region K24 of clone T417, which is a framework sequence but does not influence the antibody stability, and is also present in the human antibody sequence; and the heavy-chain variable region N35 which is a CDR sequence identified based on the Kabat numbering system, but is a framework sequence in structural terms (*Methods*, 34:184-199, 2004; http://www.vbase2.org/) (see FIG. 4 and Table 4 below).

As a result, as shown in FIG. 4, clone 308 was constructed by humanization of clone T417.

Table 5 below the CDR amino acid sequences of the clone antibody of Table 4, identified based on the Kabat numbering system.

TABLE 4

| Clones | Variable Regions | AA Sequences | SEQ ID NOS: |
|---|---|---|---|
| 308 | VH | EVQLVESGGGLVKPGGSLRLSCAASGFTFSS YAMNWVRQAPGKGLEWVSTITTGGSYTYYA DSVKGRFTISRDNAKNSLYLQMNSLRAEDTA VYYCARQDGNFLMDYWGQGTLVTVSS | 21 |
|  | VL | DVVMTQTPLSLPVTLGQPASISCKSSQSLLD SDGKTYLNWLQQRPGQSPKRLIYLVSKLDSG VPDRFTGSGSGTDFTLKISRVEAEDVGVYYC WQGTHFPFTFGQGTKVEIKR | 22 |

TABLE 5

| clones | Variable Regions | CDR1 | CDR2 | CDR3 |
|---|---|---|---|---|
| 308 | Heavy Chain | SYAMN (SEQ ID NO: 23) | TITTGGSYTYYPDSVKG (SEQ ID NO: 6) | QDGNFLMDY (SEQ ID NO: 7) |
|  | Light Chain | KSSQSLLD SDGKTYLN (SEQ ID NO: 8) | LVSKLDS (SEQ ID NO: 9) | WQGTHFPF (SEQ ID NO: 10) |

Example 3: Design of Clone 308 Antibody Mutant by in Silico Modeling

The binding between clone 308 constructed in Example 2 and TFPI KPI-2 (Kunitz domain 2) was predicted by in silico modeling, and a position that can improve the binding to the antigen was predicted (Heavy chain-52a, -64 and light chain 27d) (see FIG. 5 and Table 6 below).

Figure 17:
FIG. 17 shows the predicted binding between clone 308 among anti-TFPI antibodies and a human TFPI K2 domain. The molecule indicated by red indicates the human TFPI K2 domain, and the molecule indicated by green indicates the clone 308 antibody.

Using homology modeling that is the BioLuminate module (Schrodinger, USA), the structure of the clone 308 antibody that binds to TFPI was produced. To produce the structure, a template search was performed through the PDB database using the sequence of clone 308. As a result, a 3QOS (PDB number) structure having a similar structure and a high composite score was selected. It could be seen that 3QOS and clone 308 are similar in sequences other than the HV CDR H3 region having an antigen-specific structure and are templates suitable for producing the structure. A total of clone 308 models were produced and compared with the structure of 3QOS, and the most similar structure was finally selected. The selected model was similar in structures other than the HV CDR H3 region, and the interaction between clone 308 and the TFPI structure was predicted using the protein-protein binding prediction program PIPER (see FIG. 17 in which the molecule indicated by green indicates the 308 clone antibody and the molecule indicated by red indicates the TFPI antigen). Thus, the predicted paratope of the clone 308 antibody and the predicted epitope of the human TFPI antibody that binds thereto could be identified (Table 8). Based on the predicted binding structure, a mutation was introduced into the amino acid sequence of clone 308 in order to increase the affinity of clone 308. In other words, K64 was replaced with Q and E so as to induce an ionic bond with R17 of TFPI.

Figure 19:
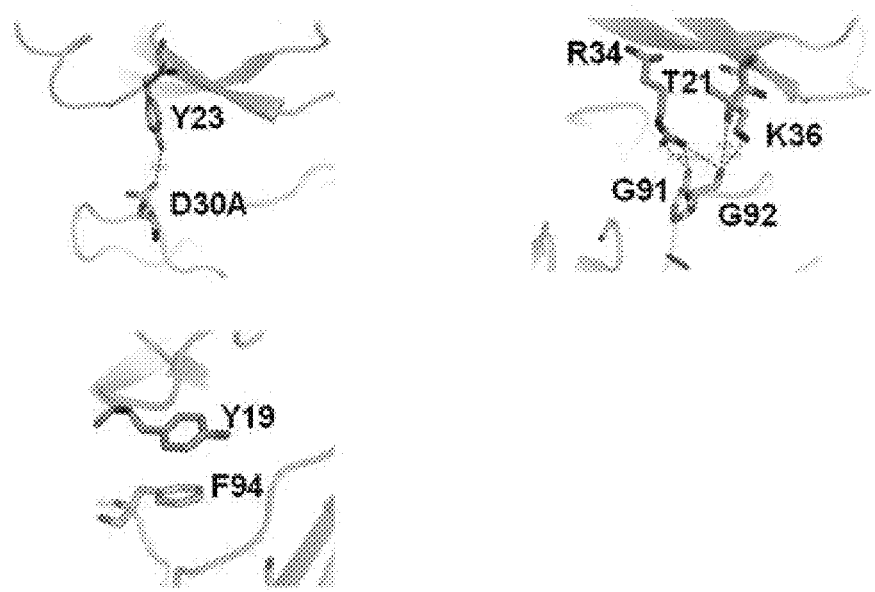
FIG. 19 shows the predicted binding between the light-chain variable region of clone 308 among anti-TFPI antibodies and a human TFPI antigen.

As a result, as shown in Table 6 below, DNA sequencing indicated that a total of two clone 308 mutants were constructed. The predicted binding between the heavy-chain variable region or light-chain variable region of clone 308 and the human TFPI antigen is shown in FIGS. 18 and 19.

Table 7 below shows the CDR amino acid sequences of the clone antibodies of Table 6, identified based on the Kabat numbering system.

Table 8 below shows the predicted paratope of the clone 308 antibody and the predicted epitope of the human TFPI antigen that binds thereto.

TABLE 6

| Clones | Variable Regions | AA Sequences | SEQ ID NOS: |
|---|---|---|---|
| 308-2 | Heavy Chain | EVQLVESGGGLVKPG GSLRLSCAASGFTFS SYAMNWVRQAPGKGL EWVSTITTGGSYTYY ADSVQGRFTISRDNA KNSLYLQMNSLRAED TAVYYCARQDGNFLM DYWGQGTLVTVSS | 24 |
| 308-4 | Heavy Chain | EVQLVESGGGLVKPG GSLRLSCAASGFTFS SYAMNWVRQAPGKGL EWVSTITTGGSYTYY ADSVEGRFTISRDNA KNSLYLQMNSLRAED TAVYYCARQDGNFLM DYWGQGTLVTVSS | 25 |

TABLE 7

| clones | Variable Regions | CDR1 | CDR2 | CDR3 |
|---|---|---|---|---|
| 308-2 | Heavy Chain | SYAMN (SEQ ID NO: 23) | TITTGGSYTYYPDSVQG (SEQ ID NO: 26) | QDGNFLMDY (SEQ ID NO: 7) |
| 308-4 | Heavy Chain | SYAMN (SEQ ID NO: 23) | TITTGGSYTYYPDSVEG (SEQ ID NO: 27) | QDGNFLMDY (SEQ ID NO: 7) |

TABLE 8

| Paratope of Clone 308 | Epitope of hTFPI | Type of binding |
|---|---|---|
| HCDR1 | S31 | Q28 | Hydrogen bond |
| HCDR2 | T52 | E11 | Hydrogen bond |
| HCDR2 | T52a | E10 | Hydrogen bond |
| HCDR2 | Y56 | P13 | Hydrophobic interaction |
| HCDR2 | Y58 | K36 | Hydrogen bond |
| HCDR2 | Y59 | R17 | Hydrogen bond |
| HCDR2 | D61 | R17 | Salt bridge |
| HCDR3 | Q98 | R34 | Hydrogen bond |
| LCDR1 | D30a | Y23 | Hydrogen bond |
| LCDR3 | G91 | R34 | Hydrogen bond |
| LCDR3 | T92 | T21 | Hydrogen bond |
| LCDR3 | T92 | R34 | Hydrogen bond |
| LCDR3 | T92 | K35 | Hydrogen bond |
| LCDR3 | F94 | Y19 | Hydrophobic interaction |

Example 4: Preparation of Clone 308 Antibody Mutant

4-1: Cloning of IgG Gene of Clone 308 Antibody Mutant

Using each of the synthesized 308-2 and 308-4 genes (Bioneer, Korea) as a template, the heavy-chain variable region was subjected to PCR using PrimeSTAR HS DNA polymerase (Cat.No.R010B; Takara) together with a KpnI-containing forward primer (Table 9; SEQ ID NO: 28) and an ApaI-containing reverse primer (Table 9; SEQ ID NO: 29). The PCR was performed under the following conditions: 2 min at 98° C.; and then 30 cycles, each consisting of 10 sec at 98° C., 10 sec at 58° C. and 30 sec at 72° C.; followed by 5 min at 72° C. The amplified gene was electrophoresed on 1% agarose gel to confirm the DNA band having the expected size, and was isolated using a gel extraction kit (Cat.No.287041, QIAGEN). The isolated gene was treated with KpnI and ApaI enzyme at 37° C. for 4 hours, and then separated on 1% agarose gel. A pcIW plasmid vector was also digested in the same manner and separated on agarose gel. Using T4 DNA ligase (Cat.No.M0203S, NEB), the isolated gene was ligated into the KpnI and ApaI of a linear pcIW vector. The ligation product was transformed into XL1-Blue bacteria (Electroporation-Competent Cells; Cat.No.200228, Stratagene), and the bacterial cells were plated on a carbenicillin-containing LB plate (Cat.No.LN004CA, NaraeBiotech) and cultured at 37° C. for 12 hours or more, and single colonies were selected from the plate and cultured. Next, a plasmid was isolated from the cells using a plasmid mini-kit (Cat.No.27405, QIAGEN) and identified by DNA sequencing.

TABLE 9

| Names | DNA Sequences | SEQ ID NOS: |
|---|---|---|
| VH Fo | TGCTGTGGGTGAGTGGTACC TGTGGGGAAGTGCAGCTCGT GGAGAGCGGT | 28 |
| VH Re | AGTGGGAACACGGAGGGCCC CTTGGTGCTGGCGGATGAGA CAGTCACAAGTGTCCC | 29 |

4-2: Production and Purification of Clone 308 Antibody Mutant IgG

In order to produce and purify 308-2 and 308-4 clones that are clone 308-2 and 308-4 antibody mutants, Expi293F™ cells were seeded at a concentration of 2.5×10⁶ cells/mL on one day before transfection. After 24 hours of culture (37° C., 8% $CO_2$, 125 rpm), Expi293™ Expression medium (Cat.No.A1435101, Gibco) was added to prepare 30 mL of the cells at a concentration of 2.5×10⁶ cells/mL (viability ≥95%). 30 μg of DNA (pcIw-anti-TFPI heavy chain: 15 μg, pcIw-anti-TFPI light chain: 15 μg) was diluted in OptiPro™SEM medium (Cat.No.12309019, Gibco) to a total volume of 1.5 mL and incubated at room temperature for 5 minutes. 80 μL of ExpiFectamine™293 reagent (Cat.No.A14524, Gibco) was added to 1.5 mL of OptiPro™SEM medium (Cat.No.12309019, Gibco) to a total volume of 1.5 mL, and then incubated at room temperature for 5 minutes. After 5 minutes of incubation, 1.5 mL of the diluted DNA and 1.5 mL of the ExpiFectamine™ 293 reagent were mixed well with each other and incubated at room temperature for 20-30 minutes. Expi293F™ cells were treated with 3 mL of the mixture of the DNA and the ExpiFectamine™ 293 reagent. After 16-18 hours of suspension culture (37° C., 8% $CO_2$, 125 rpm), 150 μL of ExpiFectamine™ 293 Enhancer 1 (Cat.No.A14524, Gibco) and 1.5 mL of ExpiFectamine™ 293 Enhancer 2 (Cat.No.A14524, Gibco) were added to the cells, followed by suspension culture for 5 days. After completion of the culture, the cells were centrifuged at 4000 rpm for 20 minutes to remove cell debris, and the supernatant was passed through a 0.22 μm filter. 100 μL of the protein A resin MabSelect Xtra (Cat.No.17-5269-02, GE Healthcare) was prepared per 30 mL of the culture medium, centrifuged at 1000 rpm for 2 minutes to remove the storage solution, and washed three times with 400 μL of protein A binding buffer (Cat.No.21007, Pierce) for each washing. Protein A resin was added to the prepared culture medium, followed by rotating incubation at room temperature for 30 minutes. The mixture of the culture medium and the resin was added to the Pierce spin column-snap cap (Cat.No.69725, Thermo), and extracted using the QIAvac 24 Plus (Cat.No.19413, QIAGEN) vacuum manifold so that only the resin remained in the column. The resin was washed with 5 mL of protein A binding buffer, and then resuspended in 200 μL of protein A elution buffer (Cat.No.21009, Pierce), after which it was incubated at room temperature for 2 minutes and eluted by centrifugation at 1000 rpm for 1 minute. The eluate was neutralized by addition of 2.5 μL of 1.5M Tris-HCl (pH 9.0). Elution was performed 4-6 times, and each fraction was quantified using Nanodrop 200C (Thermo Scientific). Fractions having the protein detected therein were collected, and the buffer was replaced with PBS (phosphate-buffered saline) buffer using 5 mL of 7K MWCO (Cat.No.0089892, Pierce) in Zeba Spin Desalting Columns. Next, electrophoresis (SDS-PAGE) of the protein was performed under reducing and non-reducing conditions to finally quantify the concentration of the antibody and verify the state of the antibody, and the antibody was stored at 4° C.

Figure 6:
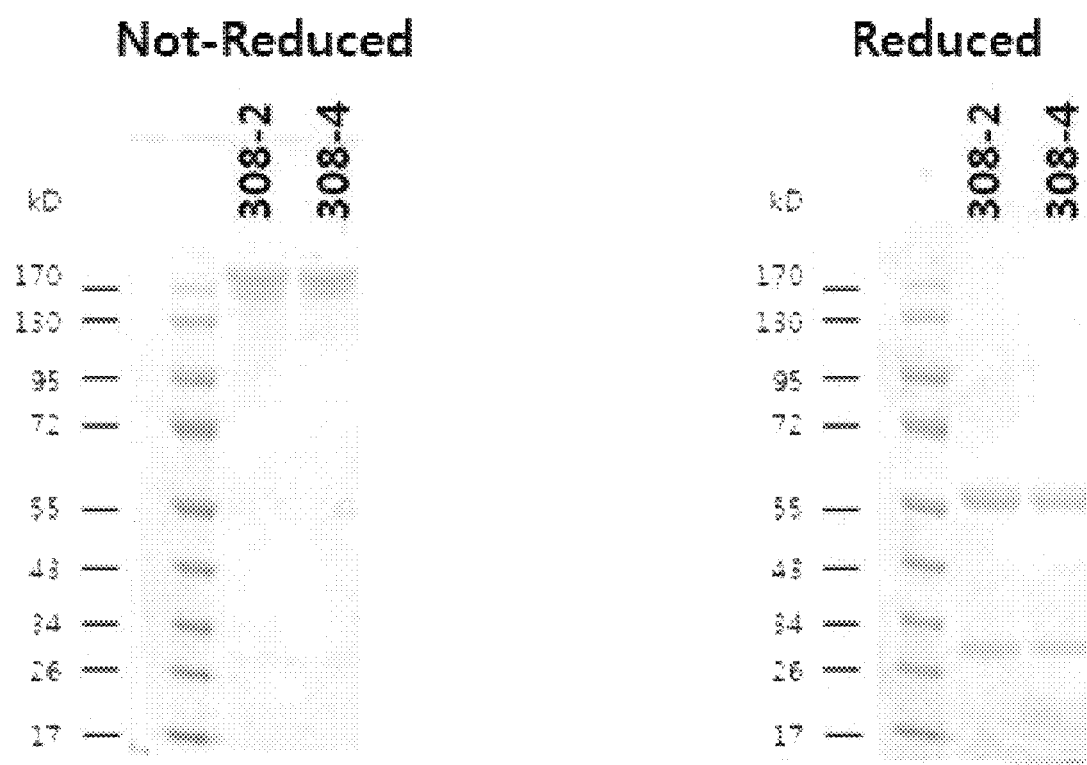
FIG. 6 shows the results of protein electrophoresis (SDS-PAGE) of IgG of 308-2 and 302-4 clone antibodies that are clone 308 antibody mutants among anti-TFPI antibodies.

As a result, a total of 18 clone antibodies were prepared by introducing one or more mutations into four positions of the amino acid sequence of clone 308, which can enhance the binding of the antibody to the antigen (human recombinant TFPI protein and were selected based on the prediction of Example 3 (FIG. 5 and Tables 4 to 7; the amino acid sequences of the 308, 308-2 and 308-4 clone antibodies). Protein electrophoresis (SDS-PAGE) indicated that the antibodies were purified in a good state (FIG. 6). Among these antibodies, clone 308-2 and clone 308-4 have a glutamine (Q) or glutamate (E) mutation introduced into the heavy-chain lysine (K) of clone 308.

Tables 4 and 6 show the heavy-chain and light-chain amino acid sequences of the anti-TFPI clone antibodies.

Tables 5 and 7 show the CDR amino acid sequences of the clone antibodies of Tables 4 and 6, identified based on the Kabat numbering system.

Example 5: Preparation of TFPI KPI-2

5-1: Cloning of Human TFPI KPI-2 (Kunitz Domain 2), Rabbit KPI-2 and Mouse TFPI KPI-2 Genes In order to construct human TFPI KPI-2 (Kunitz domain 2), rabbit TFPI KPI-2 and mouse TFPI KPI-2 genes (see Table 10), the restriction enzyme sites NcoI (Cat.No.R0193S, NEB) and NotI (Cat.No.R0189S, NEB) were introduced into pET22b plasmid vectors. Each gene (synthesized by GeneScript) was subjected to PCR using an NcoI-containing forward primer (Table 11; SEQ ID NOs: 33 to 35) and an NotI-containing reverse primer (Table 11; SEQ ID NOs: 36 to 38). The PCR was performed under the following conditions: 2 min at 94° C.; and then 30 cycles, each consisting of 30 sec at 94° C., 30 sec at 55° C. and sec at 72° C.; followed by 5 min at 72° C. The amplified genes were electrophoresed on 1% agarose gel to confirm the DNA bands having the expected sizes, and were isolated using a gel extraction kit (Cat.No.28704, QIAGEN). The three isolated genes were treated with NcoI and NotI restriction enzymes at 37° C. for 4 hours. The treated genes were separated on 1% agarose gel. A pET22b plasmid vector was also digested with NcoI and NotI in the same manner and separated on agarose gel. The prepared pET22b NcoI/NotI vector and the insert were mixed at a molar ratio of 1:3, and then T4 DNA ligase (Cat.No.M0202S; NEB) and ligase buffer (Cat.No.B0202S; N EB) were added thereto, followed by incubation at 25° C. for 3 hours. 5 μL of the ligation product was added to DH5α (chemical competent cells; Invitrogen) and incubated on ice for 10 minutes. For heat shock, the cells were incubated at 42° C. for 1 minute, and for cell recovery, the cells were suspension-cultured in SOC medium at 37° C. for 40 minutes. 50 μL of the transformed DH5a cells were plated on a carbenicillin plate and cultured at 37° C. for 12 hours or more. 6 of the produced colonies were selected, seeded into a carbenicillin-containing LB medium, and suspension-cultured at 37° C. at 220 rpm for 12 hours or more. From the plasmid-containing cells, the plasmid was separated using a plasmid mini kit (Cat.No.27405, QIAGEN). The separated plasmid was identified by DNA sequencing.

Table 10 below shows the amino acid sequences of TFPI KPI-2 (Kunitz domain 2) for each animal type.

TABLE 10

| Types | AA Sequences | SEQ ID NOS: |
|---|---|---|
| Human | KPDFCFLEEDPGTCRGYITR YFYNNQTKQCERFKYGGCLG NMNNFETLEECKNICEDG | 30 |
| Rabbit | KPDFCFLEEDPGTCRGFMTR YFYNNQSKQCEQFKYGGCLG NSNNFETLEECRNTCEDP | 31 |
| Mouse | RPDFCFLEEDPGLCRGYMKR YLYNNQTKQCERFVYGGCLG NRNNFETLDECKKICENP | 32 |

Table 11 below shows the primers used in the TFPI KPI-2 (Kunitz domain 2) gene cloning of Example 5.

TABLE 11

| Names | DNA Sequences | SEQ ID NOS: |
|---|---|---|
| HTK2 For | CCATGGAAACCCGACTTTTG CTTCCTGGA | 33 |
| RTK2 For | CCATGGAAACCCGATTTCTG CTTTCTGGAG | 34 |
| MTK2 For | CCATGGAGACCTGACTTCTG CTTTCTGGAG | 35 |
| HTK2 Re | GCGGCCGCCTAGCCGTCTTC ACAGATGTTCTTG | 36 |
| RTK2 Re | GCGGCCGCCTAGGGGTCCTC ACAGGTGTTG | 37 |
| MTK2 Re | GCGGCCGCCTAGGGGTTCTC ACAGATTTTCTTGCATT | 38 |

5-2: Production and Purification of Human TFPI KPI-2 (Kunitz Domain 2), Rabbit TFPI KPI-2 and Mouse TFPI KPI-2 Proteins The clones with identified TFPI gene sequences were transformed into BL21(DE3) bacteria (chemical competent cell; Cat.No.C2527I, NEB). Each of human TFPI KPI-2 (Kunitz domain 2), rabbit KPI-2 and mouse KPI-2 genes was added to the bacterial cells which were then incubated on ice for about 10 minutes. For heat shock, the cells were incubated at 42° C. for 1 minute, and for cell recovery, the cells were suspension-cultured in SOC at 37° C. for 40 minutes. 50 μL of the transformed bacterial cells were plated on a carbenicillin plate and cultured at 37° C. for 12 hours or more. One of the produced colonies was seeded into a carbenicillin-containing LB medium and suspension-cultured at 37° C. at 220 rpm for 12 hours or more. On the next day, the cultured bacterial cells were seeded into 500 ml of SB-glucose medium and suspension-cultured at 37° C. at 220 rpm for 2 hours. When the OD of the bacterial culture medium reached 0.6, 0.1 mM IPTG was added using Nano-Drop for induction. Next, the cells were suspension-cultured at 25° C. at 180 rpm for 12 hours or more. The bacterial cells were recovered by centrifugation at 6000 rpm for 20 minutes, and freezing and thawing were repeated three times to recover the protein expression in the periplasm region, followed by centrifugation. The supernatant was passed through a 0.22 μm filter to remove cell debris, followed by purification. The purification process was performed using Talon metal affinity resin (Cat.No.635501, Clonetech), and the resin was stabilized with phosphate buffer and incubated with the filtered culture medium at 4° C. for 12 hours or more. A washing process was performed using 10 mM imidazole, and an elution process was performed using 250 mM imidazole. The purified protein was electrophoresed on NuPAGE 4-12% Bis-Tris gel, and then the isolated protein was visualized by Coomassie blue staining. The eluted protein was filtered through a Vivaspin (Cat.No.28-9322-18, GE) column, and the buffer was replaced with PBS (phosphate-buffered saline) buffer.

Figure 7:
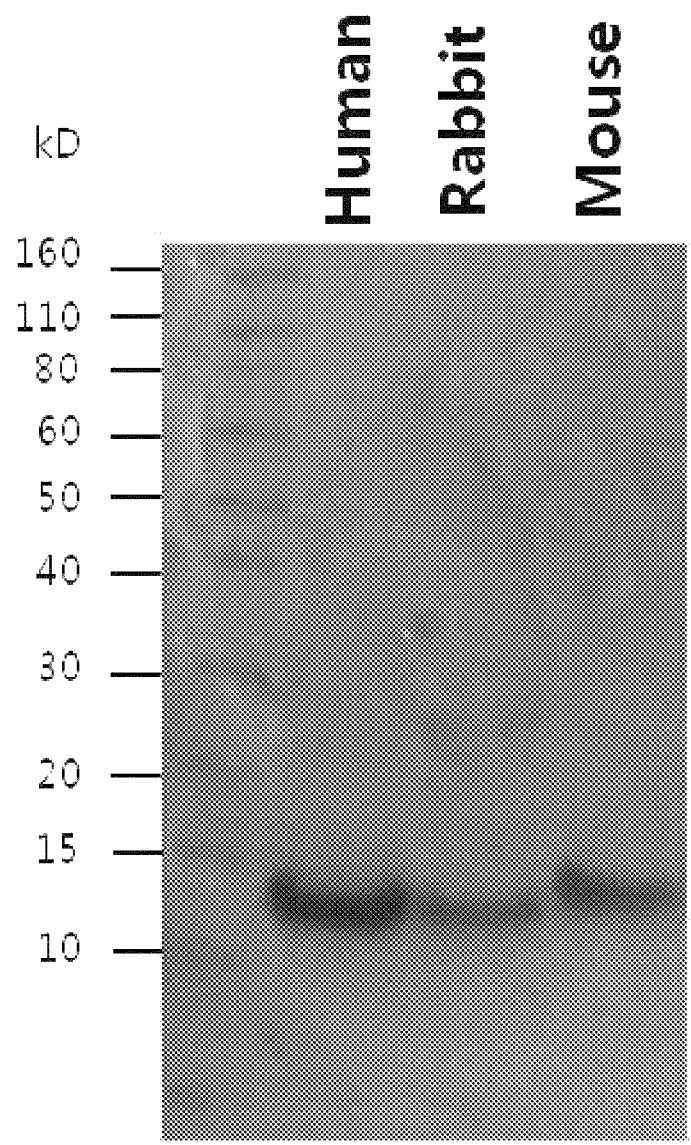
FIG. 7 shows the results of protein electrophoresis (SDS-PAGE) of the TFPI KPI-2 (Kunitz domain 2) protein according to the type of animal.

As a result, as shown in FIG. 7, protein electrophoresis (SDS-PAGE) indicated that the TFPI KPI-2 (Kunitz domain 2) protein for each animal type was purified in a good state.

Example 6: Measurement of Quantitative Affinity for Anti-TFPI Antibody for TFPI Antigen The quantitative affinity of clone T417, clone T308, clone 308, clone 308-2 or clone 308-4, which is the purified anti-TFPI antibody, for recombinant human TFPI, was measured using a Biacore T-200 (GE Healthcare, USA) biosensor. TFPI (Cat.No.TFPI-875H, Creative Biomart, USA) purified from HEK293 cells was immobilized on a CM5 chip (GE Healthcare, USA) to an Rmax of 200 by an amine-carboxyl reaction, and then the clone T417, clone T308, clone 308, clone 308-2 or clone 308-4 antibody serially diluted in HBS-EP buffer (10 mM HEPES, pH7.4, 150 mM NaCl, 3 mM EDTA, 0.005% surfactant P20) was run on the chip at a concentration of 0.078-10 nM at a flow rate 30 μL/min for 120 seconds for association and 600 seconds for dissociation (Table 12). 10 mM of glycine-HCl (pH 1.5) was run at a flow rate of 30 μL/min for 30 seconds, thereby inducing the dissociation of the antibody associated with the TFPI. The affinity in terms of kinetic rate constants ($K_{on}$ and $K_{off}$) and equilibrium dissociation constant ($K_D$) was evaluated using Biacore T-200 evaluation software.

Figure 8:
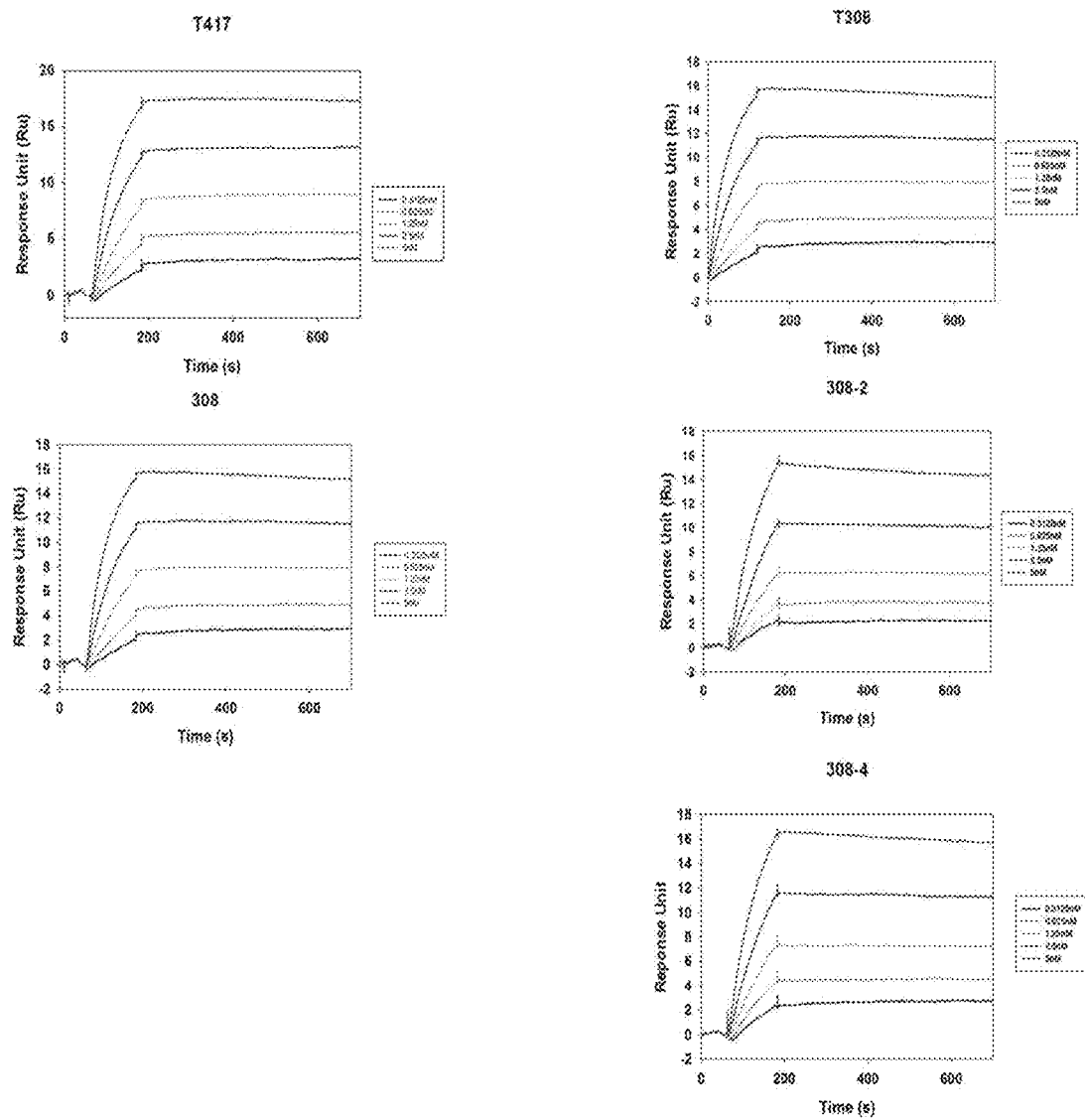
FIG. 8 graphically shows the affinities of anti-TFPI antibodies.

As a result, as shown in Table 13 below and FIG. 8, it was shown that the affinities of the prepared clone 308-2 and clone 308-4 antibodies were higher than that of clone 308.

TABLE 12

| SPR | Biacore 1200 |
|---|---|
| Chip | CM5 |
| Running Buffer | HBS-EP pH 7.4 |
| Flow rate | 30 ul/min |
| Association/dissociation time | 120 sec/600 sec |
| IgG Conc. | 0.3125~5 nM, ½ serial dilution |
| Regeneration | 10 mM Glycine-HCl pH 1.5, 30 sec |

TABLE 13

| | $K_{on}$ | $K_{off}$ | $K_D$ |
|---|---|---|---|
| T417 | $5.3 \times 10^6$ | $3.5 \times 10^{-5}$ | $6.7 \times 10^{-12}$ |
| T308 | $4.4 \times 10^6$ | $4.2 \times 10^{-5}$ | $9.4 \times 10^{-12}$ |
| 308 | $3.5 \times 10^6$ | $1.7 \times 10^{-4}$ | $5.0 \times 10^{-11}$ |
| 308-2 | $3.0 \times 10^6$ | $9.9 \times 10^{-5}$ | $3.3 \times 10^{-11}$ |
| 308-4 | $3.5 \times 10^6$ | $8.2 \times 10^{-5}$ | $2.4 \times 10^{-11}$ |

Example 7: Measurement of Fxa Activity

Blood coagulation is induced by an intrinsic pathway and an extrinsic pathway, and the two pathways activate thrombin through a common pathway that activates factor X, thereby forming fibrin to induce blood coagulation. In addition, TFPI consists of Kunitz 1 (K1), Kunitz 2 (K2) and Kunitz 3 (K3) domains. It is known that the K1 domain binds to FVIIa and the K2 domain binds to FXa. It is known that blood coagulation is inhibited by the binding between TFPI and the blood clotting factor. Thus, in order to determine the effects of anti-TFPI candidate antibodies on the blood coagulation process, the FXa activity was evaluated. An assay system was composed only of FXa, TFPI and a candidate antibody so as to minimize the effects of several factors. When the candidate antibody binds to TFPI, it does not inhibit the function of FXa, and thus the FXa activity appears. However, when the candidate antibody does not effectively bind to TFPI, TFPI binds to FXa to thereby inhibit the function of FXa, and thus the degree of color development decreases. Thus, the residual activity of FXa which is not inhibited by TFPI is measured by the degree of substrate degradation. The substrate used herein is the FXa-specific substrate S-2765, and the substrate is degraded to generate measurable chromophoric pNA at 405 nm. This measurement method is based on an amidolytic assay.

Each of FXa, TFPI, mAb2021 and S-2765 was diluted with an assay buffer (20 mM HEPES, 150 mM NaCl, 1 mg/mL BSA, 0.02% $NaN_3$, 5 mM $CaCl_2$, pH7.4) with reference to Table 14 below and dispensed in a 1.5 ml tube.

TABLE 14

| materials) | Pre-dilution Conc.(nM) | Working conc.(nM) | Others |
|---|---|---|---|
| FXa | 2 nM | 0.5 nM | |
| TFPI | 40 nM | 10 nM | |
| S-2765 | 2 mM | 0.5 mM | |
| Standard curve | 10 nM | 0.02, 0.1, 0.5, 2.5 nM | FXa |
| mAb2021 | 160 nM | 0.625, 2.5, 10, 40 nM | Positive Control |

50 μL of each of the positive control (mAb2021, anti-TFPI Ab, Novo Nordisk) and the anti-TFPI candidate antibodies was added to each well to a concentration of 40, 10, 2.5 or 0.625 nM. 50 μL of 40 nM TFPI solution was added to each well and allowed to stand at room temperature for 30 minutes. To obtain a standard curve, 50 μL of FXa solution was added to each well at varying concentrations, and 50 μL of 2 mM FXa solution was added to each well and incubated at 37° C. for 10 minutes. 50 μL of 2 mM S-2765 solution was added to each well and incubated at 37° C. for 30 minutes. Then, the absorbance of each well at a wavelength of 405 nm was read by a microplate reader in endpoint mode.

As a result, as shown in FIG. 9, both clone T308 and clone T417 that are chimeric antibodies among the anti-TFPI candidate antibodies showed increases in the absorbance in an antibody concentration-dependent manner, indicating that the TFPI inhibitory effects of the two antibodies increase in a concentration-dependent manner. Clone T308 showed the effect of inhibiting TFPI by 91% in the sample treated with 40 nM, and the effect of inhibiting TFPI by 89% in the sample treated with 10 nM, compared to the sample not treated with TFPI, which is the positive control (mAb2021, anti-TFPI Ab). Clone T417 showed the effect of inhibiting TFPI by 89% in the sample treated with 40 nM, and the effect of inhibiting TFPI by 72% in the sample treated with 10 nM, compared to the sample not treated with TFPI, which is the positive control (mAb2021, anti-TFPI Ab). When the effects were compared at a TFPI concentration of 10 nM, it could be seen that clone T417 has a better TFPI inhibitory activity than clone T308.

In addition, as shown in FIG. 10, clone 308 was obtained by humanization of clone T417 determined to have a better effect in the above assay. Clone 308 also showed an increase in the absorbance in a concentration-dependent manner, indicating that it could inhibit TFPI. Clone 308 showed a TFPI inhibitory activity of about 85.1% in the sample treated with 40 nM, and a TFPI inhibitory activity of about 58.2% in the sample treated with 10 nM, compared to the positive control (mAb2021, anti-TFPI Ab), indicating that it has an inferior effect to clone T417 that showed a TFPI inhibitory activity of 78.4% in the sample treated with 10 nM.

In addition, as shown in FIG. 11, back mutation was performed in order to increase the effect of clone 308, and clone 308-2 and clone 308-4 were obtained. It could be seen that both clone 308-2 and clone 308-4 inhibited TFPI in a concentration-dependent manner. Also, in the samples treated with 40 nM and 10 nM, it could be seen that the TFPI inhibitory activities of clone 308-2 and clone 308-4 increased compared to that of clone 308. At a concentration of 40 nM, clone 308-2 and clone 308-4 showed TFPI inhibitory activities of 85% and 82%, respectively, compared to the positive control (mAb2021, anti-TFPI Ab), but at a concentration of 10 nM, clone 308-2 showed a TFPI inhibitory activity of 72%, and clone 308-4 showed a TFPI inhibitory activity of 78%, which is higher than that of clone 308-2. Additionally, it was shown that these antibodies were comparable to the clone T417 chimeric antibody showing a TFPI inhibitory activity of 77%.

Example 8: Measurement of TF/FVIIa/FXa Complex

The most important factors in the extrinsic pathway of blood coagulation include TF (tissue factor), FVII (factor VII), FX (factor X) and the like. When TF and FVIIa form a complex by an external signal, FX is activated into FXa. Then, FXa activates prothrombin into thrombin, which then converts fibrinogen into fibrin which acts on blood coagulation. However, TFPI (tissue factor pathway inhibitor) inhibits the function of FXa by binding to FXa, thereby interfering with blood coagulation. In order to evaluate the effect of anti-TFPI antibodies in the above-described pathway, a TF/FVIIa/FXa complex assay was performed. In a state in which TFPI was present together with or independently of anti-TFPI antibodies, the extents of production and inhibition of FXa by a TF/FVIIa complex were measured based on the extent of color development of a substrate (S2765) degraded by FXa, thereby evaluating the effect of the anti-TFPI antibody. In other words, as the TFPI inhibitory effect of the anti-TFPI antibody increases, the production of FXa increases, and the amount of substrate degraded increases, resulting in an increase in absorbance.

In 1.5 mL tubes, TF (4500L/B, Sekisui diagnostics), FVIIa (Novo Nordisk, Novo Seven), and FX (PP008A, Hyphen biomed) were diluted with assay buffer (20 mM HEPES, 150 mM NaCl, 1 mg/mL BSA, 0.02% $NaN_3$, 5 mM $CaCl_2$, pH 7.4) to the concentrations shown in Table 15 below, thereby preparing a mixture solution.

TABLE 15

| Material | TF | FVIIa | FX |
|---|---|---|---|
| Conc. | 6 ng/mL | 800 nM | 30 nM |

70 μL of the mixture solution was added to each well of a 96-well plate. To a blank well, 70 μL of assay buffer was added. Each well was incubated at 37° C. for 15 minutes, and then 30 μL of TFPI was added to each well to a concentration of 50 nM. However, 30 μL of assay buffer was added to each of the blank well and a positive control well (a sample not treated with the anti-TFPI antibody and TFPI). 30 μL of the anti-TFPI antibody was added to each well to concentrations of 12.5, 25, 50 and 100 nM. To each of the blank well, the positive control well (a sample not treated with the anti-TFPI antibody and TFPI) and the negative control well (a sample not treated with the anti-TFPI antibody), 30 μL of assay buffer was added, followed by incubation at 37° C. for 15 minutes. 20 μL of EDTA (E7889, Sigma-Aldrich) was added to each well to a concentration of 50 mM. Next, 50 μL of S2765 was added to each well to a concentration of 200 μM, followed by incubation at 37° C. for 10 minutes. Next, the absorbance of each well at 405 nm was measured using a microplate reader.

As a result, as shown in FIG. 12, the effects of clone T308 and clone T417 that are chimeric antibodies among the anti-TFPI candidate antibodies were confirmed. It was shown that the two antibodies all showed an increase in the absorbance in an antibody concentration-dependent manner, indicating that the TFPI inhibitory effects of the two antibodies increase in a concentration-dependent manner. Clone T308 showed the effect of inhibiting TFPI by 100% in the sample treated with 100 nM, and the effect of inhibiting TFPI by about 87% in the sample treated with 50 nM, compared to the positive control (the sample not treated with the anti-TFPI antibody and TFPI). Clone T417 showed the effect of inhibiting TFPI by 100% in the samples treated with 100 nM and 50 nM, compared to the positive control (the sample not treated with the anti-TFPI antibody and TFPI). Thus, it could be seen that the TFPI inhibitory activity of clone T417 is higher than that of clone T308.

In addition, as shown in FIG. 13, clone 308 was obtained by humanization of the clone T417 antibody having a better effect than clone T308. Clone 308 also showed an increase in the absorbance in a concentration-dependent manner, indicating that it inhibited TFPI. Clone 308 showed TFPI inhibitory activities of about 94.3% in the sample treated with 100 nM and about 54.2% in the sample treated with 50 nM, compared to the positive control (the sample not treated with the anti-TFPI antibody and TFPI), indicating that the effect of clone 308 is inferior to that of clone T417 showing a TFPI inhibitory activity of 100%.

Furthermore, as shown in FIG. 14, back mutation was performed in order to increase the effect of the humanized clone 308 antibody, and clone 308-2 and clone 308-4 were obtained. It could be seen that both clone 308-2 and clone 308-4 inhibited TFPI in a concentration-dependent manner. In addition, in the samples treated with 50 nM, it could be seen that the TFPI inhibitory activities of clone 308-2 and clone 308-4 increased compared to that of clone 308. At concentrations of 100 nM and 50 nM, clone 308-2 and clone 308-4 all showed a TFPI inhibitory activity of 100% compared to the positive control (the sample not treated with the anti-TFPI antibody and TFPI). At a concentration of 25 nM, clone 308-2 showed a TFPI inhibitory activity of 37.8%, and clone 308-4 showed a TFPI inhibitory activity of 68.4%, which is higher than that of clone 308-2. However, it could be seen that the TFPI inhibitory activities of the back-mutated antibodies were lower than that the clone T417 chimeric antibody.

Example 9: Measurement of Thrombin Generation

The blood coagulation mechanism is divided into an intrinsic pathway and an extrinsic pathway. It is known that the function of TF (tissue factor) in the extrinsic pathway is the activity feedback function in the blood coagulation mechanism and is the explosive production of thrombin that is produced very fast. The most important factors in this blood coagulation mechanism include TF (tissue factor), FVII (factor VII), FX (factor X) and the like. When TF and FVIIa form a complex by an external signal, FX is activated into FXa. Then, FXa activates prothrombin into thrombin, which then cleaves fibrinogen into fibrin which acts on blood coagulation. However, TFPI (tissue factor pathway inhibitor) acts to inhibit the function of FXa by binding to FXa, thereby interfering with blood coagulation. A thrombin generation assay comprises: treating plasma with a test sample to be evaluated; and then inspecting the amount of thrombin produced in the plasma, based on the amount of a fluorescent product produced when the produced thrombin converts a fluorogenic substrate into the fluorescent product in the presence of PPP-reagent low; and calibrating the inspected amount of thrombin with the known amount of thrombin calibrator, thereby measuring the actual generation of thrombin.

20 μL of PPP-reagent low solution was added to the sample loading well of a prewarmed 96-well plate (round bottom immulon 2HB 96 well plate), and 20 μL of calibrator solution was added to the calibrator well of the plate. An anti-TFPI candidate antibody was diluted in a pre-dissolved sample dilution (FVIII-deficient plasma) at a concentration of 0.3125, 0.625, 1.25 or 2.5 nM, and then incubated at room temperature for 10 minutes so that it could bind to TFPI.

80 μL of each of the sample dilution was added to each of the calibrator and blank wells, and 80 μL of the diluted antibody solution was added to each of the remaining wells. A start button at the bottom of the software screen was pressed to execute washing. Washing was performed in a state in which an inlet tube was placed in distilled water in a water bath at 37° C. and in which an outlet tube was placed in an empty container. After completion of the washing, the next button was pressed to perform an empty process. The inlet tube was placed in a FluCa solution warmed to 37° C. and was primed to fill the tube with the solution. The outlet tube was mounted in an M hole in a dispenser, and then the next button was pressed to automatically dispense 20 μL of FluCa solution into each well, after which a shaking process was performed and analysis was initiated.

As a result, as shown in FIG. 15, a thrombin generation assay was performed using the clone T417 chimeric antibody and humanized clone 308 antibody selected through the above-described Fxa activity assay and TF/FVIIa/FXa complex assay. At 2.5 nM, clone T417 showed an increase in thrombin peak of 208% compared with the blank treated with only the sample dilution, and clone 308 showed an increase in thrombin peak of 162% compared to the blank. In the case of ETP indicating the total generation of thrombin, in the samples treated with 2.5 nM, clone T417 showed an increase in ETP of 131%, and clone 308 showed an increase in ETP of 122%, compared to the negative control (having no antibody). When the two antibodies were compared, it was shown that clone T417 has a better effect than the clone 308 antibody.

In addition, as shown in FIG. 16, for the clone 308-2 and clone 308-4 antibodies selected through the FXa activity assay and the TF/FVIIa/FXa complex assay after performing back mutation in order to increase the effect of the humanized clone 308 antibody, a thrombin generation assay was performed. It was shown that both clone 308-2 and clone 308-4 showed an increase in thrombin generation in a concentration-dependent manner. When the samples treated with 2.5 nM were compared, it could be seen that clone 308-2 and clone 308-4 showed increases in thrombin peak and total thrombin generation compared to the clone 308 antibody. In the samples treated with 2.5 nM, clone 308-2 and clone 308-4 showed increases in thrombin peak of 183% and 191%, respectively, compared to the negative control (having no antibody), and the ETP value was 126% in both clone 308-2 and clone 308-4, suggesting that clone 308-2 and clone 308-4 have an increased ability to generate thrombin. In addition, the ability of the two antibodies to generate thrombin was superior to that of the clone 308 antibody and was comparable to that of the clone T417 chimeric antibody.

Example 10: Prediction of Binding Between Anti-TFPI Antibody 308-4 Clone and Kunitz Domain-2

As an antibody against TFPI (tissue factor pathway inhibitor) that inhibits the activity of factor X, an antibody for treating or preventing hemophilia, which can prevent the inhibition of blood coagulation, was constructed.

Blood coagulation is induced by an intrinsic pathway and an extrinsic pathway, and the two pathways activate thrombin through a common pathway that activates factor X, thereby forming fibrin to induce blood coagulation. In addition, TFPI consists of Kunitz 1 (K1), Kunitz 2 (K2) and Kunitz 3 (K3) domains. It is known that the K1 domain binds to FVIIa and the K2 domain binds to FXa.

As described in Korean Patent Application No. 10-2015-0026555, entitled "Novel Anti-TFPI Antibody and Composition Comprising the Same", 308-4 clone that is an anti-TFPI antibody was prepared. It could be seen that the 308-4 clone has a $K_D$ of $2.64 \times 10^{-11}$ M or lower, preferably $2.52 \times 10^{-11}$ M or lower, more preferably $2.4 \times 10^{-11}$ M or lower.

In the present invention, it was attempted to prepare an antibody having a higher affinity for TFPI by affinity maturation of the 308-4 clone.

In order to predict the binding between the anti-TFPI antibody 308-4 clone and the Kunitz domain-2, homology search was performed in the Igblast (http://blast.ncbi.nlm.nih.gov/Blast.cgi) using the amino acid sequence of the 308-4 clone. As a result, it was found that the 3QOS (PDB number) structure is similar. Based on 3QOS, the structure of the 308-4 clone was designed using homology modeling that is the bioluminate module (Schrodinger, Germany). The designed structure was subjected to docking simulation with Kunitz domain-2 using the protein-protein binding prediction program PIPER to obtain binding prediction data. To select paratopes from the obtained binding structure, the interaction between the 308-4 clone and the Kunitz domain-2 was analyzed, and the amino acids of the 308- clone, which produce a non-covalent bond, were selected (Table 16). The selected paratopes were subjected to affinity maturation using the bioluminate module to calculate the binding energy value of each paratope and to predict the binding energy value that would be changed by substitution with other amino acids. Thus, amino acids having stable binding energy values were selected and reflected in the design of primers (Table 17).

Table 16 below shows the selected amino acids of the anti-TFPI antibody 308-4 clone, which were determined to produce a non-covalent bond in the analysis of the interaction between the 308-4 clone and the Kunitz domain-2.

Table 17 below shows the selected amino acids of Table 16, which were determined to have the stable binding energy values of paratopes by affinity maturation.

TABLE 16

| Variable regions | Selected amino acids (based on kabat) |
|---|---|
| Heavy chain | S31, T52a, Y56, E64, N98 |
| Light chain | S31a, T92, H93 |

TABLE 17

| Variable Regions | Selected amino acids |
|---|---|
| VH_S31 | H, K, R, T, Y, I, L |
| VH_T52a | F, Y, L, H, K, R, I |
| VH_Y56 | H, R, K |
| VH_E64 | Q, D, H |
| VH_N98 | F, H, K, Q, R, Y |
| VL_S31a | I, L, N, Q, R, F, K, T, V |
| VL_T92 | F, Y, I, N |
| VL_H93 | Y, L, I, Q, N, K |

Example 11: Preparation of Novel Antibody by Affinity Maturation of 308-4 Clone Using Yeast Display scFv Library 11-1: Construction of Yeast Display scFv Library In order to introduce a mutation into a yeast library, three heavy-chain variable region fragments and two light-chain variable region fragments were subjected to polymerase chain reaction (PCR). Specifically, for the PCR of heavy-chain variable region fragment 1, the heavy-chain variable region gene sequence of the anti-TFPI 308-4 clone was used as a template together with a forward primer (Table 18; SEQ ID NO: 40) and a reverse primer (Table 18; SEQ ID NOs: 41 to 48); for the PCR of heavy-chain variable region fragment 2, the heavy-chain variable region gene sequence of the anti-TFPI 308-4 clone was used as a template together with a forward primer (Table 18; SEQ ID NO: 49) and a reverse primer (Table 18; SEQ ID NOs: 50 to 61); and for the PCR of heavy-chain variable region fragment 3, the heavy-chain variable region gene sequence of the anti-TFPI 308-4 clone was used as a template together with a forward primer (Table 18; SEQ ID NO: 62) and a reverse primer (Table 18; SEQ ID NOs: 63 to 69). The PCR of each of the fragments was performed using AccuPower Pfu PCR Pre-Mix (CAT.No.K-2015, Bioneer). The PCR was performed under the following conditions: 2 min at 95° C.; and then 30 cycles, each consisting of 30 sec at 95° C., 30 sec at 55° C. and 60 sec at 72° C.; and followed by 10 min at 72° C. The amplified genes were electrophoresed on 1% agarose gel to confirm the DNA band having the expected size, and were isolated using a gel extraction kit (QIAquick Gel Extraction Kit, CAT.No.28706, QIAGEN). For the PCR of light-chain variable region fragment 1, the light-chain variable region gene sequence of the anti-TFPI 308-4 clone was used as a template together with a forward primer (Table 18; SEQ ID NO: 72) and a reverse primer (Table 18; SEQ ID NOs: 73 to 82); and for the PCR of light-chain variable region fragment 2, the light-chain variable region gene sequence of the anti-TFPI 308-4 clone was used as a template together with a forward primer (Table 18; SEQ ID NO: 83) and a reverse primer (Table 18; SEQ ID NOs: 84 to 87). The PCR of each of the fragments was performed using AccuPower Pfu PCR PreMix (Bioneer) under the following conditions: 2 min at 95° C.; and then 30 cycles, each consisting of 30 sec at 95° C., 30 sec at 55° C. and 60 sec at 72° C.; and then 10 min at 72° C. The amplified genes were electrophoresed on 1% agarose gel to confirm the DNA band having the expected size, and were isolated using a gel extraction kit (QIAquick Gel Extraction Kit, QIAGEN).

The obtained heavy-chain variable region fragment genes were adjusted to a molar ratio of 1:1:1 and used as a template together with a forward primer (Table 18; SEQ ID NO: 70) and a reverse primer (Table 18; SEQ ID NO: 71) in PCR. The PCR of the fragment genes was performed using Takara primer star PCR premix (CAT.NO.R040B, Takara) under the following conditions: 2 min at 95° C.; and then 20 cycles, each consisting of 10 sec at 95° C., 20 sec at 55° C. and 30 sec at 72° C.; and then 5 min at 72° C. The amplified gene was electrophoresed on 1% agarose gel to confirm the DNA band having the expected size, and was isolated using a gel extraction kit (QIAquick Gel Extraction Kit, QIAGEN), thereby obtaining a heavy-chain variable region gene.

The obtained light-chain variable region fragment genes were adjusted to a molar ratio of 1:1 and used as a template together with a forward primer (Table 18; SEQ ID NO: 91) and a reverse primer (Table 18; SEQ ID NO: 92) in PCR. The PCR of the fragment genes was performed using Takara primer star PCR premix (CAT.No.R040B, Takara) under the following conditions: 2 min at 95° C.; and then 20 cycles, each consisting of 10 sec at 95° C., 30 sec at 55° C. and 40 sec at 72° C.; and then 5 min at 72° C. The amplified gene was electrophoresed on 1% agarose gel to confirm the DNA band having the expected size, and was isolated using a gel extraction kit (QIAquick Gel Extraction Kit, QIAGEN), thereby obtaining a light-chain variable region gene.

The obtained heavy-chain and light-chain variable region genes were adjusted to a molar ratio of 1:1 and used as a template together with a forward primer (Table 18; SEQ ID NO: 93) and a reverse primer (Table 18; SEQ ID NO: 94) in PCR. The PCR of the genes was performed using Takara primer star PCR premix (Takara) under the following conditions: 2 min at 95° C.; and then 20 cycles, each consisting of 10 sec at 95° C., 20 sec at 55° C. and 30 sec at 72° C.; and then 5 min at 72° C. The amplified gene was electrophoresed on 1% agarose gel to confirm the DNA band having the expected size, and was isolated using a gel extraction kit (QIAquick Gel Extraction Kit, QIAGEN), thereby constructing a 308-4 affinity maturation scFv library gene. 200 ng of the constructed library gene was mixed with 1 μg of the pCTCON gene treated with the restriction enzymes NheI (CAT.No.R0131L, NEB) and BamHI (CAT.No.R0136L, NEB), and the mixture was transformed into yeast (EBY100 electro-competent cell). The transformed yeast was suspended in 100 mL of YPD medium and shake-cultured at 30° C. at 200 rpm for 1 hour. The cultured yeast was inoculated into 1 L of SD medium and cultured at 30° C. at 200 rpm for 12 hours or more, after which it was centrifuged to remove the supernatant, and resuspended in yeast storage buffer and stored at −70° C. To determine the size of the library, 100 μl of the culture medium was collected at 1 hour after transformation, plated on SD plate by a serial dilution method, incubated at 30° C. for 12 hours or more, and then subjected to colony counting.

Table 18 below shows the primers used in the construction of the yeast display scFv library.

TABLE 18

| Names | Nucleic acid sequences | SEQ ID NOS: |
|---|---|---|
| VH FR1 Fo | GAA GTC CAG CTG GTG GAG TCT GGA GGT | 40 |
| VH FR1 Re_S | CGG GGC CTG ACG AAC CCA GTT CAT GGC ATA GCT GCT GAA GGT GAA GCC GCT CGC TGC | 41 |
| VH FR1 Re_H | CGG GGC CTG ACG AAC CCA GTT CAT GGC ATA ATG GCT GAA GGT GAA GCC GCT CGC TGC | 42 |
| VH FR1 Re_K | CGG GGC CTG ACG AAC CCA GTT CAT GGC ATA TTT GCT GAA GGT GAA GCC GCT CGC TGC | 43 |

TABLE 18-continued

| Names | Nucleic acid sequences | SEQ ID NOS: |
|---|---|---|
| VH FR1 Re_R | CGG GGC CTG ACG AAC CCA GTT CAT GGC ATA TCT GCT GAA GGT GAA GCC GCT CGC TGC | 44 |
| VH FR1 Re_T | CGG GGC CTG ACG AAC CCA GTT CAT GGC ATA AGT GCT GAA GGT GAA GCC GCT CGC TGC | 45 |
| VH FR1 Re_Y | CGG GGC CTG ACG AAC CCA GTT CAT GGC ATA ATA GCT GAA GGT GAA GCC GCT CGC TGC | 46 |
| VH FR1 Re_I | CGG GGC CTG ACG AAC CCA GTT CAT GGC ATA AAT GCT GAA GGT GAA GCC GCT CGC TGC | 47 |
| VH FR1 Re_L | CGG GGC CTG ACG AAC CCA GTT CAT GGC ATA AAG GCT GAA GGT GAA GCC GCT CGC TGC | 48 |
| VH FR2 Fo | TAT GCC ATG AAC TGG GTT CGT CAG GCC | 49 |
| VH FR2 Re_T-YH-EQDH | GTT ATC GCG GGA AAT GGT GAA GCG CCC X3TX2 AAC GCT ATC GGC GTA GTA GGT GTX1 TGA CCC ACC GGT TGT GAT GGT GCT GAC CCA TTC CAA GCC | 50 |
| VH FR2 Re_T-RK-EQDH | GTT ATC GCG GGA AAT GGT GAA GCG CCC X3TX2 AAC GCT ATC GGC GTA GTA GGT TYT TGA CCC ACC GGT TGT GAT GGT GCT GAC CCA TTC CAA GCC | 51 |
| VH FR2 Re_FYLH-YH-EQDH | GTT ATC GCG GGA AAT GGT GAA GCG CCC X3TX2 AAC GCT ATC GGC GTA GTA GGT GTX1 TGA CCC ACC TWR TGT GAT GGT GCT GAC CCA TTC CAA GCC | 52 |
| VH FR2 Re_FYLH-RK-EQDH | GTT ATC GCG GGA AAT GGT GAA GCG CCC X3TX2 AAC GCT ATC GGC GTA GTA GGT TYT TGA CCC ACC TWR TGT GAT GGT GCT GAC CCA TTC CAA GCC | 53 |
| VH FR2 Re_KRI-YH-EQDH | GTT ATC GCG GGA AAT GGT GAA GCG CCC X3TX2 AAC GCT ATC GGC GTA GTA GGT GTX1 TGA CCC ACC THT TGT GAT GGT GCT GAC CCA TTC CAA GCC | 54 |
| VH FR2 Re_KRI-RK-EQDH | GTT ATC GCG GGA AAT GGT GAA GCG CCC X3TX2 AAC GCT ATC GGC GTA GTA GGT TYT TGA CCC ACC THT TGT GAT GGT GCT GAC CCA TTC CAA GCC | 55 |
| VH FR2 Re_T-YH-EQDH_#2 | GTT ATC GCG GGA AAT GGT GAA GCG CCC NTS AAC GCT ATC GGC GTA GTA GGT ATR TGA CCC ACC GGT TGT GAT GGT GCT GAC CCA TTC CAA GCC | 56 |
| VH FR2 Re_T-RK-EQDH_#2 | GTT ATC GCG GGA AAT GGT GAA GCG CCC NTS AAC GCT ATC GGC GTA GTA GGT TYT TGA CCC ACC GGT TGT GAT GGT GCT GAC CCA TTC CAA GCC | 57 |
| VH FR2 Re_FYLH-YH-EQDH_#2 | GTT ATC GCG GGA AAT GGT GAA GCG CCC NTS AAC GCT ATC GGC GTA GTA GGT ATR TGA CCC ACC TWR TGT GAT GGT GCT GAC CCA TTC CAA GCC | 58 |
| VH FR2 Re_FYLH-RK-EQDH_#2 | GTT ATC GCG GGA AAT GGT GAA GCG CCC NTS AAC GCT ATC GGC GTA GTA GGT TYT TGA CCC ACC TWR TGT GAT GGT GCT GAC CCA TTC CAA GCC | 59 |
| VH FR2 Re_KRI-YH-EQDH_#2 | GTT ATC GCG GGA AAT GGT GAA GCG CCC NTS AAC GCT ATC GGC GTA GTA GGT ATR TGA CCC ACC THT TGT GAT GGT GCT GAC CCA TTC CAA GCC | 60 |
| VH FR2 Re_KRI-RK-EQDH_#2 | GTT ATC GCG GGA AAT GGT GAA GCG CCC NTS AAC GCT ATC GGC GTA GTA GGT TYT TGA CCC ACC THT TGT GAT GGT GCT GAC CCA TTC CAA GCC | 61 |
| VH FR3 Fo | GGG CGC TTC ACC ATT TCC CGC GAT AAC | 62 |
| VH FR3 Re_N | GCC CTG GCC CCA ATA ATC CAT CAG AAA ATT GCC ATC CTG GCG CGC GCA ATA ATA TAC CGC | 63 |
| VH FR3 Re_F | GCC CTG GCC CCA ATA ATC CAT CAG AAA AAA GCC ATC CTG GCG CGC GCA ATA ATA TAC CGC | 64 |
| VH FR3 Re_H | GCC CTG GCC CCA ATA ATC CAT CAG AAA ATG GCC ATC CTG GCG CGC GCA ATA ATA TAC CGC | 65 |

TABLE 18-continued

| Names | Nucleic acid sequences | SEQ ID NOS: |
|---|---|---|
| VH FR3 Re_K | GCC CTG GCC CCA ATA ATC CAT CAG AAA TTT GCC ATC CTG GCG CGC GCA ATA ATA TAC CGC | 66 |
| VH FR3 Re_Q | GCC CTG GCC CCA ATA ATC CAT CAG AAA TTG GCC ATC CTG GCG CGC GCA ATA ATA TAC CGC | 67 |
| VH FR3 Re_R | GCC CTG GCC CCA ATA ATC CAT CAG AAA TCT GCC ATC CTG GCG CGC GCA ATA ATA TAC CGC | 68 |
| VH FR3 Re_Y | GCC CTG GCC CCA ATA ATC CAT CAG AAA ATA GCC ATC CTG GCG CGC GCA ATA ATA TAC CGC | 69 |
| VH Final Fo | GGT TCT GGT GGT GGT GGT TCT GCT AGC GAC GTG GTG ATG ACA CAG ACG CCG CTG | 70 |
| VH Final Re | GGA GCT CAC AGT CAC CAG CGT GCC CTG GCC CCA ATA ATC CAT CAG AAA | 71 |
| VL FR1 Fo | GAC GTG GTG ATG ACA CAG ACG CCG CTG | 72 |
| VL FR1 Re_S | GAG CCA ATT CAG ATA CGT CTT GCC GTC GGA GTC CAG CAG CGA CTG GCT TGA TTT GCA | 73 |
| VL FR1 Re_I | GAG CCA ATT CAG ATA CGT CTT GCC GTC AAT GTC CAG CAG CGA CTG GCT TGA TTT GCA | 74 |
| VL FR1 Re_L | GAG CCA ATT CAG ATA CGT CTT GCC GTC AAG GTC CAG CAG CGA CTG GCT TGA TTT GCA | 75 |
| VL FR1 Re_N | GAG CCA ATT CAG ATA CGT CTT GCC GTC AGC GTC CAG CAG CGA CTG GCT TGA TTT GCA | 76 |
| VL FR1 Re_Q | GAG CCA ATT CAG ATA CGT CTT GCC GTC TTG GTC CAG CAG CGA CTG GCT TGA TTT GCA | 77 |
| VL FR1 Re_R | GAG CCA ATT CAG ATA CGT CTT GCC GTC TCT GTC CAG CAG CGA CTG GCT TGA TTT GCA | 78 |
| VL FR1 Re_F | GAG CCA ATT CAG ATA CGT CTT GCC GTC AAA GTC CAG CAG CGA CTG GCT TGA TTT GCA | 79 |
| VL FR1 Re_K | GAG CCA ATT CAG ATA CGT CTT GCC GTC TTT GTC CAG CAG CGA CTG GCT TGA TTT GCA | 80 |
| VL FR1 Re_T | GAG CCA ATT CAG ATA CGT CTT GCC GTC AGT GTC CAG CAG CGA CTG GCT TGA TTT GCA | 81 |
| VL FR1 Re_V | GAG CCA ATT CAG ATA CGT CTT GCC GTC AAC GTC CAG CAG CGA CTG GCT TGA TTT GCA | 82 |
| VL FR2 Fo | GAC GGC AAG ACG TAT CTG AAT TGG CTC CAG | 83 |
| VL FR2 Re_T-YH | GCG TTT AAT TTC AAC CTT AGT GCC TTG GCC GAA CGT AAA CGG AAA GTR GGT GCC CTG CCA GCA ATA GTA GAC GCC | 84 |
| VL FR2 Re_T-LIHQNK | GCG TTT AAT TTC AAC CTT AGT GCC TTG GCC GAA CGT AAA CGG AAA WWK GGT GCC CTG CCA GCA ATA GTA GAC GCC | 85 |
| VL FR2 Re_FYIN-YH | GCG TTT AAT TTC AAC CTT AGT GCC TTG GCC GAA CGT AAA CGG AAA GTR AWW GCC CTG CCA GCA ATA GTA GAC GCC | 86 |
| VL FR2 Re_FYIN-LIHQNK | GCG TTT AAT TTC AAC CTT AGT GCC TTG GCC GAA CGT AAA CGG AAA WWK AWW GCC CTG CCA GCA ATA GTA GAC GCC | 87 |
| VL Final Re | GCG TTT AAT TTC AAC CTT AGT GCC TTG GCC GAA CGT AAA | 88 |
| VL Final Fo SfiI | Cgtggcccaggcggcc GAC GTG GTG ATG ACA CAG ACG CCG CTG | 89 |
| VL Final Fo NruI | Cta TCG CGA TTG CAG TGG CAC TGG CTG GTT TCG | 90 |

TABLE 18-continued

| Names | Nucleic acid sequences | SEQ ID NOS: |
|---|---|---|
| VL Overlapping Fo | GGC ACG CTG GTG ACT GTG AGC TCC Gga ggc ggc gga agt ggc gga gga ggc agc ggc Gga ggc ggc agt GAC GTG GTG ATG ACA CAG ACG CCG CTG | 91 |
| VL Final Re | GTC CTC TTC AGA AAT AAG CTT TTG TTC GGA TCC GCG TTT AAT TTC AAC CTT AGT GCC TTG GCC GAA CGT AAA | 92 |
| VH Homologous recombination | GCT CTG CAG GCT AGT GGT GGT GGT GGT TCT GGT GGT GGT GGT TCT GGT GGT GGT GGT TCT gct agc | 93 |
| VL Homologous recombination | TTG TTA TCA GAT CTC GAG CTA TTA CAA GTC CTC TTC AGA AAT AAG CTT TTG TTC GGA TCC | 94 |

11-2: Antibody Selection

The library yeast cells constructed in Example 11-1 were inoculated into SD medium and cultured at 30° C. at 200 rpm for 12 hours or more, and then the medium was replaced with SG medium, and the cells were cultured at 25° C. at 200 rpm for 12 hours to express the antibody on the yeast surface. Next, the yeast cells collected by centrifugation were washed with PBSM (3% BSA containing PBS) buffer, resuspended in 1 mL of PBSM buffer and incubated with a biotin-conjugated recombinant human TFPI protein at room temperature for 1 hour. The yeast cells incubated with the recombinant human TFPI protein were washed with PBSM, and then incubated with streptavidin microbeads (CAT.NO.130-048-101, Miltenyi biotech) on ice for 15 minutes. Next, the cells were washed once with PBSM buffer, resuspended in PBSM buffer, and then passed through an MACS column (CAT.NO.130-042-901, Milternyi biotech) to separate TFPI protein-conjugated yeast cells. The separated yeast cells were inoculated into SD medium and cultured for 48 hours or more, and the above procedure was repeated twice, thereby selecting the antibody.

11-3: Preparation of Individual Clones by FACS

The finally amplified single colonies were collected from the yeast display library, and then cultured in SD medium at 30° C. at 200 rpm for 12 hours. Then, the medium was replaced with SG medium, and the cells were cultured at 25° C. at 200 rpm for 12 hours or more, thereby expressing the antibody on the yeast surface. Next, the yeast cells recovered by centrifugation were washed with PBSF (1% BSA containing PBS) buffer, resuspended in 50 µl of PBSF buffer, and then incubated with a biotin-conjugated recombinant human TFPI protein and anti-c-myc mouse antibody (CAT.No.M4439, Sigma) at room temperature for 30 minutes. The incubated yeast cells were washed with PBSF, resuspended in 50 µl of PBSF buffer, and then incubated with FITC-conjugated anti-mouse antibody (CAT.No.F0257, Sigma) and PE-conjugated streptavidin on ice under a light-shielded condition for 15 minutes. Next, the cells were washed with PBSF buffer, resuspended in 500 µl of PBSF buffer, and then clones showing high values in the FITC and PE wavelength ranges were selected by FACS, thereby obtaining individual clones.

As a result, as shown in Table 19 below, clones that bind specifically to human TFPI could be selected, and the amino acid sequences thereof were analyzed. Among the antibodies described in Korean Patent Application No. 10-2015-0026555, the antibody used in the present invention was described as '2015-26555_(SEQ ID NO of the previous application)'.

Table 20 below shows the CDR amino acid sequences of the clone antibodies of Table 19, identified based on the Kabat numbering system.

TABLE 19

| Clones | Variable regions | Amino acid sequences | SEQ ID NOS: |
|---|---|---|---|
| 1001 | Heavy chain | EVQLVESGGGLVKPGGSLRLSCAASGFTFSSYAMNWVRQAP GKGLEWVSTITTGGSYTYYADSVDGRFTISRDNAKNSLYLQ MNSLRAEDTAVYYCARQDGNFLMDYWGQGTLVTVSS | 95 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 1015 | Heavy Chain | EVQLVESGGGLVKPGGSLRLSCAASGFTFSSYAMNWVRQAP GKGLEWVSTITTGGSHTYYADSVEGRFTISRDNAKNSLYLQ MNSLRAEDTAVYYCARQDGNFLMDYWGQGTLVTVSS | 97 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 1021 | Heavy Chain | EVQLVESGGGLVKPGGSLRLSCAASGFTFSSYAMNWVRQAP GKGLEWVSTITTGGSYTYYADSVDGRFTISRDNAKNSLYLQ MNSLRAEDTAVYYCARQDGHFLMDYWGQGTLVTVSS | 98 |

TABLE 19-continued

| Clones | Variable regions | Amino acid sequences | SEQ ID NOS: |
|---|---|---|---|
| | Light Chain | DVVMTQTPLSLPVTLGQPASISCKSSQSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |
| 1023 | Heavy Chain | EVQLVESGGGLVKPGGSLRLSCAASGFTFSSYAMNWVRQAP GKGLEWV<u>G</u>TITTGGSYTYYADSV<u>D</u>GRFTISRDNAKNSLYLQ MNSLRAEDTAVYYCARQDGNFLMDYWGQGTLVTVSS | 99 |
| | Light Chain | DVVMTQTPLSLPVTLGQPASISCKSSQSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |
| 1024 | Heavy Chain | EVQLVESGGGLVKPGGSLRLSCAASGFTFSSYAM<u>S</u>WVRQAP GKGLEWVSTITTGGSYTYYADSV<u>D</u>GRFTISRDNAKNSLYLQ MNSLRAEDTAVYYCARQDGNFLMDYWGQGTLVTVSS | 100 |
| | Light Chain | DVVMTQTPLSLPVTLGQPASISCKSSQSLLD<u>L</u>DGKTYLNWL QQRPGQSPKRLIYLVSKLDSGVPDRFTGSGSGTDFTLKISR VEAEDVGVYYCWQGTHFPFTFGQGTKVEIKR | 101 |
| 1104 | Heavy Chain | EVQLVESGGGLVKPGGSLRLSCAASGFTFSSYAMNWVRQAP GKGLEWV<u>G</u>TITTGG<u>SH</u>TYYADSV<u>Q</u>GRFTISRDNAKNSLYLQ MNSLRAEDTAVYYCARQDGNFLMDYWGQGTLVTVSS | 102 |
| | Light Chain | DVVMTQTPLSLPVTLGQPASISCKSSQSLLD<u>V</u>DGKTYLNWL QQRPGQSPKRLIYLVSKLDSGVPDRFTGSGSGTDFTLKISR VEAEDVGVYYCWQGTHFPFTFGQGTKVEIKR | 103 |
| 1123 | Heavy Chain | EVQLVESGGGLVKPGGSLRLSCAASGFTFSSYAMNWVRQAP GKGLEWVSTITTGG<u>SH</u>TYYADSVEGRFTISRDNAKNSLYLQ MNSLRAEDTAVYYCARQDG<u>H</u>FLMDYWGQGTLVTVSS | 104 |
| | Light Chain | DVVMTQTPLSLPVTLGQPASISCKSSQSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |
| 1202 | Heavy Chain | EVQLVESGGGLVKPGGSLRLSCAASGFTFSSYAMNWVRQAP GKGLEWV<u>G</u>TITTGGSYTYYADSV<u>D</u>GRFTISRDNAKNSLYLK MNSLRAEDTAVYYCARQDGNFLMDYWGQGTLVTVSS | 105 |
| | Light Chain | DVVMTQTPLSLPVTLGQPASISCKSSQSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |
| 1208 | Heavy Chain | EVQLVESGGGLVKPGGSLRLSCAASGFTFSSYAMNWVRQAP GKGLEWVSTITTGG<u>SH</u>TYYADSVEGRFTISRDNAKNSLYLQ MNSLRAEDTAVYYCARQDG<u>H</u>FLMDYWGQGTLVTVSS | 104 |
| | Light Chain | DVVMTQTPLSLPVTLGQPASISCKSSQSLLD<u>V</u>DGKTYLNWL QQRPGQSPKRLIYLVSKLDSGVPDRFTGSGSGTDFTLKISR VEAEDVGVYYCWQGTYLPFTFGQGTKVEIKR | 106 |
| 1214 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGNFLMDYWGQGTLVTVSS | 25 |
| | Light Chain | DVVMTQTPLSLPVTLGQPASISCKSSQSLLD<u>V</u>DGKTYLNWL QQRPGQSPKRLIYLVSKLDSGVPDRFTGSGSGTDFTLKISR VEAEDVGVYYCWQGTHFPFTFGQGTKVEIKR | 103 |
| 1216 | Heavy Chain | EVQLVESGGGLVKPGGSLRLSCAASGFTFS<u>H</u>YAMNWVRQAP GKGLEWVSTITTGGSYTYYADSVEGRFTISRDNAKNSLYLQ MNSLRAEDTAVYYCARQDG<u>H</u>FLMDYWGQGTLVTVSS | 107 |
| | Light Chain | DVVMTQTPLSLPVTLGQPASISCKSSQSLLD<u>I</u>DGKTYLNWL QQRPGQSPKRLIYLVSKLDSGVPDRFTGSGSGTDFTLKISR VEAEDVGVYYCWQGTHLPFTFGQGTKVEIKR | 108 |
| 1223 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDG<u>H</u>FLMDYWGQGTLVTVSS | 109 |
| | Light Chain | DVVMTQTPLSLPVTLGQPASISCKSSQSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |

TABLE 19-continued

| Clones | Variable regions | Amino acid sequences | SEQ ID NOS: |
|---|---|---|---|
| 1224 | Heavy Chain | EVQLVESGGGLVKPGGSLRLSCAASGFTFSSYAMSWVRQAP GKGLEWVSTITTGGSYTYYADSVDGRFTISRDNAKNSLYLQ MNSLRAEDTAVYYCARQDGNFLMDYWGQGTLVTVSS | 100 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 1232 | Heavy Chain | EVQLVESGGGLVKPGGSLRLSCAASGFTFSSYAMNWVRQAP GKGLEWVSTITTGGSYTYYADSVDGRFTISRDNAKNSLYLQ MNSLRAEDTAVYYCARQDGHFLMDYWGQGTLVTVSS | 98 |
| | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 1234 | Heavy Chain | EVQLVESGGGLVKPGGSLRLSCAASGFTFSSYAMNWVRQAP GKGLEWVSTITTGGSYTYYADSVQGRFTISRDNAKNSLYLQ MNSLRAEDTAVYYCARQDGNFLMDYWGQGTLVTVSS | 110 |
| | Light Chain | DVVMTQTPLSLPVTLGQPASISCKSSQSLLDIDGKTYLNWL QQRPGQSPKRLIYLVSKLDSGVPDRFTGSGSGTDFTLEISR VEAEDVGVYYCWQGTHFPFTFGQGTKVEIKR | 111 |
| 1238 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGHFLMDYWGQGTLVTVSS | 109 |
| | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 1243 | Heavy Chain | EVQLVESGGGLVKPGGSLRLSCAASGFTFSSYAMNWVRQAP GKGLEWVSTITTGGSHTYYADSVHGRFTISRDNAKNSLYLQ MNSLRAEDTAVYYCARQDGHFLMDYWGQGTLVTVSS | 112 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 1248 | Heavy Chain | EVQLVESGGGLVKPGGSLRLSCAASGFTFSSYAMNWVRQAP GKGLEWVSTITTGGSHTYYADSVDGRFTISRDNAKNSLYLQ MNSLRAEDTAVYYCARQDGHFLMDYWGQGTLVTVSS | 113 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 3007 | Heavy Chain | EVQLVESGGGLVKPGGSLRLSCAASGFTFTSYAMNWVRQAP GKGLEWVSTITLGGSYTYYADSVQGRFTISRDNAKNSLYLQ MNSLRAEDTAVYYCARQDGNFLMDYWGQGTLVTVSS | 114 |
| | Light Chain | DVVMTQTPLSLPVTLGQPASISCKSSQSLLDLDGKTYLNWL QQRPGQSPKRLIYLVSKLDSGVPDRFTGSGSGTDFTLKISR VEAEDVGVYYCWQGTHFPFTFGQGTKVEIKR | 101 |
| 3016 | Heavy Chain | EVQLVESGGGLVKPGGSLRLSCAASGFTFSSYAMNWVRQAP GKGLEWVSTITTGGSHTYYADSVEGRFTISRDNAKNSLYLQ MNSLRAEDTAVYYCARQDGNFLMDYWGQGTLVTVSS | 115 |
| | Light Chain | DVVMTQTPLSLPVTLGQPASISCKSSQSLLDSDGKTYLNWL QQRPGQSPKRLIYLVSKLDSGVPDRFTGSGSGTDFTLKISR VEAEDVGVYYCWQGTHLPFTFGQGTKVEIKR | 116 |
| 3024 | Heavy Chain | EVQLVESGGGLVKPGGSLRLSCAASGFTFSSYAMSWVRQAP GKGLEWVSTITTGGSYTYYADSVQGRFTISRDNAKNSLYLQ MNSLRAEDTAVYYCARQDGNFLMDYWGQGTLVTVSS | 117 |
| | Light Chain | DVVMTQTPLSLPVTLGQPASISCKSSQSLLDSDGKTYLNWL QQRPGQSPKRLIYLVSKLDSGVPDRFTGSGSGTDFTLKISR VEAEDVGVYYCWQGTHLPFTFGQGTKVEIKR | 116 |
| 3115 | Heavy Chain | EVQLVESGGGLVKPGGSLRLSCAASGFTFSSYAMNWVRQAP GKGLEWVGTITTGGSHTYYADSVDGRFTISRDNAKNSLYLQ MNSLRAEDTAVYYCARQDGNFLMDYWGQGTLVTVSS | 117 |

TABLE 19-continued

| Clones | Variable regions | Amino acid sequences | SEQ ID NOS: |
|---|---|---|---|
| | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 3120 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGYFLMDYWGQGTLVTVSS | 118 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 3131 | Heavy Chain | EVQLVESGGGLVKPGGSLRLSCAASGFTFSSYAMSWVRQAP GKGLEWVSTITTGGSYTYYADSVQGRFTISRDNAKNSLYLQ MNSLRAEDTAVYYCARQDGQFLMDYWGQGTLVTVSS | 119 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 3203 | Heavy Chain | EVQLVESGGGLVKPGGSLRLSCAASGFTFSSYAMSWVRQAP GKGLEWVSTITTGGSYTYYADSVEGRFTISRDNAKNSLYLQ MNSLRAEDTAVYYCARQDGNFLMDYWGQGTLVTVSS | 120 |
| | Light Chain | DVVMTQTPLSLPVTLGQPASISCKSSQSLLDLDGKTYLNWL QQRPGQSPKRLIYLVSKLDSGVPDRFTGSGSGTDFTLKISR VEAEDVGVYYCWQGTHFPFTFGQGTKVEIKR | 101 |
| 3241 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGNFLMDYWGQGTLVTVSS | 25 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 4011 | Heavy Chain | EVQLVESGGGLVKPGGSLRLSCAASGFTFYSYAMNWVRQAP GKGLEWVSTITTGGSHTYYADSVEGRFTISRDNAKNSLYLQ MNSLRAEDTAVYYCARQDGNFLMDYWGQGTLVTVSS | 121 |
| | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHLPFTFGQGTKVEIKR | 122 |
| 4017 | Heavy Chain | EVQLVESGGGLVKPGGSLRLSCAASGFTFSSYAMNWVRQAP GKGLEWVGTITTGGSYTYYADSVQGRFTISRDNAKNSLYLQ MNSLRAEDTAVYYCARQDGYFLMDYWGQGTLVTVSS | 123 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 4034 | Heavy Chain | EVQLVESGGGLVKPGGSLRLSCAASGFTFSSYAMNWVRQAP GKGLEWVSTITTGGSHTYYADSVEGRFTISRDNAKNSLYLQ MNSLRAEDTAVYYCARQDGYFLMDYWGQGTLVTVSS | 124 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 4041 | Heavy Chain | EVQLVESGGGLVKPGGSLRLSCAASGFTFSSYAMSWVRQAP GKGLEWVSTITTGGSHTYYADSVEGRFTISRDNAKNSLYLQ MNSLRAEDTAVYYCARQDGYFLMDYWGQGTLVTVSS | 125 |
| | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 4141 | Heavy Chain | EVQLVESGGGLVKPGGSLRLSCAASGFTFSSYAMNWVRQAP GKGLEWVGTITTGGSHTYYADSVEGRFTISRDNAKNSLYLQ MNSLRAEDTAVYYCARQDGYFLMDYWGQGTLVTVSS | 126 |
| | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |

TABLE 19-continued

| Clones | Variable regions | Amino acid sequences | SEQ ID NOS: |
|---|---|---|---|
| 4146 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGYFLMDYWGQGTLVTVSS | 127 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 4206 | Heavy Chain | EVQLVESGGGLVKPGGSLRLSCAASGFTFSSYAMNWVRQAP GKGLEWVSTITTGGSHTYYADSVEGRFTISRDNAKNSLYLQ MDSLRAEDTAVYYCARQDGNFLMDYWGQGTLVTVSS | 128 |
| | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHLPFTFGQGTKVEIKR | 122 |
| 4208 | Heavy Chain | EVQLVESGGGLVKSGGSLRLSCAASGFTFSSYAMSWVRQAP GKGLEWVGTITTGGSYTYYADSVQGRFTISRDNAKNSLYLQ MNSLRAEDTAVYYCARQDGNFLMDYWGQGTLVTVSS | 129 |
| | Light Chain | DVVMTQTPLSLPVTLGQPASISCKSSQSLLDTDGKTYLNWL QQRPGQSPKRLIYLVSKLDSGVPDRFTGSGSGTDFTLKISR VEAEDVGVYYCWQGTHFPFTFGQGTKVEIKR | 130 |
| 4278 | Heavy Chain | EVQLVESGGGLVKPGGSLRLSCAASGFTFSKYAMNWFRQAP GKGLEWVSTITLGGSYTYYADSVDGRFTISRDNAKNSLYLQ MNSLRAEDTAVYYCARQYLDGNFLMDYWGQGTLVTVSS | 131 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 4287 | Heavy Chain | EVQLVESGGGLVKPGGSLRLSCAASGFTFSKYAMNWFRQAP GKGLEWVSTITTGGSYTYYADSVEGRFTISRDNAKNSLYLQ MNSLRAEDTAVYYCARQHPYGNFLMDYWGQGTLVTVSS | 132 |
| | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 1 | Heavy Chain | EVQLVESGGGLVKPGGSLRLSCAASGFTFSSYAMNWVRQAP GKGLEWVGTITTGGSYTYYADSVDGRFTISRDNAKNSLYLQ MNSLRAEDTAVYYCARQDGNFLMDYWGQGTLVTVSS | 99 |
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQGTHFPFTFGQGTKVEIKR | 22 |
| 2 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGNFLMDYWGQGTLVTVSS | 25 |
| | Light Chain | DVVMTQTPLSLPVTLGQPASISCKSSPSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 3 | Heavy Chain | EVQLVESGGGLVKPGGSLRLSCAASGFTFSSYAMNWVRQAP GKGLEWVGTITTGGSHTYYADSVDGRFTISRDNAKNSLYLQ MNSLRAEDTAVYYCARQDGNFLMDYWGQGTLVTVSS | 117 |
| | Light Chain | DVVMTQTPLSLPVTLGQPASISCKSSPSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 4 | Heavy Chain | EVQLVESGGGLVKPGGSLRLSCAASGFTFSSYAMNWVRQAP GKGLEWVGTITTGGSHTYYADSVEGRFTISRDNAKNSLYLQ MNSLRAEDTAVYYCARQDGNFLMDYWGQGTLVTVSS | 133 |
| | Light Chain | DVVMTQTPLSLPVTLGQPASISCKSSPSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 5 | Heavy Chain | EVQLVESGGGLVKPGGSLRLSCAASGFTFSSYAMNWVRQAP GKGLEWVSTITTGGSYTYYADSVDGRFTISRDNAKNSLYLQ MNSLRAEDTAVYYCARQDGNFLMDYWGQGTLVTVSS | 95 |

TABLE 19-continued

| Clones | Variable regions | Amino acid sequences | SEQ ID NOS: |
|---|---|---|---|
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQGTHFPFTFGQGTKVEIKR | 22 |
| 6 | Heavy Chain | EVQLVESGGGLVKPGGSLRLSCAASGFTFSSYAMNWVRQAP GKGLEWVGTITTGGSYTYYADSVEGRFTISRDNAKNSLYLQ MNSLRAEDTAVYYCARQDGNFLMDYWGQGTLVTVSS | 134 |
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQGTHFPFTFGQGTKVEIKR | 22 |
| 7 | Heavy Chain | EVQLVESGGGLVKPGGSLRLSCAASGFTFSSYAMNWVRQAP GKGLEWVGTITTGGSYTYYADSVDGRFTISRDNAKNSLYLQ MNSLRAEDTAVYYCARQDGNFLMDYWGQGTLVTVSS | 99 |
| | Light Chain | DVVMTQTPLSLPVTLGQPASISCKSSPSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 8 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGNFLMDYWGQGTLVTVSS | 25 |
| | Light Chain | DVVMTQTPLSLPVTLGQPASISCKSSPSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 9 | Heavy Chain | EVQLVESGGGLVKPGGSLRLSCAASGFTFSSYAMNWVRQAP GKGLEWVGTITTGGSYTYYADSVQGRFTISRDNAKNSLYLQ MNSLRAEDTAVYYCARQDGNFLMDYWGQGTLVTVSS | 135 |
| | Light Chain | DVVMTQTPLSLPVTLGQPASISCKSSPSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 10 | Heavy Chain | EVQLVESGGGLVKPGGSLRLSCAASGFTFSSYAMNWVRQAP GKGLEWVSTITTGGSYTYYADSVQGRFTISRDNAKNSLYLQ MNSLRAEDTAVYYCARQDGNFLMDYWGQGTLVTVSS | 110 |
| | Light Chain | DVVMTQTPLSLPVTLGQPASISCKSSPSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| 11 | Heavy Chain | EVQLVESGGGLVKPGGSLRLSCAASGFTFSSYAMNWVRQAP GKGLEWVGTITTGGSYTYYADSVEGRFTISRDNAKNSLYLQ MNSLRAEDTAVYYCARQDGNFLMDYWGQGTLVTVSS | 136 |
| | Light Chain | DVVMTQTPLSLPVTLGQPASISCKSSPSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 12 | Heavy Chain | EVQLVESGGGLVKPGGSLRLSCAASGFTFSSYAMNWVRQAP GKGLEWVGTITTGGSHTYYADSVEGRFTISRDNAKNSLYLQ MNSLRAEDTAVYYCARQDGHFLMDYWGQGTLVTVSS | 137 |
| | Light Chain | DVVMTQTPLSLPVTLGQPASISCKSSPSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 13 | Heavy Chain | EVQLVESGGGLVKPGGSLRLSCAASGFTFSSYAMNWVRQAP GKGLEWVGTITTGGSHTYYADSVEGRFTISRDNAKNSLYLQ MNSLRAEDTAVYYCARQDGNFLMDYWGQGTLVTVSS | 138 |
| | Light Chain | DVVMTQTPLSLPVTLGQPASISCKSSPSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| 14 | Heavy Chain | EVQLVESGGGLVKPGGSLRLSCAASGFTFSKYAMNWFRQAP GKGLEWVSTITLGGSYTYYADSVDGRFTISRDNAKNSLYLQ MNSLRAEDTAVYYCARQYLDGNFLMDYWGQGTLVTVSS | 131 |
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQGTYFPFTFGQGTKVEIKR | 139 |

TABLE 19-continued

| Clones | Variable regions | Amino acid sequences | SEQ ID NOS: |
|---|---|---|---|
| 15 | Heavy Chain | EVQLVESGGGLVKPGGSLRLSCAASGFTFS<u>KY</u>AMNW<u>F</u>RQAP GKGLEWVSTITTGGSYTYYADSVEGRFTISRDNAKNSLYLQ MNSLRAEDTAVYYCARQ<u>HPY</u>GNFLMDYWGQGTLVTVSS | 132 |
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQG<u>FY</u>FPFTFGQGTKVEIKR | 140 |
| 16 | Heavy Chain | EVQLVESGGGLVKPGGSLRLSCAASGFTFS<u>H</u>YAMTWVRQAP GKGLEWVSTITTGGS<u>H</u>TYYADSVEGRFTISRDNAKNSLYLQ MNSLRAEDTAVYYCARQDGNFLMDYWGQGTLVTVSS | 141 |
| | Light Chain | DVVMTQTPLSLPVTLGQPASISCKSSPSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |
| 17 | Heavy Chain | EVQLVESGGGLVKPGGSLRLSCAASGFTFSSYAMTWVRQAP GKGLEWVSTITTGGS<u>H</u>TYYADSV<u>Q</u>GRFTISRDNAKNSLYLQ MNSLRAEDTAVYYCARQDGNFLMDYWGQGTLVTVSS | 142 |
| | Light Chain | DVVMTQTPLSLPVTLGQPASISCKSSPSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |
| 18 | Heavy Chain | EVQLVESGGGLVKPGGSLRLSCAASGFTFS<u>H</u>YAMTWVRQAP GKGLEWVSTITTGGS<u>H</u>TYYADSV<u>D</u>GRFTISRDNAKNSLYLQ MNSLRAEDTAVYYCARQDGNFLMDYWGQGTLVTVSS | 143 |
| | Light Chain | DVVMTQTPLSLPVTLGQPASISCKSSPSLLD<u>I</u>DGKTYLNWL QQRPGQSPKRLIYLVSKLDSGVPDRFTGSGSGTDFTLKISR VEAEDVGVYYCWQGTHFPFTFGQGTKVEIKR | 96 |
| 19 | Heavy Chain | EVQLVESGGGLVKPGGSLRLSCAASGFTFSQYAMNWVRQAP GKGLEWVSTIT<u>KK</u>GS<u>F</u>TYYADSV<u>D</u>GRFTISRDNAKNSLYLQ MNSLRAEDTAVYYCARQDG<u>E</u>FLMDYWGQGTLVTVSS | 144 |
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQGTHFPFTFGQGTKVEIKR | 22 |
| 20 | Heavy Chain | EVQLVESGGGLVKPGGSLRLSCAASGFTFSQYAMNWVRQAP GKGLEWVSTI<u>KK</u>GGS<u>F</u>TYYADSVDGRFTISRDNAKNSLYLQ MNSLRAEDTAVYYCARQDG<u>E</u>FLMDYWGQGTLVTVSS | 145 |
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQGTHFPFTFGQGTKVEIKR | 22 |
| 21 | Heavy Chain | EVQLVESGGGLVKPGGSLRLSCAASGFTFSSYAMNWVRQAP GKGLEWVSTIT<u>K</u>GGSYTYYADSVDGRFTISRDNAKNSLYLQ MNSLRAEDTAVYYCARQDGNFLMDYWGQGTLVTVSS | 146 |
| | Light Chain | DVVMTQTPLSLPVTLGQPASISCKSSPSLLDSDGKTYLNWL QQRPGQSPKRLIYLVSKLDSGVPDRFTGSGSGTDFTLKISR VEAEDVGVYYCWQGTHFPFTFGQGTKVEIKR | 22 |
| 22 | Heavy Chain | EVQLVESGGGLVKPGGSLRLSCAASGFTFSSYAMNWVRQAP GKGLEWVSTITTGGS<u>H</u>TYYADSVEGRFTISRDNAKNSLYLQ MNSLRAEDTAVYYCARQDG<u>H</u>FLMDYWGQGTLVTVSS | 109 |
| | Light Chain | DVVMTQTPLSLPVTLGQPASISCKSSPSLLD<u>V</u>DGKTYLNWL QQRPGQSPKRLIYLVSKLDSGVPDRFTGSGSGTDFTLKISR VEAEDVGVYYCWQGT<u>Y</u>FPFTFGQGTKVEIKR | 147 |
| 23 | Heavy Chain | EVQLVESGGGLVKPGGSLRLSCAASGFTFS<u>H</u>YAMNWVRQAP GKGLEWVSTITTGGSYTYYADSVEGRFTISRDNAKNSLYLQ MNSLRAEDTAVYYCARQDG<u>H</u>FLMDYWGQGTLVTVSS | 148 |
| | Light Chain | DVVMTQTPLSLPVTLGQPASISCKSSPSLLD<u>I</u>DGKTYLNWL QQRPGQSPKRLIYLVSKLDSGVPDRFTGSGSGTDFTLKISR VEAEDVGVYYCWQGTH<u>L</u>PFTFGQGTKVEIKR | 108 |

TABLE 20

| Clones | Variable regions | CDR1 Amino acid sequences | SEQ ID NOS: | CDR2 Amino acid sequences | SEQ ID NOS: | CDR3 Amino acid sequences | SEQ ID NOS: |
|---|---|---|---|---|---|---|---|
| 1001 6 | Heavy Chain | SYAMN | 149 | TITTGGSYTYY ADSVDG | 150 | QDGNFLMDY | 151 |
| | Light Chain | KSSQSLLDID GKTYLN | 152 | LVSKLDS | 153 | WQGTHFPF | 154 |
| 1015 7 | Heavy Chain | SYAMN | 149 | TITTGGSHTYY ADSVEG | 155 | QDGNFLMDY | 151 |
| | Light Chain | KSSQSLLDID GKTYLN | 152 | LVSKLDS | 153 | WQGTHFPF | 154 |
| 1021 8 | Heavy Chain | SYAMN | 149 | TITTGGSYTYY ADSVDG | 150 | QDGHFLMDY | 156 |
| | Light Chain | KSSQSLLDID GKTYLN | 152 | LVSKLDS | 153 | WQGTHFPF | 154 |
| 1023 6 | Heavy Chain | SYAMN | 149 | TITTGGSYTYY ADSVDG | 150 | QDGNFLMDY | 151 |
| | Light Chain | KSSQSLLDID GKTYLN | 152 | LVSKLDS | 153 | WQGTHFPF | 154 |
| 1024 9 | Heavy Chain | SYAMS | 157 | TITTGGSYTYY ADSVDG | 150 | QDGNFLMDY | 151 |
| | Light Chain | KSSQSLLDLD GKTYLN | 158 | LVSKLDS | 153 | WQGTHFPF | 154 |
| 1104 | Heavy Chain | SYAMN | 149 | TITTGGSHTYY ADSVQG | 159 | QDGNFLMDY | 151 |
| | Light Chain | KSSQSLLDVD GKTYLN | 160 | LVSKLDS | 153 | WQGTHFPF | 154 |
| 1123 11 | Heavy Chain | SYAMN | 149 | TITTGGSHTYY ADSVEG | 155 | QDGHFLMDY | 156 |
| | Light Chain | KSSQSLLDID GKTYLN | 152 | LVSKLDS | 153 | WQGTHFPF | 154 |
| 1202 6 | Heavy Chain | SYAMN | 149 | TITTGGSYTYY ADSVDG | 150 | QDGNFLMDY | 151 |
| | Light Chain | KSSQSLLDID GKTYLN | 152 | LVSKLDS | 153 | WQGTHFPF | 154 |
| 1208 12 | Heavy Chain | SYAMN | 149 | TITTGGSHTYY ADSVEG | 155 | QDGHFLMDY | 156 |
| | Light Chain | KSSQSLLDVD GKTYLN | 160 | LVSKLDS | 153 | WQGTYLPF | 161 |
| 1214 13 | Heavy Chain | SYAMN | 149 | TITTGGSYTYY ADSVEG | 162 | QDGNFLMDY | 151 |
| | Light Chain | KSSQSLLDVD GKTYLN | 160 | LVSKLDS | 153 | WQGTHFPF | 154 |
| 1216 | Heavy Chain | HYAMN | 163 | TITTGGSYTYY ADSVEG | 162 | QDGHFLMDY | 156 |
| | Light Chain | KSSQSLLDID GKTYL | 152 | LVSKLDS | 153 | WQGTHLPF | 164 |
| 1223 | Heavy Chain | SYAMN | 149 | TITTGGSYTYY ADSVEG | 162 | QDGHFLMDY | 156 |
| | Light Chain | KSSQSLLDID GKTYLN | 152 | LVSKLDS | 153 | WQGTHFPF | 154 |
| 1224 | Heavy Chain | SYAMS | 157 | TITTGGSYTYY ADSVDG | 150 | QDGNFLMDY | 151 |
| | Light Chain | KSSQSLLDID GKTYLN | 152 | LVSKLDS | 153 | WQGTHFPF | 154 |
| 1232 | Heavy Chain | SYAMN | 149 | TITTGGSYTYY ADSVDG | 150 | QDGHFLMDY | 156 |
| | Light Chain | KSSQSLLDVD GKTYLN | 160 | LVSKLDS | 153 | WQGTHFPF | 154 |
| 1234 | Heavy Chain | SYAMN | 149 | TITTGGSYTYY ADSVQG | 165 | QDGNFLMDY | 151 |
| | Light Chain | KSSQSLLDID GKTYLN | 152 | LVSKLDS | 153 | WQGTHFPF | 154 |

TABLE 20-continued

| Clones | Variable regions | CDR1 Amino acid sequences | SEQ ID NOS: | CDR2 Amino acid sequences | SEQ ID NOS: | CDR3 Amino acid sequences | SEQ ID NOS: |
|---|---|---|---|---|---|---|---|
| 1238 | Heavy Chain | SYAMN | 149 | TITTGGSYTYY ADSVEG | 162 | QDG<u>H</u>FLMDY | 156 |
| | Light Chain | KSSQSLLD<u>VD</u> GKTYLN | 160 | LVSKLDS | 153 | WQGTHFPF | 154 |
| 1243 | Heavy Chain | SYAMN | 149 | TITTGGS<u>H</u>TYY ADSV<u>H</u>G | 166 | QDG<u>H</u>FLMDY | 156 |
| | Light Chain | KSSQSLLD<u>I</u>D GKTYLN | 152 | LVSKLDS | 153 | WQGTHFPF | 154 |
| 1248 | Heavy Chain | SYAMN | 149 | TITTGGS<u>H</u>TYY ADSV<u>D</u>G | 167 | QDG<u>H</u>FLMDY | 156 |
| | Light Chain | KSSQSLLD<u>I</u>D GKTYLN | 152 | LVSKLDS | 153 | WQGTHFPF | 154 |
| 3007 | Heavy Chain | SYAMN | 149 | TIT<u>L</u>GGSYTYY ADSV<u>Q</u>G | 168 | QDGNFLMDY | 151 |
| | Light Chain | KSSQSLLD<u>L</u>D GKTYLN | 158 | LVSKLDS | 153 | WQGTHFPF | 154 |
| 3016 | Heavy Chain | SYAMN | 149 | TITTGGS<u>H</u>TYY ADSVEG | 155 | QDGNFLMDY | 151 |
| | Light Chain | KSSQSLLD<u>SD</u> GKTYLN | 169 | LVSKLDS | 153 | WQGTH<u>L</u>PF | 164 |
| 3024 | Heavy Chain | SYAM<u>S</u> | 157 | TITTGGSYTYY ADSV<u>Q</u>G | 165 | QDGNFLMDY | 151 |
| | Light Chain | KSSQSLLD<u>SD</u> GKTYLN | 169 | LVSKLDS | 153 | WQGTH<u>L</u>PF | 164 |
| 3115 | Heavy Chain | SYAMN | 149 | TITTGGS<u>H</u>TYY ADSV<u>D</u>G | 167 | QDGNFLMDY | 151 |
| | Light Chain | KSSQSLLD<u>VD</u> GKTYLN | 160 | LVSKLDS | 153 | WQGTHFPF | 154 |
| 3120 | Heavy Chain | SYAMN | 149 | TITTGGSYTYY ADSVEG | 162 | QDG<u>Y</u>FLMDY | 170 |
| | Light Chain | KSSQSLLD<u>I</u>D GKTYLN | 152 | LVSKLDS | 153 | WQGTHFPF | 154 |
| 3131 | Heavy Chain | SYAM<u>S</u> | 157 | TITTGGSYTYY ADSV<u>Q</u>G | 165 | QDG<u>Q</u>FLMDY | 171 |
| | Light Chain | KSSQSLLD<u>I</u>D GKTYLN | 152 | LVSKLDS | 153 | WQGTHFPF | 154 |
| 3203 | Heavy Chain | SYAM<u>S</u> | 157 | TITTGGSYTYY ADSVEG | 162 | QDGNFLMDY | 151 |
| | Light Chain | KSSQSLLD<u>L</u>D GKTYLN | 158 | LVSKLDS | 153 | WQGTHFPF | 154 |
| 3241 | Heavy Chain | SYAMN | 149 | TITTGGSYTYY ADSVEG | 162 | QDGNFLMDY | 151 |
| | Light Chain | KSSQSLLD<u>I</u>D GKTYLN | 152 | LVSKLDS | 153 | WQGTHFPF | 154 |
| 4011 | Heavy Chain | SYAMN | 149 | TITTGGS<u>H</u>TYY ADSVEG | 155 | QDGNFLMDY | 151 |
| | Light Chain | KSSQSLLD<u>VD</u> GKTYLN | 160 | LVSKLDS | 153 | WQGTH<u>L</u>PF | 164 |
| 4017 | Heavy Chain | SYAMN | 149 | TITTGGSYTYY ADSV<u>Q</u>G | 165 | QDG<u>Y</u>FLMDY | 131 |
| | Light Chain | KSSQSLLD<u>I</u>D GKTYLN | 152 | LVSKLDS | 153 | WQGTHFPF | 154 |
| 4034 | Heavy Chain | SYAMN | 149 | TITTGGS<u>H</u>TYY ADSVEG | 155 | QDG<u>Y</u>FLMDY | 131 |
| | Light Chain | KSSQSLLD<u>I</u>D GKTYLN | 152 | LVSKLDS | 153 | WQGTHFPF | 154 |
| 4041 | Heavy Chain | SYAM<u>S</u> | 157 | TITTGGS<u>H</u>TYY ADSVEG | 155 | QDG<u>Y</u>FLMDY | 131 |
| | Light Chain | KSSQSLLD<u>VD</u> GKTYL | 160 | LVSKLDS | 153 | WQGTHFPF | 154 |

TABLE 20-continued

| Clones | Variable regions | CDR1 Amino acid sequences | SEQ ID NOS: | CDR2 Amino acid sequences | SEQ ID NOS: | CDR3 Amino acid sequences | SEQ ID NOS: |
|---|---|---|---|---|---|---|---|
| 4141 | Heavy Chain | SYAMN | 149 | TITTGGS<u>H</u>TYY ADSVEG | 155 | QDG<u>Y</u>FLMDY | 131 |
| | Light Chain | KSSQSLLD<u>VD</u> GKTYLN | 160 | LVSKLDS | 153 | WQGTHFPF | 154 |
| 4146 | Heavy Chain | SYAMN | 149 | TITTGGSYTYY ADSVEG | 162 | QDG<u>Y</u>FLMDY | 131 |
| | Light Chain | KSSQSLLD<u>I</u>D GKTYLN | 152 | LVSKLDS | 153 | WQGTHFPF | 154 |
| 4206 | Heavy Chain | SYAMN | 149 | TITTGGS<u>H</u>TYY ADSVEG | 155 | QDGNFLMDY | 151 |
| | Light Chain | KSSQSLLD<u>VD</u> GKTYLN | 160 | LVSKLDS | 153 | WQGTHL<u>P</u>F | 164 |
| 4208 | Heavy Chain | SYAM<u>S</u> | 157 | TITTGGSYTYY ADSV<u>Q</u>G | 165 | QDGNFLMDY | 151 |
| | Light Chain | KSSQSLLD<u>T</u>D GKTYLN | 171 | LVSKLDS | 153 | WQGTHFPF | 154 |
| 4278 | Heavy Chain | <u>K</u>YAMN | 172 | TIT<u>L</u>GGSYTYY ADSVDG | 173 | Q<u>YL</u>DGNFLMDY | 174 |
| | Light Chain | KSSQSLLD<u>I</u>D GKTYLN | 152 | LVSKLDS | 153 | WQGTHFPF | 154 |
| 4287 | Heavy Chain | <u>K</u>YAMN | 172 | TITTGGSYTYY ADSVEG | 162 | Q<u>HPY</u>GNFLMDY | 175 |
| | Light Chain | KSSQSLLD<u>I</u>D GKTYLN | 152 | LVSKLDS | 153 | WQGTHFPF | 154 |
| 1 | Heavy Chain | SYAMN | 149 | TITTGGSYTYY ADSVDG | 150 | QDGNFLMDY | 151 |
| | Light Chain | KSSPSLLDSD GKTYLN | 176 | LVSKLDS | 153 | WQGTHFPF | 154 |
| 2 | Heavy Chain | SYAMN | 149 | TITTGGSYTYY ADSVEG | 162 | QDGNFLMDY | 151 |
| | Light Chain | KSSPSLLD<u>I</u>D GKTYLN | 177 | LVSKLDS | 153 | WQGTHFPF | 154 |
| 3 | Heavy Chain | SYAMN | 149 | TITTGGS<u>H</u>TYY ADSVDG | 167 | QDGNFLMDY | 151 |
| | Light Chain | KSSPSLLD<u>V</u>D GKTYLN | 178 | LVSKLDS | 153 | WQGTHFPF | 154 |
| 4 | Heavy Chain | SYAMN | 149 | TITTGGS<u>H</u>TYY ADSVEG | 155 | QDGNFLMDY | 151 |
| | Light Chain | KSSPSLLD<u>V</u>D GKTYLN | 178 | LVSKLDS | 153 | WQGTHFPF | 154 |
| 5 | Heavy Chain | SYAMN | 149 | TITTGGSYTYY ADSVDG | 150 | QDGNFLMDY | 151 |
| | Light Chain | KSSPSLLDSD GKTYLN | 176 | LVSKLDS | 153 | WQGTHFPF | 154 |
| 6 | Heavy Chain | SYAMN | 149 | TITTGGSYTYY ADSVEG | 162 | QDGNFLMDY | 151 |
| | Light Chain | KSSPSLLDSD GKTYLN | 176 | LVSKLDS | 153 | WQGTHFPF | 154 |
| 7 | Heavy Chain | SYAMN | 149 | TITTGGSYTYY ADSVDG | 150 | QDGNFLMDY | 151 |
| | Light Chain | KSSPSLLD<u>V</u>D GKTYLN | 178 | LVSKLDS | 153 | WQGTHFPF | 154 |
| 8 | Heavy Chain | SYAMN | 149 | TITTGGSYTYY ADSVEG | 162 | QDGNFLMDY | 151 |
| | Light Chain | KSSPSLLD<u>V</u>D GKTYLN | 178 | LVSKLDS | 153 | WQGTHFPF | 154 |
| 9 | Heavy Chain | SYAMN | 149 | TITTGGSYTYY ADSV<u>Q</u>G | 165 | QDGNFLMDY | 151 |
| | Light Chain | KSSPSLLD<u>V</u>D GKTYLN | 178 | LVSKLDS | 153 | WQGTHFPF | 154 |

TABLE 20-continued

| Clones | Variable regions | CDR1 Amino acid sequences | SEQ ID NOS: | CDR2 Amino acid sequences | SEQ ID NOS: | CDR3 Amino acid sequences | SEQ ID NOS: |
|---|---|---|---|---|---|---|---|
| 10 | Heavy Chain | SYAMN | 149 | TITTGGSYTYY ADSVQG | 165 | QDGNFLMDY | 151 |
|  | Light Chain | KSSPSLLDVD GKTYLN | 178 | LVSKLDS | 153 | WQGTHFPF | 154 |
| 11 | Heavy Chain | SYAMN | 149 | TITTGGSYTYY ADSVEG | 162 | QDGNFLMDY | 151 |
|  | Light Chain | KSSPSLLDID GKTYLN | 177 | LVSKLDS | 153 | WQGTHFPF | 154 |
| 12 | Heavy Chain | SYAMN | 149 | TITTGGSHTYY ADSVEG | 155 | QDGHFLMDY | 156 |
|  | Light Chain | KSSPSLLDID GKTYLN | 177 | LVSKLDS | 153 | WQGTHFPF | 154 |
| 13 | Heavy Chain | SYAMN | 149 | TITTGGSHTYY ADSVEG | 155 | QDGNFLMDY | 151 |
|  | Light Chain | KSSPSLLDID GKTYLN | 177 | LVSKLDS | 153 | WQGTHFPF | 154 |
| 14 | Heavy Chain | KYAMN | 172 | TITLGGSYTYY ADSVDG | 173 | QYLDGNFLMDY | 174 |
|  | Light Chain | KSSPSLLDSD GKTYLN | 176 | LVSKLDS | 153 | WQGTYFPF | 179 |
| 15 | Heavy Chain | KYAMN | 172 | TITTGGSYTYY ADSVEG | 162 | QHPYGNFLMDY | 175 |
|  | Light Chain | KSSPSLLDSD GKTYLN | 176 | LVSKLDS | 153 | WQGFYFPF | 180 |
| 16 | Heavy Chain | HYAMT | 181 | TITTGGSHTYY ADSVEG | 155 | QDGNFLMDY | 151 |
|  | Light Chain | KSSPSLLDID GKTYLN | 177 | LVSKLDS | 153 | WQGTHFPF | 154 |
| 17 | Heavy Chain | SYAMT | 182 | TITTGGSHTYY ADSVQG | 159 | QDGNFLMDY | 151 |
|  | Light Chain | KSSPSLLDID GKTYLN | 177 | LVSKLDS | 153 | WQGTHFPF | 154 |
| 18 | Heavy Chain | HYAMT | 181 | TITTGGSHTYY ADSVDG | 167 | QDGNFLMDY | 151 |
|  | Light Chain | KSSPSLLDID GKTYLN | 177 | LVSKLDS | 153 | WQGTHFPF | 154 |
| 19 | Heavy Chain | QYAMN | 183 | TITKKGSFTYY ADSVDG | 184 | QDGEFLMDY | 185 |
|  | Light Chain | KSSPSLLDSD GKTYLN | 176 | LVSKLDS | 153 | WQGTHFPF | 154 |
| 20 | Heavy Chain | QYAMN | 183 | TIKKGGSFTYY ADSVDG | 186 | QDGEFLMDY | 185 |
|  | Light Chain | KSSPSLLDSD GKTYLN | 176 | LVSKLDS | 153 | WQGTHFPF | 154 |
| 21 | Heavy Chain | SYAMN | 149 | TITKGGSYTYY ADSVDG | 187 | QDGNFLMDY | 151 |
|  | Light Chain | KSSPSLLDSD GKTYLN | 176 | LVSKLDS | 153 | WQGTHFPF | 154 |
| 22 | Heavy Chain | SYAMN | 149 | TITTGGSHTYY ADSVEG | 155 | QDGHFLMDY | 156 |
|  | Light Chain | KSSPSLLDVD GKTYLN | 178 | LVSKLDS | 153 | WQGTYFPF | 179 |
| 23 | Heavy Chain | HYAMN | 188 | TITTGGSYTYY ADSVEG | 162 | QDGHFLMDY | 156 |
|  | Light Chain | KSSPSLLDID GKTYLN | 177 | LVSKLDS | 153 | WQGTHLPF | 164 |

11-4: Cloning of IgG Gene of Clone 308-4 Antibody Mutant that is Anti-TFPI Antibody Obtained by Yeast Display The light-chain variable region gene of the 308-4 antibody mutant that is the anti-TFPI antibody obtained in Examples 11-2 and 11-3 were subjected to PCR using PrimeSTAR HS DNA polymerase (CAT.NO.R040B, Takara) together with a KpnI-containing forward primer (Table 21; SEQ ID NO: 189) and a reverse primer (Table 21; SEQ ID NO: 190). In addition, the kappa constant light region of the human antibody was subjected to PCR using a forward primer (Table 21; SEQ ID NO: 191) and a reverse primer (Table 21; SEQ ID NO: 192). The PCR was performed under the following conditions: 10 min at 94° C.; and then 30 cycles, each consisting of 15 sec at 94° C., 30 sec at 56° C. and 90 sec at 72° C.; and then 10 min at 72° C. The amplified genes were electrophoresed on 1% agarose gel to confirm the DNA bands having the expected size, and were isolated using a gel extraction kit. Next, the light-chain variable region and the light-chain constant region were mixed with each other at a ratio of 1:1, and the mixture was subjected to overlapping PCR using a forward primer (Table 20; SEQ ID NO: 189) and a reverse primer (Table 20; SEQ ID NO: 192) under the following conditions: 10 min at 94° C.; and then 30 cycles, each consisting of 15 sec at 94° C., 30 sec at 56° C. and 90 sec at 72° C.; followed by 10 min at 72° C. The amplified gene was electrophoresed on 1% agarose gel to confirm the DNA band having the expected size, and was isolated using a gel extraction kit. The isolated gene was treated with a KpnI (CAT.NO.R0142L,NEB) and HindIII (CAT.NO.R0104L, NEB) restriction enzymes at 37° C. for 12 hours, and then separated on 1% agarose gel. A pcIW plasmid vector was digested in the same manner and separated on agarose gel. Using T4 DNA ligase (Cat.No.M0203S, NEB), the isolated light-chain region gene was ligated into the NotI and HindIII sites of a linear pcIW vector. The ligation product was transformed into XL1-Blue bacteria (Electroporation-Competent Cells; Cat.No.200228, Stratagene), and the bacterial cells were plated on a carbenicillin-containing LB plate (Cat.No.LN004CA, NaraeBiotech) and cultured at 37° C. for 12 hours or more, and single colonies were selected from the plate and cultured. Next, a plasmid was isolated from the cells using a plasmid mini-kit (Cat.No.27405, QIAGEN) and identified by DNA sequencing.

The heavy-chain variable region was subjected to PCR using the heavy-chain variable region gene of the 308-4 antibody mutant as a template and PrimeSTAR HS DNA polymerase (Takara) together with a KpnI-containing reverse primer (Table 21; SEQ ID NO: 193) and an ApaI-containing reverse primer (Table 21; SEQ ID NO: 194). The PCR was performed under the following conditions: 2 min at 98° C.; and then 30 cycles, each consisting of 10 sec at 98° C., 10 sec at 58° C. and 30 sec at 72° C.; followed by 5 min at 72° C. The amplified gene was electrophoresed on 1% agarose gel to confirm the DNA band having the expected size, and was isolated using a gel extraction kit. Next, the three isolated genes were treated with KpnI and ApaI restriction enzymes at 37° C. for 4 hours. The gene treated with the restriction enzymes was separated on 1% agarose gel. A pCIW plasmid vector was also digested in the same manner and separated on agarose gel. Using T4 DNA ligase, the separated gene was ligated into the KpnI (CAT. NO.R0142L, NEB) and ApaI (CAT.NO.R0114L, NEB) sites of a linear pcIw vector containing the human heavy-chain constant region. The ligation product was transformed into XL1-Blue bacteria (Electroporation-Competent Cells; Stratagene), and the bacterial cells were plated on a carbenicillin-containing LB plate (Cat.No.LN004CA, NaraeBiotech) and cultured at 37° C. for 12 hours or more, and single colonies were selected from the plate and cultured. Then, a plasmid was isolated from the cells using a plasmid mini-kit (Cat.No.27405, QIAGEN), and DNA sequencing of the isolated plasmid was performed.

Table 21 below shows the primers used in IgG gene cloning of the clone 308-4 antibody mutant that is the anti-TFPI antibody obtained by yeast display.

TABLE 21

| Names | Nucleic acid sequences | SEQ ID NOS: |
|---|---|---|
| VH Fo | TGCTGTGGGTGAGTGGTACCTGTGGG GAA GTC CAG CTG GTG GAG TCT GGA GGT | 189 |
| VH Re | AGT GGG AAC ACG GAG GGC CCC TTG GTG CTG GCG GAG CTC ACA GTC ACC AGC GTG CC | 190 |
| VL Fo | TGCTGTGGGTGAGTGGTACCTGTGGG GAC GTG GTG ATG ACA CAG ACG CCG CTG | 191 |
| VL Re_CL overlap | GAT GAA CAC AGA AGG GGC AGC CAC GTG CGC TTT AAT TTC AAC CTT AGT GCC TTG GCC GAA CGT AAA | 192 |
| Ck Fo | ACG GTG GCT GCC CCT TCT GTG TTC ATC | 193 |
| Ck Re | GAT TGG ATC CAA GCT TAC TAG CAC TCA CCC CTG TTG AAA GAC TTA | 194 |

11-5: Production and Purification of Anti-TFPI 308-4 Clone Antibody Mutant IgG

In order to produce and purify the anti-TFPI clone antibody mutant cloned in Example 11-4, Expi293F™ cells were seeded at a concentration of 2.5×10⁶ cells/mL on one day before transfection. After 24 hours of culture (37° C., 8% CO₂, 125 rpm), Expi293™ Expression medium (Cat.No.A1435101, Gibco) was added to prepare 30 mL of the cells at a concentration of 2.5×10⁶ cells/mL (viability ≥95%). 30 µg of DNA (pcIw-anti-TFPI heavy chain: 15 µg, pcIw-anti-TFPI light chain: 15 µg) was diluted in OptiPro™SEM medium (Cat.No.12309019, Gibco) to a total volume of 1.5 mL and incubated at room temperature for 5 minutes. 80 µL of ExpiFectamine™293 reagent (Cat.No.A14524, Gibco) was added to 1.5 mL of OptiPro™SEM medium (Cat.No.12309019, Gibco) to a total volume of 1.5 mL, and then incubated at room temperature for minutes. After 5 minutes of incubation, 1.5 mL of the diluted DNA and 1.5 mL of the ExpiFectamine™ 293 reagent were mixed well with each other and incubated at room temperature for 20-30 minutes. Expi293F™ cells were treated with 3 mL of the mixture of the DNA and the ExpiFectamine™ 293 reagent. After 16-18 hours of suspension culture (37° C., 8% CO$_2$, 125 rpm), 150 μL of Expi-Fectamine™ 293 Enhancer 1 (Cat.No.A14524, Gibco) and 1.5 mL of ExpiFectamine™ 293 Enhancer 2 (Cat.No.A14524, Gibco) were added to the cells, followed by suspension culture for 5 days. After completion of the culture, the cells were centrifuged at 4000 rpm for 20 minutes to remove cell debris, and the supernatant was passed through a 0.22 μm filter. 100 μL of the protein A resin MabSelect Xtra (Cat.No.17-5269-02, GE Healthcare) was prepared per 30 mL of the culture medium, centrifuged at 1000 rpm for 2 minutes to remove the storage solution, and washed three times with 400 μL of protein A binding buffer (Cat.No.21007, Pierce) for each washing. Protein A resin was added to the prepared culture medium, followed by rotating incubation at room temperature for 30 minutes. The mixture of the culture medium and the resin was added to the Pierce spin column-snap cap (Cat.No.69725, Thermo), and extracted using the QIAvac 24 Plus (Cat.No.19413, QIAGEN) vacuum manifold so that only the resin remained in the column. The resin was washed with 5 mL of protein A binding buffer, and then resuspended in 200 μL of protein A elution buffer (Cat.No.21009, Pierce), after which it was incubated at room temperature for 2 minutes and eluted by centrifugation at 1000 rpm for 1 minute. The eluate was neutralized by addition of 2.5 μL of 1.5M Tris-HCl (pH 9.0). Elution was performed 4-6 times, and each fraction was quantified using Nanodrop 200C (Thermo Scientific). Fractions having the protein detected therein were collected, and the buffer was replaced with PBS (phosphate-buffered saline) buffer using 5 mL of 7K MWCO (Cat.No.0089892, Pierce) in Zeba Spin Desalting Columns. Next, electrophoresis (SDS-PAGE) of the protein was performed under reducing and non-reducing conditions to finally quantify the concentration of the antibody and verify the state of the antibody, and the antibody was stored at 4° C.

As a result, protein electrophoresis (SDS-PAGE) indicated that the anti-TFPI 308-4 clone antibody mutant was purified in a good state.

Example 12: Preparation of Anti-TFPI 308-4 Clone Affinity-Matured Antibody Using Phage Display Fab Library 12-1: Construction of Phage Display Fab Library In order to construct an Fab library, a heavy-chain variable region library was constructed, and then a light-chain variable region library was constructed. Specifically, for the PCR of heavy-chain variable region fragment 1, the heavy-chain variable region gene sequence of the anti-TFPI 308-4 clone was used as a template together with a forward primer (Table 18; SEQ ID NO: 40) and a reverse primer (Table 18; SEQ ID NOs: 41 to 48); for the PCR of heavy-chain variable region fragment 2, the heavy-chain variable region gene sequence of the anti-TFPI 308-4 clone was used as a template together with a forward primer (Table 18; SEQ ID NO: 49) and a reverse primer (Table 18; SEQ ID NOs: 50 to 61); and for the PCR of heavy-chain variable region fragment 2, the heavy-chain variable region gene sequence of the anti-TFPI 308-4 clone was used as a template together with a forward primer (Table 18; SEQ ID NO: 62) and a reverse primer (Table 18; SEQ ID NOs: 63 to 69). The PCR of each of the fragments was performed using AccuPower Pfu PCR PreMix (CAT.NO.K-2015, Bioneer) under the following conditions: 2 min at 95° C.; and then 30 cycles, each consisting of 30 sec at 95° C., 30 sec at 55° C. and 60 sec at 72° C.; followed by 10 min at 72° C. The amplified genes were electrophoresed on 1% agarose gel to confirm the DNA bands having the expected sizes, and was isolated using a gel extraction kit (QIAquick Gel Extraction Kit, QIAGEN). The isolated heavy-chain variable region fragment genes were adjusted to a molar ratio of 1:1:1 and used as a template together with a forward primer (Table 18; SEQ ID NO: 70) and a reverse primer (Table 18; SEQ ID NO: 71) in PCR. The PCR of the amplified genes was performed using Takara primer star PCR premix (Takara) under the following conditions: 2 min at 95° C.; and then 20 cycles, each consisting of 10 sec at 95° C., 20 sec at 55° C. and 30 sec at 72° C.; followed by 5 min at 72° C. The amplified gene was electrophoresed on 1% agarose gel to confirm the DNA band having the expected size, and was isolated using a gel extraction kit (QIAquick Gel Extraction Kit, QIAGEN), thereby obtaining a heavy-chain variable region gene. The obtained gene was treated with XhoI (CAT.No.R0146L, NEB) and ApaI (Cat.No.R0114L, NEB) restriction enzymes at 37° C. for 4 hours. The gene was separated on 1% agarose gel. Using T4 DNA ligase (Cat.No.M0203S, NEB), the separated gene was ligated into the XhoI and ApaI sites of a linear pComb3x vector containing the 308-4 light-chain variable-constant regions. The ligation product was transformed into XL1-Blue bacteria (Electroporation-competent cells; Cat.No.200228, Stratagene), and then the bacterial cells were cultured in 300 ml of LB medium at 37° C. at 220 rpm for 1 hour, and then treated with 150 μL of Carbenicillin and 300 μL of tetracycline, followed by suspension culture at 37° C. at 220 rpm for 12 hours or more. Next, the constructed heavy-chain variable region library plasmid was isolated using a Midi prep kit (CAT.No.12143, QIAGEN). To determine the size of the library, 100 μl of the culture medium was collected at 1 hour after transformation, and plated on a Carbenicillin-containing LB plate (Cat.No.LN004CA, NaraeBiotech) by a serial dilution method, after which it was incubated at 37° C. for 12 hours or more, and then subjected to colony counting.

For the PCR of light-chain variable region fragment 1, the light-chain variable region gene sequence of the anti-TFPI 308-4 clone was used as a template together with a forward primer (Table 18; SEQ ID NO: 72) and a reverse primer (Table 18; SEQ ID NOs: 73 to 82); and for the PCR of light-chain variable region fragment 2, the light-chain variable region gene sequence of the anti-TFPI 308-4 clone was used as a template together with a forward primer (Table 18; SEQ ID NO: 83) and a reverse primer (Table 18; SEQ ID NOs: 84 to 87). The PCR of each of the fragments was performed using AccuPower Pfu PCR PreMix (CAT. NO. K-2015, Bioneer) under the following conditions: 2 min at 95° C.; and then 30 cycles, each consisting of 30 sec at 95° C., 30 sec at 55° C. and 60 sec at 72° C.; followed by 10 min at 72° C. The amplified genes were electrophoresed on 1% agarose gel to confirm the DNA bands having the expected sizes, and were isolated using a gel extraction kit (QIAquick Gel Extraction Kit, QIAGEN). The light-chain variable region fragment genes were adjusted to a molar ratio of 1:1 and used as a template together with a forward primer (Table 18; SEQ ID NO: 91) and a reverse primer (Table 18; SEQ ID NO: 92) in PCR. The PCR of the amplified genes was performed using Takara primer star PCR premix (Takara) under the following conditions: 2 min at 95° C.; and then 20 cycles, each consisting of 10 sec at 95° C., 30 sec at 55° C.

and 40 sec at 72° C.; followed by 5 min at 72° C. The amplified gene was electrophoresed on 1% agarose gel to confirm the DNA band having the expected size, and was isolated using a gel extraction kit (QIAquick Gel Extraction Kit, QIAGEN), thereby obtaining a light-chain variable region gene. The obtained gene was treated with NruI (CAT.No.R0192L, NEB) and XbaI (Cat.No.R0145L, NEB) restriction enzymes at 37° C. for 4 hours. The gene treated with the restriction enzymes was separated on 1% agarose gel. Using T4 DNA ligase (Cat.No.M0203S, NEB), the separated gene was ligated into the NruI and XbaI sites of a linear pComb3x library containing the 308-4 heavy-chain variable region library. The ligation product was transformed into XL1-Blue bacteria (Electroporation-competent cells; Cat.No.200228, Stratagene), and then the bacterial cells were cultured in 300 ml of LB medium at 37° C. at 220 rpm for 1 hour, and then treated with 150 µL of carbencillin and 300 µL of tetracycline, followed by shake culture at 37° C. at 220 rpm for 1 hour. Next, the cells were treated with 4.5 mL ($10^{11}$ pfu) of VCS M13 helper phage, and then shake-cultured at 37° C. at 220 rpm for 1 hour. Next, the cells were treated with 300 µL of kanamycin and 300 µL of carbenicillin and cultured overnight at 37° C. at 220 rpm. On the next day, the cultured cells were centrifuged at 4000 rpm for 20 minutes, and the supernatant was transferred onto a fresh container. To precipitate the phage, 5×PEG/NaCl was added to the supernatant at 1×, and then allowed to stand on ice for 30 minutes or more. The precipitated phage was centrifuged at 8000 rpm for 30 minutes. The supernatant was discarded, and the precipitated phage was resuspended in 10 mL of PBS. To remove cell debris, the phage suspended in 10 mL of PBS was centrifuged at 14,000 rpm for 10 minutes, and the supernatant was isolated and stored at 4° C. To determine the size of the library, 100 µl of the culture medium was collected at 1 hour after transformation, and plated on a Carbenicillin-containing LB plate (NaraeBiotech) by a serial dilution method, after which it was incubated at 37° C. for 12 hours or more, and then subjected to colony counting.

12-2: Selection of Anti-TFPI Antibody Mutant 1 mL of the human recombinant protein TFPI was added to a solid phase polystyrene tube (Cat.No.444202, Nunc) at a concentration of 1 µg/ml, and the tube was coated with the protein at 4° C. for 12 hours or more and washed three times with 5 mL of 0.05% PBST. The TFPI-coated Immuno tube was blocked with 5 mL of 1% BSA/PBS at room temperature for 2 hours. The blocking buffer was removed from the Immuno tube, and then the tube was treated with the phage library and incubated at room temperature for 2 hours. Next, the tube was washed four times with 5 mL of PBST. The Immuno tube was treated with 1 mL glycine (pH 2.0) elution buffer and incubated at room temperature for 10 minutes, and the eluted phage of the supernatant was neutralized by addition of 100 µl of 1.5M Tris-Cl (pH 8.8). 10 mL of XLI-Blue electroporation-competent cells (OD600=0.8-1.0) cultured for about 2 hours were treated with the neutralized phage. After infection at room temperature for 30 minutes, 10 mL of SB, 20 µl of tetracycline (50 mg/mL) and 10 µl of carbenicillin (100 mg/mL) were added to 10 mL of the infected XLI-Blue electroporation-competent cells which were then shake-cultured at 200 rpm at 37° C. for 1 hour. Then, the cells were treated with 1 mL of VCSM13 helper phage (>$10^{11}$ pfu/mL) and shake-cultured at 200 rpm at 37° C. for 1 hour. After 1 hour of culture, the cells were treated with 80 mL of SB, 100 µl of kanamycin and 100 µl of carbenicillin (100 mg/mL) and cultured overnight at 37° C. at 200 rpm. The library cultured for 12 hours or more was centrifuged at 4000 rpm for 15 minutes to isolate the supernatant, and 5×PEG/NaCl buffer was added to the supernatant at 1×, and then allowed to stand on ice for 30 minutes. The supernatant was removed by centrifugation at 8000 rpm for 30 minutes. The pellets were resuspended in 2 mL of 1% BSA/PBS, and then centrifuged at 12000 rpm for 10 minutes, and the supernatant was collected and used in the next panning. The above-described procedure was repeated four times.

12-3: Preparation of Anti-TFPI Individual Clone Antibodies by ELISA

Single colonies were collected from the finally amplified library, and then cultured in 1.5 mL of SB/carbenicillin at 37° C. at 220 rpm until an OD600 of about 0.8-1.0 was reached, followed by incubation with 1 mM IPTG at 30° C. at 200 rpm for 12 hours. Next, the cells were centrifuged at 5500 rpm for 5 minutes, and the supernatant was added to a TFPI antigen-coated ELISA plate, incubated at room temperature for 2 hours, and then washed four times with PBST (1×PBS, 0.05% tween 20). Next, a 1:5000 dilution of an HRP/anti-hFab-HRP conjugate (CAT.No.A0293, Sigma) with 1% BSA/1×PBS was added to the cells, after which the cells were incubated at room temperature for 1 hour and washed four times with PBST (1×PBS, 0.05% tween 20). Then, the cells treated with a TMB solution for 5-10 minutes, and a TMB stop solution was added to the cells. Next, the absorbance at a wavelength of 450 nm was measured using the TECAN sunrise, and clones having high O.D values were selected as individual clones.

As a result, as shown in Table 22 below, clones that bind specifically to human TFPI could be selected, and the amino acid sequences thereof were analyzed. Among the antibodies described in Korean Patent Application No. 10-2015-0026555, the antibody used in the present invention was described as '2015-26555_(SEQ ID NO of the previous application)'.

Table 23 below shows the CDR amino acid sequences of the clone antibodies of Table 22, identified based on the Kabat numbering system.

TABLE 22

| Clones | Variable Regions | Amino Acid Sequences | SEQ ID NOS: |
|---|---|---|---|
| A24 | Heavy Chain | EVQLVESGGGLVKPGGSLRLSCAASGFTF<u>H</u>SYAMNWVRQAPGKGLEWVSTITT<u>R</u>GSYTYYADSVEGRFTISRDNAKNSLYLQMNSLRAEDTAVYYCARQDGNFLMDYWGQGTLVTVSS | 195 |
|  | Light Chain | DVVMTQTPLSLPVTLGQPASISCKSSQSLLD<u>V</u>DGKTYLNWLQQRPGQSPKRLIYLVSKLDSGVPDRFTGSGSGTDFTLKISRVEAEDVGVYYCWQGTHFPFTFGQGTKVEIKR | 103 |

TABLE 22-continued

| Clones | Variable Regions | Amino Acid Sequences | SEQ ID NOS: |
|---|---|---|---|
| A25 | Heavy Chain | EVQLVESGGGLVKPGGSLRLSCAASGFTFSSYAMNWVRQAP GKGLEWVSTITTGGSHTYYADSVEGRFTISRDNAKNSLYLQ MNSLRAEDTAVYYCARQDGNFLMDYWGQGTLVTVSS | 97 |
|  | Light Chain | DVVMTQTPLSLPVTLGQPASISCKSSQSLLDRDGKTYLNWL QQRPGQSPKRLIYLVSKLDSGVPDRFTGSGSGTDFTLKISR VEAEDVGVYYCWQGTHFPFTFGQGTKVEIKR | 196 |
| A52 | Heavy Chain | EVQLVESGGGLVKPGGSLRLSCAASGFTFSSYAMNWVRQAP GKGLEWVSTITTGGSHTYYADSVDGRFTISRDNAKNSLYLQ MNSLRAEDTAVYYCARQDGNFLMDYWGQGTLVTVSS | 197 |
|  | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |
| A63 | Heavy Chain | EVQLVESGGGLVKPGGSLRLSCAASGFTFSSYAMNWVRQAP GKGLEWVSTITTGGSYTYYADSVQGRFTISRDNAKNSLYLQ MNSLRAEDTAVYYCARQDGNFLMDYWGQGTLVTVSS | 198 |
|  | Light Chain | DVVMTQTPLSLPVTLGQPASISCKSSQSLLDVDGKTYLNWL QQRPGQSPKRLIYLVSKLDSGVPDRFTGSGSGTDFTLKISR VEAEDVGVYYCWQGTHFPFTFGQGTKVEIKR | 103 |
| A67 | Heavy Chain | EVQLVESGGGLVKPGGSLRLSCAASGFTFSSYAMNWVRQAP GKGLEWVSTITTGGSYTYYADSVEGRFTISRDNAKNSLYLQ MNSLRAEDTAVYYCARQDGNFLMDYWGQGTLVTVSS | 25 |
|  | Light Chain | DVVMTQTPLSLPVTLGQPASISCKSSQSLLDLDGKTYLNWL QQRPGQSPKRLIYLVSKLDSGVPDRFTGSGSGTDFTLKISR VEAEDVGVYYCWQGTHFPFTFGQGTKVEIKR | 101 |
| A71 | Heavy Chain | EVQLVESGGGLVKPGGSLRLSCAASGFTFSSYAMNWVRQAP GKGLEWVSTITTGGSYTYYADSVHGRFTISRDNAKNSLYLQ MNSLRAEDTAVYYCARQDGNFLMDYWGQGTLVTVSS | 199 |
|  | Light Chain | DVVMTQTPLSLPVTLGQPASISCKSSQSLLDTDGKTYLNWL QQRPGQSPKRLIYLVSKLDSGVPDRFTGSGSGTDFTLKISR VEAEDVGVYYCWQGTHFPFTFGQGTKVEIKR | 130 |
| A74 | Heavy Chain | EVQLVESGGGLVKPGGSLRLSCAASGFTFSSYAMHWVRQAP GKGLEWVSTITTGGSYTYYADSVQGRFTISRDNAKNSLYLQ MNSLRAEDTAVYYCARQDGNFLMDYWGQGTLVTVSS | 200 |
|  | Light Chain | DVVMTQTPLSLPVTLGQPASISCKSSQSLLDIDGKTYLNWL QQRPGQSPKRLIYLVSKLDSGVPDRFTGSGSGTDFTLKISR VEAEDVGVYYCWQGTHFPFTFGQGTKVEIKR | 96 |

TABLE 23

| Clones | Variable Regions | CDR1 AA sequences | SEQ ID NOS: | CDR2 AA sequences | SEQ ID NOS: | CDR3 AA sequences | SEQ ID NOS: |
|---|---|---|---|---|---|---|---|
| A24 | Heavy Chain | SYAMN | 149 | TITTRGSYTYY ADSVEG | 200 | QDGNFLMDY | 151 |
|  | Light Chain | KSSQSLLDV DGKTYLN | 160 | LVSKLDS | 153 | WQGTHFPF | 154 |
| A25 | Heavy Chain | SYAMN | 149 | TITTGGSHTYY ADSVEG | 155 | QDGNFLMDY | 151 |
|  | Light Chain | KSSQSLLDR DGKTYLN | 201 | LVSKLDS | 153 | WQGTHFPF | 154 |
| A52 | Heavy Chain | SYAMN | 149 | TITTGGSHTYY ADSVDG | 167 | QDGNFLMDY | 151 |
|  | Light Chain | KSSQSLLDI DGKTYLN | 152 | LVSKLDS | 153 | WQGTHFPF | 154 |

TABLE 23-continued

| Clones | Variable Regions | CDR1 AA sequences | SEQ ID NOS: | CDR2 AA sequences | SEQ ID NOS: | CDR3 AA sequences | SEQ ID NOS: |
|---|---|---|---|---|---|---|---|
| A63 | Heavy Chain | SYAMN | 149 | TITTGGSYTYY ADSVQG | 165 | QDGNFLMDY | 151 |
|  | Light Chain | KSSQSLLDV DGKTYLN | 160 | LVSKLDS | 153 | WQGTHFPF | 154 |
| A67 | Heavy Chain | SYAMN | 149 | TITTGGSYTYY ADSVEG | 162 | QDGNFLMDY | 151 |
|  | Light Chain | KSSQSLLDL DGKTYLN | 158 | LVSKLDS | 153 | WQGTHFPF | 154 |
| A71 | Heavy Chain | SYAMN | 149 | TITTGGSYTYY ADSVHG | 202 | QDGNFLMDY | 151 |
|  | Light Chain | KSSQSLLDT DGKTYLN | 171 | LVSKLDS | 153 | WQGTHFPF | 154 |
| A74 | Heavy Chain | SYAMH | 203 | TITTGGSYTYY ADSVQG | 165 | QDGNFLMDY | 151 |
|  | Light Chain | KSSQSLLDI DGKTYLN | 152 | LVSKLDS | 153 | WQGTHFPF | 154 |

12-4: Cloning of IgG Gene of Anti-TFPI 308-4 Clone Antibody Mutant

Using the obtained anti-TFPI 308-4 clone antibody mutant light-chain variable region gene as a template, PCR was performed using PrimeSTAR HS DNA polymerase (Takara) together with a KpnI-containing forward primer (Table 21; SEQ ID NO: 189) and a reverse primer (Table 21; SEQ ID NO: 190). In addition, using the human antibody kappa constant light region as a template, PCR was performed with a forward primer (Table 21; SEQ ID NO: 191) and a reverse primer (Table 21; SEQ ID NO: 192). The PCR was performed under the following conditions: 10 min at 94° C.; and then 30 cycles, each consisting of 15 sec at 94° C., 30 sec at 56° C. and 90 sec at 72° C.; followed by 10 min at 72° C. The amplified genes were electrophoresed on 1% agarose gel to confirm the DNA bands having the expected sizes, and were isolated using a gel extraction kit. Next, the light-chain variable region gene and the light-chain constant region gene were mixed with each other at a ratio of 1:1, and the mixture was subjected to overlapping PCR using a forward primer (Table 20; SEQ ID NO: 189) and a reverse primer (Table 20; SEQ ID NO: 192) under the following conditions: 10 min at 94° C.; and then 30 cycles, each consisting of 15 sec at 94° C., 30 sec at 56° C. and 90 sec at 72° C.; followed by 10 min at 72° C. The amplified gene was electrophoresed on 1% agarose gel to confirm the DNA band having the expected size, and was isolated using a gel extraction kit. The isolated gene was treated with KpnI (CAT.NO.R0142L, NEB) and HindIII (CAT.NO.R0104L, NEB) restriction enzymes at 37° C. for 12 hours or more, and then separated on 1% agarose gel. A pcIW plasmid vector was digested in the same manner and separated on agarose gel. Using T4 DNA ligase (Cat.No.M0203S, NEB), the isolated light-chain region gene was ligated into the NotI and HindIII sites of a linear pcIW vector. The ligation product was transformed into XL1-Blue bacteria (Electroporation-Competent Cells; Stratagene, Cat.No.200228), and the bacterial cells were plated on a carbenicillin-containing LB plate (Cat.No.LN004CA, NaraeBiotech) and cultured at 37° C. for 12 hours or more, and single colonies were selected from the plate and cultured. Next, a plasmid was isolated from the cells using a plasmid mini-kit (Cat.No.27405, QIAGEN) and analyzed by DNA sequencing.

The heavy-chain variable region was subjected to PCR using the heavy-chain variable region gene of the 308-4 antibody mutant as a template and PrimeSTAR HS DNA polymerase (Takara) together with a KpnI-containing reverse primer (Table 21; SEQ ID NO: 193) and an ApaI-containing reverse primer (Table 21; SEQ ID NO: 194). The PCR was performed under the following conditions: 2 min at 98° C.; and then 30 cycles, each consisting of 10 sec at 98° C., 10 sec at 58° C. and 30 sec at 72° C.; followed by 5 min at 72° C. The amplified gene was electrophoresed on 1% agarose gel to confirm the DNA band having the expected size, and was isolated using a gel extraction kit. Next, the three isolated genes were treated with KpnI and ApaI restriction enzymes at 37° C. for 4 hours. The gene treated with the restriction enzymes was separated on 1% agarose gel. A pCIW plasmid vector was also digested in the same manner and separated on agarose gel. Using T4 DNA ligase, the separated gene was ligated into the KpnI (CAT. NO. R0142L, NEB) and ApaI (NEB, CAT. NO. R0114L) sites of a linear pcIw vector containing the human heavy-chain constant region. The ligation product was transformed into XL1-Blue bacteria (Electroporation-Competent Cells; Stratagene, Cat.No.200228), and the bacterial cells were plated on a carbenicillin-containing LB plate (NaraeBiotech, Cat.No.LN004CA) and cultured at 37° C. for 12 hours or more, and single colonies were selected from the plate and cultured. Then, a plasmid was isolated from the cells using a plasmid mini-kit (Cat.No.27405, QIAGEN) and was analyzed by DNA sequencing.

12-5: Production and Purification of Anti-TFPI 308-4 Clone Antibody Mutant IgG

In order to produce and purify the anti-TFPI clone antibody mutant cloned in Example 12-4, Expi293F™ cells were seeded at a concentration of $2.5 \times 10^6$ cells/mL on one day before transfection. After 24 hours of culture (37° C., 8% $CO_2$, 125 rpm), Expi293™ Expression medium (Cat- .No.A1435101, Gibco) was added to prepare 30 mL of the cells at a concentration of $2.5 \times 10^6$ cells/mL (viability ≥95%). 30 μg of DNA (pcIw-anti-TFPI heavy chain: 15 μg, pcIw-anti-TFPI light chain: 15 μg) was diluted in OptiPro™SEM medium (Cat.No.12309019, Gibco) to a total volume of 1.5 mL and incubated at room temperature for 5 minutes. 80 μL of ExpiFectamine™293 reagent (Cat.No.A14524, Gibco) was added to 1.5 mL of OptiPro™SEM medium (Cat.No.12309019, Gibco) to a total volume of 1.5 mL, and then incubated at room temperature for minutes. After 5 minutes of incubation, 1.5 mL of the diluted DNA and 1.5 mL of the ExpiFectamine™ 293 reagent were mixed well with each other and incubated at room temperature for 20-30 minutes. Expi293F™ cells were treated with 3 mL of the mixture of the DNA and the ExpiFectamine™ 293 reagent. After 16-18 hours of suspension culture (37° C., 8% $CO_2$, 125 rpm), 150 μL of ExpiFectamine™ 293 Enhancer 1 (Cat.No.A14524, Gibco) and 1.5 mL of ExpiFectamine™ 293 Enhancer 2 (Cat-.No.A14524, Gibco) were added to the cells, followed by suspension culture for 5 days. After completion of the culture, the cells were centrifuged at 4000 rpm for 20 minutes to remove cell debris, and the supernatant was passed through a 0.22 μm filter. 100 μL of the protein A resin MabSelect Xtra (Cat.No.17-5269-02, GE Healthcare) was prepared per 30 mL of the culture medium, centrifuged at 1000 rpm for 2 minutes to remove the storage solution, and washed three times with 400 μL of protein A binding buffer (Cat.No.21007, Pierce) for each washing. Protein A resin was added to the prepared culture medium, followed by rotating incubation at room temperature for 30 minutes. The mixture of the culture medium and the resin was added to the Pierce spin column-snap cap (Cat.No.69725, Thermo), and extracted using the QIAvac 24 Plus (Cat.No.19413, QIAGEN) vacuum manifold so that only the resin remained in the column. The resin was washed with 5 mL of protein A binding buffer, and then resuspended in 200 μL of protein A elution buffer (Cat.No.21009, Pierce), after which it was incubated at room temperature for 2 minutes and eluted by centrifugation at 1000 rpm for 1 minute. The eluate was neutralized by addition of 2.5 μL of 1.5M Tris-HCl (pH 9.0). Elution was performed 4-6 times, and each fraction was quantified using Nanodrop 200C (Thermo Scientific). Fractions having the protein detected therein were collected, and the buffer was replaced with PBS (phosphate-buffered saline) buffer using 5 mL of 7K MWCO (Cat.No.0089892, Pierce) in Zeba Spin Desalting Columns. Next, electrophoresis (SDS-PAGE) of the protein was performed under reducing and non-reducing conditions to finally quantify the concentration of the antibody and verify the state of the antibody, and the antibody was stored at 4° C.

As a result, protein electrophoresis (SDS-PAGE) indicated that the anti-TFPI 308-4 clone antibody mutant was purified in a good state.

Example 13: Measurement of Quantitative Affinity of 308-4 Antibody Mutant for TFPI Antigen The quantitative affinities of 308-4 clone heavy-chain variable region antibody mutants 12, 1023, 1202, 3241, which are the anti-TFPI antibodies purified in Examples 11 and 12, for human recombinant TFPI, were measured using a Biacore T-200 (GE Healthcare) biosensor. Specifically, protein A was immobilized on a CM5 chip (CAT. No. BR-1005-30, GE Healthcare) to an Rmax of 200 by an amine-carboxyl reaction, and then each of the purified 12, 1023, 1202 and 3241 clones was bound to the immobilized protein A. Next, recombinant human TFPI serially diluted in HBS-EP buffer (10 mM HEPES (pH7.4), 150 mM NaCl, 3 mM EDTA, 0.005% surfactant P20) was run on the chip at a concentration of 0.078-5 nM at a flow rate of 30 μL/min for 120 seconds for association and 3600 seconds for dissociation. Dissociation of the TFPI associated with the antibody was induced by running 10 mM glycine-HCl (pH 1.5) at a flow rate for 30 seconds. The affinities in terms of kinetic rate constants ($K_{on}$ and $K_{off}$) and equilibrium dissociation constant ($K_D$) were evaluated using Biacore T-200 evaluation software, and the results are shown in Table 24 below.

Table 24 below shows the affinities of the anti-TFPI antibodies for recombinant human TFPI protein in terms of rate constants ($K_{on}$ and $K_{off}$) and equilibrium dissociation constant ($K_D$).

TABLE 24

| Antibodies | $K_{on}$ | $K_{off}$ | $K_D$ |
|---|---|---|---|
| 12 | $4.87 \times 10^6$ | $3.99 \times 10^{-5}$ | $8.19 \times 10^{-12}$ |
| 1023 | $4.91 \times 10^6$ | $1.5 \times 10^{-4}$ | $3.01 \times 10^{-11}$ |
| 1202 | $7.56 \times 10^6$ | $7.16 \times 10^{-5}$ | $9.47 \times 10^{-12}$ |
| 3241 | $1.91 \times 10^6$ | $1.4 \times 10^{-4}$ | $7.4 \times 10^{-11}$ |

Example 14: Measurement of Fxa Activity

Blood coagulation is induced by an intrinsic pathway and an extrinsic pathway, and the two pathways activate thrombin through a common pathway that activates factor X, thereby forming fibrin to induce blood coagulation. In addition, TFPI consists of Kunitz 1 (K1), Kunitz 2 (K2) and Kunitz 3 (K3) domains. It is known that the K1 domain binds to FVIIa and the K2 domain binds to FXa. It is known that blood coagulation is inhibited by the binding between TFPI and the blood clotting factor. Thus, in order to determine the effect of MG1113 (anti-TFPI antibody) on the blood coagulation process, the FXa activity was evaluated.

An assay system was composed only of FXa, TFPI and a candidate antibody so as to minimize the effects of several factors. When the candidate antibody binds to TFPI, it does not inhibit the function of FXa, and thus the FXa activity appears. However, when the candidate antibody does not effectively bind to TFPI, TFPI binds to FXa to thereby inhibit the function of FXa, and thus the degree of color development decreases. Thus, the residual activity of FXa which is not inhibited by TFPI is measured by the degree of substrate degradation. The substrate used herein is the FXa-specific substrate S-2765, and the substrate is degraded to generate measurable chromophoric pNA at 405 nm. This measurement method is based on an amidolytic assay.

Each of FXa, TFPI, mAb2021 and S-2765 was diluted with assay buffer (20 mM HEPES, 150 mM NaCl, 1 mg/mL of BSA, 0.02% $NaN_3$, 5 mM $CaCl_2$, pH7.4) with reference to Table 25 below and dispensed in a 1.5 ml tube.

TABLE 25

| Materials | Pre-dilution conc. (nM) | Working conc. (nM) | Others |
|---|---|---|---|
| FXa | 2 nM | 0.5 nM | |
| TFPI | 40 nM | 10 nM | |
| S-2765 | 2 mM | 0.5 mM | |
| Standard curve | 10 nM | 0.02, 0.1, 0.5, 2.5 nM | FXa |
| mAb2021 | 160 nM | 2.5, 5, 10, 20 nM | Positive Control |

50 μL of each of the positive control mAb2021 antibody (anti-TFPI Ab, Novo Nordisk) and the candidate antibodies was added to each well at concentrations of 20, 10, 5 and 2.5 nM. 50 μL of 40 nM TFPI solution was added to each well and allowed to stand at room temperature for 30 minutes. To obtain a standard curve, 50 μL of FXa solution was added to each well at varying concentrations, and 50 μL of 2 nM FXa solution was added to each well and incubated at 37° C. for 10 minutes. 50 μL of 2 mM S-2765 solution was added to each well and incubated at 37° C. for 30 minutes. Then, the absorbance of each well at a wavelength of 405 nm was read by a microplate reader in endpoint mode.

Figure 20:
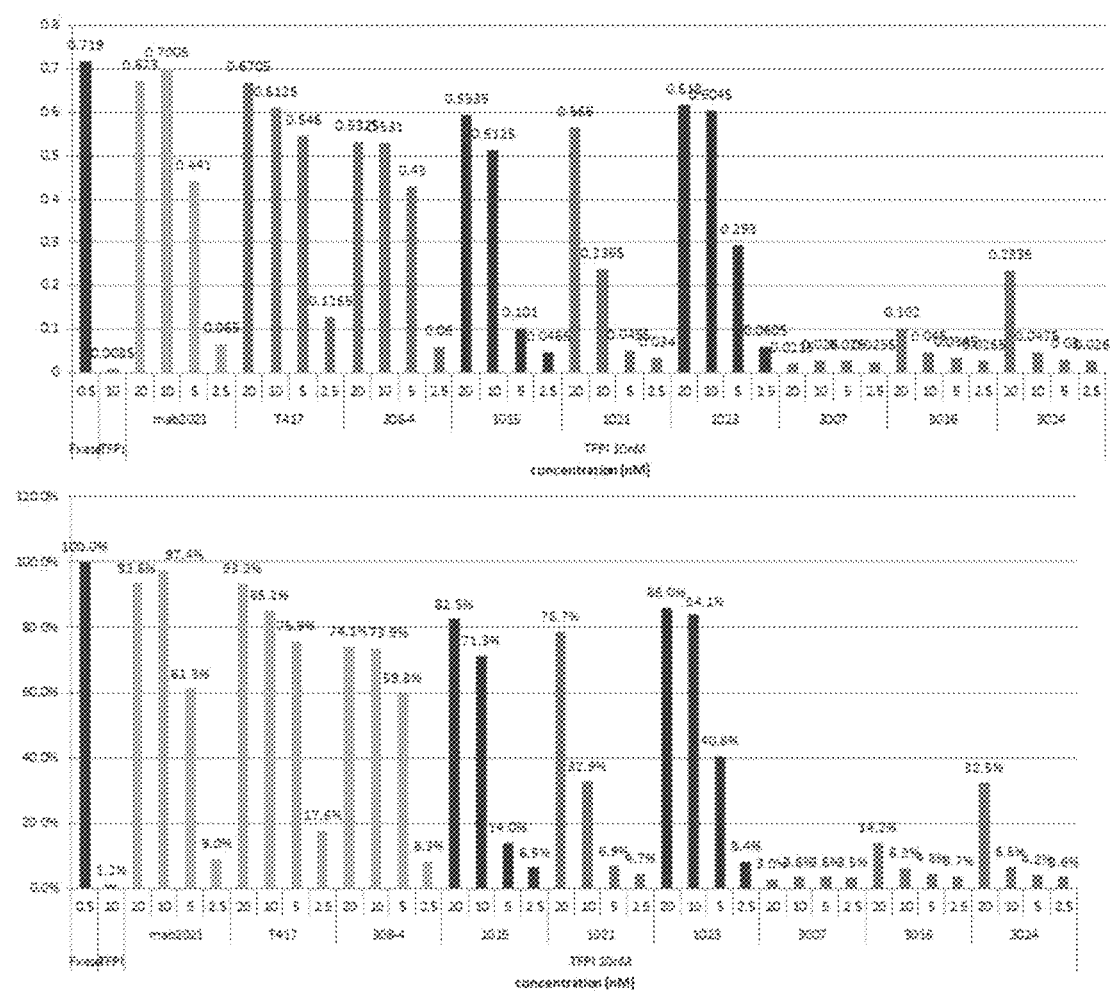
FIGS. 20 to 28 show the results of evaluating the effects of affinity-matured anti-TFPI antibodies by an Fxa activity assay.

As a result, as shown in FIG. 20, the effects of No. 1015, 1021, 1023, 3007, 3016 and 3024 antibodies that are affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 1015 antibody showed the effect of inhibiting TFPI by about 83% in the sample treated with 20 nM, and the effect of inhibiting TFPI by about 71% in the sample treated with 10 nM, compared to the positive control sample not treated with TFPI. In addition, No. 1023 antibody showed the effect of inhibiting TFPI by about 86% in the sample treated with 20 nM, and the effect of inhibiting TFPI by about 84% in the sample treated with 10 nM, compared to the positive control sample. When the effects were compared at a TFPI concentration of 10 nM, it was shown that No. 1023 antibody had a better TFPI inhibitory activity than No. 1015 antibody.

Figure 21:
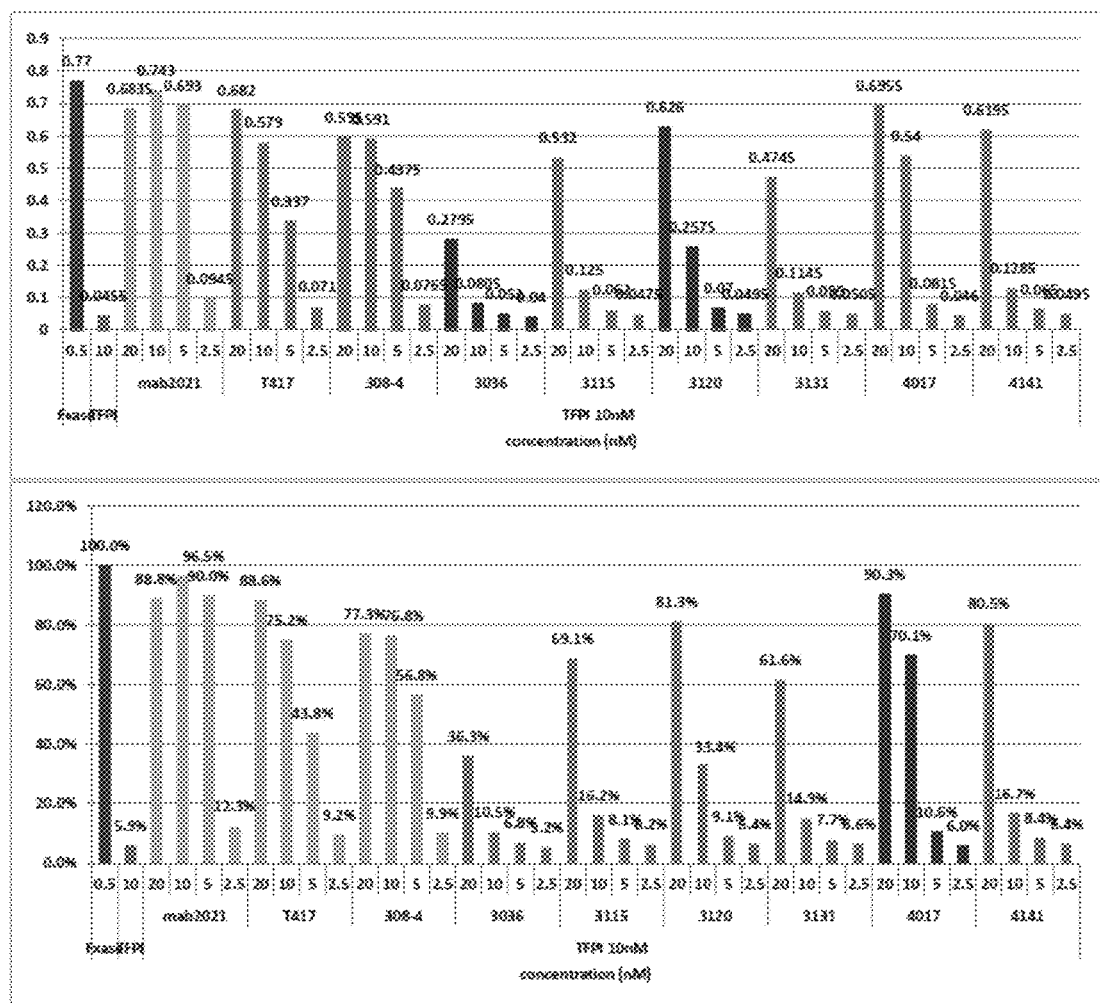

In addition, as shown in FIG. 21, the effects of No. 3036, 3115, 3120, 3131, 4017 and 4141 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 4017 antibody showed the effect of inhibiting TFPI by about 90% in the sample treated with 20 nM, and the effect of inhibiting TFPI by about 70% in the sample treated with 10 nM, compared to the positive control sample not treated with TFPI.

Figure 22:
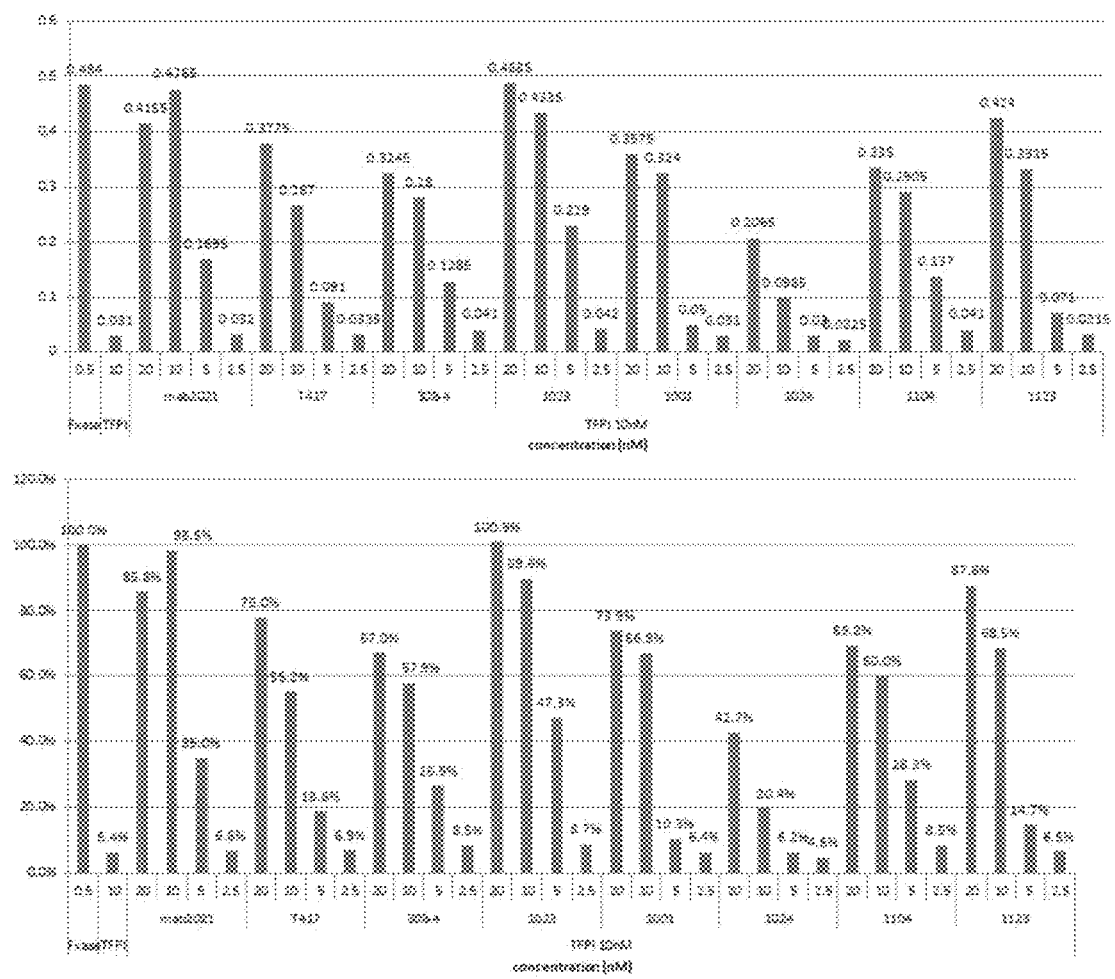

In addition, as shown in FIG. 22, the effects of No. 1001, 1024, 1104 and 1123 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 1123 antibody showed the effect of inhibiting TFPI by about 88% in the sample treated with 20 nM, and the effect of inhibiting TFPI by about 69% in the sample treated with 10 nM, compared to the positive control sample not treated with TFPI.

Figure 23:
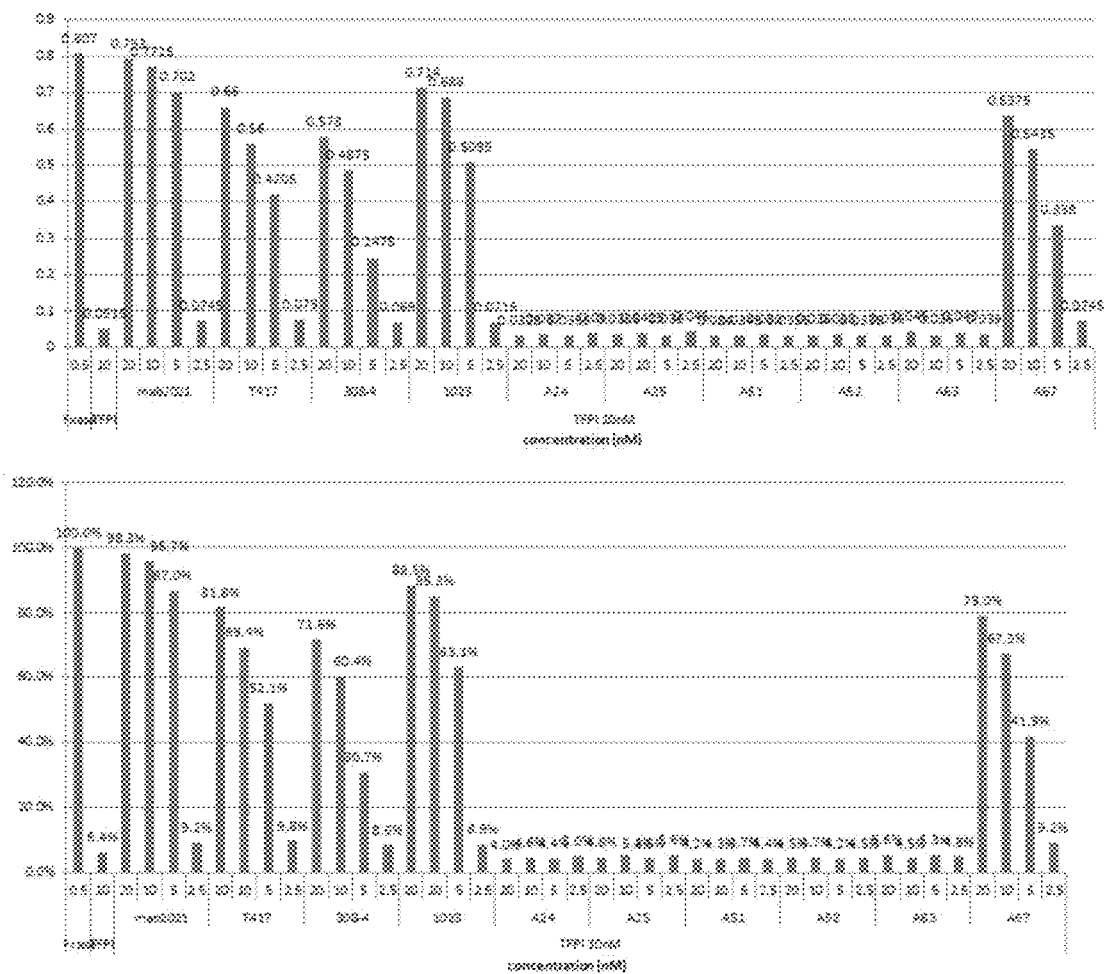

In addition, as shown in FIG. 23, the effects of A24, A25, A51, A52, A63 and A67 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, A67 antibody showed the effect of inhibiting TFPI by about 79% in the sample treated with 20 nM, and the effect of inhibiting TFPI by about 67% in the sample treated with 10 nM, compared to the positive control sample not treated with TFPI.

Figure 24:
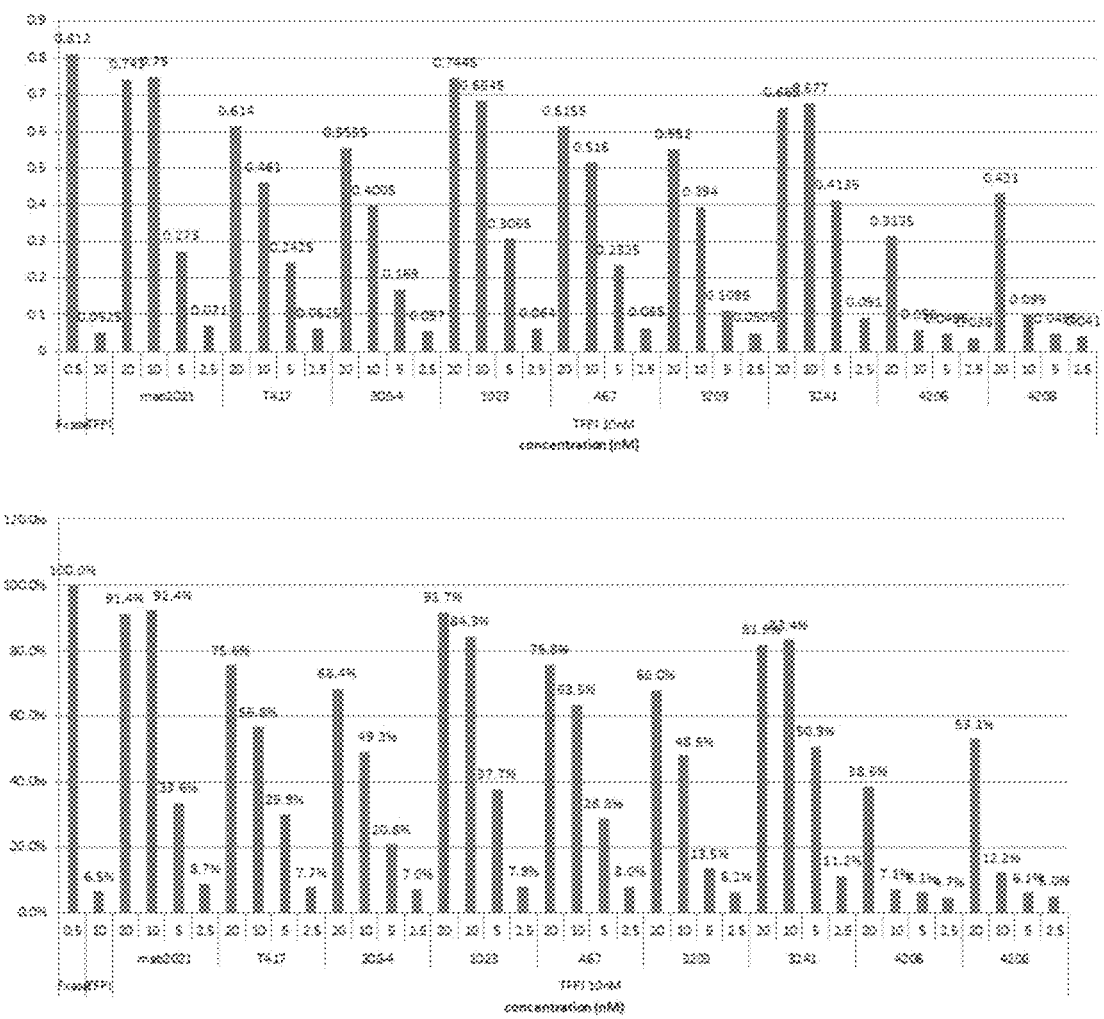
Figure 25:
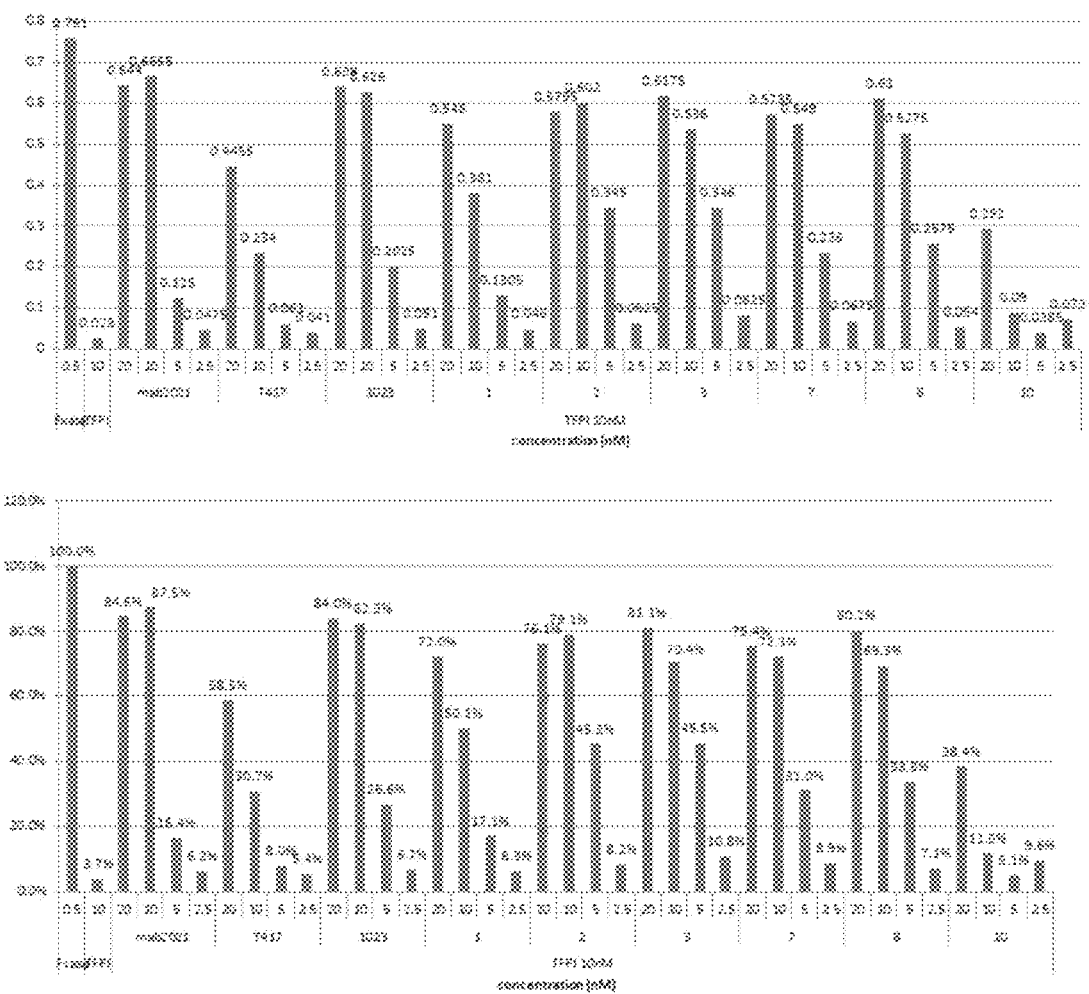
Figure 26:
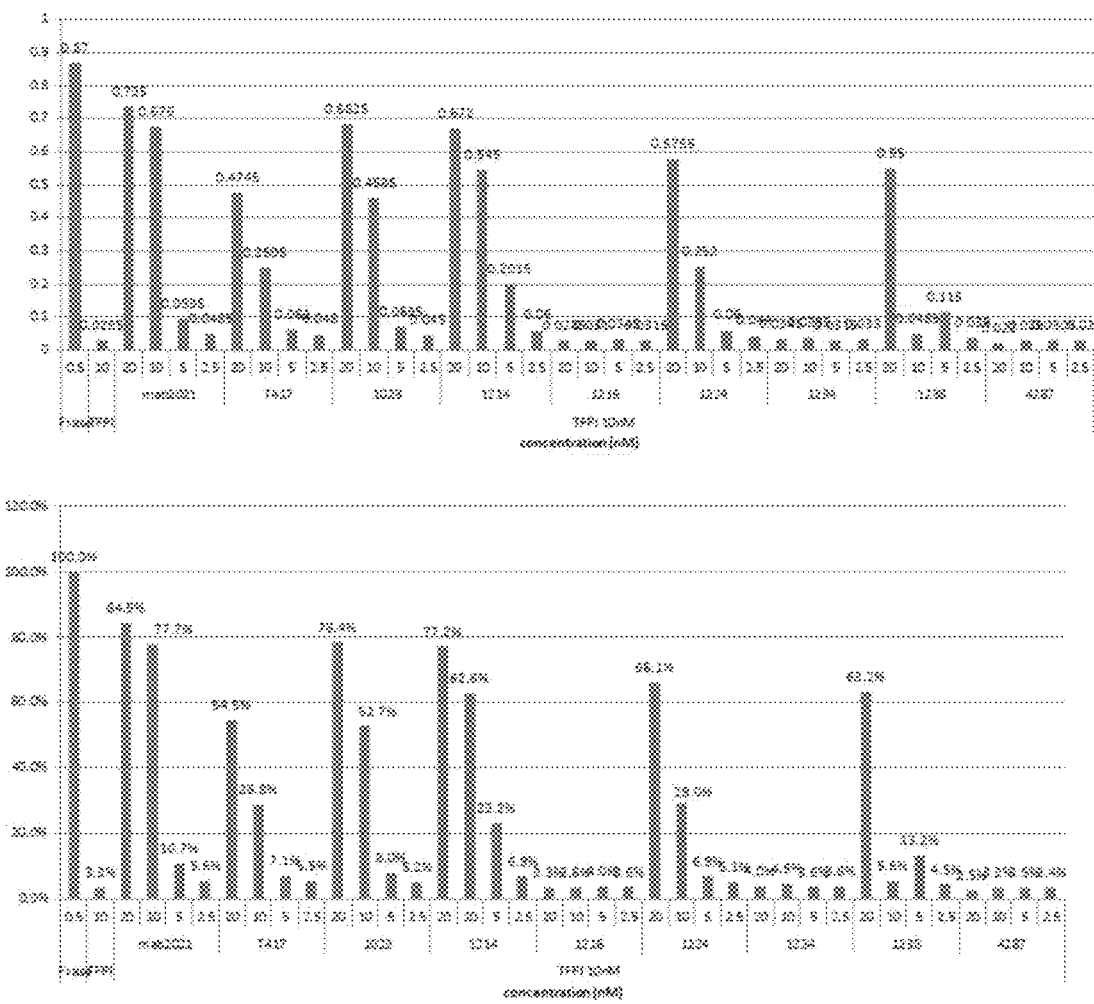
Figure 27:
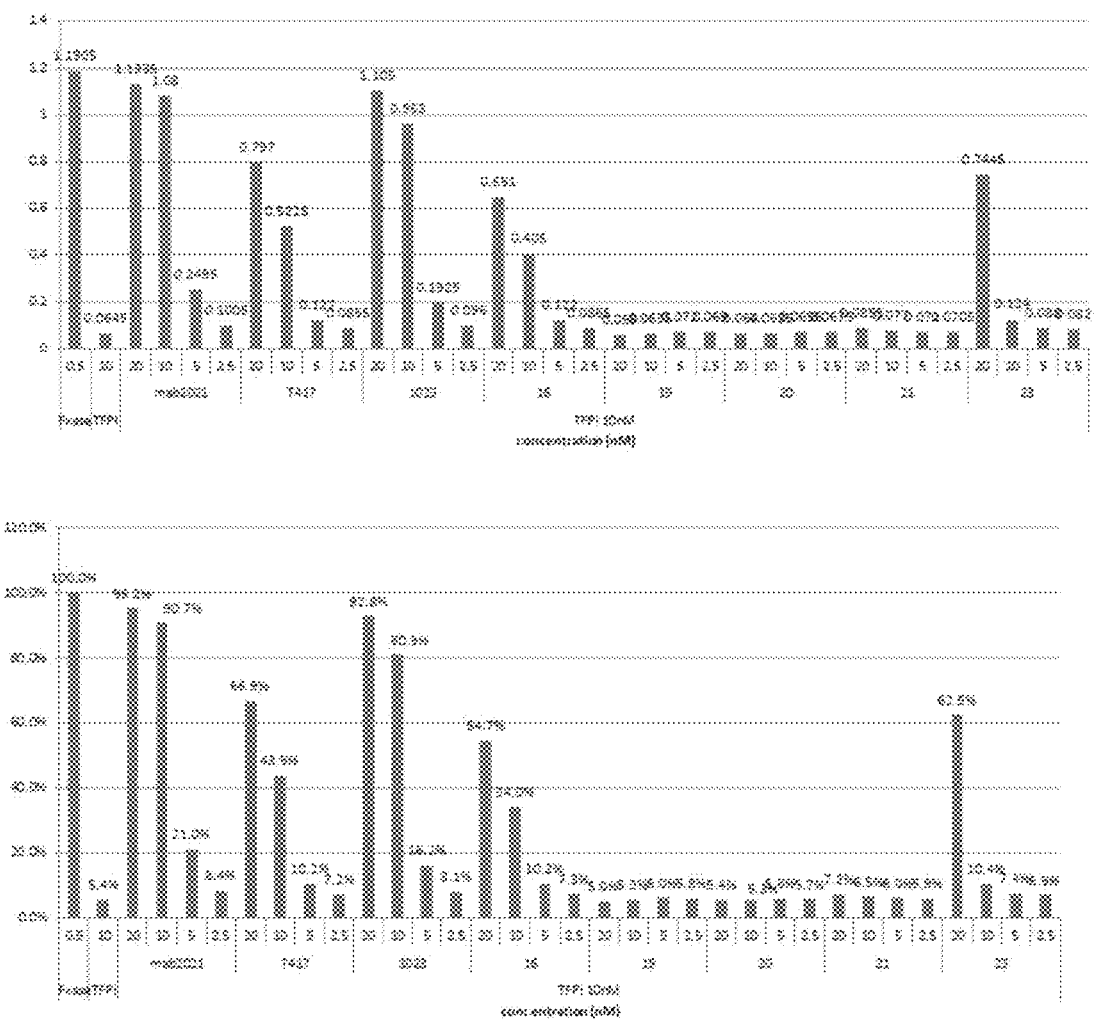

In addition, as shown in FIG. 24, the effects of No. 3203, 3241, 4206 and 4208 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 3241 antibody showed the effect of inhibiting TFPI by about 82% in the sample treated with 20 nM, and the effect of inhibiting TFPI by about 83% in the sample treated with 10 nM, compared to the positive control sample not treated with TFPI.

In addition, as shown in FIG. 25, the effects of No. 1, 2, 3, 7, 8 and 10 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 2 antibody showed the effect of inhibiting TFPI by about 76% in the sample treated with 20 nM, and the effect of inhibiting TFPI by about 79% in the sample treated with 10 nM, compared to the positive control sample not treated with TFPI. No. 3 antibody showed the effect of inhibiting TFPI by about 81% in the sample treated with 20 nM, and the effect of inhibiting TFPI by about 70% in the sample treated with 10 nM, compared to the positive control sample not treated with TFPI. No. 8 antibody showed the effect of inhibiting TFPI by about 80% in the sample treated with 20 nM, and the effect of inhibiting TFPI by about 69% in the sample treated with 10 nM, compared to the positive control sample not treated with TFPI.

In addition, as shown in FIG. 26, the effects of No. 1214, 1216, 1224, 1234, 1238 and 4287 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 1214 antibody showed the effect of inhibiting TFPI by about 77% in the sample treated with 20 nM, and the effect of inhibiting TFPI by about 63% in the sample treated with 10 nM, compared to the positive control sample not treated with TFPI.

In addition, as shown in FIG. 27, the effects of No. 16, 19, 20, 21 and 23 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 16 antibody showed the effect of inhibiting TFPI by about 55% in the sample treated with 20 nM, and the effect of inhibiting TFPI by about 34% in the sample treated with 10 nM, compared to the positive control sample not treated with TFPI.

Figure 28:
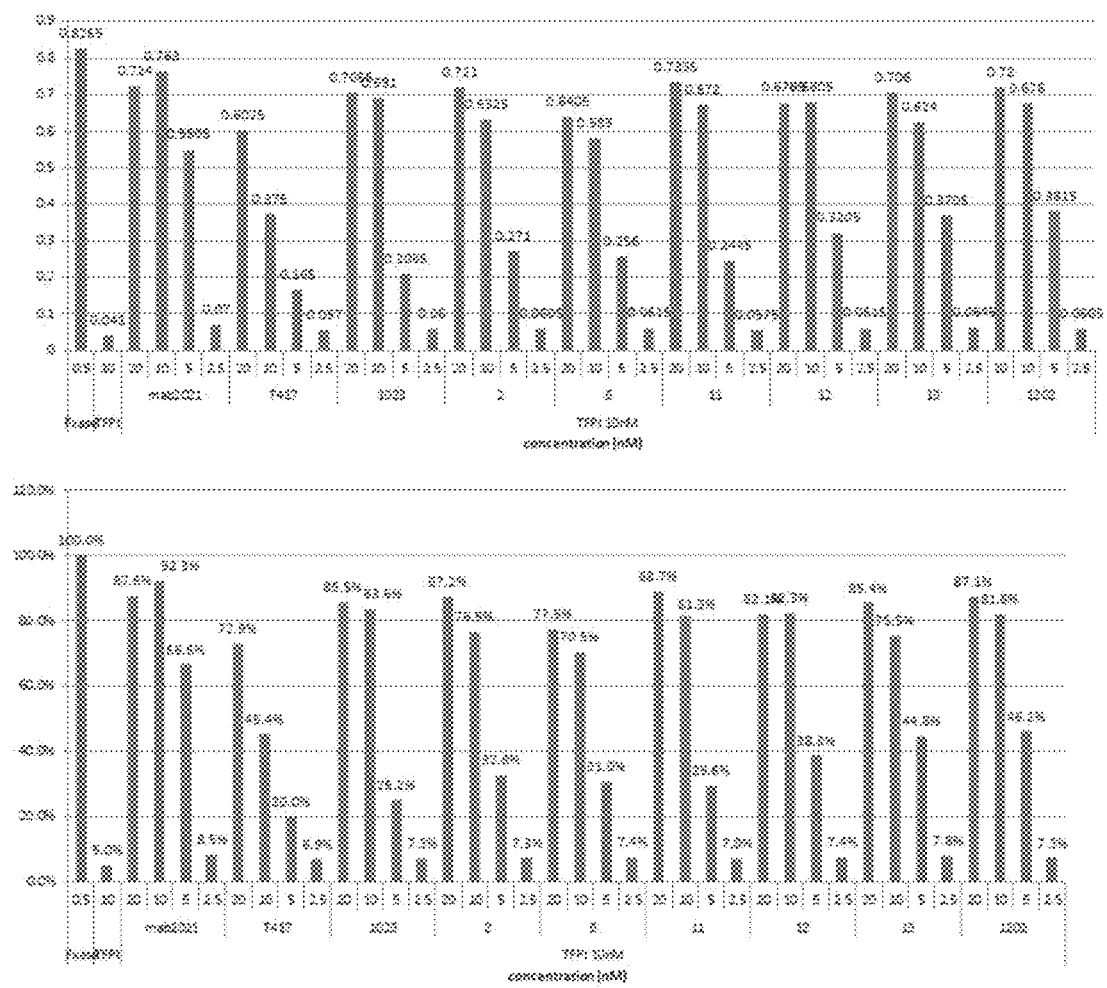

In addition, as shown in FIG. 28, the effects of No. 11, 12, 13 and 1202 antibodies that are the affinity-matured antibodies among the anti-TFPI MG1113 candidate antibodies were analyzed. It was shown that all the antibodies showed increases in the absorbance in an antibody concentration-dependent manner, indicating that the TFPI inhibitory effects of the antibodies increase in a concentration-dependent manner. Among these antibodies, No. 11 antibody showed the effect of inhibiting TFPI by about 89% in the sample treated with 20 nM, and the effect of inhibiting TFPI by about 81% in the sample treated with 10 nM, compared to the positive control sample not treated with TFPI. No. 12 antibody showed the effect of inhibiting TFPI by about 82% in the sample treated with 20 nM, and the effect of inhibiting TFPI by about 82% in the sample treated with 10 nM, compared to the positive control sample not treated with TFPI. No. 13 antibody showed the effect of inhibiting TFPI by about 85% in the sample treated with 20 nM, and the effect of inhibiting TFPI by about 76% in the sample treated with 10 nM, compared to the positive control sample not treated with TFPI. No. 1202 antibody showed the effect of inhibiting TFPI by about 87% in the sample treated with 20 nM, and the effect of inhibiting TFPI by about 82% in the sample treated with 10 nM, compared to the positive control sample not treated with TFPI.

Example 15: Measurement of TF/FVIIa/FX Complex

The most important factors in the extrinsic pathway of blood coagulation include TF (tissue factor), FVII (factor VII), FX (factor X) and the like. When TF and FVIIa form a complex by an external signal, FX is activated into FXa. Then, FXa activates prothrombin into thrombin, which then cleaves fibrinogen into fibrin which acts on blood coagulation. However, TFPI (tissue factor pathway inhibitor) inhibits the function of FXa by binding to FXa, thereby interfering with blood coagulation. In order to evaluate the effect of the anti-TFPI antibody MG1113 in the above-described pathway, a TF/FVIIa/FXa complex assay was performed. In a state in which TFPI was present together with or independently of the anti-TFPI antibody MG1113, the extents of production and inhibition of FXa by a TF/FVIIa complex were measured based on the extent of color development of a substrate (S2765) degraded by FXa, thereby evaluating the effect of the anti-TFPI antibody MG1113. In other words, as the TFPI inhibitory effect of the anti-TFPI antibody MG1113 increases, the production of FXa increases, and the amount of substrate degraded increases, resulting in an increase in absorbance.

In 1.5 mL tubes, TF (4500L/B, Sekisui diagnostics), FVIIa (Novo Nordisk, Novo Seven) and FX (PP008A, Hyphen biomed) were diluted with assay buffer (20 mM HEPES, 150 mM NaCl, 1 mg/mL BSA, 0.02% $NaN_3$, 5 mM $CaCl_2$, pH 7.4) to the concentrations shown in Table 26 below, thereby preparing a mixture solution.

TABLE 26

| Material | TF | FVIIa | FX |
| --- | --- | --- | --- |
| Concentration | 0.6 ng/mL | 1 nM | 17 nM --> 5 nM |

70 μL of the mixture solution was added to each well of a 96-well plate. To a blank well, 70 μL of assay buffer was added. Each well was incubated at 37° C. for 15 minutes, and then 30 μL of TFPI was added to each well to a concentration of 50 nM. However, 30 μL of assay buffer was added to each of the blank well and a positive control well (a sample not treated with the anti-TFPI antibody MG1113 and TFPI). 30 μL of the anti-TFPI antibody MG1113 was added to each well to concentrations of 12.5, 25, 50 and 100 nM. To each of the blank well, the positive control well (a sample not treated with the anti-TFPI antibody and TFPI) and the negative control well (a sample not treated with the anti-TFPI antibody MG1113), 30 μL of assay buffer was added, followed by incubation at 37° C. for 15 minutes. 20 μL of EDTA (E7889, Sigma-Aldrich) was added to each well to a concentration of 50 mM. Next, 50 μL of 52765 (Chromogenix, S-2765) was added to each well to a concentration of 200 μM, followed by incubation at 37° C. for 10 minutes. Next, the absorbance of each well at 405 nm was measured using a microplate reader.

Table 27 shows the numerical results obtained by evaluating the effects of the affinity-matured anti-TFPI MG1113 antibodies by the TF/FVIIa/FX complex assay.

TABLE 27

| Ab Conc. | Normalized | TFPI (50 nM) | mAb2021 | T417 | 308-4 | 1015 | 1023 | 4017 |
| --- | --- | --- | --- | --- | --- | --- | --- | --- |
| 100 nM | 0.918 | 0.119 | 0.937 | 0.949 | 0.938 | 0.944 | 0.951 | 0.943 |
| 50 nM |  |  | 0.929 | 0.945 | 0.926 | 0.919 | 0.947 | 0.919 |
| 25 nM |  |  | 0.918 | 0.873 | 0.664 | 0.269 | 0.795 | 0.307 |
| 12.5 nM |  |  | 0.218 | 0.242 | 0.223 | 0.179 | 0.228 | 0.181 |
| 6.25 nM |  |  | 0.168 | 0.179 | 0.177 | 0.158 | 0.168 | 0.150 |
| 3.13 nM |  |  | 0.145 | 0.147 | 0.155 | 0.148 | 0.152 | 0.138 |
| 1.56 nM |  |  | 0.125 | 0.134 | 0.135 | 0.141 | 0.143 | 0.134 |

Table 28 below shows the numerical results obtained by evaluating the effects of the affinity-matured anti-TFPI MG1113 antibodies by the TF/FVIIa/FX complex assay.

TABLE 28

| Ab Conc. | Normalized | TFPI (50 nM) | mAb2021 | T417 | 308-4 | 1015 | 1023 | 4017 |
|---|---|---|---|---|---|---|---|---|
| 100 nM | 100.0% | 13.0% | 102.0% | 103.3% | 102.1% | 102.8% | 103.6% | 102.7% |
| 50 nM | | | 101.2% | 102.9% | 100.8% | 100.1% | 103.1% | 100.1% |
| 25 nM | | | 100.0% | 95.0% | 72.3% | 29.3% | 86.5% | 33.4% |
| 12.5 nM | | | 23.7% | 26.3% | 24.2% | 19.4% | 24.8% | 19.7% |
| 6.25 nM | | | 18.2% | 19.4% | 19.2% | 17.2% | 18.2% | 16.3% |
| 3.13 nM | | | 15.7% | 16.0% | 16.8% | 16.1% | 16.5% | 15.0% |
| 1.56 nM | | | 13.6% | 14.5% | 14.7% | 15.4% | 15.6% | 14.5% |

Figure 29:
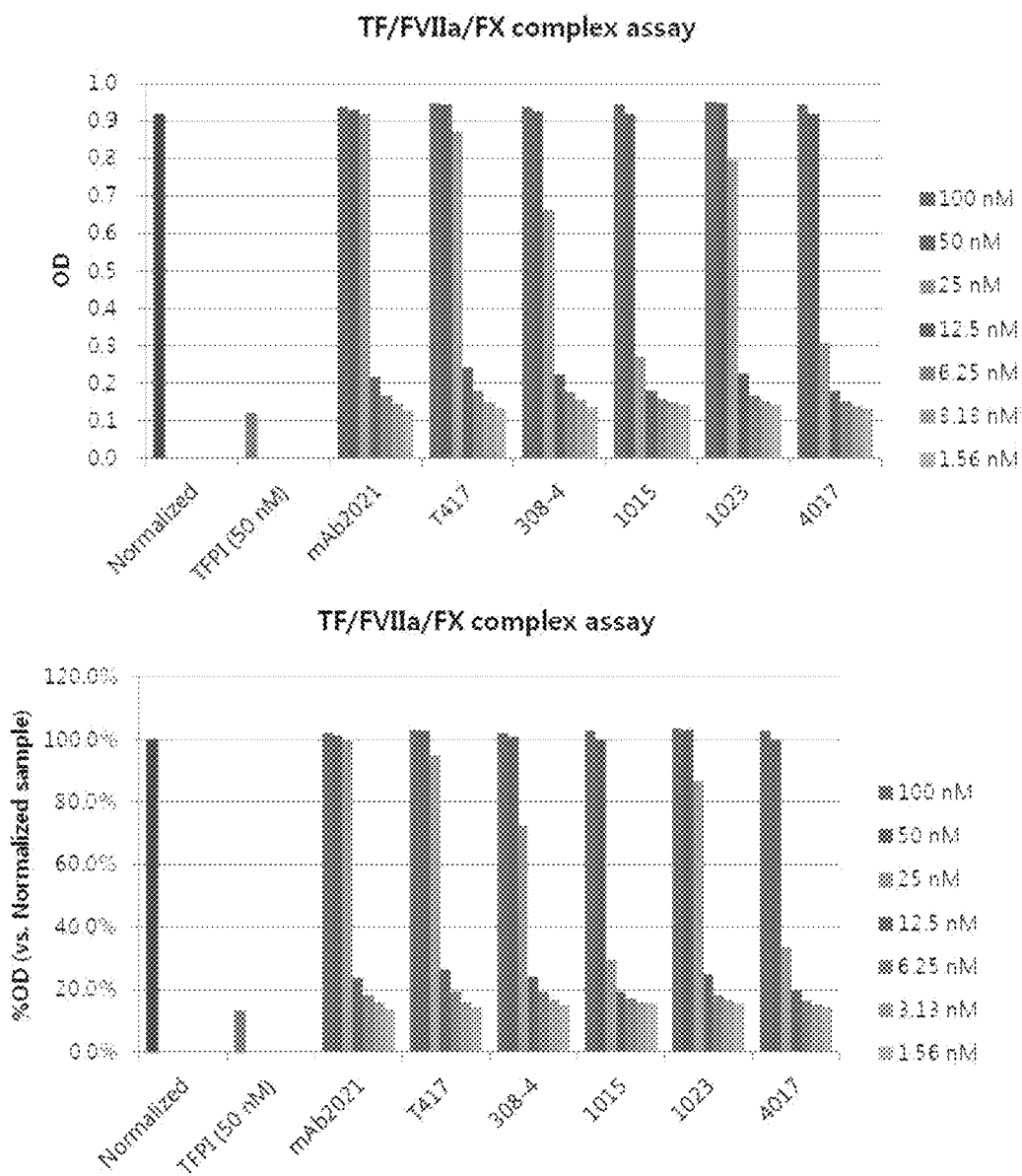

As a result, as shown in FIG. 29 and Tables 27 and 28 above, the effects of No. 1015, 1023 and 4017 antibodies that are affinity-matured antibodies among the anti-TFPI MG1113 candidate antibodies were confirmed. It was shown that all the candidate antibodies showed increases in the absorbance in an antibody concentration-dependent manner, indicating that the TFPI inhibitory effects of the antibodies increase in a concentration-dependent manner. No. 1015 antibody showed the effect of inhibiting TFPI by 100% in the sample treated with 50 nM, and the effect of inhibiting TFPI by about 29.3% in the sample treated with 25 nM, compared to the positive control sample not treated with TFPI. No. 1023 antibody showed the effect of inhibiting TFPI by 100% in the sample treated with 50 nM, and the effect of inhibiting TFPI by about 86.5% in the sample treated with 25 nM, compared to the positive control sample. No. 4017 antibody showed the effect of inhibiting TFPI by 100% in the sample treated with 50 nM, and the effect of inhibiting TFPI by about 33.4% in the sample treated with 25 nM, compared to the positive control sample. Thus, it was found that No. 1023 antibody has the high ability to inhibit TFPI.

Table 29 below shows the numerical results obtained by evaluating the effects of the affinity-matured anti-TFPI MG1113 antibodies by the TF/FVIIa/FX complex assay.

TABLE 29

| Ab Conc. | Normalized | TFPI (50 nM) | mAb2021 | T417 | 308-4 | 1023 | 1123 | A67 |
|---|---|---|---|---|---|---|---|---|
| 100 nM | 0.955 | 0.143 | 0.966 | 0.945 | 0.926 | 0.935 | 0.905 | 0.907 |
| 50 nM | | | 0.951 | 0.908 | 0.909 | 0.905 | 0.770 | 0.895 |
| 25 nM | | | 0.955 | 0.880 | 0.716 | 0.923 | 0.272 | 0.914 |
| 12.5 nM | | | 0.233 | 0.251 | 0.222 | 0.259 | 0.157 | 0.290 |
| 6.25 nM | | | 0.180 | 0.186 | 0.185 | 0.190 | 0.150 | 0.196 |
| 3.13 nM | | | 0.171 | 0.160 | 0.164 | 0.167 | 0.151 | 0.177 |
| 1.56 nM | | | 0.151 | 0.145 | 0.154 | 0.153 | 0.140 | 0.154 |

Table 30 below shows the numerical results obtained by evaluating the effects of the affinity-matured anti-TFPI MG1113 antibodies by the TF/FVIIa/FX complex assay.

TABLE 30

| Ab Conc. | Normalized | TFPI (50 nM) | mAb2021 | T417 | 308-4 | 1023 | 1123 | A67 |
|---|---|---|---|---|---|---|---|---|
| 100 nM | 100.0% | 15.0% | 101.2% | 99.0% | 97.0% | 98.0% | 94.8% | 95.0% |
| 50 nM | | | 99.6% | 95.1% | 95.2% | 94.8% | 80.7% | 93.7% |
| 25 nM | | | 100.1% | 92.2% | 75.0% | 96.6% | 28.5% | 95.8% |
| 12.5 nM | | | 24.4% | 26.3% | 23.2% | 27.1% | 16.4% | 30.3% |
| 6.25 nM | | | 18.8% | 19.5% | 19.4% | 19.9% | 15.7% | 20.5% |
| 3.13 nM | | | 17.9% | 16.8% | 17.2% | 17.5% | 15.8% | 18.5% |
| 1.56 nM | | | 15.8% | 15.2% | 16.1% | 16.0% | 14.7% | 16.1% |

In addition, as shown in FIG. 30 and Tables 29 and 30 above, No. 1023 antibody determined to have the highest effect in the above-described assay, together with No. 1123 antibody that is another affinity-matured antibody and the A67 antibody, was evaluated. It was shown that all the candidate antibodies showed increases in the absorbance in an antibody concentration-dependent manner, indicating that the TFPI inhibitory effects of the antibodies increase in a concentration-dependent manner. No. 1023 antibody showed the effect of inhibiting TFPI by 94.8% in the sample treated with 50 nM, and the effect of inhibiting TFPI by about 96.6% in the sample treated with 25 nM, compared to the positive control sample not treated with TFPI. No. 1123 antibody showed the effect of inhibiting TFPI by 80.7% in the sample treated with 50 nM, and the effect of inhibiting TFPI by about 28.5% in the sample treated with 25 nM, compared to the positive control sample. A67 antibody showed the effect of inhibiting TFPI by 93.7% in the sample treated with 50 nM, and the effect of inhibiting TFPI by about 95.8% in the sample treated with 25 nM, compared to the positive control sample. Thus, it was found that No. 1023 and A67 antibodies are similar to each other in the ability to inhibit TFPI.

Table 31 below shows the numerical results obtained by evaluating the effects of the affinity-matured anti-TFPI MG1113 antibodies by the TF/FVIIa/FX complex assay.

Figure 31:
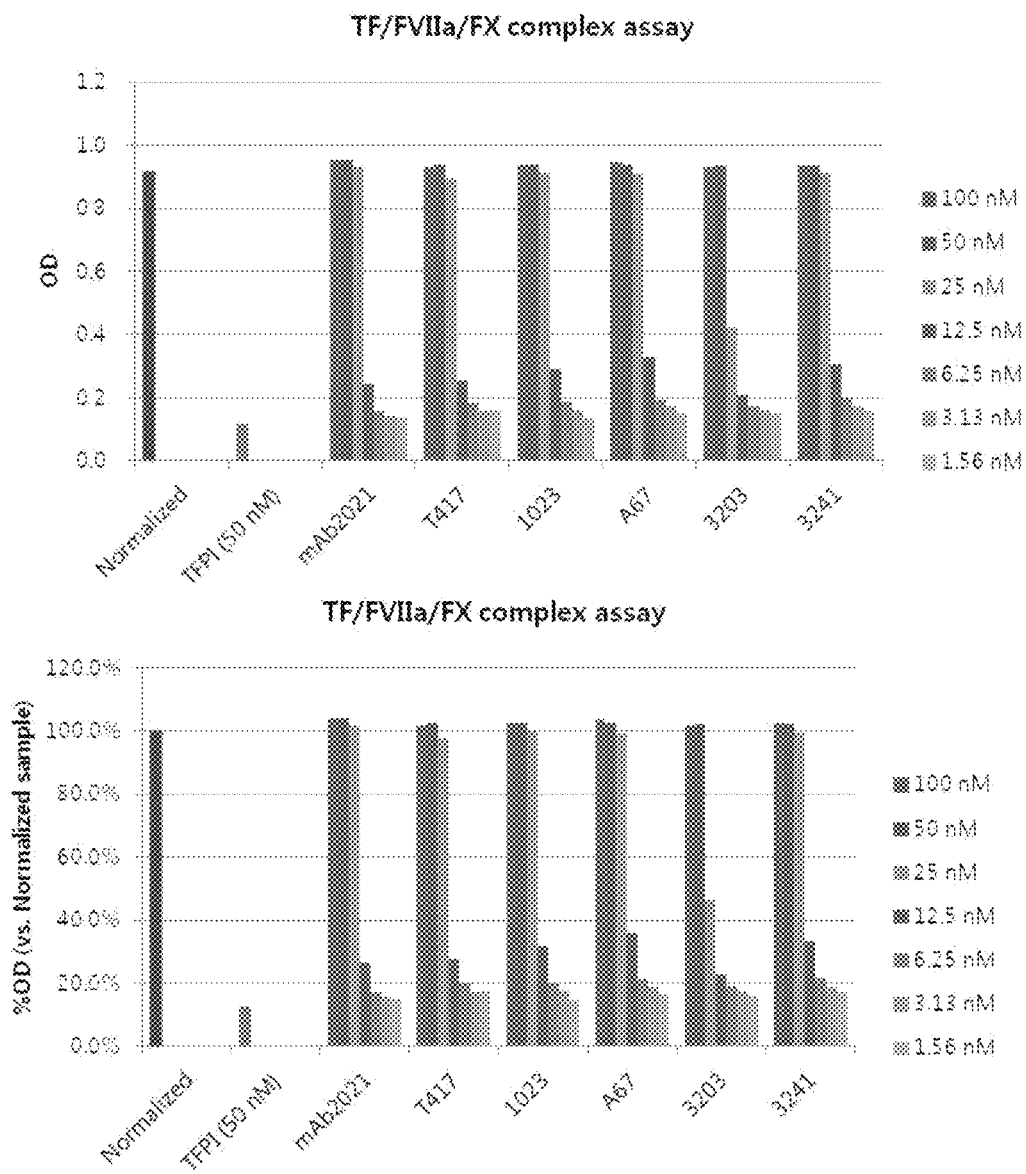

In addition, as shown in FIG. 31 and Tables 31 and 32 above, No. 1023 antibody determined to have the highest effect in the above-described assay, the A67 antibody, and No. 3203 antibody and No. 3241 antibody which are additional affinity-matured antibodies, were evaluated. It was shown that all the candidate antibodies showed increases in the absorbance in an antibody concentration-dependent manner, indicating that the TFPI inhibitory effects of the antibodies increase in a concentration-dependent manner. No. 1023 antibody showed the effect of inhibiting TFPI by 100% in the sample treated with 50 nM, and the effect of inhibiting TFPI by about 99.8% in the sample treated with 25 nM, compared to the positive control sample not treated with TFPI. A67 antibody showed the effect of inhibiting TFPI by 100% in the sample treated with 50 nM, and the effect of inhibiting TFPI by about 99.2% in the sample treated with 25 nM, compared to the positive control sample. No. 3203 antibody showed the effect of inhibiting TFPI by 100% in the sample treated with 50 nM, and the effect of inhibiting TFPI by about 46.3% in the sample treated with 25 nM, compared to the positive control sample. No. 3241 antibody showed the effect of inhibiting TFPI by 100% in the sample treated with 50 nM, and the effect of inhibiting TFPI by about 99.6% in the sample treated with 25 nM, compared to the positive control sample. Thus, it was found

TABLE 31

| Ab Conc. | Normalized | TFPI (50 nM) | mAb2021 | T417 | 1023 | A67 | 3203 | 3241 |
|---|---|---|---|---|---|---|---|---|
| 100 nM | 0.915 | 0.115 | 0.952 | 0.931 | 0.939 | 0.947 | 0.932 | 0.937 |
| 50 nM | | | 0.953 | 0.938 | 0.938 | 0.938 | 0.934 | 0.935 |
| 25 nM | | | 0.932 | 0.894 | 0.914 | 0.908 | 0.424 | 0.911 |
| 12.5 nM | | | 0.241 | 0.253 | 0.290 | 0.330 | 0.208 | 0.305 |
| 6.25 nM | | | 0.156 | 0.183 | 0.185 | 0.195 | 0.173 | 0.197 |
| 3.13 nM | | | 0.143 | 0.158 | 0.160 | 0.172 | 0.162 | 0.171 |
| 1.56 nM | | | 0.137 | 0.160 | 0.135 | 0.149 | 0.147 | 0.157 |

Table 32 below shows the numerical results obtained by evaluating the effects of the affinity-matured anti-TFPI MG1113 antibodies by the TF/FVIIa/FX complex assay.

TABLE 32

| Ab Conc. | Normalized | TFPI (50 nM) | mAb2021 | T417 | 1023 | A67 | 3203 | 3241 |
|---|---|---|---|---|---|---|---|---|
| 100 nM | 100.0% | 12.6% | 104.0% | 101.7% | 102.6% | 103.5% | 101.8% | 102.3% |
| 50 nM | | | 104.1% | 102.5% | 102.5% | 102.5% | 102.1% | 102.1% |
| 25 nM | | | 101.9% | 97.7% | 99.8% | 99.2% | 46.3% | 99.6% |
| 12.5 nM | | | 26.3% | 27.7% | 31.6% | 36.1% | 22.7% | 33.3% |
| 6.25 nM | | | 17.0% | 20.0% | 20.2% | 21.3% | 18.9% | 21.5% |
| 3.13 nM | | | 15.6% | 17.2% | 17.5% | 18.7% | 17.7% | 18.7% |
| 1.56 nM | | | 15.0% | 17.5% | 14.7% | 16.3% | 16.1% | 17.2% | that No. 1023, A67 and No. 3241 antibodies are similar to each other in the ability to inhibit TFPI.

Table 33 below shows the numerical results obtained by evaluating the effects of the affinity-matured anti-TFPI MG1113 antibodies by the TF/FVIIa/FX complex assay.

TABLE 33

| Ab Conc. | Normalized | TFPI (50 nM) | mAb2021 | T417 | 1023 | 2 | 3 | 8 |
|---|---|---|---|---|---|---|---|---|
| 100 nM | 0.809 | 0.04 | 0.805 | 0.745 | 0.810 | 0.835 | 0.842 | 0.834 |
| 50 nM | | | | 0.733 | 0.509 | 0.652 | 0.735 | 0.743 | 0.673 |

TABLE 33-continued

| Ab Conc. | Normalized | TFPI (50 nM) | mAb2021 | T417 | 1023 | 2 | 3 | 8 |
|---|---|---|---|---|---|---|---|---|
| 25 nM | | | 0.344 | 0.154 | 0.216 | 0.416 | 0.527 | 0.391 |
| 12.5 nM | | | 0.082 | 0.072 | 0.079 | 0.083 | 0.141 | 0.088 |
| 6.25 nM | | | 0.050 | 0.050 | 0.056 | 0.052 | 0.059 | 0.052 |
| 3.13 nM | | | 0.047 | 0.049 | 0.048 | 0.045 | 0.046 | 0.050 |
| 1.56 nM | | | 0.043 | 0.045 | 0.050 | 0.045 | 0.045 | 0.041 |

Table 34 below shows the numerical results obtained by evaluating the effects of the affinity-matured anti-TFPI MG1113 antibodies by the TF/FVIIa/FX complex assay.

TABLE 34

| Ab Conc. | Normalized | TFPI(50M) | mAb2021 | T417 | 1023 | 2 | 3 | 8 |
|---|---|---|---|---|---|---|---|---|
| 100 nM | 100.0% | 4.9% | 99.4% | 92.0% | 100.1% | 103.2% | 104.1% | 103.0% |
| 50 nM | | | 90.6% | 62.9% | 80.5% | 90.9% | 91.8% | 83.2% |
| 25 nM | | | 42.5% | 19.0% | 26.6% | 51.4% | 65.1% | 48.3% |
| 12.5 nM | | | 10.1% | 8.9% | 9.7% | 10.3% | 17.4% | 10.8% |
| 6.25 nM | | | 6.1% | 6.2% | 6.9% | 6.4% | 7.2% | 6.4% |
| 3.13 nM | | | 5.7% | 6.0% | 5.9% | 5.6% | 5.7% | 6.1% |
| 1.56 nM | | | 5.3% | 5.5% | 6.2% | 5.5% | 5.6% | 5.1% |

In addition, as shown in FIG. 32 and Tables 33 and 34 above, the concentration of FX used for treatment was changed from 17 nM to 5 nM to reduce the reaction rate to thereby increase resolution for analyzing the effects of the candidate antibodies. No. 1023 antibody selected through the above-described assay, and No. 2, 3 and 8 antibodies which are additional affinity-matured antibodies, were evaluated. It was observed that the candidate antibodies showed increases in the absorbance in an antibody concentration-dependent manner, indicating that the TFPI inhibitory effects of the antibodies increase in a concentration-dependent manner. It was shown that all the candidate antibodies showed increases in the absorbance in an antibody concentration-dependent manner, indicating that the TFPI inhibitory effects of the antibodies increase in a concentration-dependent manner. No. 1023 antibody showed the effect of inhibiting TFPI by 80.5% in the sample treated with 50 nM, and the effect of inhibiting TFPI by about 26.6% in the sample treated with 25 nM, compared to the positive control sample not treated with TFPI. No. 2 antibody showed the effect of inhibiting TFPI by about 99.9% in the sample treated with 50 nM, and the effect of inhibiting TFPI by about 51.4% in the sample treated with 25 nM, compared to the positive control sample. No. 3 antibody showed the effect of inhibiting TFPI by about 91.8% in the sample treated with 50 nM, and the effect of inhibiting TFPI by about 61.5% in the sample treated with 25 nM, compared to the positive control sample. No. 8 antibody showed the effect of inhibiting TFPI by about 83.2% in the sample treated with 50 nM, and the effect of inhibiting TFPI by about 48.3% in the sample treated with 25 nM, compared to the positive control sample.

Table 35 below shows the numerical results obtained by evaluating the effects of the affinity-matured anti-TFPI MG1113 antibodies by the TF/FVIIa/FX complex assay.

TABLE 35

| Ab Conc. | Normalized | TFPI (50 nM) | mAb2021 | T417 | 1023 | 12 | 13 | 1202 |
|---|---|---|---|---|---|---|---|---|
| 100 nM | 0.848 | 0.035 | 0.852 | 0.810 | 0.846 | 0.847 | 0.859 | 0.859 |
| 50 nM | | | 0.730 | 0.600 | 0.681 | 0.803 | 0.818 | 0.843 |
| 25 nM | | | 0.462 | 0.273 | 0.371 | 0.489 | 0.528 | 0.509 |
| 12.5 nM | | | 0.105 | 0.074 | 0.088 | 0.097 | 0.101 | 0.091 |
| 6.25 nM | | | 0.062 | 0.050 | 0.071 | 0.067 | 0.075 | 0.059 |
| 3.13 nM | | | 0.046 | 0.047 | 0.051 | 0.048 | 0.054 | 0.051 |
| 1.56 nM | | | 0.044 | 0.045 | 0.041 | 0.041 | 0.046 | 0.043 |

Table 36 below shows the numerical results obtained by evaluating the effects of the affinity-matured anti-TFPI MG1113 antibodies by the TF/FVIIa/FX complex assay.

TABLE 36

| Ab Conc. | Normalized | TFPI (50 nM) | mAb2021 | T417 | 1023 | 12 | 13 | 1202 |
|---|---|---|---|---|---|---|---|---|
| 100 nM | 100.0% | 4.1% | 100.4% | 95.5% | 99.8% | 99.9% | 101.3% | 101.2% |
| 50 nM | | | 86.1% | 70.7% | 80.3% | 94.6% | 96.5% | 99.4% |
| 25 nM | | | 54.4% | 32.1% | 43.7% | 57.7% | 62.2% | 60.0% |

TABLE 36-continued

| Ab Conc. | Normalized | TFPI (50 nM) | mAb2021 | T417 | 1023 | 12 | 13 | 1202 |
|---|---|---|---|---|---|---|---|---|
| 12.5 nM | | | 12.4% | 8.7% | 10.3% | 11.4% | 11.9% | 10.7% |
| 6.25 nM | | | 7.3% | 5.8% | 8.3% | 7.8% | 8.8% | 6.9% |
| 3.13 nM | | | 5.4% | 5.5% | 6.0% | 5.6% | 6.4% | 6.0% |
| 1.56 nM | | | 5.2% | 5.2% | 4.8% | 4.8% | 5.4% | 5.1% |

Figure 33:
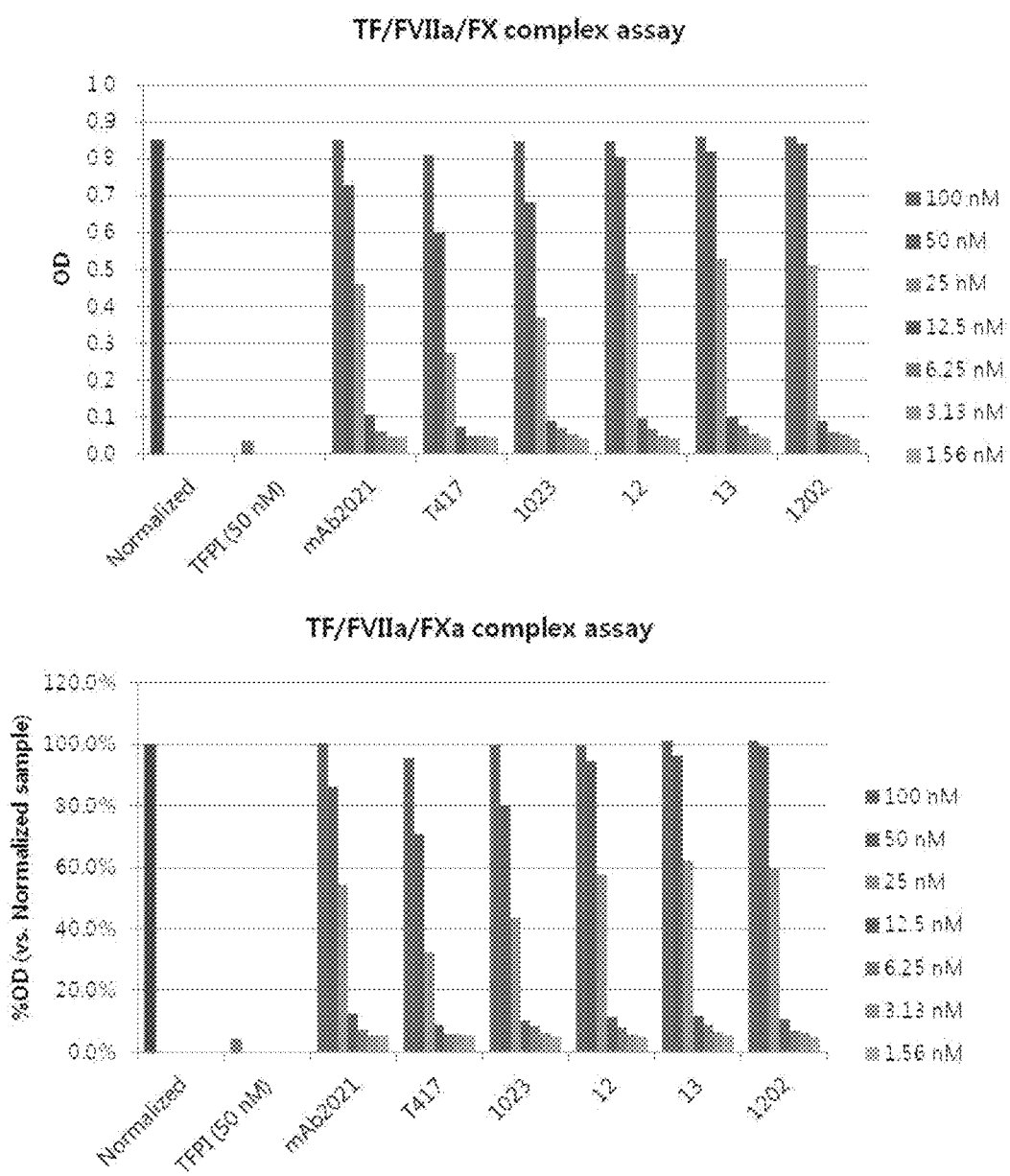

As shown in FIG. 33 and Tables 35 and 36 above, No. 1023 antibody and No. 12, 13 and 1202 antibodies that are additional affinity-matured antibodies were evaluated. It was observed that the candidate antibodies showed increases in the absorbance in an antibody concentration-dependent manner, indicating that the TFPI inhibitory effects of the antibodies increase in a concentration-dependent manner. It was shown that all the candidate antibodies showed increases in the absorbance in an antibody concentration-dependent manner, indicating that the TFPI inhibitory effects of the antibodies increase in a concentration-dependent manner. No. 1023 antibody showed the effect of inhibiting TFPI by 80.3% in the sample treated with 50 nM, and the effect of inhibiting TFPI by about 43.7% in the sample treated with 25 nM, compared to the positive control sample not treated with TFPI. No. 12 antibody showed the effect of inhibiting TFPI by about 94.6% in the sample treated with 50 nM, and the effect of inhibiting TFPI by about 57.7% in the sample treated with 25 nM, compared to the positive control sample. No. 13 antibody showed the effect of inhibiting TFPI by about 96.5% in the sample treated with 50 nM, and the effect of inhibiting TFPI by about 62.2% in the sample treated with 25 nM, compared to the positive control sample. No. 1202 antibody showed the effect of inhibiting TFPI by about 99.4% in the sample treated with 50 nM, and the effect of inhibiting TFPI by about 60.0% in the sample treated with 25 nM, compared to the positive control sample.

Example 16: Measurement of Thrombin Generation

The blood coagulation mechanism is divided into an intrinsic pathway and an extrinsic pathway. It is known that the function of TF (tissue factor) in the extrinsic pathway is the activity feedback function in the blood coagulation mechanism and is the explosive production of thrombin that is produced very fast. The most important factors in this blood coagulation mechanism include TF (tissue factor), FVII (factor VII), FX (factor X) and the like. When TF and FVIIa form a complex by an external signal, FX is activated into FXa. Then, FXa activates prothrombin into thrombin, which then cleaves fibrinogen into fibrin which acts on blood coagulation. However, TFPI (tissue factor pathway inhibitor) acts to inhibit the function of FXa by binding to FXa, thereby interfering with blood coagulation. A thrombin generation assay comprises: treating plasma with a test sample to be evaluated; and then inspecting the amount of thrombin produced in the plasma, based on the amount of a fluorescent product produced when the produced thrombin converts a fluorogenic substrate into the fluorescent product in the presence of PPP-reagent low; and calibrating the inspected amount of thrombin with the known amount of thrombin calibrator, thereby measuring the actual generation of thrombin.

20 μL of PPP-reagent low solution was added to the sample loading well of a prewarmed 96-well plate (round bottom immulon 2HB 96 well plate), and 20 μL of calibrator solution was added to the calibrator well of the plate. An anti-TFPI candidate antibody was diluted in a pre-dissolved sample dilution (FVIII-deficient plasma) at a concentration of 0.3125, 0.625, 1.25 or 2.5 nM, and then incubated at room temperature for 10 minutes so that it could bind to TFPI.

80 μL of each of the sample dilution (FVIII-deficient plasma) was added to each of the calibrator and blank wells, and 80 μL of the diluted antibody solution was added to each of the remaining wells. A start button at the bottom of the software screen was pressed to execute washing. Washing was performed in a state in which an inlet tube was placed in distilled water in a water bath at 37° C. and in which an outlet tube was placed in an empty container. After completion of the washing, the next button was pressed to perform an empty process. The inlet tube was placed in a FluCa solution warmed to 37° C. and was primed to fill the tube with the solution. The outlet tube was mounted in an M hole in a dispenser, and then the next button was pressed to automatically dispense 20 μL of FluCa solution into each well, after which a shaking process was performed and analysis was initiated.

As a result, as shown in FIG. 34, for No. 1023 antibody among the affinity-matured antibodies selected through the Fxa activity assay and the TF/FVIIa/FXa complex assay, a thrombin generation comparison assay was performed using T417 chimeric antibody. At a concentration of 2.5 nM, the T417 antibody showed an increase in thrombin peak of about 401%, and No. 1023 antibody showed an increase in thrombin peak of about 401%, compared to the blank treated with only the sample dilution. In the case of ETP indicating the total generation of thrombin, in the sample treated with 2.5 nM, the T417 antibody showed an increase in ETP of about 293%, and No. 1023 antibody showed an increase in ETP of about 309%, compared to the negative control group (having no antibody). When the two antibodies were compared, it was shown that No. 1023 antibody obtained by affinity maturation has a better effect than the T417 antibody.

INDUSTRIAL APPLICABILITY

As described above, the antibody of the present invention, which binds specifically to TFPI, can activate the extrinsic pathway of blood coagulation by inhibiting TFPI. Thus, the antibody of the present invention can be effectively used for the treatment of antibody-induced hemophilia patients and for the prevention of blood coagulation disease in hemophilia-A or hemophilia-B patients.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An antibody that binds specifically to a TFPI (tissue factor pathway inhibitor) of SEQ ID NO: 39 and comprises:
  1) a heavy-chain CDR1 comprising the amino acid sequence of SEQ ID NO: 149, a heavy-chain CDR2 comprising the amino acid sequence of SEQ ID NO: 150, and a heavy-chain CDR3 comprising the amino acid sequence of SEQ ID NO: 151; and a light-chain CDR1 comprising the amino acid sequence of SEQ ID NO: 152, a light-chain CDR2 comprising the amino acid sequence of SEQ ID NO: 153, and a light-chain CDR3 comprising the amino acid sequence of SEQ ID NO: 154;
  2) a heavy-chain CDR1 comprising the amino acid sequence of SEQ ID NO: 5, a heavy-chain CDR2 comprising the amino acid sequence of SEQ ID NO: 6, and a heavy-chain CDR3 comprising the amino acid sequence of SEQ ID NO: 7; and a light-chain CDR1 comprising the amino acid sequence of SEQ ID NO: 8, a light-chain CDR2 comprising the amino acid sequence of SEQ ID NO: 9, and a light-chain CDR3 comprising the amino acid sequence of SEQ ID NO: 10;
  3) a heavy-chain CDR1 comprising the amino acid sequence of SEQ ID NO: 23, a heavy-chain CDR2 comprising the amino acid sequence of SEQ ID NO: 6, and a heavy-chain CDR3 comprising the amino acid sequence of SEQ ID NO: 7; and a light-chain CDR1 comprising the amino acid sequence of SEQ ID NO: 8, a light-chain CDR2 comprising the amino acid sequence of SEQ ID NO: 9, and a light-chain CDR3 comprising the amino acid sequence of SEQ ID NO: 10;
  4) a heavy-chain CDR1 comprising the amino acid sequence of SEQ ID NO: 23, a heavy-chain CDR2 comprising the amino acid sequence of SEQ ID NO: 27, and a heavy-chain CDR3 comprising the amino acid sequence of SEQ ID NO: 7; and a light-chain CDR1 comprising the amino acid sequence of SEQ ID NO: 8, a light-chain CDR2 comprising the amino acid sequence of SEQ ID NO: 9, and a light-chain CDR3 comprising the amino acid sequence of SEQ ID NO: 10;
  5) a heavy-chain CDR1 comprising the amino acid sequence of SEQ ID NO: 149, a heavy-chain CDR2 comprising the amino acid sequence of SEQ ID NO: 162, and a heavy-chain CDR3 comprising the amino acid sequence of SEQ ID NO: 151; and a light-chain CDR1 comprising the amino acid sequence of SEQ ID NO: 177, a light-chain CDR2 comprising the amino acid sequence of SEQ ID NO: 153, and a light-chain CDR3 comprising the amino acid sequence of SEQ ID NO: 154;
  6) a heavy-chain CDR1 comprising the amino acid sequence of SEQ ID NO: 149, a heavy-chain CDR2 comprising the amino acid sequence of SEQ ID NO: 155, and a heavy-chain CDR3 comprising the amino acid sequence of SEQ ID NO: 156; and a light-chain CDR1 comprising the amino acid sequence of SEQ ID NO: 177, a light-chain CDR2 comprising the amino acid sequence of SEQ ID NO: 153, and a light-chain CDR3 comprising the amino acid sequence of SEQ ID NO: 154;
  7) a heavy-chain CDR1 comprising the amino acid sequence of SEQ ID NO: 149, a heavy-chain CDR2 comprising the amino acid sequence of SEQ ID NO: 155, and a heavy-chain CDR3 comprising the amino acid sequence of SEQ ID NO: 151; and a light-chain CDR1 comprising the amino acid sequence of SEQ ID NO: 177, a light-chain CDR2 comprising the amino acid sequence of SEQ ID NO: 153, and a light-chain CDR3 comprising the amino acid sequence of SEQ ID NO: 154; or
  8) a heavy-chain CDR1 comprising the amino acid sequence of SEQ ID NO: 149, a heavy-chain CDR2 comprising the amino acid sequence of SEQ ID NO: 162, and a heavy-chain CDR3 comprising the amino acid sequence of SEQ ID NO: 151; and a light-chain CDR1 comprising the amino acid sequence of SEQ ID NO: 152, a light-chain CDR2 comprising the amino acid sequence of SEQ ID NO: 153, and a light-chain CDR3 comprising the amino acid sequence of SEQ ID NO: 154.

2. The antibody of claim 1, wherein the antibody contains a heavy-chain variable region comprising the amino acid sequence of SEQ ID NO: 1, 21, 25, 95, 99, 105, 137, or 138.

3. The antibody of claim 1, wherein the antibody contains a light-chain variable region comprising the amino acid sequence of SEQ ID NO: 2, 22, or 96.

4. A pharmaceutical composition, which comprises the antibody of claim 1 as an active ingredient.

5. A pharmaceutical composition, which comprises the antibody of claim 2 as an active ingredient.

6. A pharmaceutical composition, which comprises the antibody of claim 3 as an active ingredient.

* * * * *